United States Patent
McGarvey et al.

(10) Patent No.: US 12,257,340 B2
(45) Date of Patent: Mar. 25, 2025

(54) PHARMACEUTICAL COMPOSITIONS COMPRISING ANTI-191P4D12 ANTIBODY DRUG CONJUGATES AND METHODS OF USE THEREOF

(71) Applicants: AGENSYS, INC., Santa Monica, CA (US); SEAGEN INC., Bothell, WA (US)

(72) Inventors: Orla McGarvey, Basel (CH); Gayathri Ratnaswamy, Encino, CA (US); Yingqing Sun, San Diego, CA (US); Marie Rose Van Schravendijk, Seattle, WA (US)

(73) Assignees: AGENSYS, INC., Northbrook, IL (US); SEAGEN INC., Bothell, WA (US)

( * ) Notice: Subject to any disclaimer, the term of this patent is extended or adjusted under 35 U.S.C. 154(b) by 966 days.

(21) Appl. No.: 17/298,865

(22) PCT Filed: Oct. 15, 2019

(86) PCT No.: PCT/US2019/056214
§ 371 (c)(1),
(2) Date: Jun. 1, 2021

(87) PCT Pub. No.: WO2020/117373
PCT Pub. Date: Jun. 11, 2020

(65) Prior Publication Data
US 2022/0175950 A1  Jun. 9, 2022

Related U.S. Application Data

(60) Provisional application No. 62/774,819, filed on Dec. 3, 2018.

(51) Int. Cl.
| | |
|---|---|
| A61K 39/395 | (2006.01) |
| A61K 9/00 | (2006.01) |
| A61K 38/07 | (2006.01) |
| A61K 47/02 | (2006.01) |
| A61K 47/12 | (2006.01) |
| A61K 47/54 | (2017.01) |
| A61K 47/68 | (2017.01) |

(52) U.S. Cl.
CPC ............ *A61K 9/0019* (2013.01); *A61K 38/07* (2013.01); *A61K 39/3955* (2013.01); *A61K 47/02* (2013.01); *A61K 47/12* (2013.01); *A61K 47/545* (2017.08); *A61K 47/68031* (2023.08); *A61K 47/6849* (2017.08)

(58) Field of Classification Search
CPC .......... A61K 39/3955; A61K 47/68031; A61K 47/68; A61K 47/545
See application file for complete search history.

(56) References Cited

U.S. PATENT DOCUMENTS

| | | |
|---|---|---|
| 4,179,337 A | 12/1979 | Davis et al. |
| 4,301,144 A | 11/1981 | Iwashita et al. |
| 4,496,689 A | 1/1985 | Mitra |
| 4,640,835 A | 2/1987 | Shimizu et al. |
| 4,670,417 A | 6/1987 | Iwashita et al. |
| 4,791,192 A | 12/1988 | Nakagawa et al. |
| 4,816,567 A | 3/1989 | Cabilly et al. |
| 4,880,935 A | 11/1989 | Thorpe |
| 4,946,778 A | 8/1990 | Ladner et al. |
| 5,122,368 A | 6/1992 | Greenfield et al. |
| 5,260,203 A | 11/1993 | Ladner et al. |
| 5,476,786 A | 12/1995 | Huston |
| 5,482,858 A | 1/1996 | Huston |
| 5,622,929 A | 4/1997 | Willner et al. |
| 5,624,821 A | 4/1997 | Winter et al. |
| 5,635,483 A | 6/1997 | Pettit et al. |
| 5,648,260 A | 7/1997 | Winter et al. |
| 5,663,149 A | 9/1997 | Pettit et al. |
| 5,677,425 A | 10/1997 | Bodmer et al. |
| 5,780,588 A | 7/1998 | Pettit et al. |
| 5,811,097 A | 9/1998 | Allison et al. |
| 5,824,805 A | 10/1998 | King et al. |
| 5,837,242 A | 11/1998 | Holliger et al. |
| 5,855,887 A | 1/1999 | Allison et al. |
| 5,869,046 A | 2/1999 | Presta et al. |
| 6,051,227 A | 4/2000 | Allison et al. |
| 6,054,297 A | 4/2000 | Carter et al. |
| 6,075,181 A | 6/2000 | Kucherlapati et al. |

(Continued)

FOREIGN PATENT DOCUMENTS

| | | |
|---|---|---|
| AU | 2008202217 B2 | 6/2008 |
| CA | 2496923 | 2/2004 |

(Continued)

OTHER PUBLICATIONS

Bam et al., 1998, "Tween protects recombinant human growth hormone against agitation-induced damage via hydrophobic interactions," J. Pharm. Sci., 87(12):1554-1559.

(Continued)

*Primary Examiner* — Xiaozhen Xie
(74) *Attorney, Agent, or Firm* — JONES DAY

(57) ABSTRACT

A pharmaceutical composition comprising an antibody drug conjugate comprising an antibody or antigen binding fragment thereof that binds to 191P4D12 conjugated to one or more units of monomethyl auristatin E (MMAE) and a pharmaceutically acceptable excipient comprising L-histidine, polysorbate-20 (TWEEN-20), and at least one of trehalose dihydrate and sucrose.

31 Claims, 25 Drawing Sheets
Specification includes a Sequence Listing.

(56) References Cited

U.S. PATENT DOCUMENTS

| | | |
|---|---|---|
| 6,121,022 A | 9/2000 | Presta et al. |
| 6,150,584 A | 11/2000 | Kucherlapati et al. |
| 6,165,745 A | 12/2000 | Ward et al. |
| 6,207,157 B1 | 3/2001 | Gu et al. |
| 6,214,345 B1 | 4/2001 | Firestone et al. |
| 6,264,949 B1 | 7/2001 | Friedman |
| 6,277,375 B1 | 8/2001 | Ward |
| 6,407,213 B1 | 6/2002 | Carter et al. |
| 6,436,703 B1 | 8/2002 | Tanq et al. |
| 6,492,123 B1 | 12/2002 | Holliger et al. |
| 6,639,055 B1 | 10/2003 | Carter et al. |
| 6,682,736 B1 | 1/2004 | Hanson et al. |
| 6,719,971 B1 | 4/2004 | Carter et al. |
| 6,794,501 B2 | 9/2004 | Chen et al. |
| 6,800,738 B1 | 10/2004 | Carter et al. |
| 6,984,720 B1 | 1/2006 | Korman et al. |
| 7,098,316 B2 | 8/2006 | Ni et al. |
| 7,171,311 B2 | 1/2007 | Dai et al. |
| 7,175,849 B2 | 2/2007 | Baum et al. |
| 7,189,507 B2 | 3/2007 | Mack et al. |
| 7,332,582 B2 | 2/2008 | Hardy et al. |
| 7,488,802 B2 | 2/2009 | Collins et al. |
| 7,521,051 B2 | 4/2009 | Collins et al. |
| 7,563,869 B2 | 7/2009 | Honjo et al. |
| 7,595,048 B2 | 9/2009 | Honjo et al. |
| 7,605,238 B2 | 10/2009 | Korman et al. |
| 7,612,181 B2 | 11/2009 | Wu et al. |
| 7,659,241 B2 | 2/2010 | Senter et al. |
| 7,745,394 B2 | 6/2010 | Doronina et al. |
| 7,829,531 B2 | 11/2010 | Senter et al. |
| 7,851,437 B2 | 12/2010 | Senter et al. |
| 7,943,743 B2 | 5/2011 | Korman et al. |
| 7,951,546 B2 | 5/2011 | Genetech |
| 7,964,566 B2 | 6/2011 | Doronina et al. |
| 7,968,090 B2 | 6/2011 | Raitano et al. |
| 8,008,449 B2 | 8/2011 | Korman et al. |
| 8,168,757 B2 | 5/2012 | Finnefrock et al. |
| 8,217,149 B2 | 7/2012 | Irving et al. |
| 8,354,509 B2 | 1/2013 | Carven et al. |
| 8,383,796 B2 | 2/2013 | Korman et al. |
| 8,609,089 B2 | 12/2013 | Langermann et al. |
| 8,637,642 B2 | 1/2014 | Satpayev et al. |
| 8,735,553 B1 | 5/2014 | Li et al. |
| 8,758,758 B1 | 6/2014 | Sievers et al. |
| 9,078,931 B2 | 7/2015 | Satpayev et al. |
| 9,314,538 B2 | 4/2016 | Satpayev et al. |
| 9,683,048 B2 | 6/2017 | Freeman et al. |
| 9,962,454 B2 | 5/2018 | Satpayev et al. |
| 10,344,090 B2 | 7/2019 | Yuan et al. |
| RE48,389 E | 1/2021 | Satpayev et al. |
| 10,894,090 B2 | 1/2021 | Satpayev et al. |
| 11,559,582 B2 | 1/2023 | Satpayev et al. |
| 2001/0051344 A1 | 12/2001 | Shalon et al. |
| 2002/0065220 A1 | 5/2002 | Young et al. |
| 2002/0090672 A1 | 7/2002 | Rosen et al. |
| 2002/0137160 A1 | 9/2002 | Byatt et al. |
| 2003/0065156 A1 | 4/2003 | Williams et al. |
| 2003/0073144 A1 | 4/2003 | Benson et al. |
| 2003/0077606 A1 | 4/2003 | Rosen et al. |
| 2003/0083263 A1 | 5/2003 | Doronina et al. |
| 2003/0099974 A1 | 5/2003 | Lillie et al. |
| 2003/0109690 A1 | 6/2003 | Ruben et al. |
| 2003/0148408 A1 | 8/2003 | Frantz et al. |
| 2003/0165831 A1 | 9/2003 | Lee et al. |
| 2003/0170621 A1 | 9/2003 | McCarthy et al. |
| 2003/0232350 A1 | 12/2003 | Afar et al. |
| 2004/0005563 A1 | 1/2004 | Mack et al. |
| 2004/0009491 A1 | 1/2004 | Birse et al. |
| 2004/0029114 A1 | 2/2004 | Mack et al. |
| 2004/0053348 A1 | 3/2004 | Faris et al. |
| 2004/0076955 A1 | 4/2004 | Mack et al. |
| 2004/0081653 A1 | 4/2004 | Raitano et al. |
| 2004/0083497 A1 | 4/2004 | Raitano et al. |
| 2004/0259086 A1 | 12/2004 | Schlegel et al. |
| 2005/0112568 A1 | 5/2005 | Friedman et al. |
| 2005/0238649 A1 | 10/2005 | Doronina et al. |
| 2006/0024317 A1 | 2/2006 | Boyd et al. |
| 2006/0074008 A1 | 4/2006 | Senter et al. |
| 2006/0275211 A1 | 12/2006 | Jakobovits et al. |
| 2008/0268476 A1 | 10/2008 | Lopez |
| 2009/0203538 A1 | 8/2009 | Sugioka et al. |
| 2010/0266617 A1 | 10/2010 | Carven et al. |
| 2011/0064753 A1 | 3/2011 | Senter et al. |
| 2011/0201052 A1 | 8/2011 | Raitano et al. |
| 2011/0268751 A1* | 11/2011 | Sievers ............ C07K 16/2878 530/391.7 |
| 2011/0271358 A1 | 11/2011 | Freeman et al. |
| 2012/0078028 A1* | 3/2012 | Satpayev ........... C07K 16/3015 424/179.1 |
| 2013/0189286 A1 | 7/2013 | Satpayev et al. |
| 2014/0308370 A1 | 10/2014 | Frendewey et al. |
| 2015/0079109 A1 | 3/2015 | Li et al. |
| 2015/0292030 A1 | 10/2015 | McConkey et al. |
| 2015/0306245 A1 | 10/2015 | Satpayev et al. |
| 2015/0353640 A1* | 12/2015 | Adler .............. A61K 39/39591 424/133.1 |
| 2016/0022814 A1 | 1/2016 | Petit et al. |
| 2016/0263243 A1* | 9/2016 | Satpayev .......... C07K 16/3069 |
| 2016/0311919 A1 | 10/2016 | Xiao et al. |
| 2016/0355597 A1 | 12/2016 | Rhee et al. |
| 2018/0030144 A1 | 2/2018 | Chanteux et al. |
| 2018/0051085 A1 | 2/2018 | Chang et al. |
| 2018/0296693 A1 | 10/2018 | Satpayev et al. |
| 2019/0142939 A1 | 5/2019 | Chang et al. |
| 2019/0290775 A1 | 9/2019 | Cao et al. |
| 2019/0314362 A1 | 10/2019 | Iwata et al. |
| 2019/0330149 A1 | 10/2019 | Zhao et al. |
| 2020/0277383 A1 | 9/2020 | Chang et al. |
| 2021/0030869 A1 | 2/2021 | Smith et al. |
| 2021/0283268 A1 | 9/2021 | Satpayev et al. |
| 2022/0106389 A1 | 4/2022 | Hu et al. |
| 2023/0001005 A1 | 1/2023 | Abidoye |
| 2023/0025600 A1 | 1/2023 | Gartner et al. |
| 2023/0270871 A1 | 8/2023 | Gartner et al. |
| 2023/0330251 A1 | 10/2023 | Gartner et al. |
| 2023/0346968 A1 | 11/2023 | Satpayev et al. |
| 2023/0364254 A1 | 11/2023 | Gartner et al. |

FOREIGN PATENT DOCUMENTS

| | | |
|---|---|---|
| CN | 1313297 A | 9/2001 |
| CN | 101500590 A | 8/2009 |
| EP | 1074617 A2 | 2/2001 |
| JP | 2006513724 A | 4/2006 |
| JP | 2008521411 A | 6/2008 |
| JP | 2010523469 A | 7/2010 |
| JP | 2012514651 A | 6/2012 |
| JP | 6083871 B2 | 8/2013 |
| JP | 2013543498 A | 12/2013 |
| JP | 6726258 B2 | 7/2020 |
| JP | 7042872 B2 | 3/2022 |
| TW | I524901 B | 3/2016 |
| TW | 201642908 A | 12/2016 |
| TW | 201818968 A | 6/2018 |
| WO | WO 1993011161 A1 | 6/1993 |
| WO | WO 1999052942 A2 | 10/1999 |
| WO | WO 2001002568 A2 | 1/2001 |
| WO | WO 2001018016 A1 | 3/2001 |
| WO | WO 2001022920 A2 | 4/2001 |
| WO | WO 2001051628 A2 | 7/2001 |
| WO | WO 2001054474 A2 | 8/2001 |
| WO | WO 2001055315 A2 | 8/2001 |
| WO | WO 2001057188 A2 | 8/2001 |
| WO | WO 2001060860 A2 | 8/2001 |
| WO | WO 2001070979 A2 | 9/2001 |
| WO | WO 2001090304 A2 | 11/2001 |
| WO | WO 2001094629 A2 | 12/2001 |
| WO | WO 2002010449 A2 | 2/2002 |
| WO | WO 2002028902 A2 | 4/2002 |
| WO | WO 2002059377 A2 | 8/2002 |
| WO | WO 2002060317 A2 | 8/2002 |
| WO | WO 2002086084 A2 | 10/2002 |
| WO | WO 2002086443 A2 | 10/2002 |
| WO | WO 2002088172 A2 | 11/2002 |

(56) References Cited

FOREIGN PATENT DOCUMENTS

| | | |
|---|---|---|
| WO | WO 2002088172 A3 | 11/2002 |
| WO | WO 2002099040 A2 | 12/2002 |
| WO | WO 2002102235 A2 | 12/2002 |
| WO | WO 2003003906 A2 | 1/2003 |
| WO | WO 2003008444 A2 | 1/2003 |
| WO | WO 2003024392 A2 | 3/2003 |
| WO | WO 2003042402 A2 | 5/2003 |
| WO | WO 2003042402 A3 | 5/2003 |
| WO | WO 2003042661 A2 | 5/2003 |
| WO | WO 2004004771 A1 | 7/2003 |
| WO | WO 2004005458 A2 | 1/2004 |
| WO | WO 2004010957 A2 | 2/2004 |
| WO | WO 2004016736 A2 | 2/2004 |
| WO | WO 2004016736 A3 | 2/2004 |
| WO | WO 2004016799 A2 | 2/2004 |
| WO | WO 2004056875 A1 | 7/2004 |
| WO | WO 2004065545 A1 | 8/2004 |
| WO | WO 2004072286 A1 | 8/2004 |
| WO | WO 2005030124 A2 | 4/2005 |
| WO | WO 2005092380 A2 | 10/2005 |
| WO | WO 2005092380 A3 | 10/2005 |
| WO | WO 2005111076 A1 | 11/2005 |
| WO | WO 2006034488 A2 | 3/2006 |
| WO | WO 2006034488 A3 | 3/2006 |
| WO | WO 2006071441 A2 | 7/2006 |
| WO | WO 2006071441 A3 | 7/2006 |
| WO | WO 2008052187 A2 | 5/2008 |
| WO | WO 2008052187 A3 | 5/2008 |
| WO | WO 2008156712 A1 | 12/2008 |
| WO | WO 2010036959 A2 | 4/2010 |
| WO | WO 2010036959 A3 | 4/2010 |
| WO | WO 2010081004 A1 | 7/2010 |
| WO | WO 2010089411 A2 | 8/2010 |
| WO | WO 2010089411 A3 | 8/2010 |
| WO | WO 2011066342 A2 | 6/2011 |
| WO | WO 2011066342 A3 | 6/2011 |
| WO | WO 2011082400 A2 | 7/2011 |
| WO | WO 2011082400 A3 | 7/2011 |
| WO | WO 2011159877 A2 | 12/2011 |
| WO | WO 2011159877 A3 | 12/2011 |
| WO | WO 2011161699 A2 | 12/2011 |
| WO | WO 2011161699 A3 | 12/2011 |
| WO | WO 2012047724 A1 | 4/2012 |
| WO | WO 2012047724 A4 | 4/2012 |
| WO | WO 2014179664 A2 | 11/2014 |
| WO | WO 2014179664 A3 | 11/2014 |
| WO | WO 2014194302 A2 | 12/2014 |
| WO | WO 2014194302 A3 | 12/2014 |
| WO | WO 2015085847 A1 | 6/2015 |
| WO | WO 2015112800 A1 | 7/2015 |
| WO | WO 2015112900 A1 | 7/2015 |
| WO | WO 2016067013 A1 | 5/2016 |
| WO | WO 2006105488 A2 | 10/2016 |
| WO | WO 2018017714 A1 | 1/2018 |
| WO | WO 2018226578 A1 | 12/2018 |
| WO | WO 2019183438 A1 | 9/2019 |
| WO | WO 2020061060 A1 | 3/2020 |
| WO | WO 2021030240 A1 | 2/2021 |
| WO | WO 2021108353 A1 | 6/2021 |
| WO | WO 2021257938 A1 | 12/2021 |
| WO | WO 2022060955 A1 | 3/2022 |
| WO | WO 2022076767 A1 | 4/2022 |
| WO | WO 2023019236 A1 | 2/2023 |
| WO | WO 2023133388 A2 | 7/2023 |
| WO | WO 2023133388 A3 | 7/2023 |
| WO | WO 2024026253 A1 | 2/2024 |

OTHER PUBLICATIONS

Banks et al., 2012, "Native-state solubility and transfer free energy as predictive tools for selecting excipients to include in protein formulation development studies," J. Pharm. Sci., 101(8):2720-2732.

Chang et al., 2002, "Chapter 1—Practical Approaches to Protein Formulation Development," Rational Design of Stable Protein Formulations Theory and Practice, Pharmaceutical Biotechnolocy, vol. 13, Ed. Carpenter et al., Springer US, pp. 1-25 and Preface, Contents, and Index (51 pages).

Chi et al., 2003, "Physical stability of proteins in aqueous solution: mechanism and driving forces in nonnative protein aggregation," Pharm. Res., 20(9):1325-1336.

Cleland et al., 1993, "The development of stable protein formulations: a close look at protein aggregation, deamidation, and oxidation," Crit. Rev. Ther. Drug Carrier Syst., 10(4):307-377.

International Search Report and Written Opinion for International Patent Application No. PCT/US2019/056214 (Pub No. WO 2020117373) mailed Mar. 19, 2020 (14 pages).

Johns Hopkins Medicine, The Sidney Kimmel Comprehensive Cancer Center, 2018, "A single-arm, open-label, multicenter study of enfortumab vedotin (ASG-22CE) for treatment of patients with locally advanced or metastatic urothelial cancer who previously received immune checkpoint inhibitor (CPI) therapy (sponsor protocol #SGN22E-001), " Protocol No. J1797, Phase II (2 pages).

Krishnamurthy et al., 2002, "The stability factor: importance in formulation development," Curr. Pharm. Biotechnol., 3(4):361-371.

Nayar et al., 2002, "Chapter 8—High Throughput Formulation: Strategies for Rapid Development of Stable Protein Products," Rational Design of Stable Protein Formulations Theory and Practice, Pharmaceutical Biotechnolocy, vol. 13, Ed. Carpenter et al., Springer US, pp. 177-198 and Preface, Contents, and Index (48 pages).

Randolph et al., 2007, "Engineering challenges of protein formulations," AIChE J., 53(8):1902-1907.

Van De Weert et al., 2012, "Physical Instability of Peptides and Proteins," Pharmaceutical Formulation Development of Peptides and Proteins, Second Edition, pp. 107-129.

Wang et al., 2007, "Antibody structure, instability, and formulation," J. Pharm. Sci., 96(1):1-26.

Wang, 1999, "Instability, stabilization, and formulation of liquid protein pharmaceuticals," Int. J. Pharm., 185(2):129-188.

Wang, 2015, "Advanced protein formulations," Protein Sci., 24(7):1031-1039.

Wang, 2019, "Science and art of protein formulation development," Int. J. Pharm., 568:118505 (24 pages).

Advanced Bladder Cancer (ABC) Meta-Analysis Collaboration, 2005, "Neoadjuvant chemotherapy in invasive bladder cancer: update of a systematic review and meta-analysis of individual patient data advanced bladder cancer (ABC) meta-analysis collaboration," Eur. Urol., 48(2):202-206.

Ahmadzadeh et al., 2009, "Tumor antigen-specific CD8 T cells infiltrating the tumor express high levels of PD-1 and are functionally impaired," Blood, 114(8):1537-1544.

Alberts et al., 1994, "Molecular Biology of the Cell, " 3rd Ed., p. 465.

Alley et al., 2004, "Abstract 627—Controlling the location of drug attachment in antibody-drug conjugates," American Association for Cancer Research, 2004 Annual Meeting, Mar. 27-31, 2004, Proceedings of the AACR, vol. 45, Mar. 2004.

Altschul et al., 1990, "Basic local alignment search tool," J. Mol. Biol., 215(3):403-410.

Altschul et al., 1997, "Gapped BLAST and PSI-BLAST: a new generation of protein database search programs," Nucleic Acids Res., 25(17):3389-3402.

American Medical Association (AMA), 2014, "Enfortumab Vedotin—United States Adopted Name (USAN) Drug Finder," [online] Jun. 25, 2014, [retrieved on Jun. 7, 2024]. Retrieved from the Internet:< URL: https://searchusan.ama-assn.org/usan/documentDownload?uri=/unstructured/binary/usan/enfortumab-vedotin.pdf >.

Amsberry et al., 1990, "The lactonization of 2'-hydroxyhydrocinnamic acid amides: a potential prodrug for amines," J. Org. Chem., 55(23):5867-5877.

Anastasiadis et al., 2012, "Follow-up procedures for non-muscle-invasive bladder cancer: an update," Expert Rev. Anticancer Ther., 12(9):1229-1241.

Andersson et al., 2004, "Urinary bladder contraction and relaxation: physiology and pathophysiology," Physiol. Rev., 84(3):935-986.

(56) References Cited

OTHER PUBLICATIONS

Aragon-Ching et al., 2018, "Multidisciplinary Management of Muscle-Invasive Bladder Cancer: Current Challenges and Future Directions," Am. Soc. Clin. Oncol. Educ. Book, 38:307-318.
Astellas, 2020, "PADCEV™ (enfortumab vedotin-ejfv) for Injection—Safety Data Sheet," issued Sep. 22, 2020, Version 1.0. Retrieved from the Internet:< URL: https://www.astellas.com/us/system/files/padcev_enfotumab_vedotin_for_injection_30_mg_sds_na2015_092220_final.pdf> (8 pages).
Australian Patent Office, Examiner's Report No. 3 for Australian Patent Application No. 2003228717 mailed Aug. 31, 2007 (2 pages).
Babjuk et al., 2020, "EAU Guidelines on Non-muscle-invasive Bladder Cancer (TaT1 and CIS)" European Association of Urology (54 pages).
Bai et al., 1990, "Structure-activity studies with chiral isomers and with segments of the antimitotic marine peptide dolastatin 10," Biochem. Pharmacol., 40(8):1859-1864.
Balar et al., 2017, "Atezolizumab as first-line treatment in cisplatin-ineligible patients with locally advanced and metastatic urothelial carcinoma: a single-arm, multicentre, phase 2 trial," Lancet, 389(10064):67-76 (Epub 2016).
Beck et al., 2008, "Trends in glycosylation, glycoanalysis and glycoengineering of therapeutic antibodies and Fc-fusion proteins," Curr. Pharm. Biotechnol., 9(6):482-501.
Bellmunt et al., 2009, "Phase III trial of vinflunine plus best supportive care compared with best supportive care alone after a platinum-containing regimen in patients with advanced transitional cell carcinoma of the urothelial tract," J. Clin. Oncol., 27(27):4454-4461.
Bellmunt et al., 2011, "Bladder cancer: ESMO Clinical Practice Guidelines for diagnosis, treatment and follow-up," Ann. Oncol., 22 Suppl 6:vi45-49 (5 pages).
Bellmunt et al., 2013, "Long-term survival results of a randomized phase III trial of vinflunine plus best supportive care versus best supportive care alone in advanced urothelial carcinoma patients after failure of platinum-based chemotherapy," Ann. Oncol., 24(6):1466-1472.
Bellmunt et al., 2017, "Pembrolizumab as Second-Line Therapy for Advanced Urothelial Carcinoma," N. Engl. J. Med., 376(11):1015-1026, Protocol, Supplementary Appendix (362 pages).
Boerner et al., 1991, "Production of antigen-specific human monoclonal antibodies from in vitro-primed human splenocytes," J. Immunol., 147(1):86-95.
Brancati et al., 2010, "Mutations in PVRL4, Encoding Cell Adhesion Molecule Nectin-4, Cause Ectodermal Dysplasia-Syndactyly Syndrome," The American Journal of Human Genetics, 87:265-273.
Brignone et al., 2007, "A soluble form of lymphocyte activation gene-3 (IMP321) induces activation of a large range of human effector cytotoxic cells," J. Immunol., 179(6):4202-4211.
Bruggemann et al., 1997, "Production of human antibody repertoires in transgenic mice," Curr. Opin. Biotechnol., 8(4):455-458.
Cardoso et al., 2017, "Research needs in breast cancer," Ann. Oncol., 28(2):208-217.
Carpenter et al., 1997, "Rational design of stable lyophilized protein formulations: some practical advice," Pharm. Res., 14(8):969-975.
Carter et al., 1992, "Humanization of an anti-p185HER2 antibody for human cancer therapy," Proc. Natl. Acad. Sci. USA, 89(10):4285-4289.
Carter et al., 2008, "Antibody-drug conjugates for cancer therapy," Cancer J., 14(3):154-169.
Carter, 1986, "Site-directed mutagenesis," Biochem. J., 237(1):1-7.
Cathomas et al., 2015, "First-line treatment of metastatic disease: cisplatin-ineligible patients," Hematol. Oncol. Clin. North Am., 29(2):329-340 (Epub 2014).
Challita-Eid et al., 2016, "Enfortumab Vedotin Antibody-Drug Conjugate Targeting Nectin-4 Is a Highly Potent Therapeutic Agent in Multiple Preclinical Cancer Models," Cancer Res., 76(10):3003-3013.

Chang et al., 2016, "Diagnosis and Treatment of Non-Muscle Invasive Bladder Cancer: AUA/SUO Guideline," J. Urol., 196(4):1021-1029.
Chao et al., 2006, "Isolating and engineering human antibodies using yeast surface display," Nat. Protoc., 1(2):755-768.
Chen et al., 1999, "Selection and analysis of an optimized anti-VEGF antibody: crystal structure of an affinity-matured Fab in complex with antigen," J. Mol. Biol., 293(4):865-881.
Choi et al., 2014, "Intrinsic basal and luminal subtypes of muscle-invasive bladder cancer," Nat. Rev. Urol., 11(7):400-410.
Chothia et al., 1987, "Canonical structures for the hypervariable regions of immunoglobulins, " J. Mol. Biol., 196(4):901-917.
Choueiri et al., 2012, "Double-blind, randomized trial of docetaxel plus vandetanib versus docetaxel plus placebo in platinum-pretreated metastatic urothelial cancer," J. Clin. Oncol., 30(5):507-512 (Epub 2011).
Choueiri et al., 2014, "Neoadjuvant dose-dense methotrexate, vinblastine, doxorubicin, and cisplatin with pegfilgrastim support in muscle-invasive urothelial cancer: pathologic, radiologic, and biomarker correlates," J. Clin. Oncol., 32(18):1889-1894.
Clackson et al., 1991, "Making antibody fragments using phage display libraries," Nature, 352(6336):624-628.
ClinicalTrials Identifier: NCT01409135, "A Study of the Safety and Pharmacokinetics of AGS-22M6E in Subjects With Malignant Solid Tumors That Express Nectin-4," first posted: Aug. 4, 2011, last update posted: Oct. 7, 2015, [retrieved on Aug. 31, 2022]. Retrieved from the Internet:< URL: https://clinicaltrials.gov/ct2/show/NCT01409135> (9 pages).
ClinicalTrials Identifier: NCT02091999 (v23), 2019 "A Phase 1 Study of the Safety and Pharmacokinetics of Escalating Doses of ASG-22CE Given as Monotherapy in Subjects With Metastatic Urothelial Cancer and Other Malignant Solid Tumors That Express Nectin-4," first posted: Mar. 19, 2014, last update posted: Apr. 16, 2019, [retrieved on Jul. 23, 2024]. Retrieved from the Internet:< https://www.clinicaltrials.gov/study/NCT02091999?term=NCT02091999&rank=1&tab=history&a=23#version-content-panel> (9 pages).
Cortes et al., 2011, "Eribulin monotherapy versus treatment of physician's choice in patients with metastatic breast cancer (EMBRACE): a phase 3 open-label randomised study," Lancet, 377(9769):914- 23.
Crew et al., 2006, "Epidemiology of gastric cancer," World J. Gastroenterol., 12(3):354-362.
Dash et al., 2006, "Impact of renal impairment on eligibility for adjuvant cisplatin-based chemotherapy in patients with urothelial carcinoma of the bladder," Cancer, 107(3):506-513.
Davidoff et al., 2001, "Bone marrow-derived cells contribute to tumor neovasculature and, when modified to express an angiogenesis inhibitor, can restrict tumor growth in mice," Clin. Cancer Res., 7(9):2870-2879.
De Santis et al., 2009, "Randomized phase II/III trial assessing gemcitabine/ carboplatin and methotrexate/carboplatin/vinblastine in patients with advanced urothelial cancer "unfit" for cisplatin-based chemotherapy: phase II—results of EORTC study 30986," J. Clin. Oncol., 27(33):5634-5639.
Decker et al., 1982, "Risk factors in head and neck cancer," N. Engl. J. Med., 306(19):1151-1155.
Dong et al., 2002, "Tumor-associated B7-H1 promotes T-cell apoptosis: a potential mechanism of immune evasion," Nat. Med., 8(8):793-800.
Doronina et al., 2003, "Development of potent monoclonal antibody auristatin conjugates for cancer therapy," Nat. Biotechnol., 21(7):778-784.
Doronina et al., 2006, "Enhanced activity of monomethylauristatin F through monoclonal antibody delivery: effects of linker technology on efficacy and toxicity," Bioconjug Chem., 17(1):114-124.
Drakaki et al., 2018, "Docetaxel with or without ramucirumab after immune checkpoint inhibition in platinum-refractory metastatic urothelial carcinoma (mUC): Prespecified subgroup analysis from the phase 3 RANGE trial, " J. Clin. Oncol., 36(6_suppl):Abstract 434 (4 pages).

(56) References Cited

OTHER PUBLICATIONS

Dubowchik et al., 1999, "Receptor-mediated and enzyme-dependent targeting of cytotoxic anticancer drugs," Pharmacol. Ther., 83(2):67-123.
European Patent Office, Communication Pursuant to Article 94(3) EPC for European Patent Application No. 10012141.7 mailed Jun. 1, 2015 (8 pages).
European Patent Office, European Search Report and European Search Opinion for European Patent Application No. 10012141.7 mailed Mar. 25, 2011 (8 pages).
European Patent Office, Supplementary European Search Report and European Search Opinion for European Patent Application No. 11831345.1 mailed May 8, 2014 (6 pages).
European Patent Office, Supplementary Partial European Search Report for European Patent Application No. 03726484.3 mailed Jun. 23, 2008 (8 pages).
Fabre et al., 2002, "Prominent role of the Ig-like V domain in trans-interactions of nectins. Nectin3 and nectin 4 bind to the predicted C-C'-C"-D beta-strands of the nectin1 V domain," The Journal of Biological Chemistry, 277(30):27006-27013.
Fabre-Lafay et al., 2005, "Nectin-4, a new serological breast cancer marker, is a substrate for tumor necrosis factor-alpha-converting enzyme (TACE)/ADAM-17," The Journal of Biological Chemistry, 280(20):19543-19550.
Fabre-Lafay et al., 2007, "Nectin-4 is a new histological and serological tumor associated marker for breast cancer," BMC Cancer, 7:73 (16 pages).
Fourcade et al., 2010, "Upregulation of Tim-3 and PD-1 expression is associated with tumor antigen-specific CD8+ T cell dysfunction in melanoma patients," J. Exp. Med., 207(10):2175-2186 and Supplemental Material (17 pages).
Francisco et al., 2003, "cAC10-vcMMAE, an anti-CD30-monomethyl auristatin E conjugate with potent and selective antitumor activity," Blood, 102(4):1458-1465.
Fu et al., 1996, "Translational regulation of human p53 gene expression," EMBO Journal, 15:4392-4401.
Fucikova et al., 2020, "Detection of immunogenic cell death and its relevance for cancer therapy," Cell Death Dis., 11(11):1013 (13 pages).
Galsky et al., 2021, "Perioperative pembrolizumab therapy in muscle-invasive bladder cancer: Phase III KEYNOTE-866 and KEYNOTE-905/EV-303," Future Oncol., 17(24):3137-3152.
Gao et al., 2009, "Overexpression of PD-L1 significantly associates with tumor aggressiveness and postoperative recurrence in human hepatocellular carcinoma," Clin. Cancer Res., 15(3):971-979.
GBD 2015 Disease and Injury Incidence and Prevalence Collaborators, 2016, "Global, regional, and national incidence, prevalence, and years lived with disability for 310 diseases and injuries, 1990-2015: a systematic analysis for the Global Burden of Disease Study 2015," Lancet, 388(10053):1545-1602.
GBD 2015 Mortality and Causes of Death Collaborators, 2016, "Global, regional, and national life expectancy, all-cause mortality, and cause-specific mortality for 249 causes of death, 1980-2015: a systematic analysis for the Global Burden of Disease Study 2015," Lancet, 388(10053):1459-1544.
Ghebeh et al., 2006, "The B7-H1 (PD-L1) T lymphocyte-inhibitory molecule is expressed in breast cancer patients with infiltrating ductal carcinoma: correlation with important high-risk prognostic factors," Neoplasia, 8(3):190-198.
Ghebeh et al., 2008, "FOXP3+ Tregs and B7-H1+/PD-1+ T lymphocytes co-infiltrate the tumor tissues of high-risk breast cancer patients: Implication for immunotherapy," BMC Cancer, 8:57 (12 pages).
Goswami et al., 2013, "Developments and Challenges for mAb-Based Therapeutics," Antibodies, 2(3):452-500.
Greenbaum et al., 2003, "Comparing protein abundance and mRNA expression levels on a genomic scale," Genome Biology, 4(9):117.1-117.8.
Greene et al., 2015, "The role of anthracyclines in the treatment of early breast cancer," J. Oncol. Pharm. Pract., 21(3):201-212 (Epub 2014).
Gutka, 2018, "Rational Selection of Sugars for Biotherapeutic Stabilization: A Practitioner's Perspective," BioProcess International [online], Oct. 15, 2018 [retrieved on Feb. 9, 2023]. Retrieved from the Internet:< URL: https://bioprocessintl.com/manufacturing/formulation/rational-selection-of-sugars-for-biotherapeutic-stabilization-a-practitioners-perspective/> (21 pages).
Hacker, 1997, "Lack of association between an interleukin-1 receptor antagonist gene polymorphism and ulcerative colitis," Gut., 40:623-627.
Hamanishi et al., 2007, "Programmed cell death 1 ligand 1 and tumor-infiltrating CD8+ T lymphocytes are prognostic factors of human ovarian cancer," Proc. Natl. Acad. Sci. USA, 104(9):3360-3365.
Hamblett et al., 2004, "Abstract 624—Effect of drug loading on the pharmacology, pharmacokinetics, and toxicity of an anti-CD30 antibody-drug conjugate," American Association for Cancer Research, 2004 Annual Meeting, Mar. 27-31, 2004, Proceedings of the AACR, vol. 45, Mar. 2004.
Hanna, 2020, "Advancements in Therapy for Bladder Cancer: Enfortumab Vedotin," J. Adv. Pract. Oncol., 11(4):412-417.
Hay et al., 1999, "A 2-nitroimidazole carbamate prodrug of 5-amimo-1-(chloromethyl)-3-[(5,6,7-trimethoxyindol-2-yl)carbony 1]-1,2-dihydro-3H--benz[E]indole (amino-seco-CBI-TMI) for use with ADEPT and GDEPT," Bioorg. Med. Chem. Lett., 9(15):2237-2242.
Henikoff et al., 1992, "Amino acid substitution matrices from protein blocks," Proc. Natl. Acad. Sci. USA, 89(22):10915-10919.
Hino et al., 2010, "Tumor cell expression of programmed cell death-1 ligand 1 is a prognostic factor for malignant melanoma," Cancer, 116(7):1757-1766.
Hoimes et al., 2018, "EV-103 Study: A phase 1b dose-escalation and dose-expansion study of enfortumab vedotin in combination with immune checkpoint inhibitor (CPI) therapy for treatment of patients with locally advanced or metastatic urothelial cancer," Eur. Urol. Suppl., Abstract 805, 17(2);e1151 (3 pages).
Holliger et al., 1993, ""Diabodies": small bivalent and bispecific antibody fragments," Proc. Natl. Acad. Sci. USA, 90(14):6444-6448.
Holmes et al., 2021, "KEYNOTE-B15/EV-304: Randomized phase 3 study of perioperative enfortumab vedotin plus pembrolizumab versus chemotherapy in cisplatin-eligible patients with muscle-invasive bladder cancer (MIBC)," 2021 ASCO Annual Meeting, Genitourinary Cancer-Kidney and Bladder, May 28, 2021, J. Clin. Oncol., 39(15_suppl), Abstract TPS4587.
Holmes, 2018, "EV-103 study : A phase 1b dose—escalation and dose—expansion study of enfortumab vedotin in combination with immune checkpoint inhibitor (CPI) therapy for treatment of patients with locally advanced or metastatic urothelial cancer," Elsevier, Accession No. EMB-625350146 (2 pages).
Honegger et al., 2001, "Yet another numbering scheme for immunoglobulin variable domains: an automatic modeling and analysis tool," J. Mol. Biol., 309(3):657-670.
Hoogenboom et al., 1992, "By-passing immunisation. Human antibodies from synthetic repertoires of germline VH gene segments rearranged in vitro," J. Mol. Biol., 227(2):381-388.
Hudson et al., 2003, "Engineered antibodies," Nat. Med., 9(1):129-134.
Hur Vitz et al., 2016, "Triple-negative breast cancer: advancements in characterization and treatment approach," Curr. Opin. Obstet. Gynecol., 28(1):59-69.
Huston et al., 1993, "Antigen recognition and targeted delivery by the single-chain Fv," Cell Biophys., 22(1-3):189-224.
Inman et al., 2007, "PD-L1 (B7-H1) expression by urothelial carcinoma of the bladder and BCG-induced granulomata: associations with localized stage progression," Cancer, 109(8):1499-1505.
International Searching Authority, International Preliminary Examination Report for International Patent Application No. PCT/US2003/013013 (Pub No. WO 2004016799) dated Mar. 15, 2007 (4 pages).

(56) References Cited

OTHER PUBLICATIONS

International Searching Authority, International Search Report and Written Opinion for International Patent Application No. PCT/US2011/054054 (Pub No. WO 2012047724) mailed Feb. 15, 2012 (7 pages).
International Searching Authority, International Search Report and Written Opinion for International Patent Application No. PCT/US2020/045567 (Pub No. WO 2021030240) mailed Jan. 19, 2021 (11 pages).
International Searching Authority, International Search Report and Written Opinion for International Patent Application No. PCT/US2020/061923 (Pub No. WO 2021108353) mailed Mar. 12, 2021 (12 pages).
International Searching Authority, International Search Report and Written Opinion for International Patent Application No. PCT/US2021/037994 (Pub No. WO 2021257938) mailed Oct. 20, 2021 (21 pages).
International Searching Authority, International Search Report and Written Opinion for International Patent Application No. PCT/US2021/050627 (Pub No. WO 2022060955) mailed Jan. 20, 2022 (12 pages).
International Searching Authority, International Search Report and Written Opinion for International Patent Application No. PCT/US2021/054084 (Pub No. WO 2022076767) mailed Jan. 21, 2022 (8 pages).
International Searching Authority, International Search Report and Written Opinion for International Patent Application No. PCT/US2022/074897 (Pub No. WO 2023019236) mailed Oct. 28, 2022 (9 pages).
International Searching Authority, International Search Report and Written Opinion for International Patent Application No. PCT/US2023/060062 (Pub No. WO 2023133388) mailed Jul. 21, 2023 (13 pages).
International Searching Authority, International Search Report and Written Opinion for International Patent Application No. PCT/US2023/070812 (Pub No. WO 2024026253) mailed Nov. 16, 2023 (8 pages).
International Searching Authority, International Search Report for International Patent Application No. PCT/US2003/013013 (Pub No. WO 2004016799) mailed Sep. 14, 2006 (4 pages).
International Union of Pure and Applied Chemistry (IUPAC), 1960, "Definitive Rules for Nomenclature of Organic Chemistry," J. Am. Chem. Soc., 82(21):5545-5574.
Jakobovits, 1995, "Production of fully human antibodies by transgenic mice," Curr. Opin. Biotechnol., 6(5):561-566.
Jamil et al., 2019, "Protocol for phase I study of pembrolizumab in combination with Bacillus Calmette-Guérin for patients with high-risk non-muscle invasive bladder cancer," BMJ Open, 9(7):e028287 (9 pages).
Japanese Patent Office, English translation of Decision of Rejection for Japanese Patent Application No. 2013-531875 mailed Aug. 15, 2016 (5 pages).
Johnson et al., 1995, "Anti-tumor activity of CC49-doxorubicin immunoconjugates," Anticancer Res., 15(4):1387-1393.
Jones et al., 1986, "Replacing the complementarity-determining regions in a human antibody with those from a mouse," Nature, 321(6069):522-525.
Jones et al., 1995, "Randomized comparison of vinorelbine and melphalan in anthracycline-refractory advanced breast cancer," J. Clin. Oncol., 13(10):2567-2574.
Kaneko et al., 1991, "New hydrazone derivatives of adriamycin and their immunoconjugates—a correlation between acid stability and cytotoxicity," Bioconjug. Chem., 2(3):133-141.
Karakiewicz et al., 2006, "Nomogram for predicting disease recurrence after radical cystectomy for transitional cell carcinoma of the bladder," J. Urol., 176(4 Pt 1):1354-1362.
Karlin et al., 1990, "Methods for assessing the statistical significance of molecular sequence features by using general scoring schemes, " Proc. Natl. Acad. Sci. USA, 87(6):2264-2268.
Karlin et al., 1993, "Applications and statistics for multiple high-scoring segments in molecular sequences," Proc. Natl. Acad. Sci. USA, 90(12):5873-5877.
Kassouf et al., 2015, "CUA guidelines on the management of non-muscle invasive bladder cancer," Can. Urol. Assoc. J., 9(9-10):E690-704.
Kates et al., 2020, "Adaptive Immune Resistance to Intravesical BCG in Non-Muscle Invasive Bladder Cancer: Implications for Prospective BCG-Unresponsive Trials," Clin. Cancer Res., 26(4):882-891 (Epub 2019).
Kaufman et al., 2015, "Phase III open-label randomized study of eribulin mesylate versus capecitabine in patients with locally advanced or metastatic breast cancer previously treated with an anthracycline and a taxane," J. Clin. Oncol., 33(6):594-601.
Kawai et al., 2013, "Bacillus Calmette-Guerin (BCG) immunotherapy for bladder cancer: current understanding and perspectives on engineered BCG vaccine," Cancer Sci., 104(1):22-27.
KEYTRUDA® (pembrolizumab) Prescribing Information, revised Mar. 2021 (106 pages).
KEYTRUDA® (pembrolizumab) Prescribing Information, revised May 2017 (46 pages).
Kingsburry et al., 1984, "A novel peptide delivery system involving peptidase activated prodrugs as antimicrobial agents. Synthesis and biological activity of peptidyl derivatives of 5-fluorouracil," J. Med. Chem., 27(11):1447-1451.
Kirkali et al., 2005, "Bladder cancer: epidemiology, staging and grading, and diagnosis," Urology, 66(6 Suppl 1):4-34.
Kohler et al., 1975, "Continuous cultures of fused cells secreting antibody of predefined specificity," Nature, 256(5517):495-497.
Kroese et al., 2004, "Genetic tests and their evaluation: Can we answer the key questions?" Genetics in Medicine, 6:475-480.
Lau et al., 1995, "Conjugation of doxorubicin to monoclonal anti-carcinoembryonic antigen antibody via novel thiol-directed cross-linking reagents," Bioorg. Med. Chem., 3(10):1299-1304.
Lau et al., 1995, "Novel doxorubicin-monoclonal anti-carcinoembryonic antigen antibody immunoconjugate activity in vitro," Bioorg. Med. Chem., 3(10):1305-1312.
Leemans et al., 2011, "The molecular biology of head and neck cancer," Nat. Rev. Cancer, 11(1):9-22.
Lefranc et al., 2003, "IMGT unique numbering for immunoglobulin and T cell receptor variable domains and Ig superfamily V-like domains," Dev. Comp. Immunol., 27(1):55-77.
Lei et al., 1995, "Structure-function analysis of human glucose-6-phosphatase, the enzyme deficient in glycogen storage disease type 1a," J. Biol. Chem., 270(20):11882-11886.
Li et al., 2006, "Human antibodies for immunotherapy development generated via a human B cell hybridoma technology," Proc. Natl. Acad. Sci. USA, 103(10):3557-3562.
Li et al., 2020, "Intravesical gemcitabine versus mitomycin for non-muscle invasive bladder cancer: a systematic review and meta-analysis of randomized controlled trial," BMC Urol., 20(1):97 (8 pages).
Loo et al., 2012, "Development of an Fc-enhanced anti-B7-H3 monoclonal antibody with potent antitumor activity," Clin. Cancer Res., 18(14):3834-3845.
Lotan et al., 2005, "Lymphovascular invasion is independently associated with overall survival, cause-specific survival, and local and distant recurrence in patients with negative lymph nodes at radical cystectomy," J. Clin. Oncol., 23(27):6533-6539.
Lu et al., 2005, "A fully human recombinant IgG-like bispecific antibody to both the epidermal growth factor receptor and the insulin-like growth factor receptor for enhanced antitumor activity," J. Biol. Chem., 280(20):19665-19672.
Lucentini, 2004, "Gene Association Studies Typically Wrong," The Scientist, 18:20 (4 pages).
Mallampalli et al., 1996, "Betamethasone modulation of sphingomyelin hydrolysis up-regulates CTP: cholinephosphate cytidylyltransferase activity in adult rat lung," Biochem. J., 38:333-341.
Mandai et al., 2015, "Nectins and nectin-like molecules in development and disease," Curr. Top Dev. Biol., 112:197-231.
Marks et al., 1991, "By-passing immunization. Human antibodies from V-gene libraries displayed on phage," J. Mol. Biol., 222(3):581-597.

(56) References Cited

OTHER PUBLICATIONS

Martin, 2010, "Chapter 3: Protein Sequence and Structure Analysis of Antibody Variable Domains," R. Kontermann and S. Dubel (eds.), Antibody Engineering vol. 2, Springer-Verlag Berlin Heidelberg, pp. 33-51.
Masters et al., 2015, "Systemic Therapy for Stage IV Non-Small-Cell Lung Cancer: American Society of Clinical Oncology Clinical Practice Guideline Update," J. Clin. Oncol., 33(30):3488-3515.
Mcgregor et al., 2019, "Enfortumab Vedotin, a fully human monoclonal antibody against Nectin 4 conjugated to monomethyl auristatin E for metastatic urothelial Carcinoma," Expert Opin. Investig. Drugs, 28(10):821-826.
Morrison et al., 1984, "Chimeric human antibody molecules: mouse antigen-binding domains with human constant region domains," Proc. Natl. Acad. Sci. USA, 81(21):6851-6855.
Mullane et al., 2016, "Cancer immunotherapy: new applications in urologic oncology," Curr. Opin. Urol., 26(6):556-563.
Myers et al., 1988, "Optimal alignments in linear space," Comput. Appl. Biosci., 4(1):11-17.
Nakanishi et al., 2007, "Overexpression of B7-H1 (PD-L1) significantly associates with tumor grade and postoperative prognosis in human urothelial cancers," Cancer Immunol. Immunother, 56(8):1173-1182 (Epub 2006).
Navai et al., 2016, "Phase 1b Trial to Evaluate Tissue Response to a Second Dose of Intravesical Recombinant Adenoviral Interferon α2b Formulated in Syn3 for Failures of Bacillus Calmette-Guerin (BCG) Therapy in Nonmuscle Invasive Bladder Cancer," Ann. Surg. Oncol., 23(12):4110-4114.
Necchi et al., 2018, "Pembrolizumab as Neoadjuvant Therapy Before Radical Cystectomy in Patients With Muscle-Invasive Urothelial Bladder Carcinoma (PURE-01): An Open-Label, Single-Arm, Phase II Study," J. Clin. Oncol., 36(34):3353-3360 with Appendix (11 pages).
Neville et al., 1989, "Enhancement of immunotoxin efficacy by acid-cleavable cross-linking agents utilizing diphtheria toxin and toxin mutants," J. Biol. Chem., 264(25):14653-14661.
Nomi et al., 2007, "Clinical significance and therapeutic potential of the programmed death-1 ligand/programmed death-1 pathway in human pancreatic cancer," Clin. Cancer Res., 13(7):2151-2157.
Novello et al., 2016, "Metastatic non-small-cell lung cancer: ESMO Clinical Practice Guidelines for diagnosis, treatment and follow-up," Ann. Oncol., 27(suppl 5):v1-v27.
Ohigashi et al., 2005, "Clinical significance of programmed death-1 ligand-1 and programmed death-1 ligand-2 expression in human esophageal cancer," Clin. Cancer Res., 11(8):2947-2953.
PADCEV™ (enfortumab vedotin-ejfv) Prescribing Information, revised Dec. 31, 2019 (19 pages).
Pardoll, 2012, "The blockade of immune checkpoints in cancer immunotherapy," Nat. Rev. Cancer, 12(4):252-264.
Pasin et al., 2008, "Superficial bladder cancer: an update on etiology, molecular development, classification, and natural history," Rev. Urol., 10(1):31-43.
Pennisi, 1998, "A Closer Look at SNPs Suggests Difficulties," Science, 281(5384):1787-1789.
Perez et al., 2007, "Efficacy and safety of ixabepilone (BMS-247550) in a phase II study of patients with advanced breast cancer resistant to an anthracycline, a taxane, and capecitabine," J. Clin. Oncol., 25(23):3407-3414.
Petrylak et al., 2018, "Enfortumab vedotin (EV) in patients (Pts) with metastatic urothelial carcinoma (mUC) with prior checkpoint inhibitor (CPI) failure: A prospective cohort of an ongoing phase 1 study," J. Clin. Oncol., 36(6_suppl 1) (3 pages).
Petrylak et al., 2022, "Study EV-103 Cohort H: Antitumor activity of neoadjuvant treatment with enfortumab vedotin monotherapy in patients (pts) with muscle invasive bladder cancer (MIBC) who are cisplatin-ineligible," 2022 ASCO Genitourinary Cancers Symposium, Urothelial Carcinoma, Feb. 16, 2022, J. Clin. Oncol., 40(6_suppl), Abstract 435.
Pettit et al., 1996, "Dolastatins 24: synthesis of (-)-dolastatin 10. X-Ray molecular structure of N,N-dimethylvaly1-valy1-dolaisoleuine tert-butyl ester," J. Chem. Soc., Perkin Trans. 1, 8:859-863.
Pettit et al., 1998, "Antineoplastic agents 365. Dolastatin 10 SAR probes," Anticancer. Drug Des., 13(4):243-277.
Pettit et al., 1998, "Specific activities of dolastatin 10 and peptide derivatives against Cryptococcus neoformans," Antimicrob. Agents Chemother., 42(11):2961-2965.
Piccart, 2008, "Circumventing de novo and acquired resistance to trastuzumab: new hope for the care of ErbB2-positive breast cancer," Clin. Breast Cancer, 8 Suppl 3:S100-113.
Plasilova et al., 2016, "Features of triple-negative breast cancer: Analysis of 38,813 cases from the national cancer database," Medicine (Baltimore), 95(35):e4614 (6 pages).
Plimack et al., 2014, "Accelerated methotrexate, vinblastine, doxorubicin, and cisplatin is safe, effective, and efficient neoadjuvant treatment for muscle-invasive bladder cancer: results of a multicenter phase II study with molecular correlates of response and toxicity," J. Clin. Oncol., 32(18):1895-1901.
Pluckthun et al., 1989, "Expression of functional antibody Fv and Fab fragments in *Escherichia coli*," Methods Enzymol, 178:497-515.
Powles et al., 2018, "A phase II study investigating the safety and efficacy of neoadjuvant atezolizumab in muscle invasive bladder cancer (ABACUS).," 2018 ASCO Annual Meeting, Genitourinary (Nonprostate) Cancer, Jun. 1, 2018, J. Clin. Oncol., 36(15), Abstract 4506.
Press Release, 2017, "Roche Provides Update on Phase III Study of Tecentriq (atezolizumab) in People with Previously Treated Advanced Bladder Cancer," May 10, 2017 (4 pages).
Press Release, 2020, "Seattle Genetics and Astellas Announce PADCEV® (enfortumab vedotin-ejfv) Significantly Improved Overall Survival in Phase 3 Trial in Previously Treated Locally Advanced or Metastatic Urothelial Cancer," Business Wire, Sep. 18, 2020 (8 pages).
Presta, 1992, "Antibody engineering," Curr. Op. Struct. Biol., 2(4):593-596.
Rabet et al., 2017, "Nectin-4: a new prognostic biomarker for efficient therapeutic targeting of primary and metastatic triple-negative breast cancer," Ann. Oncol., 28(4):769-776.
Rajc et al., 2017, "Prognostic role of Nectin-4 expression in luminal B (HER2 negative) breast cancer," Patho. Res. Pract., 213(9):1102-1108.
Reck et al., 2010, "Overall survival with cisplatin-gemcitabine and bevacizumab or placebo as first-line therapy for nonsquamous non-small-cell lung cancer: results from a randomised phase III trial (AVAiL)," Ann. Oncol., 21(9):1804-1809.
Reymond et al., 2001, "Nectin4/PRR4, a new afadin-associated member of the nectin family that trans-interacts with nectin1/PRR1 through V domain interaction," J. Biol. Chem., 276(46):43205-43215.
Riechmann et al., 1988, "Reshaping human antibodies for therapy," Nature, 332(6162):323-327.
Rikitake et al., 2008, "Interactions of the cell adhesion molecule nectin with transmembrane and peripheral membrane proteins for pleiotropic functions," Cell Mol. Life Sci., 65(2):253-263.
Robson et al., 2017, "Olaparib for Metastatic Germline BRCA-Mutated Breast Cancer," N. Engl. J. Med., 377(18):1792-1793.
Roche, 2017, "Roche provides update on phase III study of TECENTRIQ® (atezolizumab) in people with previously treated advanced bladder cancer," Media Release, Basel, May 10, 2017 (5 pages).
Rodig et al., 2018, "MHC proteins confer differential sensitivity to CTLA-4 and PD-1 blockade in untreated metastatic melanoma," Sci. Transl. Med., 10(450):eaar3342 (13 pages).
Rodrigues et al., 1995, "Synthesis and beta-lactamase-mediated activation of a cephalosporin-taxol prodrug," Chem. Biol., 2(4):223-227.
Rofstad et al., 1984, "Tumour growth delay, cell inactivation and vascular damage following hyperthermic treatment of a human melanoma xenograft," Eur. J. Cancer Clin. Oncol., 20(10):1295-1305.

(56) References Cited

OTHER PUBLICATIONS

Rosenberg et al., 2016, "Atezolizumab in patients with locally advanced and metastatic urothelial carcinoma who have progressed following treatment with platinum-based chemotherapy: a single-arm, multicentre, phase 2 trial, " Lancet, 387(10031):1909-1920.

Rosenberg et al., 2018, "EV-201 Study: A single-arm, open-label, multicenter study of enfortumab vedotin for treatment of patients with locally advanced or metastatic urothelial cancer who previously received immune checkpoint inhibitor therapy," 33rd Annual EAU Congress Copenhagen, Eur. Urol. Suppl., Abstract 805, 17(2);e1152.

Rosenberg et al., 2019, "Pivotal Trial of Enfortumab Vedotin in Urothelial Carcinoma After Platinum and Anti-Programmed Death 1/Programmed Death Ligand 1 Therapy," J. Clin. Oncol., 37(29):2592-2600 and Supplementary Study Protocol (147 pages).

Saffran et al., 2001, "Anti-PSCA mAbs inhibit tumor growth and metastasis formation and prolong the survival of mice bearing human prostate cancer xenografts," PNAS, 98(5):2658-2663.

Sakisaka et al., 2007, "The roles of nectins in cell adhesions: cooperation with other cell adhesion molecules and growth factor receptors," Curr. Opin. Cell Biol., 19(5):593-602.

Sakuishi et al., 2010, "Targeting Tim-3 and PD-1 pathways to reverse T cell exhaustion and restore anti-tumor immunity," J. Exp. Med., 207(10):2187-2194 and Supplemental Material (10 pages).

Sandler et al., 2006, "Paclitaxel-carboplatin alone or with bevacizumab for non-small-cell lung cancer," N. Engl. J. Med., 355(24):2542-2450.

Schmid et al., 2019, "Atezolizumab and Nab-Paclitaxel in Advanced Triple-Negative Breast Cancer. Reply," N. Engl. J. Med., 380(10):987-988.

Seattle Genetics, Inc., 2019, "A single-aim, open-label, multicenter study of enfortumab vedotin (ASG-22CE) for treatment of patients with locally advanced or metastatic urothelial cancer who previously received immune checkpoint inhibitor (CPI) therapy," Protocol No. SGN22E-001, Amendment 5 (Nov. 14, 2018), NEJM Redaction Package, Mar. 25, 2019 [retrieved on Feb. 6, 2024]. Retrieved from the Internet:< URL: https://ascopubs.org/doi/suppl/10.1200/JCO.19.01140/suppl_file/protocol_jco.19.01140.pdf> (125 pages).

Senter et al., 2004, "Abstract 623—Immunoconjugates comprised of drugs with impaired cellular permeability: A new approach to targeted therapy," Proceedings of the American Association for Cancer Research, vol. 45, presented Mar. 28, 2004.

Senter, 2009, "Potent antibody drug conjugates for cancer therapy," Curr Opin Chem Biol., 13(3):235-244.

Sharpe et al., 2007, "The function of programmed cell death 1 and its ligands in regulating autoimmunity and infection," Nat. Immunol., 8(3):239-245.

Shi et al., 2019, "Unravel the molecular mechanism of XBP1 in regulating the biology of cancer cells," J. Cancer, 10(9):2035-2046.

Shimauchi et al., 2007, "Augmented expression of programmed death-1 in both neoplastic and non-neoplastic CD4+ T-cells in adult T-cell leukemia/lymphoma," Int. J. Cancer, 121(12):2585-2590.

Socinski et al., 2018, "Current and Emergent Therapy Options for Advanced Squamous Cell Lung Cancer," J. Thorac. Oncol., 13(2):165-183 (Epub 2017).

Streltsov et al., 2004, "Structural evidence for evolution of shark Ig new antigen receptor variable domain antibodies from a cell-surface receptor," Proc. Natl. Acad. Sci. USA, 101(34):12444-12449.

Takai et al., 2008, "Nectins and nectin-like molecules: roles in contact inhibition of cell movement and proliferation," Nat. Rev. Mol. Cell Biol., 9(8):603-615.

Takai et al., 2008, "The immunoglobulin-like cell adhesion molecule nectin and its associated protein afadin," Annu. Rev. Cell Dev. Biol., 24:309-342.

Takano et al., 2009, "Identification of Nectin-4 Oncoprotein as a Diagnostic and Therapeutic Target for Luna Cancer," Cancer Res., 69(16):6694-6703.

Taylor et al., 1992, "A transgenic mouse that expresses a diversity of human sequence heavy and light chain immunoglobulins," Nucleic Acids Res., 20(23):6287-6295.

Taylor et al., 2020, "Update on the guideline of guidelines: non-muscle-invasive bladder cancer," BJU Int., 125(2):197-205.

Teklu et al., 1972, "Nitrogen-hydrogen tautomerism in porphyrins and chlorins," J. Am. Chem. Soc., 94(5):1745-1747.

Thompson et al., 2006, "Significance of B7-H1 overexpression in kidney cancer," Clin. Genitourin. Cancer, 5(3):206-211.

Thompson et al., 2007, "PD-1 is expressed by tumor-infiltrating immune cells and is associated with poor outcome for patients with renal cell carcinoma," Clin. Cancer Res., 13(6):1757-1761.

Toki et al., 2002, "Protease-mediated fragmentation of p-amidobenzyl ethers: a new strategy for the activation of anticancer prodrugs," J. Org. Chem., 67(6):1866-1872.

U.S. Department of Health and Human Services, 2010, "Common Terminology Criteria for Adverse Events (CTCAE)—Version 4.0," Published: May 28, 2009 (v4.03: Jun. 14, 2010). Retrieved from the Internet:< URL: https://evs.nci.nih.gov/ftp1/CTCAE/CTCAE_4.03/CTCAE_4.03_2010-06-14 QuickReference_8.5x11.pdf> (80 pages).

U.S. Food and Drug Administration, 2005, "Guidance for Industry Estimating the Maximum Safe Starting Dose in Initial Clinical Trials for Therapeutics in Adult Healthy Volunteers," Jul. 2005, Pharmacology and Toxicology (30 pages).

UniProt Identifier: Q96NY8, "NECT4_HUMAN," last updated Dec. 1, 2001, [retrieved on Aug. 31, 2022]. Retrieved from the Internet:< URL:https://rest.uniprot.org/unisave/Q96NY8?format=txt&versions=1> (1 page).

United States Patent and Trademark Office, Non-Final Office Action in U.S. Appl. No. 12/820,279, filed Dec. 21, 2010.

Valliere-Douglass et al., 2015, "Solid-state mAbs and ADCs subjected to heat-stress stability conditions can be covalently modified with buffer and excipient molecules," J. Pharm. Sci., 104(2):652-665 (Epub 2014).

Van Dijk et al., 2001, "Human antibodies as next generation therapeutics," Curr. Opin. Chem. Biol., 5(4):368-374.

Von Der Maase et al., 2005, "Long-term survival results of a randomized trial comparing gemcitabine plus cisplatin, with methotrexate, vinblastine, doxorubicin, plus cisplatin in patients with bladder cancer," J. Clin. Oncol., 23(21):4602-4608.

Walsh, 2010, "Post-translational modifications of protein biopharmaceuticals," Drug Discov. Today, 15(17-18):773-780.

Watkingson et al., 2017, "Antibody-Drug Conjugates: Fast-Track Development from Gene to Product," BioProcess International (14 pages).

Wells et al., 1985, "Cassette mutagenesis: an efficient method for generation of multiple mutations at defined sites," Gene, 34(2-3):315-323.

Woldu et al., 2017, "Guideline of guidelines: non-muscle-invasive bladder cancer," BJU Int., 119(3):371-380.

Wolff et al., 1993, "Monoclonal antibody homodimers: enhanced antitumor activity in nude mice," Cancer Res., 53(11):2560-2565.

Woolven et al., 1999, "The structure of the llama heavy chain constant genes reveals a mechanism for heavy-chain antibody formation," Immunogenetics, 50(1-2):98-101.

World Health Organization (WHO), 2013, "WHO Drug Information 2013," WHO Drug Information, nivolumab (BMS-936558), a human IgG4 mAb with the structure, 27(1):68-69.

World Health Organization (WHO), 2013, "WHO Drug Information 2013," WHO Drug Information, pembrolizumab (formerly known as MK-3475, SCH 900475 and lambrolizumab), a humanized IgG4 mAb with the structure, 27(2):161-162.

Woyke et al., 2001, "In vitro activities and postantifungal effects of the potent dolastatin 10 derivative auristatin PHE," Antimicrob. Agents Chemother., 45(12):3580-3584.

Yang et al., 2008, "PD-L1: PD-1 interaction contributes to the functional suppression of T-cell responses to human uveal melanoma cells in vitro," Invest. Ophthalmol. Vis. Sci., 49(6):2518-2525.

Yu et al., 2021, "Enfortumab vedotin after PD-1 or PD-L1 inhibitors in cisplatin-ineligible patients with advanced urothelial carcinoma (EV-201): a multicentre, single-arm, phase 2 trial," Lancet Oncol., 22(6):872-882.

(56) References Cited

OTHER PUBLICATIONS

Zhao et al., 2010, "A germline knowledge based computational approach for determining antibody complementarity determining regions," Molecular Immunology, 47:694-700.

Zoller et al., 1982, "Oligonucleotide-directed mutagenesis using M13-derived vectors: an efficient and general procedure for the production of point mutations in any fragment of DNA," Nucleic Acids Res., 10(20):6487-6500.

* cited by examiner

The cDNA (SEQ ID NO:1) and amino acid sequence (SEQ ID NO:2) of 191P4D12. The start methionine is underlined. The open reading frame extends from nucleic acid 264-1796 including the stop codon.

```
   1 ggccgtcgttgttggccacagcgtgggaagcagctctgggggagctcggagctcccgatc
  61 acggcttcttgggggtagctacggctgggtgtgtagaacgggggccggggctggggctggg
 121 tccctagtggagacccaagtgcgagaggcaagaactctgcagcttcctgccttctgggt
 181 cagttccttattcaagtctgcagccggctcccaggagatctcggtggaacttcagaaac
   1                                          M  P  L  S  L  G  A  E  M  W  G  P  E
 241 gctgggcagtctgcctttcaaccAGGCCCTGTCCTTGGGAGCCGAGATGTGGGGCCCTG
  14  A  W  L  L  L  L  L  A  S  F  T  G  R  C  P  A  G
 301 AGGCCTGGCTGCTGCTGCTGCTACTGGCTGGCATCATTTACAGGCCGGTGCCCGGCGGGTG
  34  L  E  T  S  D  V  V  T  V  V  L  G  Q  D  A  K  L  P  C  F
 361 AGCTGGAGACCTCAGACGTGGTAACTGTGGTGCTGGGCCAGGACGCAAAACTGCCCTGCT
  54  Y  R  G  D  S  G  E  Q  V  G  Q  V  A  W  A  R  V  D  A  G
 421 TCTACCGAGGAGACTCCGGAGAGCAAGTCGGCCAAGTGGCATGGGCTCGAGTGGACGCCG
  74  E  G  A  Q  E  L  A  L  L  H  S  K  Y  G  L  H  V  S  P  A
 481 GCGAAGGGGCCCAGGAACTAGCGCTACTGCACTCCAAATACGGGCTTCATGTGAGCCCGG
  94  Y  E  G  R  V  E  Q  P  P  P  P  R  N  P  L  D  G  S  V  L
 541 CTTACGAGGGCCGCGTGGAGCAGCCGCCGCCCCCACGCAACCCCCTGGACGGCTCAGTGC
 114  L  R  N  A  V  Q  A  D  E  G  E  Y  E  C  R  V  S  T  F  P
 601 TCCTCCGCAACGCAGTGCAGGCGGATGAGGGCGAGTACGAGTGCCGGGTCAGCACGTTCC
 134  A  G  S  F  Q  A  R  L  R  L  R  V  L  V  P  P  L  P  S  L
 661 CCGCCGGCAGCTTCCAGGCGCGGCTGCGGCTCCGAGTGCTGGTGCCTCCCCTGCCCTCAC
 154  N  P  G  P  A  L  E  E  G  Q  G  L  T  L  A  A  S  C  T  A
 721 TGAATCCTGGTCCAGCACTAGAAGAGGGCCAGGGCCTGACCCTGGCAGCCTCCTGCACAG
 174  E  G  S  P  A  P  S  V  T  W  D  T  E  V  K  G  T  T  S  S
 781 CTGAGGGCAGCCCAGCTCCTAGCGTGACCTGGGACACGGAGGTCAAAGGCACAACGTCCA
 194  R  S  F  K  H  S  R  S  A  A  V  T  S  E  F  H  L  V  P  S
 841 GCCGGTTCCTCAAGCACTCCCGCTCTGCTGCCGTCACCTCAGAGTTCCACTTGGTGCCTA
 214  R  S  M  N  G  Q  P  L  T  C  V  V  S  H  P  G  L  L  Q  D
 901 GCCGCAGCATGAATGGCCAGCCACTGACTTGTGTGGTGAGCCATCCTGGCCTTCTCCAGG
 234  Q  R  I  T  H  I  L  H  V  S  F  L  A  E  A  S  V  R  G  L
 961 ACCAAAGGATCACCCACATCCTCCACGTGTCCTTCCTTGCTGAGGCTTCTGTGAGGGGCC
 254  E  D  Q  N  L  W  H  I  G  R  E  G  A  M  L  K  C  L  S
1021 TTGAAGACCAAAATCTCTGGCACATTGGCAGAGAAGGAGCTATGCTCAAGTGCCTGAGTG
 274  G  Q  F  P  P  S  Y  N  W  T  R  L  D  G  P  L  P  S  G  V
1081 AAGGGCAGCCCCCTCCCCCATACAACTGGACAAGGCTGGATGGCCCTCTGCCCAGTGGAG
 294  R  V  D  G  D  T  L  G  F  P  P  L  T  T  E  H  S  G  I  Y
1141 TACGAGTGGATGGAGACACTTTGGGCTTTCCCCCACTGACCACTGAGCACAGCGGCATCT
 314  V  C  H  V  S  N  E  F  S  S  R  D  S  Q  V  T  V  D  V  L
1201 ACGTCTGCCATGTCAGCAATGAGTTCTCCTCAAGGGATTCTCAGGTCACTGTGGATGTTC
 334  D  P  Q  E  D  S  G  K  Q  V  D  L  V  S  A  S  V  V  V
```

FIG. 5A

FIG. 5A (con't)

The cDNA (SEQ ID NO:3) and amino acid sequence (SEQ ID NO:4) of Ha22-2(2,4)6.1 heavy chain. Double-underlined is the leader sequence, underlined is the heavy chain variable region, and underlined with a dashed line is the human IgG1 constant region.

The cDNA (SEQ ID NO:5) and amino acid sequence (SEQ ID NO:6) of Ha22-2(2,4)6.1 light chain. Double-underlined is the leader sequence, underlined is the light chain variable region, and underlined with a dashed line is the human kappa constant region.

FIG. 5B

The amino acid sequence (SEQ ID NO:7) of Ha22-2(2,4)6.1 heavy chain.
Double-underlined is the leader sequence, underlined is the heavy chain variable region, and underlined with a dashed line is the human IgG1 constant region.

```
  1  MELGLCWVFLVAILEGVQCEVQLVESGGGLVQPGGSLRLSCAASGFTFSS
 51  YNMNWVRQAPGKGLEWVSYISSSSSTIYYADSVKGRFTISRDNAKNSLSL
101  QMNSLRDEDTAVYYCARAYYYGMDVWGQGTTVTVSSASTKGPSVFPLAPS
151  SKSTSGGTAALGCLVKDYFPEPVTVSWNSGALTSGVHTFPAVLQSSGLYS
201  LSSVVTVPSSSLGTQTYICNVNHKPSNTKVDKKVEPKSCDKTHTCPPCPA
251  PELLGGPSVFLFPPKPKDTLMISRTPEVTCVVVDVSHEDPEVKFNWYVDG
301  VEVHNAKTKPREEQYNSTYRVVSVLTVLHQDWLNGKEYKCKVSNKALPAP
351  IEKTISKAKGQPREPQVYTLPPSREEMTKNQVSLTCLVKGFYPSDIAVEW
401  ESNGQPENNYKTTPPVLDSDGSFFLYSKLTVDKSRWQQGNVFSCSVMHEA
451  LHNHYTQKSLSLSPGK
```

The amino acid sequence (SEQ ID NO:8) of Ha22-2(2,4)6.1 light chain.
Double-underlined is the leader sequence, underlined is the light chain variable region, and underlined with a dashed line is the human kappa constant region.

```
  1  MDMRVPAQLLGLLLLWFPGSRCDIQMTQSPSSVSASVGDRVTITCRASQG
 51  ISGWLAWYQQKPGKAPKFLIYAASTLQSGVPSRFSGSGSGTDFTLTISSL
101  QPEDFATYYCQQANSFPPTFGGGTKVEIKRTVAAPSVFIFPPSDEQLKSG
151  TASVVCLLNNFYPREAKVQWKVDNALQSGNSQESVTEQDSKDSTYSLSST
201  LTLSKADYEKHKVYACEVTHQGLSSPVTKSFNRGEC
```

FIG. 5C

PHARMACEUTICAL COMPOSITIONS COMPRISING ANTI-191P4D12 ANTIBODY DRUG CONJUGATES AND METHODS OF USE THEREOF

CROSS REFERENCE TO RELATED APPLICATIONS

This application is a U.S. National Stage Application under 35 U.S.C. § 371 of International Patent Application No. PCT/US2019/056214, filed Oct. 15, 2019, which claims the benefit of U.S. Provisional Patent Application No. 62/774,819, filed Dec. 3, 2018, the disclosure of each of which is incorporated by reference herein in its entirety.

1. FIELD

Provided herein are pharmaceutical compositions comprising anti-191P4D12 antibody drug conjugates. Methods of using the pharmaceutical compositions are also provided herein.

2. BACKGROUND

Drug substances are usually administered as part of a formulation in combination with one or more other agents that serve varied and specialized pharmaceutical functions. Pharmaceutical excipients have various functions and contribute to the pharmaceutical formulations in many different ways, e.g., solubilization, dilution, thickening, stabilization, preservation, coloring, flavoring, etc. Properties that may be considered when formulating an active drug substance include bioavailability, ease of manufacture, ease of administration, and stability of the dosage form. Due to the varying properties of active drug substances being formulated, dosage forms typically require pharmaceutical excipients that are uniquely tailored to the active drug substance in order to achieve advantageous physical and pharmaceutical properties.

Thus, a need exists as to pharmaceutical compositions of anti-191P4D12 antibody drug conjugates having advantageous physical and pharmaceutical properties. The present invention satisfies this need and provides related benefits.

3. SUMMARY

In one aspect, provided herein is a pharmaceutical composition comprising (a) an antibody drug conjugate comprising an antibody or antigen binding fragment thereof that binds to 191P4D12 conjugated to one or more units of monomethyl auristatin E (MMAE), wherein the antibody or antigen binding fragment thereof comprises a heavy chain variable region comprising complementarity determining regions (CDRs) comprising the amino acid sequences of the CDRs of the heavy chain variable region set forth in SEQ ID NO:7 and a light chain variable region comprising CDRs comprising the amino acid sequences of the CDRs of the light chain variable region set forth in SEQ ID NO:8; and (b) a pharmaceutically acceptable excipient comprising L-histidine, polysorbate-20 (TWEEN-20), and at least one of trehalose dihydrate and sucrose.

In some embodiments, the antibody or antigen binding fragment thereof comprises CDR H1 comprising an amino acid sequence of SEQ ID NO:9, CDR H2 comprising an amino acid sequence of SEQ ID NO:10, CDR H3 comprising an amino acid sequence of SEQ ID NO:11; CDR L1 comprising an amino acid sequence of SEQ ID NO:12, CDR L2 comprising an amino acid sequence of SEQ ID NO:13, and CDR L3 comprising an amino acid sequence of SEQ ID NO:14.

In some embodiments, the antibody or antigen binding fragment thereof comprises a heavy chain variable region comprising the amino acid sequence ranging from the 20th amino acid (glutamic acid) to the 136th amino acid (serine) of SEQ ID NO:7 and a light chain variable region comprising the amino acid sequence ranging from the 23rd amino acid (aspartic acid) to the 130th amino acid (arginine) of SEQ ID NO:8.

In some embodiments, the antibody comprises a heavy chain comprising the amino acid sequence ranging from the 20th amino acid (glutamic acid) to the 466th amino acid (lysine) of SEQ ID NO:7 and a light chain comprising the amino acid sequence ranging from the 23rd amino acid (aspartic acid) to the 236th amino acid (cysteine) of SEQ ID NO:8.

In some embodiments, the antigen binding fragment is an Fab, F(ab')2, Fv or scFv fragment.

In some embodiments, the antibody is a fully human antibody.

In some embodiments, the antibody or antigen binding fragment thereof is recombinantly produced.

In some embodiments, the antibody drug conjugate has the following structure:

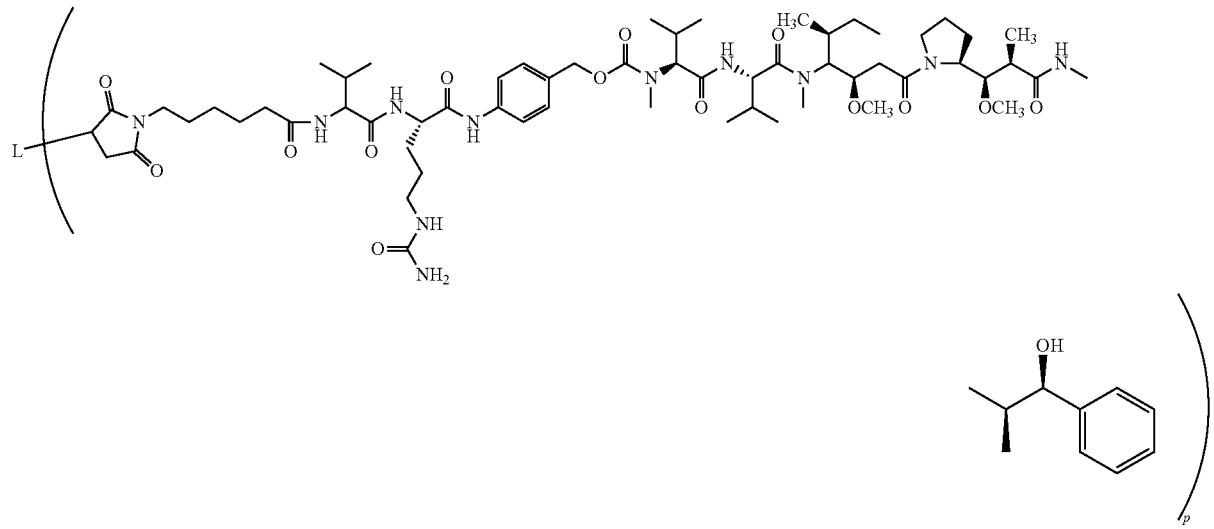

wherein L- represents the antibody or antigen binding fragment thereof and p is from 1 to 10.

In some embodiments, p is from 2 to 8.

In some embodiments, the antibody or antigen binding fragment is linked to each unit of monomethyl auristatin E (MMAE) via a linker.

In some embodiments, the linker is an enzyme-cleavable linker, and in one embodiment, the linker forms a bond with a sulfur atom of the antibody or antigen binding fragment thereof.

In some embodiments, the linker has a formula of: $-A_a-W_w-Y_y-$; wherein -A- is a stretcher unit, a is 0 or 1; —W— is an amino acid unit, w is an integer ranging from 0 to 12; and —Y— is a spacer unit, y is 0, 1, or 2.

In some embodiments, the stretcher unit has the structure of Formula (1) below; the amino acid unit is valine citrulline; and the spacer unit is a PAB group having the structure of Formula (2) below:

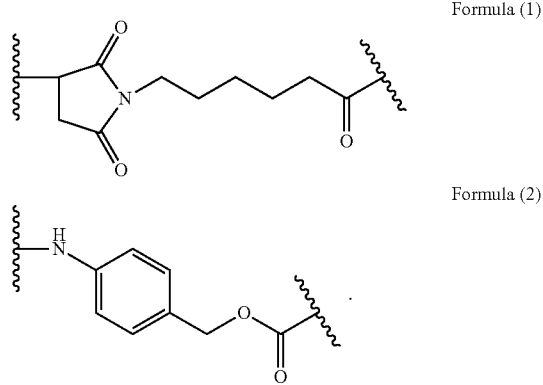

Formula (1)

Formula (2)

In some embodiments, the stretcher unit forms a bond with a sulfur atom of the antibody or antigen binding fragment thereof; and wherein the spacer unit is linked to MMAE via a carbamate group.

In some embodiments, the antibody drug conjugate comprises from 1 to 10 units of MMAE per antibody or antigen binding fragment thereof.

In some embodiments, the antibody drug conjugate comprises from 2 to 8 units of MMAE per antibody or antigen binding fragment thereof.

In some embodiments, the pharmaceutical composition comprises the antibody drug conjugate at a concentration of from about 1 to about 20 mg/mL. In some embodiments, the pharmaceutical composition comprises the antibody drug conjugate at a concentration of from about 5 to about 15 mg/mL. In other embodiments, the pharmaceutical composition comprises the antibody drug conjugate at a concentration of from about 8 to about 12 mg/mL. In yet other embodiments, the pharmaceutical composition comprises the antibody drug conjugate at a concentration of about 10 mg/mL.

In some embodiments, L-histidine is present in the range of about 5 to about 50 mM. In other embodiments, L-histidine is present in the range of about 10 to about 40 mM. In other embodiments, L-histidine is present in the range of about 15 to about 35 mM. In other embodiments, L-histidine is present in the range of about 15 to about 30 mM. In other embodiments, L-histidine is present in the range of about 15 to about 25 mM. In yet other embodiments, L-histidine is present at about 20 mM.

In some embodiments, the concentration of TWEEN-20 is in the range of from about 0.001 to about 0.1% (v/v). In other embodiments, the concentration of TWEEN-20 is in the range of from about 0.0025 to about 0.075% (v/v). In other embodiments, the concentration of TWEEN-20 is in the range of from about 0.005 to about 0.05% (v/v). In other embodiments, the concentration of TWEEN-20 is in the range of from about 0.01 to about 0.03% (v/v). In yet other embodiments, the concentration of TWEEN-20 is in the range of about 0.02% (v/v).

In some embodiments, the pharmaceutical composition provided herein comprises trehalose dihydrate. In some embodiments, the trehalose dihydrate is present in the range of about 1 to about 20% (w/v). In some embodiments, the trehalose dihydrate is present in the range of about 2 to about 15% (w/v). In other embodiments, the trehalose dihydrate is present in the range of about 3 to about 10% (w/v). In yet other embodiments, the trehalose dihydrate is present in the range of about 4 to about 6% (w/v). In yet other embodiments, the trehalose dihydrate is present at about 5.5% (w/v).

In some embodiments, the trehalose dihydrate is present in the range of about 50 mM to about 300 mM. In some embodiments, the trehalose dihydrate is present in the range of about 75 mM to about 250 mM. In other embodiments, the trehalose dihydrate is present in the range of about 100 mM to about 200 mM. In yet other embodiments, the trehalose dihydrate is present in the range of about 130 mM to about 150 mM. In yet other embodiments, the trehalose dihydrate is present at about 146 mM.

In some embodiments, the pharmaceutical composition comprises sucrose. In some embodiments, the sucrose is present in the range of about 1 to about 20% (w/v). In some embodiments, the sucrose is present in the range of about 2 to about 15% (w/v). In other embodiments, the sucrose is present in the range of about 3 to about 10% (w/v). In other embodiments, the sucrose is present in the range of about 4 to about 6% (w/v). In yet other embodiments, the sucrose is present at about 5.5% (w/v).

In some embodiments, the sucrose is present in the range of about 50 mM to about 300 mM. In other embodiments, the sucrose is present in the range of about 75 mM to about 250 mM. In other embodiments, the sucrose is present in the range of about 100 mM to about 200 mM. In yet other embodiments, the sucrose is present in the range of about 130 mM to about 150 mM. In yet other embodiments, the sucrose is present at about 146 mM.

In some embodiments, the pharmaceutical composition has a pH in a range of about 5.5 to about 6.5. In some embodiments, the pharmaceutical composition has a pH in a range of about 5.7 to about 6.3. In other embodiments, the pharmaceutical composition has a pH of about 6.0.

In some embodiments, the pH is taken at room temperature. In some embodiments, the pH is taken at about 15° C. to about 27° C. In other embodiments, the pH is taken at about 4° C. In other embodiments, the pH is taken at about 25° C.

In some embodiments, the pharmaceutical composition provided herein comprises hydrochloric acid (HCl). In some embodiments, the pH is adjusted by HCl.

In other embodiments, the pharmaceutical composition provided herein comprises succinic acid. In some embodiments, the pH is adjusted by succinic acid.

In some embodiments, the pharmaceutical composition provided herein comprises about 20 mM L-histidine, about 0.02% (w/v) TWEEN-20, and at least one of about 5.5% (w/v) trehalose dihydrate or about 5% (w/v) sucrose. In some embodiments, the pharmaceutical composition provided herein further comprises HCl or succinic acid. In some embodiments, the pH is about 6.0 at room temperature. In other embodiments, the pH is about 6.0 at 25° C.

In some specific embodiments, the pharmaceutical composition provided herein comprises:
(a) an antibody drug conjugate having the following structure:

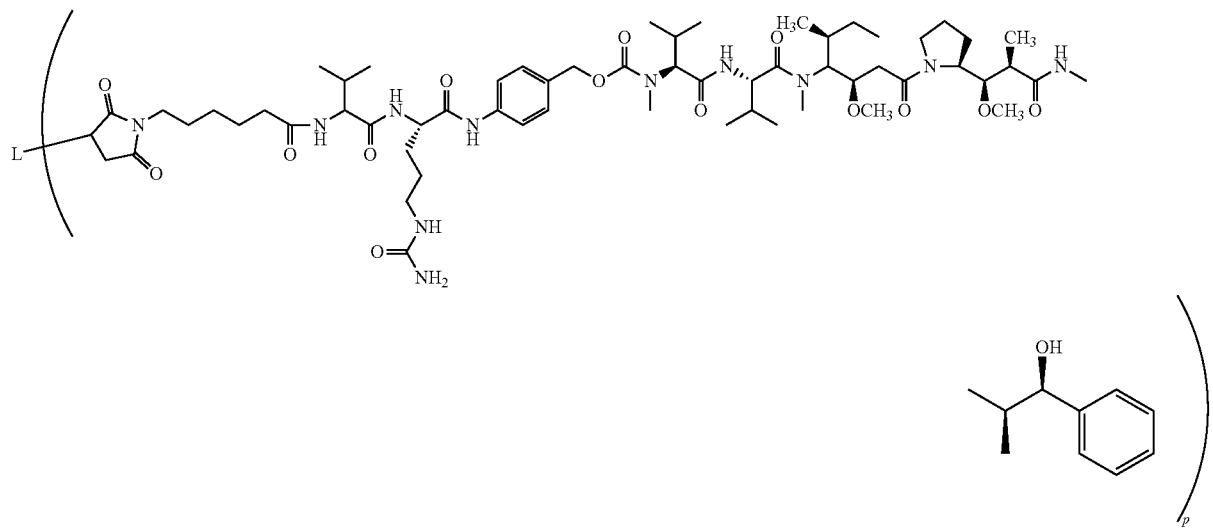

wherein L- represents the antibody or antigen binding fragment thereof and p is from 1 to 10; and (b) a pharmaceutically acceptable excipient comprising about 20 mM L-histidine, about 0.02% (w/v) TWEEN-20, about 5.5% (w/v) trehalose dihydrate, and HCl, wherein the pH is about 6.0 at 25° C.

In some embodiments, the antibody drug conjugate is at the concentration of about 10 mg/mL.

In other specific embodiments, the pharmaceutical composition provided herein comprises:
(a) an antibody drug conjugate comprising the following structure:

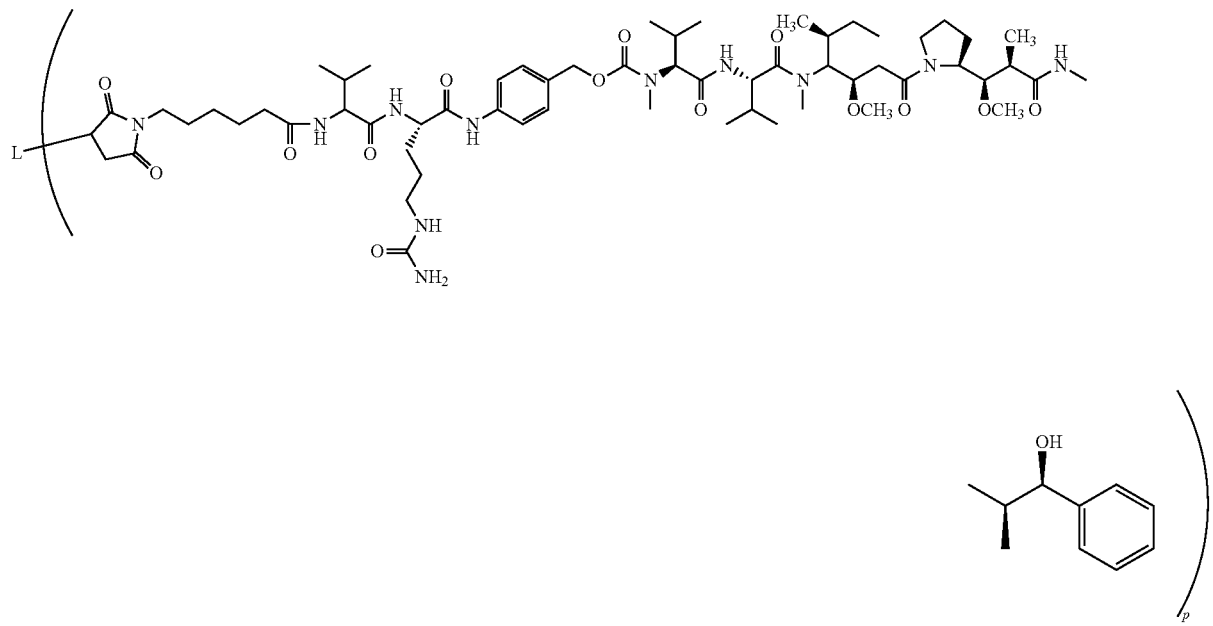

wherein L- represents the antibody or antigen binding fragment thereof and p is from 1 to 10; and
(b) a pharmaceutically acceptable excipient comprising about 20 mM L-histidine, about 0.02% (w/v) TWEEN-20, about 5.5% (w/v) trehalose dihydrate, and succinic acid, wherein the pH is about 6.0 at 25° C.

In some embodiments, the antibody drug conjugate is at the concentration of about 10 mg/mL in the pharmaceutical composition provided herein.

In yet other specific embodiments, the pharmaceutical composition provided herein comprises:
(a) an antibody drug conjugate comprising the following structure:

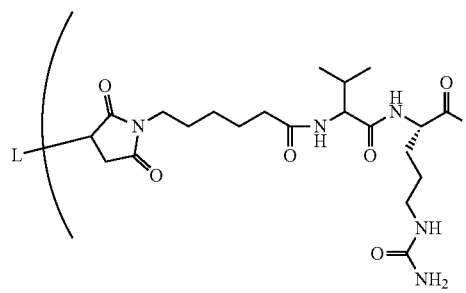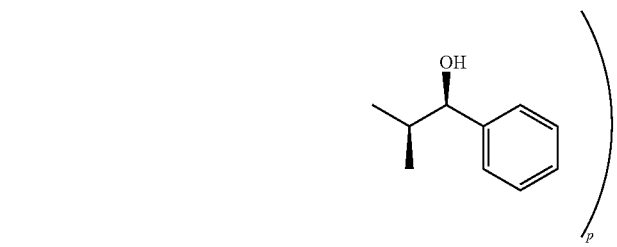

wherein L- represents the antibody or antigen binding fragment thereof and p is from 1 to 10; and
(b) a pharmaceutically acceptable excipient comprising about 20 mM L-histidine, about 0.02% (w/v) TWEEN-20, about 5.0% (w/v) sucrose, and HCl, wherein the pH is about 6.0 at 25° C.

In some embodiments, the antibody drug conjugate is at the concentration of about 10 mg/mL in the pharmaceutical composition provided herein.

In some embodiments, the pharmaceutical composition provided herein is in a liquid form.

In other embodiments, the pharmaceutical composition provided herein is lyophilized.

In another aspect, provided herein is a lyophilized composition made by freeze-drying the pharmaceutical composition provided herein.

In some embodiments, the pharmaceutical composition is stored at −80° C., 4° C., 25° C. or 37° C.

In another aspect, provided herein is a method of preventing or treating a disease or disorder in a subject, comprising administering to the subject an effective amount of the pharmaceutical composition provided herein.

In some embodiments, the subject is a human subject.

In some embodiments, the cancer is a solid tumor. In some embodiments, the cancer is colon cancer, pancreatic cancer, ovarian cancer, lung cancer, bladder cancer, breast cancer, esophageal cancer, head cancer, or neck cancer.

In a specific embodiment, the cancer is colon cancer. In a specific embodiment, the cancer is pancreatic cancer. In a specific embodiment, the cancer is ovarian cancer. In a specific embodiment, the cancer is lung cancer. In some embodiments, the lung cancer is non-small cell lung cancer. In a specific embodiment, the cancer is bladder cancer. In a specific embodiment, the cancer is advanced bladder cancer. In a specific embodiment, the cancer is metastatic bladder cancer. In a specific embodiment, the cancer is breast cancer. In a specific embodiment, the cancer is esophageal cancer. In a specific embodiment, the cancer is head cancer. In a specific embodiment, the cancer is neck cancer. In a specific embodiment, the cancer has tumor cells expressing 191P4D12.

In some embodiments, the method provided herein further comprises administering to the subject a second therapeutic agent. In some embodiments, the second therapeutic agent is an immune checkpoint inhibitor. In some embodiments, the immune checkpoint inhibitor is a PD-1 inhibitor or a PD-L1 inhibitor. In other embodiments, the immune checkpoint inhibitor is a PD-1 inhibitor. In yet other embodiments, the PD-1 inhibitor is pembrolizumab or nivolumab. In other embodiments, the immune checkpoint inhibitor is a PD-L1 inhibitor. In other embodiments, the PD-L1 inhibitor is selected from a group consisting of atezolizumab, avelumab, and durvalumab.

In some embodiments, the antibody drug conjugate formulated in the pharmaceutical composition is administered at a dose of 1 to 10 mg/kg of the subject's body weight. In other embodiments, the antibody drug conjugate formulated in the pharmaceutical composition is administered at a dose of 1 to 5 mg/kg of the subject's body weight. In yet other embodiments, the antibody drug conjugate formulated in the pharmaceutical composition is administered at a dose of 1 to 2.5 mg/kg of the subject's body weight. In some embodiments, the antibody drug conjugate formulated in the pharmaceutical composition is administered at a dose of 1 to 1.25 mg/kg of the subject's body weight. In some embodiments, the antibody drug conjugate formulated in the pharmaceutical composition is administered at a dose of about 1 mg/kg of the subject's body weight. In some embodiments, the antibody drug conjugate formulated in the pharmaceutical composition is administered at a dose of about 1.25 mg/kg of the subject's body weight.

In some embodiments, the antibody drug conjugate formulated in the pharmaceutical composition is administered by an intravenous (IV) injection or infusion.

In some embodiments, the antibody drug conjugate formulated in the pharmaceutical composition is administered by an intravenous (IV) injection or infusion over about 30 minutes twice every three-week cycle. In some embodiments, the antibody drug conjugate formulated in the pharmaceutical composition is administered by an intravenous (IV) injection or infusion over about 30 minutes on Days 1 and 8 of every three-week cycle. In some embodiments, the method further comprises administering an immune checkpoint inhibitor by an intravenous (IV) injection or infusion on Day 1 of every three-week cycle. In some embodiments, the immune checkpoint inhibitor is pembrolizumab, and wherein pembrolizumab is administered at amount of about 200 mg over about 30 minutes. In other embodiments, the immune checkpoint inhibitor is atezolizumab, and wherein atezolizumab is administered at amount of about 1200 mg over about 60 minutes or 30 minutes.

In other embodiments, the antibody drug conjugate formulated in the pharmaceutical composition is administered by an intravenous (IV) injection or infusion over about 30 minutes three times every four-week cycle. In some embodiments, the antibody drug conjugate formulated in the pharmaceutical composition is administered by an intravenous (IV) injection or infusion over about 30 minutes on Days 1, 8 and 15 of every four-week cycle. In some embodiments, the method further comprises administering an immune checkpoint inhibitor by an intravenous (IV) injection or infusion. In some embodiments, the immune checkpoint inhibitor is pembrolizumab. In other embodiments, the immune checkpoint inhibitor is atezolizumab.

4. DESCRIPTION OF THE DRAWINGS

FIGS. 1A, 1B, 1C, and 1D depict the results of SDS-PAGE analysis for the 14-day stability study for the formulations F1-F14 at 40° C.

FIG. 1E depicts the summary of the PR-HPLC study described in Section 6.1.

FIGS. 1F, 1G, and 1H depicts the results of the SE-HPLC analysis for the formulations F1-F14 at 40° C.

FIG. 2A depicts the results of the shade study for the formulations F4, F9 and F14 at TO.

FIG. 3D depicts the results of the SDS-PAGE analysis of the BDS (before lyophilization) at TO.

FIG. 3F depicts the results of the SDS-PAGE analysis of the DP after lyophilization and reconstitution at TO.

FIG. 5A depicts the nucleotide and amino acid sequences of 191P4D12 protein.

FIG. 5B depicts the nucleotide and amino acid sequences of the heavy chain and light chain of Ha22-2(2.4)6.1.

FIG. 5C depicts the amino acid sequences of the heavy chain and light chain of Ha22-2(2.4)6.1.

5. DETAILED DESCRIPTION

Figure 1A:
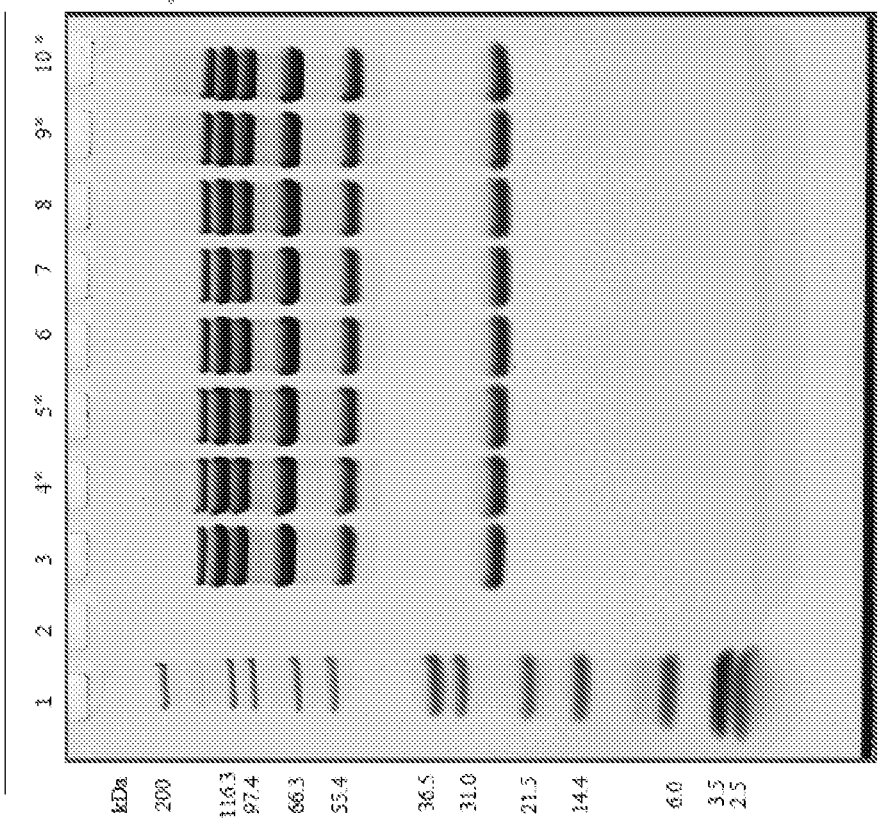
Figure 1B:
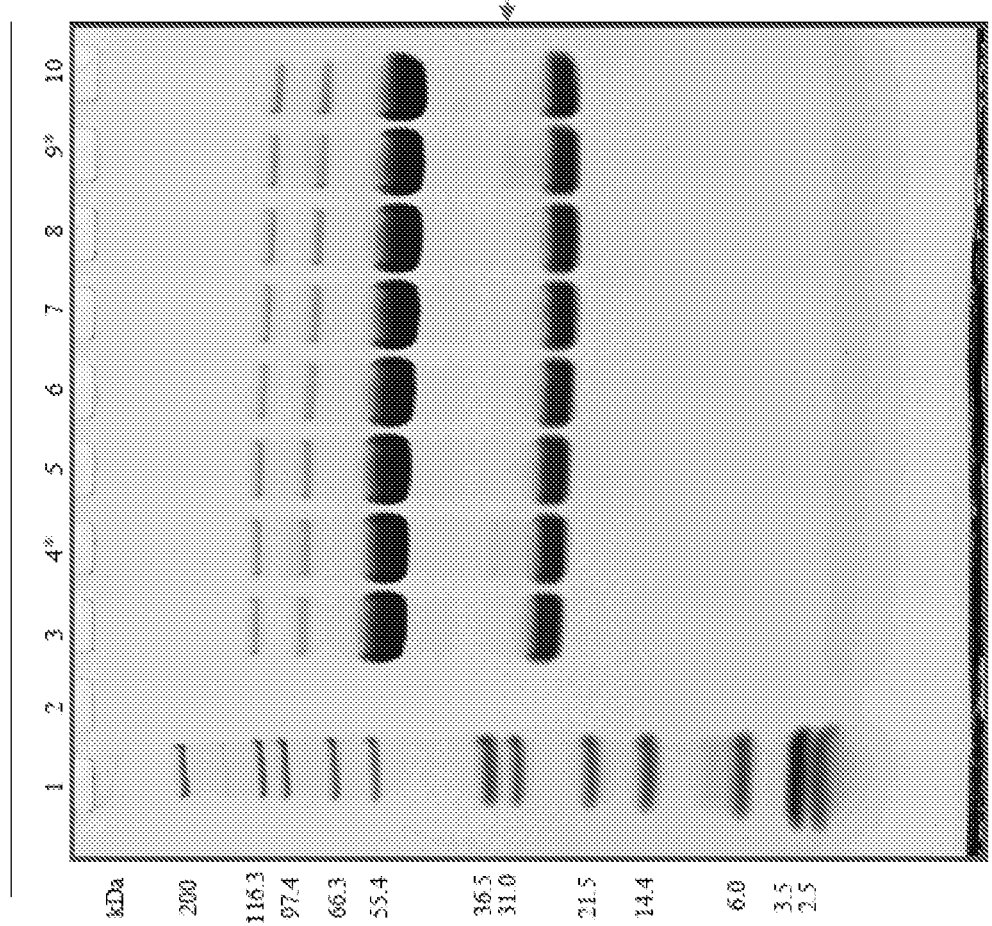
Figure 1C:
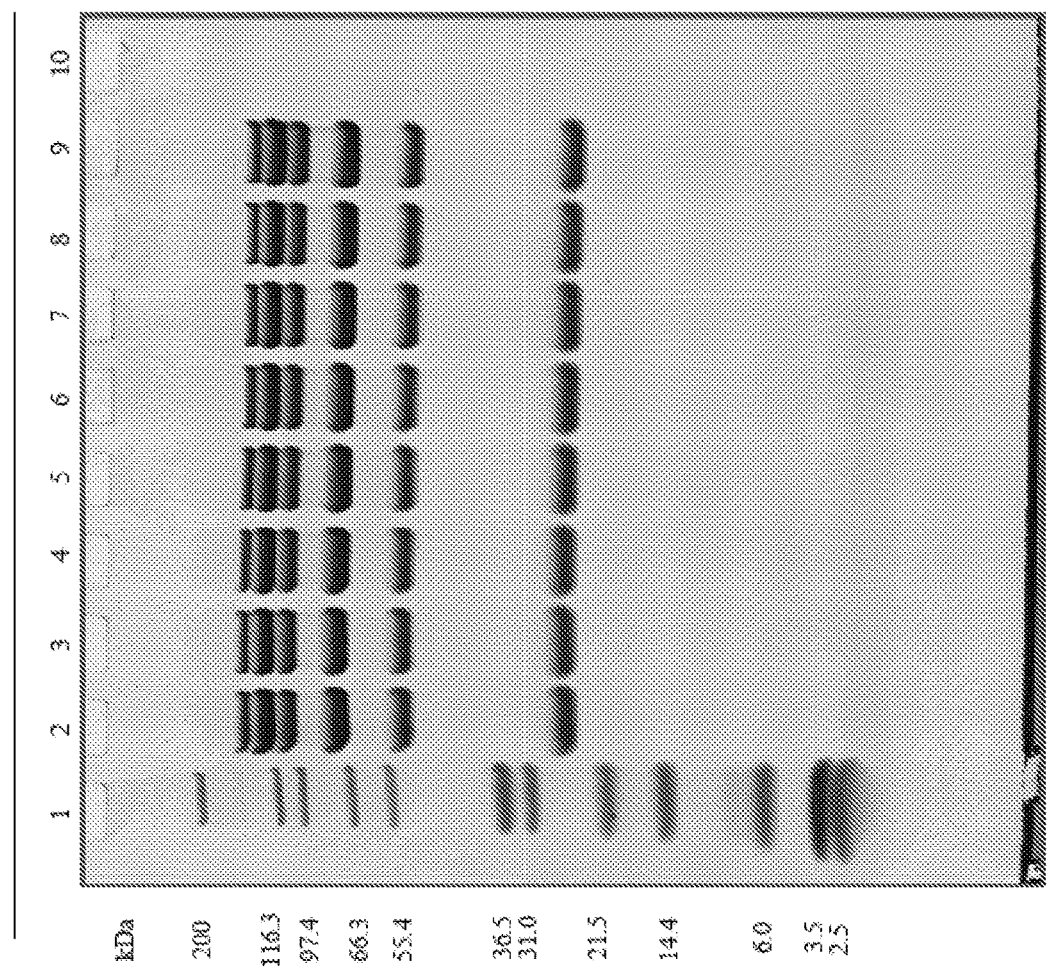
Figure 1D:
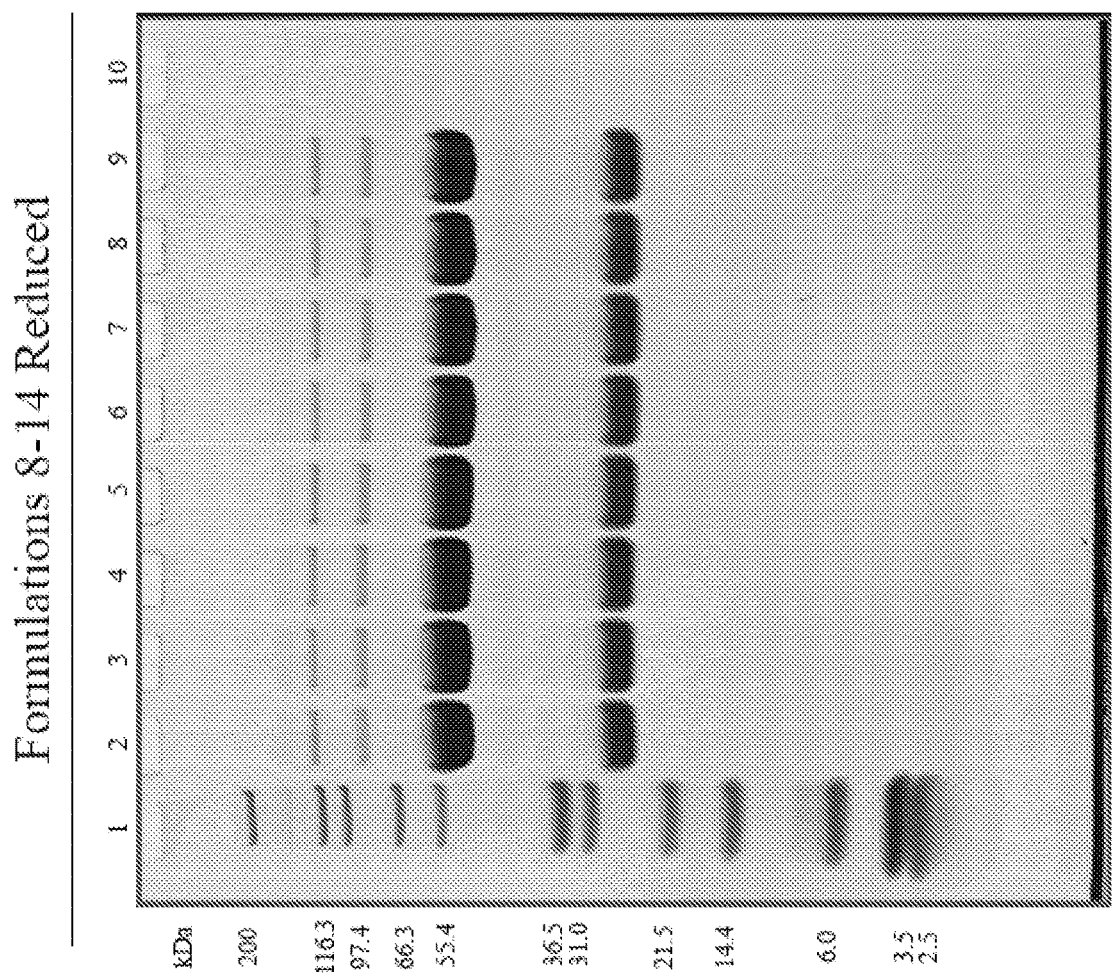

Before the present disclosure is further described, it is to be understood that the disclosure is not limited to the particular embodiments set forth herein, and it is also to be understood that the terminology used herein is for the purpose of describing particular embodiments only, and is not intended to be limiting.

5.1 Definitions

Techniques and procedures described or referenced herein include those that are generally well understood and/or commonly employed using conventional methodology by those skilled in the art, such as, for example, the widely utilized methodologies described in Sambrook et al., Molecular Cloning: A Laboratory Manual (3d ed. 2001); Current Protocols in Molecular Biology (Ausubel et al. eds., 2003); Therapeutic Monoclonal Antibodies: From Bench to Clinic (An ed. 2009); Monoclonal Antibodies: *Methods and Protocols* (Albitar ed. 2010); and *Antibody Engineering* Vols 1 and 2 (Kontermann and Dübel eds., 2d ed. 2010).

Unless otherwise defined herein, technical and scientific terms used in the present description have the meanings that are commonly understood by those of ordinary skill in the art. For purposes of interpreting this specification, the following description of terms will apply and whenever appropriate, terms used in the singular will also include the plural and vice versa. In the event that any description of a term set forth conflicts with any document incorporated herein by reference, the description of the term set forth below shall control.

The term "antibody," "immunoglobulin," or "Ig" is used interchangeably herein, and is used in the broadest sense and specifically covers, for example, monoclonal antibodies (including agonist, antagonist, neutralizing antibodies, full length or intact monoclonal antibodies), antibody compositions with polyepitopic or monoepitopic specificity, polyclonal or monovalent antibodies, multivalent antibodies, multispecific antibodies (e.g., bispecific antibodies so long as they exhibit the desired biological activity), formed from at least two intact antibodies, single chain antibodies, and fragments thereof, as described below. An antibody can be human, humanized, chimeric and/or affinity matured, as well as an antibody from other species, for example, mouse and rabbit, etc. The term "antibody" is intended to include a polypeptide product of B cells within the immunoglobulin class of polypeptides that is able to bind to a specific molecular antigen and is composed of two identical pairs of polypeptide chains, wherein each pair has one heavy chain (about 50-70 kDa) and one light chain (about 25 kDa), each amino-terminal portion of each chain includes a variable region of about 100 to about 130 or more amino acids, and each carboxy-terminal portion of each chain includes a constant region. See, e.g., *Antibody Engineering* (Borrebaeck ed., 2d ed. 1995); and Kuby, *Immunology* (3d ed. 1997). In specific embodiments, the specific molecular antigen can be bound by an antibody provided herein, including a polypeptide or an epitope. Antibodies also include, but are not limited to, synthetic antibodies, recombinantly produced antibodies, camelized antibodies, intrabodies, anti-idiotypic (anti-Id) antibodies, and functional fragments (e.g., antigen-binding fragments) of any of the above, which refers to a portion of an antibody heavy or light chain polypeptide that retains some or all of the binding activity of the antibody from which the fragment was derived. Non-limiting examples of functional fragments (e.g., antigen-binding fragments) include single-chain Fvs (scFv) (e.g., including monospecific, bispecific, etc.), Fab fragments, F(ab') fragments, F(ab)$_2$ fragments, F(ab')2 fragments, disulfide-linked Fvs (dsFv), Fd fragments, Fv fragments, diabody, triabody, tetrabody, and minibody. In particular, antibodies provided herein include immunoglobulin molecules and immunologically active portions of immunoglobulin molecules, for example, antigen-binding domains or molecules that contain an antigen-binding site that binds to an antigen (e.g., one or more CDRs of an antibody). Such antibody fragments can be found in, for example, Harlow and Lane, *Antibodies: A Laboratory Manual* (1989); *Mol. Biology and Biotechnology: A Comprehensive Desk Reference* (Myers ed., 1995); Huston et al., 1993, Cell Biophysics 22:189-224; Plückthun and Skerra, 1989, Meth. Enzymol. 178:497-515; and Day, *Advanced Immunochemistry* (2d ed. 1990). The antibodies provided herein can be of any class (e.g., IgG, IgE, IgM, IgD, and IgA) or any subclass (e.g., IgG1, IgG2, IgG3, IgG4, IgA1, and IgA2) of immunoglobulin molecule. Antibodies may be agonistic antibodies or antagonistic antibodies.

The term "monoclonal antibody" refers to an antibody obtained from a population of substantially homogeneous antibodies, that is, the individual antibodies comprising the population are identical except for possible naturally occurring mutations that can be present in minor amounts. Monoclonal antibodies are highly specific, being directed against a single antigenic site. In contrast to polyclonal antibody preparations, which can include different antibodies directed against different determinants (epitopes), each monoclonal antibody is directed against a single determinant on the antigen.

An "antigen" is a structure to which an antibody can selectively bind. A target antigen may be a polypeptide, carbohydrate, nucleic acid, lipid, hapten, or other naturally occurring or synthetic compound. In some embodiments, the target antigen is a polypeptide. In certain embodiments, an antigen is associated with a cell, for example, is present on or in a cell, for example, a cancer cell.

An "intact" antibody is one comprising an antigen-binding site as well as a CL and at least heavy chain constant regions, CH1, CH2 and CH3. The constant regions may include human constant regions or amino acid sequence variants thereof. In certain embodiments, an intact antibody has one or more effector functions.

The terms "antigen binding fragment," "antigen binding domain," "antigen binding region," and similar terms refer to that portion of an antibody, which comprises the amino acid residues that interact with an antigen and confer on the binding agent its specificity and affinity for the antigen (e.g., the CDRs). "Antigen-binding fragment" as used herein include "antibody fragment," which comprise a portion of an intact antibody, such as the antigen-binding or variable region of the intact antibody. Examples of antibody fragments include, without limitation, Fab, Fab', F(ab')$_2$, and Fv fragments; diabodies and di-diabodies (see, e.g., Holliger et al., 1993, Proc. Natl. Acad. Sci. 90:6444-48; Lu et al., 2005, J. Biol. Chem. 280:19665-72; Hudson et al., 2003, Nat. Med. 9:129-34; WO 93/11161; and U.S. Pat. Nos. 5,837,242 and 6,492,123); single-chain antibody molecules (see, e.g., U.S. Pat. Nos. 4,946,778; 5,260,203; 5,482,858; and 5,476, 786); dual variable domain antibodies (see, e.g., U.S. Pat. No. 7,612,181); single variable domain antibodies (sdAbs) (see, e.g., Woolven et al., 1999, Immunogenetics 50: 98-101; and Streltsov et al., 2004, Proc Natl Acad Sci USA. 101: 12444-49); and multispecific antibodies formed from antibody fragments.

The terms "binds" or "binding" refer to an interaction between molecules including, for example, to form a complex. Interactions can be, for example, non-covalent interactions including hydrogen bonds, ionic bonds, hydrophobic interactions, and/or van der Waals interactions. A complex can also include the binding of two or more molecules held together by covalent or non-covalent bonds, interactions, or forces. The strength of the total non-covalent interactions between a single antigen-binding site on an antibody and a single epitope of a target molecule, such as an antigen, is the affinity of the antibody or functional fragment for that epitope. The ratio of dissociation rate ($k_{off}$) to association rate ($k_{on}$) of a binding molecule (e.g., an antibody) to a monovalent antigen ($k_{off}/k_{on}$) is the dissociation constant $K_D$, which is inversely related to affinity. The lower the $K_D$ value, the higher the affinity of the antibody. The value of $K_D$ varies for different complexes of antibody and antigen and depends on both $k_{on}$ and $k_{off}$. The dissociation constant $K_D$ for an antibody provided herein can be determined using any method provided herein or any other method well-known to those skilled in the art. The affinity at one binding site does not always reflect the true strength of the interaction between an antibody and an antigen. When complex antigens containing multiple, repeating antigenic determinants, such as a polyvalent antigen, come in contact with antibodies containing multiple binding sites, the interaction of antibody with antigen at one site will increase the probability of a reaction at a second site. The strength of such multiple interactions between a multivalent antibody and antigen is called the avidity.

In connection with the antibody or antigen binding fragment thereof described herein terms such as "bind to," "that specifically bind to," and analogous terms are also used interchangeably herein and refer to binding molecules of antigen binding domains that specifically bind to an antigen, such as a polypeptide. An antibody or antigen binding fragment that binds to or specifically binds to an antigen may be cross-reactive with related antigens. In certain embodiments, an antibody or antigen binding fragment that binds to or specifically binds to an antigen does not cross-react with other antigens. An antibody or antigen binding fragment that binds to or specifically binds to an antigen can be identified, for example, by immunoassays, Octet®, Biacore®, or other techniques known to those of skill in the art. In some embodiments, an antibody or antigen binding fragment binds to or specifically binds to an antigen when it binds to an antigen with higher affinity than to any cross-reactive antigen as determined using experimental techniques, such as radioimmunoassays (MA) and enzyme linked immunosorbent assays (ELISAs). Typically, a specific or selective reaction will be at least twice background signal or noise and may be more than 10 times background. See, e.g., *Fundamental Immunology* 332-36 (Paul ed., 2d ed. 1989) for a discussion regarding binding specificity. In certain embodiments, the extent of binding of an antibody or antigen binding fragment to a "non-target" protein is less than about 10% of the binding of the binding molecule or antigen binding domain to its particular target antigen, for example, as determined by fluorescence activated cell sorting (FACS) analysis or MA. With regard terms such as "specific binding," "specifically binds to," or "is specific for" means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target. An antibody or antigen binding fragment that binds to an antigen includes one that is capable of binding the antigen with sufficient affinity such that the binding molecule is useful, for example, as a diagnostic agent in targeting the antigen. In certain embodiments, an antibody or antigen binding fragment that binds to an antigen has a dissociation constant ($K_D$) of less than or equal to 1000 nM, 800 nM, 500 nM, 250 nM, 100 nM, 50 nM, 10 nM, 5 nM, 4 nM, 3 nM, 2 nM, 1 nM, 0.9 nM, 0.8 nM, 0.7 nM, 0.6 nM, 0.5 nM, 0.4 nM, 0.3 nM, 0.2 nM, or 0.1 nM. In certain embodiments, an antibody or antigen binding fragment binds to an epitope of an antigen that is conserved among the antigen from different species (e.g., between human and cyno species).

"Binding affinity" generally refers to the strength of the sum total of noncovalent interactions between a single binding site of a molecule (e.g., a binding protein such as an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a binding molecule X for its binding partner Y can generally be represented by the dissociation constant ($K_D$). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present disclosure. Specific illustrative embodiments include the following. In one embodiment, the "$K_D$" or "$K_D$ value" may be measured by assays known in the art, for example by a binding assay. The $K_D$ may be measured in a RIA, for example, performed with the Fab version of an antibody of interest and its antigen (Chen et al., 1999, J. Mol Biol 293:865-81). The $K_D$ or $K_D$ value may also be measured by using biolayer interferometry (BLI) or surface plasmon resonance (SPR) assays by Octet®, using, for example, a Octet®QK384 system, or by Biacore®, using, for example, a Biacore®TM-2000 or a Biacore®TM-3000. An "on-rate" or "rate of association" or "association rate" or "kon" may also be determined with the same biolayer interferometry (BLI) or surface plasmon resonance (SPR) techniques described above using, for example, the Octet®QK384, the Biacore®TM-2000, or the Biacore®TM-3000 system.

In certain embodiments, the antibodies or antigen binding fragments can comprise "chimeric" sequences in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., 1984, Proc. Natl. Acad. Sci. USA 81:6851-55).

In certain embodiments, the antibodies or antigen binding fragments can comprise portions of "humanized" forms of nonhuman (e.g., murine) antibodies that are chimeric antibodies that include human immunoglobulins (e.g., recipient antibody) in which the native CDR residues are replaced by residues from the corresponding CDR of a nonhuman species (e.g., donor antibody) such as mouse, rat, rabbit, or nonhuman primate comprising the desired specificity, affinity, and capacity. In some instances, one or more FR region residues of the human immunoglobulin are replaced by corresponding nonhuman residues. Furthermore, humanized antibodies can comprise residues that are not found in the recipient antibody or in the donor antibody. These modifications are made to further refine antibody performance. A humanized antibody heavy or light chain can comprise substantially all of at least one or more variable regions, in which all or substantially all of the CDRs correspond to those of a nonhuman immunoglobulin and all or substantially all of the FRs are those of a human immunoglobulin sequence. In certain embodiments, the humanized antibody will comprise at least a portion of an immunoglobulin constant region (Fc), typically that of a human immunoglobulin. For further details, see, Jones et al., 1986, Nature 321:522-25; Riechmann et al., 1988, Nature 332:323-29; Presta, 1992, Curr. Op. Struct. Biol. 2:593-96; Carter et al., 1992, Proc. Natl. Acad. Sci. USA 89:4285-89; U.S. Pat. Nos. 6,800,738; 6,719,971; 6,639,055; 6,407,213; and 6,054,297.

In certain embodiments, the antibodies or antigen binding fragments can comprise portions of a "fully human antibody" or "human antibody," wherein the terms are used interchangeably herein and refer to an antibody that comprises a human variable region and, for example, a human constant region. In specific embodiments, the terms refer to an antibody that comprises a variable region and constant region of human origin. "Fully human" antibodies, in certain embodiments, can also encompass antibodies which bind polypeptides and are encoded by nucleic acid sequences which are naturally occurring somatic variants of human germline immunoglobulin nucleic acid sequence. The term "fully human antibody" includes antibodies comprising variable and constant regions corresponding to human germline immunoglobulin sequences as described by Kabat et al. (See Kabat et al. (1991) *Sequences of Proteins of Immunological Interest*, Fifth Edition, U.S. Department of Health and Human Services, NIH Publication No. 91-3242). A "human antibody" is one that possesses an amino acid sequence which corresponds to that of an antibody produced by a human and/or has been made using any of the techniques for making human antibodies. This definition of a human antibody specifically excludes a humanized antibody comprising non-human antigen-binding residues. Human antibodies can be produced using various techniques known in the art, including phage-display libraries (Hoogenboom and Winter, 1991, J. Mol. Biol. 227:381; Marks et al., 1991, J. Mol. Biol. 222:581) and yeast display libraries (Chao et al., 2006, Nature Protocols 1: 755-68). Also available for the preparation of human monoclonal antibodies are methods described in Cole et al., *Monoclonal Antibodies and Cancer Therapy* 77 (1985); Boerner et al., 1991, J. Immunol.

147(1):86-95; and van Dijk and van de Winkel, 2001, Curr. Opin. Pharmacol. 5: 368-74. Human antibodies can be prepared by administering the antigen to a transgenic animal that has been modified to produce such antibodies in response to antigenic challenge, but whose endogenous loci have been disabled, e.g., mice (see, e.g., Jakobovits, 1995, Curr. Opin. Biotechnol. 6(5):561-66; Bruggemann and Taussing, 1997, Curr. Opin. Biotechnol. 8(4):455-58; and U.S. Pat. Nos. 6,075,181 and 6,150,584 regarding XENO-MOUSE™ technology). See also, for example, Li et al., 2006, Proc. Natl. Acad. Sci. USA 103:3557-62 regarding human antibodies generated via a human B-cell hybridoma technology.

In certain embodiments, the antibodies or antigen binding fragments can comprise portions of a "recombinant human antibody," wherein the phrase includes human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal (e.g., a mouse or cow) that is transgenic and/or transchromosomal for human immunoglobulin genes (see e.g., Taylor, L. D. et al. (1992) *Nucl. Acids Res.* 20:6287-6295) or antibodies prepared, expressed, created or isolated by any other means that involves splicing of human immunoglobulin gene sequences to other DNA sequences. Such recombinant human antibodies can have variable and constant regions derived from human germline immunoglobulin sequences (See Kabat, E. A. et al. (1991) *Sequences of Proteins of Immunological Interest*, Fifth Edition, U.S. Department of Health and Human Services, NIH Publication No. 91-3242). In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

In certain embodiments, the antibodies or antigen binding fragments can comprise a portion of a "monoclonal antibody," wherein the term as used herein refers to an antibody obtained from a population of substantially homogeneous antibodies, e.g., the individual antibodies comprising the population are identical except for possible naturally occurring mutations that may be present in minor amounts, and each monoclonal antibody will typically recognize a single epitope on the antigen. In specific embodiments, a "monoclonal antibody," as used herein, is an antibody produced by a single hybridoma or other cell. The term "monoclonal" is not limited to any particular method for making the antibody. For example, the monoclonal antibodies useful in the present disclosure may be prepared by the hybridoma methodology first described by Kohler et al., 1975, Nature 256:495, or may be made using recombinant DNA methods in bacterial or eukaryotic animal or plant cells (see, e.g., U.S. Pat. No. 4,816,567). The "monoclonal antibodies" may also be isolated from phage antibody libraries using the techniques described in Clackson et al., 1991, Nature 352:624-28 and Marks et al., 1991, J. Mol. Biol. 222:581-97, for example. Other methods for the preparation of clonal cell lines and of monoclonal antibodies expressed thereby are well-known in the art. See, e.g., *Short Protocols in Molecular Biology* (Ausubel et al. eds., 5th ed. 2002).

A typical 4-chain antibody unit is a heterotetrameric glycoprotein composed of two identical light (L) chains and two identical heavy (H) chains. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain (VH) followed by three constant domains (CH) for each of the α and γ chains and four CH domains for μ and ε isotypes. Each L chain has at the N-terminus, a variable domain (VL) followed by a constant domain (CL) at its other end. The VL is aligned with the VH, and the CL is aligned with the first constant domain of the heavy chain (CH1). Particular amino acid residues are believed to form an interface between the light chain and heavy chain variable domains. The pairing of a VH and VL together forms a single antigen-binding site. For the structure and properties of the different classes of antibodies, see, for example, *Basic and Clinical Immunology* 71 (Stites et al. eds., 8th ed. 1994); and *Immunobiology* (Janeway et al. eds., 5$^{th}$ ed. 2001).

The term "Fab" or "Fab region" refers to an antibody region that binds to antigens. A conventional IgG usually comprises two Fab regions, each residing on one of the two arms of the Y-shaped IgG structure. Each Fab region is typically composed of one variable region and one constant region of each of the heavy and the light chain. More specifically, the variable region and the constant region of the heavy chain in a Fab region are VH and CH1 regions, and the variable region and the constant region of the light chain in a Fab region are VL and CL regions. The VH, CH1, VL, and CL in a Fab region can be arranged in various ways to confer an antigen binding capability according to the present disclosure. For example, VH and CH1 regions can be on one polypeptide, and VL and CL regions can be on a separate polypeptide, similarly to a Fab region of a conventional IgG. Alternatively, VH, CH1, VL and CL regions can all be on the same polypeptide and oriented in different orders as described in more detail the sections below.

The term "variable region," "variable domain," "V region," or "V domain" refers to a portion of the light or heavy chains of an antibody that is generally located at the amino-terminal of the light or heavy chain and has a length of about 120 to 130 amino acids in the heavy chain and about 100 to 110 amino acids in the light chain, and are used in the binding and specificity of each particular antibody for its particular antigen. The variable region of the heavy chain may be referred to as "VH." The variable region of the light chain may be referred to as "VL." The term "variable" refers to the fact that certain segments of the variable regions differ extensively in sequence among antibodies. The V region mediates antigen binding and defines specificity of a particular antibody for its particular antigen. However, the variability is not evenly distributed across the 110-amino acid span of the variable regions. Instead, the V regions consist of less variable (e.g., relatively invariant) stretches called framework regions (FRs) of about 15-30 amino acids separated by shorter regions of greater variability (e.g., extreme variability) called "hypervariable regions" that are each about 9-12 amino acids long. The variable regions of heavy and light chains each comprise four FRs, largely adopting a β sheet configuration, connected by three hypervariable regions, which form loops connecting, and in some cases form part of, the β sheet structure. The hypervariable regions in each chain are held together in close proximity by the FRs and, with the hypervariable regions from the other chain, contribute to the formation of the antigen-binding site of antibodies (see, e.g., Kabat et al., *Sequences of Proteins* of *Immunological Interest* (5th ed. 1991)). The constant regions are not involved directly in binding an antibody to an antigen, but exhibit various effector functions, such as participation of the antibody in antibody dependent cellular cytotoxicity (ADCC) and complement dependent cytotoxicity (CDC). The variable regions differ extensively in sequence between different antibodies. In specific embodiments, the variable region is a human variable region.

The term "variable region residue numbering according to Kabat" or "amino acid position numbering as in Kabat", and variations thereof, refer to the numbering system used for heavy chain variable regions or light chain variable regions of the compilation of antibodies in Kabat et al., supra. Using this numbering system, the actual linear amino acid sequence may contain fewer or additional amino acids corresponding to a shortening of, or insertion into, an FR or CDR of the variable domain. For example, a heavy chain variable domain may include a single amino acid insert (residue 52a according to Kabat) after residue 52 and three inserted residues (e.g., residues 82a, 82b, and 82c, etc. according to Kabat) after residue 82. The Kabat numbering of residues may be determined for a given antibody by alignment at regions of homology of the sequence of the antibody with a "standard" Kabat numbered sequence. The Kabat numbering system is generally used when referring to a residue in the variable domain (approximately residues 1-107 of the light chain and residues 1-113 of the heavy chain) (e.g., Kabat et al., supra). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG 1 EU antibody. Other numbering systems have been described, for example, by AbM, Chothia, Contact, IMGT, and AHon.

The term "heavy chain" when used in reference to an antibody refers to a polypeptide chain of about 50-70 kDa, wherein the amino-terminal portion includes a variable region of about 120 to 130 or more amino acids, and a carboxy-terminal portion includes a constant region. The constant region can be one of five distinct types, (e.g., isotypes) referred to as alpha (α), delta (δ), epsilon (ε), gamma (γ), and mu (μ), based on the amino acid sequence of the heavy chain constant region. The distinct heavy chains differ in size: α, δ, and γ contain approximately 450 amino acids, while μ and ε contain approximately 550 amino acids. When combined with a light chain, these distinct types of heavy chains give rise to five well-known classes (e.g., isotypes) of antibodies, IgA, IgD, IgE, IgG, and IgM, respectively, including four subclasses of IgG, namely IgG1, IgG2, IgG3, and IgG4.

The term "light chain" when used in reference to an antibody refers to a polypeptide chain of about 25 kDa, wherein the amino-terminal portion includes a variable region of about 100 to about 110 or more amino acids, and a carboxy-terminal portion includes a constant region. The approximate length of a light chain is 211 to 217 amino acids. There are two distinct types, referred to as kappa (κ) or lambda (λ) based on the amino acid sequence of the constant domains.

As used herein, the terms "hypervariable region," "HVR," "Complementarity Determining Region," and "CDR" are used interchangeably. A "CDR" refers to one of three hypervariable regions (H1, H2 or H3) within the non-framework region of the immunoglobulin (Ig or antibody) VH β-sheet framework, or one of three hypervariable regions (L1, L2 or L3) within the non-framework region of the antibody VL β-sheet framework. Accordingly, CDRs are variable region sequences interspersed within the framework region sequences.

CDR regions are well-known to those skilled in the art and have been defined by well-known numbering systems. For example, the Kabat Complementarity Determining Regions (CDRs) are based on sequence variability and are the most commonly used (see, e.g., Kabat et al., supra). Chothia refers instead to the location of the structural loops (see, e.g., Chothia and Lesk, 1987, J. Mol. Biol. 196:901-17). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software (see, e.g., *Antibody Engineering* Vol. 2 (Kontermann and Dübel eds., 2d ed. 2010)). The "contact" hypervariable regions are based on an analysis of the available complex crystal structures. Another universal numbering system that has been developed and widely adopted is ImMunoGeneTics (IMGT) Information System® (Lafranc et al., 2003, Dev. Comp. Immunol. 27(1):55-77). IMGT is an integrated information system specializing in immunoglobulins (IG), T-cell receptors (TCR), and major histocompatibility complex (MHC) of human and other vertebrates. Herein, the CDRs are referred to in terms of both the amino acid sequence and the location within the light or heavy chain. As the "location" of the CDRs within the structure of the immunoglobulin variable domain is conserved between species and present in structures called loops, by using numbering systems that align variable domain sequences according to structural features, CDR and framework residues are readily identified. This information can be used in grafting and replacement of CDR residues from immunoglobulins of one species into an acceptor framework from, typically, a human antibody. An additional numbering system (AHon) has been developed by Honegger and Plückthun, 2001, J. Mol. Biol. 309: 657-70. Correspondence between the numbering system, including, for example, the Kabat numbering and the IMGT unique numbering system, is well-known to one skilled in the art (see, e.g., Kabat, supra; Chothia and Lesk, supra; Martin, supra; Lefranc et al., supra). The residues from each of these hypervariable regions or CDRs are noted below.

TABLE 30

|  | Kabat | AbM | Chothia | Contact | IMGT |
| --- | --- | --- | --- | --- | --- |
| CDR L1 | L24--L34 | L24--L34 | L24--L34 | L30--L36 | L27--L38 |
| CDR L2 | L50--L56 | L50--L56 | L50--L56 | L46--L55 | L56--L65 |
| CDR L3 | L89--L97 | L89--L97 | L89--L97 | L89--L96 | L105--L117 |
| CDR H1 | H31--H35B (Kabat Numbering) | H26--H35B | H26--H32...34 | H30--H35B | H27--H38 |
| CDR H1 | H31--H35 (Chothia Numbering) | H26--H35 | H26--H32 | H30--H35 |  |
| CDR H2 | H50--H65 | H50--H58 | H52--H56 | H47--H58 | H56--H65 |
| CDR H3 | H95--H102 | H95--H102 | H95--H102 | H93--H101 | H105-H117 |

The boundaries of a given CDR may vary depending on the scheme used for identification. Thus, unless otherwise specified, the terms "CDR" and "complementary determining region" of a given antibody or region thereof, such as a variable region, as well as individual CDRs (e.g., "CDR-H1, CDR-H2) of the antibody or region thereof, should be understood to encompass the complementary determining region as defined by any of the known schemes described herein above. In some instances, the scheme for identification of a particular CDR or CDRs is specified, such as the CDR as defined by the Kabat, Chothia, or Contact method. In other cases, the particular amino acid sequence of a CDR is given.

Hypervariable regions may comprise "extended hypervariable regions" as follows: 24-36 or 24-34 (L1), 46-56 or 50-56 (L2), and 89-97 or 89-96 (L3) in the VL, and 26-35 or 26-35A (H1), 50-65 or 49-65 (H2), and 93-102, 94-102, or 95-102 (H3) in the VH.

The term "constant region" or "constant domain" refers to a carboxy terminal portion of the light and heavy chain which is not directly involved in binding of the antibody to antigen but exhibits various effector function, such as interaction with the Fc receptor. The term refers to the portion of an immunoglobulin molecule comprising a more conserved amino acid sequence relative to the other portion of the immunoglobulin, the variable region, which contains the antigen binding site. The constant region may contain the CH1, CH2, and CH3 regions of the heavy chain and the CL region of the light chain.

The term "framework" or "FR" refers to those variable region residues flanking the CDRs. FR residues are present, for example, in chimeric, humanized, human, domain antibodies, diabodies, linear antibodies, and bispecific antibodies. FR residues are those variable domain residues other than the hypervariable region residues or CDR residues.

The term "Fc region" herein is used to define a C-terminal region of an immunoglobulin heavy chain, including, for example, native sequence Fc regions, recombinant Fc regions, and variant Fc regions. Although the boundaries of the Fc region of an immunoglobulin heavy chain might vary, the human IgG heavy chain Fc region is often defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations comprising a mixture of antibodies with and without the K447 residue. A "functional Fc region" possesses an "effector function" of a native sequence Fc region. Exemplary "effector functions" include C1q binding; CDC; Fc receptor binding; ADCC; phagocytosis; downregulation of cell surface receptors (e.g., B cell receptor), etc. Such effector functions generally require the Fc region to be combined with a binding region or binding domain (e.g., an antibody variable region or domain) and can be assessed using various assays known to those skilled in the art. A "variant Fc region" comprises an amino acid sequence which differs from that of a native sequence Fc region by virtue of at least one amino acid modification (e.g., substituting, addition, or deletion). In certain embodiments, the variant Fc region has at least one amino acid substitution compared to a native sequence Fc region or to the Fc region of a parent polypeptide, for example, from about one to about ten amino acid substitutions, or from about one to about five amino acid substitutions in a native sequence Fc region or in the Fc region of a parent polypeptide. The variant Fc region herein can possess at least about 80% homology with a native sequence Fc region and/or with an Fc region of a parent polypeptide, or at least about 90% homology therewith, for example, at least about 95% homology therewith.

As used herein, an "epitope" is a term in the art and refers to a localized region of an antigen to which a binding molecule (e.g., an antibody) can specifically bind. An epitope can be a linear epitope or a conformational, non-linear, or discontinuous epitope. In the case of a polypeptide antigen, for example, an epitope can be contiguous amino acids of the polypeptide (a "linear" epitope) or an epitope can comprise amino acids from two or more non-contiguous regions of the polypeptide (a "conformational," "non-linear" or "discontinuous" epitope). It will be appreciated by one of skill in the art that, in general, a linear epitope may or may not be dependent on secondary, tertiary, or quaternary structure. For example, in some embodiments, a binding molecule binds to a group of amino acids regardless of whether they are folded in a natural three dimensional protein structure. In other embodiments, a binding molecule requires amino acid residues making up the epitope to exhibit a particular conformation (e.g., bend, twist, turn or fold) in order to recognize and bind the epitope.

The terms "polypeptide" and "peptide" and "protein" are used interchangeably herein and refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification. Also included within the definition are, for example, polypeptides containing one or more analogs of an amino acid, including but not limited to, unnatural amino acids, as well as other modifications known in the art. It is understood that, because the polypeptides of this disclosure may be based upon antibodies or other members of the immunoglobulin superfamily, in certain embodiments, a "polypeptide" can occur as a single chain or as two or more associated chains.

The term "vector" refers to a substance that is used to carry or include a nucleic acid sequence, including for example, a nucleic acid sequence encoding a binding molecule (e.g., an antibody) as described herein, in order to introduce a nucleic acid sequence into a host cell. Vectors applicable for use include, for example, expression vectors, plasmids, phage vectors, viral vectors, episomes, and artificial chromosomes, which can include selection sequences or markers operable for stable integration into a host cell's chromosome. Additionally, the vectors can include one or more selectable marker genes and appropriate expression control sequences. Selectable marker genes that can be included, for example, provide resistance to antibiotics or toxins, complement auxotrophic deficiencies, or supply critical nutrients not in the culture media. Expression control sequences can include constitutive and inducible promoters, transcription enhancers, transcription terminators, and the like, which are well-known in the art. When two or more nucleic acid molecules are to be co-expressed (e.g., both an antibody heavy and light chain or an antibody VH and VL), both nucleic acid molecules can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The introduction of nucleic acid molecules into a host cell can be confirmed using methods well-known in the art. Such methods include, for example, nucleic acid analysis such as Northern blots or polymerase chain reaction (PCR) amplification of mRNA, immunoblotting for expression of gene products, or other suitable analytical methods to test the expression of an introduced nucleic acid sequence or its corresponding gene product. It is understood by those skilled in the art that the nucleic acid molecules are expressed in a sufficient amount to produce a desired product and it is further understood that expression levels can be optimized to obtain sufficient expression using methods well-known in the art.

The term "host" as used herein refers to an animal, such as a mammal (e.g., a human).

The term "host cell" as used herein refers to a particular subject cell that may be transfected with a nucleic acid molecule and the progeny or potential progeny of such a cell. Progeny of such a cell may not be identical to the parent cell transfected with the nucleic acid molecule due to mutations or environmental influences that may occur in succeeding generations or integration of the nucleic acid molecule into the host cell genome.

An "isolated nucleic acid" is a nucleic acid, for example, an RNA, DNA, or a mixed nucleic acids, which is substantially separated from other genome DNA sequences as well as proteins or complexes such as ribosomes and polymerases, which naturally accompany a native sequence. An "isolated" nucleic acid molecule is one which is separated from other nucleic acid molecules which are present in the natural source of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. In a specific embodiment, one or more nucleic acid molecules encoding an antibody as described herein are isolated or purified. The term embraces nucleic acid sequences that have been removed from their naturally occurring environment, and includes recombinant or cloned DNA isolates and chemically synthesized analogues or analogues biologically synthesized by heterologous systems. A substantially pure molecule may include isolated forms of the molecule.

"Polynucleotide" or "nucleic acid," as used interchangeably herein, refers to polymers of nucleotides of any length and includes DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction. A polynucleotide may comprise modified nucleotides, such as methylated nucleotides and their analogs. "Oligonucleotide," as used herein, refers to short, generally single-stranded, synthetic polynucleotides that are generally, but not necessarily, fewer than about 200 nucleotides in length. The terms "oligonucleotide" and "polynucleotide" are not mutually exclusive. The description above for polynucleotides is equally and fully applicable to oligonucleotides. A cell that produces a binding molecule of the present disclosure may include a parent hybridoma cell, as well as bacterial and eukaryotic host cells into which nucleic acids encoding the antibodies have been introduced. Unless specified otherwise, the left-hand end of any single-stranded polynucleotide sequence disclosed herein is the 5' end; the left-hand direction of double-stranded polynucleotide sequences is referred to as the 5' direction. The direction of 5' to 3' addition of nascent RNA transcripts is referred to as the transcription direction; sequence regions on the DNA strand comprising the same sequence as the RNA transcript that are 5' to the 5' end of the RNA transcript are referred to as "upstream sequences"; sequence regions on the DNA strand comprising the same sequence as the RNA transcript that are 3' to the 3' end of the RNA transcript are referred to as "downstream sequences."

The term "pharmaceutically acceptable" as used herein means being approved by a regulatory agency of the Federal or a state government, or listed in *United States Pharmacopeia, European Pharmacopeia*, or other generally recognized Pharmacopeia for use in animals, and more particularly in humans.

"Excipient" means a pharmaceutically-acceptable material, composition, or vehicle, such as a liquid or solid filler, diluent, solvent, or encapsulating material. Excipients include, for example, encapsulating materials or additives such as absorption accelerators, antioxidants, binders, buffers, carriers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents and mixtures thereof. The term "excipient" can also refer to a diluent, adjuvant (e.g., Freunds' adjuvant (complete or incomplete) or vehicle.

In some embodiments, excipients are pharmaceutically acceptable excipients. Examples of pharmaceutically acceptable excipients include buffers, such as phosphate, citrate, and other organic acids; antioxidants, including ascorbic acid; low molecular weight (e.g., fewer than about 10 amino acid residues) polypeptide; proteins, such as serum albumin, gelatin, or immunoglobulins; hydrophilic polymers, such as polyvinylpyrrolidone; amino acids, such as 1-histidine, glycine, glutamine, asparagine, arginine, or lysine; monosaccharides, disaccharides, and other carbohydrates, including glucose, sucrose, trehalose dihydrate, mannose, or dextrins; chelating agents, such as EDTA; sugar alcohols, such as mannitol or sorbitol; salt-forming counterions, such as sodium; and/or nonionic surfactants, such as TWEEN™, polyethylene glycol (PEG), and PLURONICS™. Other examples of pharmaceutically acceptable excipients are described in Remington and Gennaro, *Remington's Pharmaceutical Sciences* (18th ed. 1990).

In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, e.g., Lippincott Williams & Wilkins: Philadelphia, PA, 2005; Handbook of Pharmaceutical Excipients, 6th ed.; Rowe et al., Eds.; The Pharmaceutical Press and the American Pharmaceutical Association: 2009; Handbook of Pharmaceutical Additives, 3rd ed.; Ash and Ash Eds.; Gower Publishing Company: 2007; Pharmaceutical Preformulation and Formulation, 2nd ed.; Gibson Ed.; CRC Press LLC: Boca Raton, FL, 2009. In some embodiments, pharmaceutically acceptable excipients are nontoxic to the cell or mammal being exposed thereto at the dosages and concentrations employed. In some embodiments, a pharmaceutically acceptable excipient is an aqueous pH buffered solution.

In some embodiments, excipients are sterile liquids, such as water and oils, including those of petroleum, animal, vegetable, or synthetic origin, such as peanut oil, soybean oil, mineral oil, sesame oil, and the like. Water is an exemplary excipient when a composition (e.g., a pharmaceutical composition) is administered intravenously. Saline solutions and aqueous dextrose and glycerol solutions can also be employed as liquid excipients, particularly for injectable solutions. A excipient can also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition, if desired, can also contain minor amounts of wetting or emulsifying agents, or pH buffering agents. Compositions can take the form of solutions, suspensions, emulsion, tablets, pills, capsules, powders, sustained-release formulations, and the like.

Compositions, including pharmaceutical compounds, may contain a binding molecule (e.g., an antibody), for example, in isolated or purified form, together with a suitable amount of excipients.

The abbreviation "MMAE" refers to monomethyl auristatin E.

Unless otherwise noted, the term "alkyl" refers to a saturated straight or branched hydrocarbon comprising from about 1 to about 20 carbon atoms (and all combinations and subcombinations of ranges and specific numbers of carbon atoms therein), with from about 1 to about 8 carbon atoms being preferred. Examples of alkyl groups are methyl, ethyl, n-propyl, isopropyl, n-butyl, iso-butyl, sec-butyl, tert-butyl, n-pentyl, 2-pentyl, 3-pentyl, 2-methyl-2-butyl, n-hexyl, n-heptyl, n-octyl, n-nonyl, n-decyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, and 3,3-dimethyl-2-butyl. Alkyl groups, whether alone or as part of another group, can be optionally substituted with one or more groups, preferably 1 to 3 groups (and any additional substituents selected from halogen), including, but not limited to, -halogen, —O—($C_1$-$C_8$ alkyl), —O—($C_2$-$C_8$ alkenyl), —O—($C_2$-$C_8$ alkynyl), -aryl, —C(O)R', —OC(O)R', —C(O)OR', —C(O)$NH_2$, —C(O)NHR', —C(O)N(R')$_2$, —NHC(O)R', —SR', —$SO_3$R', —S(O)$_2$R', —S(O)R', —OH, =O, —$N_3$, —$NH_2$, —NH(R'), —N(R')$_2$ and —CN, where each R' is independently selected from —H, —$C_1$-$C_8$ alkyl, —$C_2$-$C_8$ alkenyl, —$C_2$-$C_8$ alkynyl, or -aryl, and wherein said —O—($C_1$-$C_8$ alkyl), —O—($C_2$-$C_8$ alkenyl), —O—($C_2$-$C_8$ alkynyl), -aryl, —$C_1$-$C_8$ alkyl, —$C_2$-$C_8$ alkenyl, and —$C_2$-$C_8$ alkynyl groups can be optionally further substituted with one or more groups including, but not limited to, —$C_1$-$C_8$ alkyl, —$C_2$-$C_8$ alkenyl, —$C_2$-$C_8$ alkynyl, -halogen, —O—($C_1$-$C_8$ alkyl), —O—($C_2$-$C_8$ alkenyl), —O—($C_2$-$C_8$ alkynyl), -aryl, —C(O)R", —OC(O)R", —C(O)OR", —C(O)$NH_2$, —C(O)NHR", —C(O)N(R")$_2$, —NHC(O)R", —SR", —$SO_3$R", —S(O)$_2$R", —S(O)R", —OH, —$N_3$, —$NH_2$, —NH(R"), —N(R")$_2$ and —CN, where each R" is independently selected from —H, —$C_1$-$C_8$ alkyl, —$C_2$-$C_8$ alkenyl, —$C_2$-$C_8$ alkynyl, or -aryl.

Unless otherwise noted, the terms "alkenyl" and "alkynyl" refer to straight and branched carbon chains comprising from about 2 to about 20 carbon atoms (and all combinations and subcombinations of ranges and specific numbers of carbon atoms therein), with from about 2 to about 8 carbon atoms being preferred. An alkenyl chain has at least one double bond in the chain and an alkynyl chain has at least one triple bond in the chain. Examples of alkenyl groups include, but are not limited to, ethylene or vinyl, allyl, -1-butenyl, -2-butenyl, -isobutylenyl, -1-pentenyl, -2-pentenyl, -3-methyl-1-butenyl, -2-methyl-2-butenyl, and -2,3-dimethyl-2-butenyl. Examples of alkynyl groups include, but are not limited to, acetylenic, propargyl, acetylenyl, propynyl, -1-butynyl, -2-butynyl, -1-pentynyl, -2-pentynyl, and -3-methyl-1 butynyl. Alkenyl and alkynyl groups, whether alone or as part of another group, can be optionally substituted with one or more groups, preferably 1 to 3 groups (and any additional substituents selected from halogen), including but not limited to, -halogen, —O—($C_1$-$C_8$ alkyl), —O—($C_2$-$C_8$ alkenyl), —O—($C_2$-$C_8$ alkynyl), -aryl, —C(O)R', —OC(O)R', —C(O)OR', —C(O)$NH_2$, —C(O)NHR', —C(O)N(R')$_2$, —NHC(O)R', —SR', —$SO_3$R', —S(O)$_2$R', —S(O)R', —OH, =O, —$N_3$, —$NH_2$, —NH(R'), —N(R')$_2$ and —CN, where each R' is independently selected from —H, —$C_1$-$C_8$ alkyl, —$C_2$-$C_8$ alkenyl, —$C_2$-$C_8$ alkynyl, or -aryl and wherein said —O—($C_1$-$C_8$ alkyl), —O—($C_2$-$C_8$ alkenyl), —O—($C_2$-$C_8$ alkynyl), -aryl, —$C_1$-$C_8$ alkyl, —$C_2$-$C_8$ alkenyl, and —$C_2$-$C_8$ alkynyl groups can be optionally further substituted with one or more substituents including, but not limited to, —$C_1$-$C_8$ alkyl, —$C_2$-$C_8$ alkenyl, —$C_2$-$C_8$ alkynyl, -halogen, —O—($C_1$-$C_8$ alkyl), —O—($C_2$-$C_8$ alkenyl), —O—($C_2$-$C_8$ alkynyl), -aryl, —C(O)R", —OC(O)R", —C(O)OR", —C(O)$NH_2$, —C(O)NHR", —C(O)N(R")$_2$, —NHC(O)R", —SR", —$SO_3$R", —S(O)$_2$R", —S(O)R", —OH, —$N_3$, —$NH_2$, —NH(R"), —N(R")$_2$ and —CN, where each R" is independently selected from —H, —$C_1$-$C_8$ alkyl, —$C_2$-$C_8$ alkenyl, —$C_2$-$C_8$ alkynyl, or -aryl.

Unless otherwise noted, the term "alkylene" refers to a saturated branched or straight chain hydrocarbon radical comprising from about 1 to about 20 carbon atoms (and all combinations and subcombinations of ranges and specific numbers of carbon atoms therein), with from about 1 to about 8 carbon atoms being preferred and having two monovalent radical centers derived by the removal of two hydrogen atoms from the same or two different carbon atoms of a parent alkane. Typical alkylenes include, but are not limited to, methylene, ethylene, propylene, butylene, pentylene, hexylene, heptylene, octylene, nonylene, decaene, 1,4-cyclohexylene, and the like. Alkylene groups, whether alone or as part of another group, can be optionally substituted with one or more groups, preferably 1 to 3 groups (and any additional substituents selected from halogen), including, but not limited to, -halogen, —O—($C_1$-$C_8$ alkyl), —O—($C_2$-$C_8$ alkenyl), —O—($C_2$-$C_8$ alkynyl), -aryl, —C(O)R', —OC(O)R', —C(O)OR', —C(O)$NH_2$, —C(O)NHR', —C(O)N(R')$_2$, —NHC(O)R', —SR', —$SO_3$R', —S(O)$_2$R', —S(O)R', —OH, =O, —$N_3$, —$NH_2$, —NH(R'), —N(R')$_2$ and —CN, where each R' is independently selected from —H, —$C_1$-$C_8$ alkyl, —$C_2$-$C_8$ alkenyl, —$C_2$-$C_8$ alkynyl, or -aryl and wherein said —O—($C_1$-$C_8$ alkyl), —O—($C_2$-$C_8$ alkenyl), —O—($C_2$-$C_8$ alkynyl), -aryl, —$C_1$-$C_8$ alkyl, —$C_2$-$C_8$ alkenyl, and —$C_2$-$C_8$ alkynyl groups can be further optionally substituted with one or more substituents including, but not limited to, —$C_1$-$C_8$ alkyl, —$C_2$-$C_8$ alkenyl, —$C_2$-$C_8$ alkynyl, -halogen, —O—($C_1$-$C_8$ alkyl), —O—($C_2$-$C_8$ alkenyl), —O—($C_2$-$C_8$ alkynyl), -aryl, —C(O)R", —OC(O)R", —C(O)OR", —C(O)$NH_2$, —C(O)NHR", —C(O)N(R")$_2$, —NHC(O)R", —SR", —$SO_3$R", —S(O)$_2$R", —S(O)R", —OH, —$N_3$, —$NH_2$, —NH(R"), —N(R")$_2$ and —CN, where each R" is independently selected from —H, —$C_1$-$C_8$ alkyl, —$C_2$-$C_8$ alkenyl, —$C_2$-$C_8$ alkynyl, or -aryl.

Unless otherwise noted, the term "alkenylene" refers to an optionally substituted alkylene group containing at least one carbon-carbon double bond. Exemplary alkenylene groups include, for example, ethenylene (—CH=CH—) and propenylene (—CH=CHCH$_2$—).

Unless otherwise noted, the term "alkynylene" refers to an optionally substituted alkylene group containing at least one carbon-carbon triple bond. Exemplary alkynylene groups include, for example, acetylene (—C≡C—), propargyl (—CH$_2$C≡C—), and 4-pentynyl (—CH$_2$CH$_2$CH$_2$C≡CH—).

Unless otherwise noted, the term "aryl" refers to a monovalent aromatic hydrocarbon radical of 6-20 carbon atoms (and all combinations and subcombinations of ranges and specific numbers of carbon atoms therein) derived by the removal of one hydrogen atom from a single carbon atom of a parent aromatic ring system. Some aryl groups are represented in the exemplary structures as "Ar". Typical aryl groups include, but are not limited to, radicals derived from benzene, substituted benzene, phenyl, naphthalene, anthracene, biphenyl, and the like.

An aryl group, whether alone or as part of another group, can be optionally substituted with one or more, preferably 1 to 5, or even 1 to 2 groups including, but not limited to, -halogen, —C$_1$-C$_8$ alkyl, —C$_2$-C$_8$ alkenyl, —C$_2$-C$_8$ alkynyl, —O—(C$_1$-C$_8$ alkyl), —O—(C$_2$-C$_8$ alkenyl), —O—(C$_2$-C$_8$ alkynyl), -aryl, —C(O)R', —OC(O)R', —C(O)OR', —C(O)NH$_2$, —C(O)NHR', —C(O)N(R')$_2$, —NHC(O)R', —SR', —SO$_3$R', —S(O)$_2$R', —S(O)R', —OH, —NO$_2$, —N$_3$, —NH$_2$, —NH(R'), —N(R')$_2$ and —CN, where each R' is independently selected from —H, —C$_1$-C$_8$ alkyl, —C$_2$-C$_8$ alkenyl, —C$_2$-C$_8$ alkynyl, or -aryl and wherein said —C$_1$-C$_8$ alkyl, —C$_2$-C$_8$ alkenyl, —C$_2$-C$_8$ alkynyl, —O—(C$_1$-C$_8$ alkyl), —O—(C$_2$-C$_8$ alkenyl), —O—(C$_2$-C$_8$ alkynyl), and -aryl groups can be further optionally substituted with one or more substituents including, but not limited to, —C$_1$-C$_8$ alkyl, —C$_2$-C$_8$ alkenyl, —C$_2$-C$_8$ alkynyl, -halogen, —O—(C$_1$-C$_8$ alkyl), —O—(C$_2$-C$_8$ alkenyl), —O—(C$_2$-C$_8$ alkynyl), -aryl, —C(O)R", —OC(O)R", —C(O)OR", —C(O)NH$_2$, —C(O)NHR", —C(O)N(R")$_2$, —NHC(O)R", —SR", —SO$_3$R", —S(O)$_2$R", —S(O)R", —OH, —N$_3$, —NH$_2$, —NH(R"), —N(R")$_2$ and —CN, where each R" is independently selected from —H, —C$_1$-C$_8$ alkyl, —C$_2$-C$_8$ alkenyl, —C$_2$-C$_8$ alkynyl, or -aryl.

Unless otherwise noted, the term "arylene" refers to an optionally substituted aryl group which is divalent (i.e., derived by the removal of two hydrogen atoms from the same or two different carbon atoms of a parent aromatic ring system) and can be in the ortho, meta, or para configurations as shown in the following structures with phenyl as the exemplary aryl group.

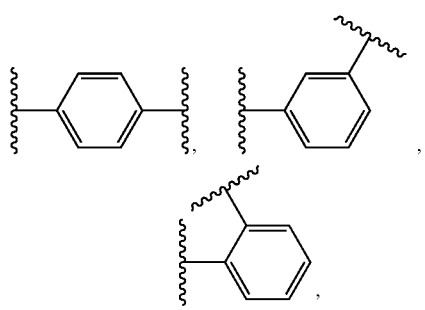

Typical "—(C$_1$-C$_8$ alkylene)aryl," "—(C$_2$-C$_8$ alkenylene)aryl", "and —(C$_2$-C$_8$ alkynylene)aryl" groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like.

Unless otherwise noted, the term "heterocycle," refers to a monocyclic, bicyclic, or polycyclic ring system having from 3 to 14 ring atoms (also referred to as ring members) wherein at least one ring atom in at least one ring is a heteroatom selected from N, O, P, or S (and all combinations and subcombinations of ranges and specific numbers of carbon atoms and heteroatoms therein). The heterocycle can have from 1 to 4 ring heteroatoms independently selected from N, O, P, or S. One or more N, C, or S atoms in a heterocycle can be oxidized. A monocyclic heterocycle preferably has 3 to 7 ring members (e.g., 2 to 6 carbon atoms and 1 to 3 heteroatoms independently selected from N, O, P, or S), and a bicyclic heterocycle preferably has 5 to 10 ring members (e.g., 4 to 9 carbon atoms and 1 to 3 heteroatoms independently selected from N, O, P, or S). The ring that includes the heteroatom can be aromatic or non-aromatic. Unless otherwise noted, the heterocycle is attached to its pendant group at any heteroatom or carbon atom that results in a stable structure. Heterocycles are described in Paquette, "*Principles of Modern Heterocyclic Chemistry*" (W. A. Benjamin, New York, 1968), particularly Chapters 1, 3, 4, 6, 7, and 9; "*The Chemistry of Heterocyclic Compounds, A series of Monographs*" (John Wiley & Sons, New York, 1950 to present), in particular Volumes 13, 14, 16, 19, and 28; and *J. Am. Chem. Soc.* 82:5566 (1960). Examples of "heterocycle" groups include by way of example and not limitation pyridyl, dihydropyridyl, tetrahydropyridyl (piperidyl), thiazolyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4H-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl. Preferred "heterocycle" groups include, but are not limited to, benzofuranyl, benzothiophenyl, indolyl, benzopyrazolyl, coumarinyl, isoquinolinyl, pyrrolyl, thiophenyl, furanyl, thiazolyl, imidazolyl, pyrazolyl, triazolyl, quinolinyl, pyrimidinyl, pyridinyl, pyridonyl, pyrazinyl, pyridazinyl, isothiazolyl, isoxazolyl and tetrazolyl. A heterocycle group, whether alone or as part of another group, can be optionally substituted with one or more groups, preferably 1 to 2 groups, including but not limited to, —C$_1$-C$_8$ alkyl, —C$_2$-C$_8$ alkenyl, —C$_2$-C$_8$ alkynyl, -halogen, —O—(C$_1$-C$_8$ alkyl), —O—(C$_2$-C$_8$ alkenyl), —O—(C$_2$-C$_8$ alkynyl), -aryl, —C(O)R', —OC(O)R', —C(O)OR', —C(O)NH$_2$, —C(O)NHR', —C(O)N(R')$_2$, —NHC(O)R', —SR', —SO$_3$R', —S(O)$_2$R', —S(O)R', —OH, —N$_3$, —NH$_2$, —NH(R'), —N(R')$_2$ and —CN, where each R' is independently selected from —H, —C$_1$-C$_8$ alkyl, —C$_2$-C$_8$ alkenyl, —C$_2$-C$_8$ alkynyl, or -aryl and wherein said —O—(C$_1$-C$_8$ alkyl), —O—(C$_2$-C$_8$ alkenyl), —O—(C$_2$-C$_8$ alkynyl), —C$_1$-C$_8$ alkyl, —C$_2$-C$_8$ alkenyl, —C$_2$-C$_8$ alkynyl, and -aryl groups can be further optionally substituted with one or more substituents including, but not limited to, —C$_1$-C$_8$ alkyl, —C$_2$-C$_8$ alkenyl, —C$_2$-C$_8$ alkynyl, -halogen, —O—(C$_1$-C$_8$ alkyl), —O—(C$_2$-C$_8$ alkenyl), —O—(C$_2$-C$_8$ alkynyl), -aryl, —C(O)R", —OC(O)R", —C(O)OR", —C(O)NH$_2$, —C(O)NHR", —C(O)N(R")$_2$, —NHC(O)R", —SR", —SO$_3$R", —S(O)$_2$R", —S(O)R", —OH, —N$_3$, —NH$_2$, —NH(R"), —N(R")$_2$ and —CN, where each R" is independently selected from —H, —C$_1$-C$_8$ alkyl, —C$_2$-C$_8$ alkenyl, —C$_2$-C$_8$ alkynyl, or aryl.

By way of example and not limitation, carbon-bonded heterocycles can be bonded at the following positions: position 2, 3, 4, 5, or 6 of a pyridine; position 3, 4, 5, or 6 of a pyridazine; position 2, 4, 5, or 6 of a pyrimidine; position 2, 3, 5, or 6 of a pyrazine; position 2, 3, 4, or 5 of a furan, tetrahydrofuran, thiofuran, thiophene, pyrrole or tetrahydropyrrole; position 2, 4, or 5 of an oxazole, imidazole or thiazole; position 3, 4, or 5 of an isoxazole, pyrazole, or isothiazole; position 2 or 3 of an aziridine; position 2, 3, or 4 of an azetidine; position 2, 3, 4, 5, 6, 7, or 8 of a quinoline; or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles can be bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, or 1H-indazole; position 2 of a isoindole, or isoindoline; position 4 of a morpholine; and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

Unless otherwise noted, the term "carbocycle," refers to a saturated or unsaturated non-aromatic monocyclic, bicyclic, or polycyclic ring system having from 3 to 14 ring atoms (and all combinations and subcombinations of ranges and specific numbers of carbon atoms therein) wherein all of the ring atoms are carbon atoms. Monocyclic carbocycles preferably have 3 to 6 ring atoms, still more preferably 5 or 6 ring atoms. Bicyclic carbocycles preferably have 7 to 12 ring atoms, e.g., arranged as a bicyclo[4,5], [5,5], [5,6] or [6,6] system, or 9 or 10 ring atoms arranged as a bicyclo[5,6] or [6,6] system. The term "carbocycle" includes, for example, a monocyclic carbocycle ring fused to an aryl ring (e.g., a monocyclic carbocycle ring fused to a benzene ring). Carbocycles preferably have 3 to 8 carbon ring atoms. Carbocycle groups, whether alone or as part of another group, can be optionally substituted with, for example, one or more groups, preferably 1 or 2 groups (and any additional substituents selected from halogen), including, but not limited to, -halogen, —C$_1$-C$_8$ alkyl, —C$_2$-C$_8$ alkenyl, —C$_2$-C$_8$ alkynyl, —O—(C$_1$-C$_8$ alkyl), —O—(C$_2$-C$_8$ alkenyl), —O—(C$_2$-C$_8$ alkynyl), -aryl, —C(O)R', —OC(O)R', —C(O)OR', —C(O)NH$_2$, —C(O)NHR', —C(O)N(R')$_2$, —NHC(O)R', —SR', —SO$_3$R', —S(O)$_2$R', —S(O)R', —OH, =O, —N$_3$, —NH$_2$, —NH(R'), —N(R')$_2$ and —CN, where each R' is independently selected from —H, —C$_1$-C$_8$ alkyl, —C$_2$-C$_8$ alkenyl, —C$_2$-C$_8$ alkynyl, or -aryl and wherein said —C$_1$-C$_8$ alkyl, —C$_2$-C$_8$ alkenyl, —C$_2$-C$_8$ alkynyl, —O—(C$_1$-C$_8$ alkyl), —O—(C$_2$-C$_8$ alkenyl), —O—(C$_2$-C$_8$ alkynyl), and -aryl groups can be further optionally substituted with one or more substituents including, but not limited to, —C$_1$-C$_8$ alkyl, —C$_2$-C$_8$ alkenyl, —C$_2$-C$_8$ alkynyl, -halogen, —O—(C$_1$-C$_8$ alkyl), —O—(C$_2$-C$_8$ alkenyl), —O—(C$_2$-C$_8$ alkynyl), -aryl, —C(O)R", —OC(O)R", —C(O)OR", —C(O)NH$_2$, —C(O)NHR", —C(O)N(R")$_2$, —NHC(O)R", —SR", —SO$_3$R", —S(O)$_2$R", —S(O)R", —OH, —N$_3$, —NH$_2$, —NH(R"), —N(R")$_2$ and —CN, where each R" is independently selected from —H, —C$_1$-C$_8$ alkyl, —C$_2$-C$_8$ alkenyl, —C$_2$-C$_8$ alkynyl, or -aryl.

Examples of monocyclic carbocylic substituents include -cyclopropyl, -cyclobutyl, -cyclopentyl, -1-cyclopent-1-enyl, -1-cyclopent-2-enyl, -1-cyclopent-3-enyl, cyclohexyl, -1-cyclohex-1-enyl, -1-cyclohex-2-enyl, -1-cyclohex-3-enyl, -cycloheptyl, -cyclooctyl, -1,3-cyclohexadienyl, -1,4-cyclohexadienyl, -1,3-cycloheptadienyl, -1,3,5-cycloheptatrienyl, and -cyclooctadienyl.

A "carbocyclo," whether used alone or as part of another group, refers to an optionally substituted carbocycle group as defined above that is divalent (i.e., derived by the removal of two hydrogen atoms from the same or two different carbon atoms of a parent carbocyclic ring system).

Unless otherwise indicated by context, a hyphen (-) designates the point of attachment to the pendant molecule. Accordingly, the term "—(C$_1$-C$_8$ alkylene)aryl" or "—C$_1$-C$_8$ alkylene(aryl)" refers to a C$_1$-C$_8$ alkylene radical as defined herein wherein the alkylene radical is attached to the pendant molecule at any of the carbon atoms of the alkylene radical and one of the hydrogen atoms bonded to a carbon atom of the alkylene radical is replaced with an aryl radical as defined herein.

When a particular group is "substituted", that group may have one or more substituents, preferably from one to five substituents, more preferably from one to three substituents, most preferably from one to two substituents, independently selected from the list of substituents. The group can, however, generally have any number of substituents selected from halogen. Groups that are substituted are so indicated. It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

Protective groups as used herein refer to groups which selectively block, either temporarily or permanently, one reactive site in a multifunctional compound. Suitable hydroxy-protecting groups for use in the present invention are pharmaceutically acceptable and may or may not need to be cleaved from the parent compound after administration to a subject in order for the compound to be active. Cleavage is through normal metabolic processes within the body. Hydroxy protecting groups are well-known in the art, see, *Protective Groups in Organic Synthesis* by T. W. Greene and P. G. M. Wuts (John Wiley & sons, 3$^{rd}$ Edition) incorporated herein by reference in its entirety and for all purposes and include, for example, ether (e.g., alkyl ethers and silyl ethers including, for example, dialkylsilylether, trialkylsilylether, dialkylalkoxysilylether), ester, carbonate, carbamates, sulfonate, and phosphate protecting groups. Examples of hydroxy protecting groups include, but are not limited to, methyl ether; methoxymethyl ether, methylthiomethyl ether, (phenyldimethylsilyl)methoxymethyl ether, benzyloxymethyl ether, p-methoxybenzyloxymethyl ether, p-nitrobenzyloxymethyl ether, o-nitrobenzyloxymethyl ether, (4-methoxyphenoxy)methyl ether, guaiacolmethyl ether, t-butoxymethyl ether, 4-pentenyloxymethyl ether, siloxymethyl ether, 2-methoxyethoxymethyl ether, 2,2,2-trichloroethoxymethyl ether, bis(2-chloroethoxy)methyl ether, 2-(trimethylsilyl)ethoxymethyl ether, menthoxymethyl ether, tetrahydropyranyl ether, 1-methoxycyclohexyl ether, 4-methoxytetrahydrothiopyranyl ether, 4-methoxytetrahydrothiopyranyl ether S,S-Dioxide, 1-[(2-choro-4-methyl) phenyl]-4-methoxypiperidin-4-yl ether, 1-(2-fluorophenyl)-4-methoxypiperidin-4-yl ether, 1,4-dioxan-2-yl ether, tetrahydrofuranyl ether, tetrahydrothiofuranyl ether; substituted ethyl ethers such as 1-ethoxyethyl ether, 1-(2-chloroethoxy)ethyl ether, 1-[2-(trimethylsilyl)ethoxy]ethyl ether, 1-methyl-1-methoxy ethyl ether, 1-methyl-1-benzyloxyethyl ether, 1-methyl-1-benzyloxy-2-fluoroethyl ether, 1-methyl-1 phenoxyethyl ether, 2-trimethylsilyl ether, t-butyl ether, allyl ether, propargyl ethers, p-chlorophenyl ether, p-methoxyphenyl ether, benzyl ether, p-methoxybenzyl ether 3,4-dimethoxybenzyl ether, trimethylsilyl ether, triethylsilyl ether, tripropylsilylether, dimethylisopropylsilyl ether, diethylisopropylsilyl ether, dimethylhexylsilyl ether, t-butyldimethylsilyl ether, diphenylmethylsilyl ether, benzoylformate ester, acetate ester, chloroacetate ester, dichloroacetate ester, trichloroacetate ester, trifluoroacetate ester, methoxyacetate ester, triphenylmethoxyacetate ester, phenylacetate ester, benzoate ester, alkyl methyl carbonate, alkyl 9-fluorenylmethyl carbonate, alkyl ethyl carbonate, alkyl 2,2,2,-trichloroethyl carbonate, 1,1,-dimethyl-2,2,2-trichloroethyl carbonate, alkylsulfonate, methanesulfonate, benzylsulfonate, tosylate, methylene acetal, ethylidene acetal, and t-butylmethylidene ketal. Preferred protecting groups are represented by the formulas —$R^a$, —$Si(R^a)(R^a)(R^a)$, —$C(O)R^a$, —$C(O)OR^a$, —$C(O)NH(R^a)$, —$S(O)_2R^a$, —$S(O)_2OH$, $P(O)(OH)_2$, and —$P(O)(OH)OR^a$, wherein $R^a$ is $C_1$-$C_{20}$ alkyl, $C_2$-$C_{20}$ alkenyl, $C_2$-$C_{20}$ alkynyl, —$C_1$-$C_{20}$ alkylene(carbocycle), —$C_2$-$C_{20}$ alkenylene(carbocycle), —$C_2$-$C_{20}$ alkynylene(carbocycle), —$C_6$-$C_{10}$ aryl, —$C_1$-$C_{20}$ alkylene(aryl), —$C_2$-$C_{20}$ alkenylene(aryl), —$C_2$-$C_{20}$ alkynylene(aryl), —$C_1$-$C_{20}$ alkylene(heterocycle), —$C_2$-$C_{20}$ alkenylene(heterocycle), or —$C_2$-$C_{20}$ alkynylene(heterocycle) wherein said alkyl, alkenyl, alkynyl, alkylene, alkenylene, alkynylene, aryl, carbocycle, and heterocycle radicals whether alone or as part of another group are optionally substituted.

The term "effective amount" or "therapeutically effective amount" as used herein refers to the amount of binding molecule (e.g., an antibody) or pharmaceutical composition provided herein which is sufficient to result in the desired outcome.

The terms "subject" and "patient" may be used interchangeably. As used herein, in certain embodiments, a subject is a mammal, such as a non-primate (e.g., cow, pig, horse, cat, dog, rat, etc.) or a primate (e.g., monkey and human). In specific embodiments, the subject is a human. In one embodiment, the subject is a mammal, e.g., a human, diagnosed with a condition or disorder. In another embodiment, the subject is a mammal, e.g., a human, at risk of developing a condition or disorder.

"Administer" or "administration" refers to the act of injecting or otherwise physically delivering a substance as it exists outside the body into a patient, such as by mucosal, intradermal, intravenous, intramuscular delivery, and/or any other method of physical delivery described herein or known in the art.

As used herein, the terms "treat," "treatment" and "treating" refer to the reduction or amelioration of the progression, severity, and/or duration of a disease or condition resulting from the administration of one or more therapies. Treating may be determined by assessing whether there has been a decrease, alleviation and/or mitigation of one or more symptoms associated with the underlying disorder such that an improvement is observed with the patient, despite that the patient may still be afflicted with the underlying disorder. The term "treating" includes both managing and ameliorating the disease. The terms "manage," "managing," and "management" refer to the beneficial effects that a subject derives from a therapy which does not necessarily result in a cure of the disease.

The terms "prevent," "preventing," and "prevention" refer to reducing the likelihood of the onset (or recurrence) of a disease, disorder, condition, or associated symptom(s) (e.g., a cancer).

The term "cancer" or "cancer cell" is used herein to denote a tissue or cell found in a neoplasm which possesses characteristics which differentiate it from normal tissue or tissue cells. Among such characteristics include but are not limited to: degree of anaplasia, irregularity in shape, indistinctness of cell outline, nuclear size, changes in structure of nucleus or cytoplasm, other phenotypic changes, presence of cellular proteins indicative of a cancerous or pre-cancerous state, increased number of mitoses, and ability to metastasize. Words pertaining to "cancer" include carcinoma, sarcoma, tumor, epithelioma, leukemia, lymphoma, polyp, and scirrus, transformation, neoplasm, and the like.

The terms "about" and "approximately" mean within 20%, within 15%, within 10%, within 9%, within 8%, within 7%, within 6%, within 5%, within 4%, within 3%, within 2%, within 1%, or less of a given value or range.

As used in the present disclosure and claims, the singular forms "a", "an" and "the" include plural forms unless the context clearly dictates otherwise.

It is understood that wherever embodiments are described herein with the term "comprising" otherwise analogous embodiments described in terms of "consisting of" and/or "consisting essentially of" are also provided. It is also understood that wherever embodiments are described herein with the phrase "consisting essentially of" otherwise analogous embodiments described in terms of "consisting of" are also provided.

The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

5.2 Pharmaceutical Compositions

In one aspect, provided herein are "pharmaceutical compositions," which include an antibody drug conjugate provided herein, and one or more pharmaceutically acceptable or physiologically acceptable excipients. In certain embodiments, the antibody drug conjugate are provided in combination with, or separate from, one or more additional agents. Also provided is a composition comprising such one or more additional agents and one or more pharmaceutically acceptable or physiologically acceptable excipients. In particular embodiments, the antibody drug conjugate and an additional agent(s) are present in a therapeutically acceptable amount. The pharmaceutical compositions may be used in accordance with the methods and uses provided herein. Thus, for example, the pharmaceutical compositions can be administered ex vivo or in vivo to a subject in order to practice treatment methods and uses provided herein. Pharmaceutical compositions provided herein can be formulated to be compatible with the intended method or route of administration; exemplary routes of administration are set forth herein.

In some embodiments, provided are pharmaceutical compositions of antibody drug conjugates that modulate a cancer or tumor.

In some aspects, the pharmaceutical compositions may further comprise other therapeutically active agents or compounds disclosed herein or known to the skilled artisan which can be used in the treatment or prevention of various diseases and disorders as set forth herein (e.g., a cancer). As set forth above, the additional therapeutically active agents or compounds may be present in a separate pharmaceutical composition(s).

Pharmaceutical compositions typically comprise a therapeutically effective amount of at least one of the antibody drug conjugates provided herein and one or more pharmaceutically acceptable formulation agents. In certain embodiments, the pharmaceutical composition further comprises one or more additional agents described herein.

In one embodiment, a pharmaceutical composition comprises an antibody drug conjugate provided herein. In some embodiments, a pharmaceutical composition comprises a therapeutically effective amount of an antibody drug conjugate provided herein. In certain embodiments, the pharmaceutical composition comprises a pharmaceutically acceptable excipient.

In some embodiments, the antibody drug conjugate in the pharmaceutical composition provided herein is selected from the antibody drug conjugates described in Section 5.3 below.

In certain embodiments, the pharmaceutical composition comprises the antibody drug conjugate at a concentration of from 0.1-100 mg/mL. In some embodiments, the pharmaceutical composition comprises the antibody drug conjugate at a concentration of from 1 to 20 mg/mL. In other embodiments, the pharmaceutical composition comprises the antibody drug conjugate at a concentration of from 5 to 15 mg/mL. In other embodiments, the pharmaceutical composition comprises the antibody drug conjugate at a concentration of from 8 to 12 mg/mL. In other embodiments, the pharmaceutical composition comprises the antibody drug conjugate at a concentration of from 9 to 11 mg/mL. In some embodiments, the pharmaceutical composition comprises the antibody drug conjugate at a concentration of about 9.5 mg/mL. In some embodiments, the pharmaceutical composition comprises the antibody drug conjugate at a concentration of about 9.6 mg/mL. In some embodiments, the pharmaceutical composition comprises the antibody drug conjugate at a concentration of about 9.7 mg/mL. In some embodiments, the pharmaceutical composition comprises the antibody drug conjugate at a concentration of about 9.8 mg/mL. In some embodiments, the pharmaceutical composition comprises the antibody drug conjugate at a concentration of about 9.9 mg/mL. In yet other embodiments, the pharmaceutical composition comprises the antibody drug conjugate at a concentration of about 10 mg/mL. In yet other embodiments, the pharmaceutical composition comprises the antibody drug conjugate at a concentration of about 10.1 mg/mL. In some embodiments, the pharmaceutical composition comprises the antibody drug conjugate at a concentration of about 10.2 mg/mL. In some embodiments, the pharmaceutical composition comprises the antibody drug conjugate at a concentration of about 10.3 mg/mL. In some embodiments, the pharmaceutical composition comprises the antibody drug conjugate at a concentration of about 10.3 mg/mL. In some embodiments, the pharmaceutical composition comprises the antibody drug conjugate at a concentration of about 10.4 mg/mL. In some embodiments, the pharmaceutical composition comprises the antibody drug conjugate at a concentration of about 10.5 mg/mL.

In some embodiments, the pharmaceutical composition provided herein comprises L-histidine, TWEEN-20, and at least one of trehalose dihydrate or sucrose. In some embodiments, the pharmaceutical composition provided herein further comprises hydrochloric acid (HCl) or succinic acid.

In some embodiments, the concentration of L-histidine useful in the pharmaceutical compositions provided herein is in the range of between 5 and 50 mM. In some embodiments, the concentration of L-histidine in the pharmaceutical compositions provided herein is in the range of between 10 and 40 mM. In some embodiments, the concentration of L-histidine in the pharmaceutical compositions provided herein is in the range of between 15 and 35 mM. In some embodiments, the concentration of L-histidine in the pharmaceutical compositions provided herein is in the range of between 15 and 30 mM. In some embodiments, the concentration of L-histidine in the pharmaceutical compositions provided herein is in the range of between 15 and 25 mM. In some embodiments, the concentration of L-histidine in the pharmaceutical compositions provided herein is in the range of between 15 and 35 mM. In some embodiments, the concentration of L-histidine in the pharmaceutical compositions provided herein is about 16 mM. In some embodiments, the concentration of L-histidine in the pharmaceutical compositions provided herein is about 17 mM. In some embodiments, the concentration of L-histidine in the pharmaceutical compositions provided herein is about 18 mM. In some embodiments, the concentration of L-histidine in the pharmaceutical compositions provided herein is about 19 mM. In some embodiments, the concentration of L-histidine in the pharmaceutical compositions provided herein is about 20 mM. In some embodiments, the concentration of L-histidine in the pharmaceutical compositions provided herein is about 21 mM. In some embodiments, the concentration of L-histidine in the pharmaceutical compositions provided herein is about 22 mM. In some embodiments, the concentration of L-histidine in the pharmaceutical compositions provided herein is about 23 mM. In some embodiments, the concentration of L-histidine in the pharmaceutical compositions provided herein is about 24 mM. In some embodiments, the concentration of L-histidine in the pharmaceutical compositions provided herein is about 25 mM.

In some embodiments, the concentration of TWEEN-20 useful in the pharmaceutical compositions provided herein is in the range of from 0.001 to 0.1% (v/v). In another embodiment, the concentration of TWEEN-20 is in the range of from 0.0025 to 0.075% (v/v). In one embodiment, the concentration of TWEEN-20 is in the range of from 0.005 to 0.05% (v/v). In another embodiment, the concentration of TWEEN-20 is in the range of from 0.0075 to 0.025% (v/v). In another embodiment, the concentration of TWEEN-20 is in the range of from 0.0075 to 0.05% (v/v). In another embodiment, the concentration of TWEEN-20 is in the range of from 0.01 to 0.03% (v/v). In one particular embodiment, the concentration of TWEEN-20 is about 0.01% (v/v). In one particular embodiment, the concentration of TWEEN-20 is about 0.015% (v/v). In one particular embodiment, the concentration of TWEEN-20 is about 0.016% (v/v). In one particular embodiment, the concentration of TWEEN-20 is about 0.017% (v/v). In one particular embodiment, the concentration of TWEEN-20 is about 0.018% (v/v). In one particular embodiment, the concentration of TWEEN-20 is about 0.019% (v/v). In one particular embodiment, the concentration of TWEEN-20 is about 0.02% (v/v). In one particular embodiment, the concentration of TWEEN-20 is about 0.021% (v/v). In one particular embodiment, the concentration of TWEEN-20 is about 0.022% (v/v). In one particular embodiment, the concentration of TWEEN-20 is about 0.023% (v/v). In one particular embodiment, the concentration of TWEEN-20 is about 0.024% (v/v). In one particular embodiment, the concentration of TWEEN-20 is about 0.025% (v/v).

In one embodiment, the concentration of trehalose dihydrate useful in the pharmaceutical compositions provided herein is in the range of between 1% and 20% (w/v). In another embodiment, the concentration of trehalose dihydrate is in the range of 2% and 15% (w/v). In one embodiment, the concentration of trehalose dihydrate is in the range of 3% and 10% (w/v). In another embodiment, the concentration of trehalose dihydrate is in the range of 4% and 9% (w/v). In another embodiment, the concentration of trehalose dihydrate is in the range of 4% and 8% (w/v). In another embodiment, the concentration of trehalose dihydrate is in the range of 4% and 7% (w/v). In another embodiment, the concentration of trehalose dihydrate is in the range of 4% and 6% (w/v). In another embodiment, the concentration of trehalose dihydrate is in the range of 4.5% and 6% (w/v). In another embodiment, the concentration of trehalose dihydrate is about 4.6% (w/v). In another embodiment, the concentration of trehalose dihydrate is about 4.7% (w/v). In another embodiment, the concentration of trehalose dihydrate is about 4.8% (w/v). In another embodiment, the concentration of trehalose dihydrate is about 4.9% (w/v). In another embodiment, the concentration of trehalose dihydrate is about 5.0% (w/v). In another embodiment, the concentration of trehalose dihydrate is about 5.1% (w/v). In another embodiment, the concentration of trehalose dihydrate is about 5.2% (w/v). In another embodiment, the concentration of trehalose dihydrate is about 5.3% (w/v). In another embodiment, the concentration of trehalose dihydrate is about 5.4% (w/v). In another embodiment, the concentration of trehalose dihydrate is about 5.5% (w/v). In another embodiment, the concentration of trehalose dihydrate is about 5.6% (w/v). In another embodiment, the concentration of trehalose dihydrate is about 5.7% (w/v). In another embodiment, the concentration of trehalose dihydrate is about 5.8% (w/v). In another embodiment, the concentration of trehalose dihydrate is about 5.9% (w/v). In another embodiment, the concentration of trehalose dihydrate is about 6.0% (w/v). In another embodiment, the concentration of trehalose dihydrate is about 6.1% (w/v). In another embodiment, the concentration of trehalose dihydrate is about 6.2% (w/v). In another embodiment, the concentration of trehalose dihydrate is about 6.3% (w/v). In another embodiment, the concentration of trehalose dihydrate is about 6.4% (w/v). In another embodiment, the concentration of trehalose dihydrate is about 6.5% (w/v).

In certain embodiments, the molarity of the trehalose dihydrate is from 50 to 300 mM. In other embodiments, the molarity of the trehalose dihydrate is from 75 to 250 mM. In some embodiments, the molarity of the trehalose dihydrate is from 100 to 200 mM. In other embodiments, the molarity of the trehalose dihydrate is from 130 to 150 mM. In some embodiments, the molarity of the trehalose dihydrate is from 135 to 150 mM. In certain embodiments, the molarity of the trehalose dihydrate is about 135 mM. In certain embodiments, the molarity of the trehalose dihydrate is about 136 mM. In certain embodiments, the molarity of the trehalose dihydrate is about 137 mM. In certain embodiments, the molarity of the trehalose dihydrate is about 138 mM. In certain embodiments, the molarity of the trehalose dihydrate is about 139 mM. In certain embodiments, the molarity of the trehalose dihydrate is about 140 mM. In certain embodiments, the molarity of the trehalose dihydrate is about 141 mM. In certain embodiments, the molarity of the trehalose dihydrate is about 142 mM. In certain embodiments, the molarity of the trehalose dihydrate is about 143 mM. In certain embodiments, the molarity of the trehalose dihydrate is about 144 mM. In certain embodiments, the molarity of the trehalose dihydrate is about 145 mM. In certain embodiments, the molarity of the trehalose dihydrate is about 146 mM. In certain embodiments, the molarity of the trehalose dihydrate is about 150 mM. In certain embodiments, the molarity of the trehalose dihydrate is about 151 mM. In certain embodiments, the molarity of the trehalose dihydrate is about 151 mM. In certain embodiments, the molarity of the trehalose dihydrate is about 152 mM. In certain embodiments, the molarity of the trehalose dihydrate is about 153 mM. In certain embodiments, the molarity of the trehalose dihydrate is about 154 mM. In certain embodiments, the molarity of the trehalose dihydrate is about 155 mM.

In one embodiment, the concentration of sucrose useful in the pharmaceutical compositions provided herein is in the range of between 1% and 20% (w/v). In another embodiment, the concentration of sucrose is in the range of 2% and 15% (w/v). In one embodiment, the concentration of sucrose is in the range of 3% and 10% (w/v). In another embodiment, the concentration of sucrose is in the range of 4% and 9% (w/v). In another embodiment, the concentration of sucrose is in the range of 4% and 8% (w/v). In another embodiment, the concentration of sucrose is in the range of 4% and 7% (w/v). In another embodiment, the concentration of sucrose is in the range of 4% and 6% (w/v). In another embodiment, the concentration of sucrose is in the range of 4.5% and 6% (w/v). In another embodiment, the concentration of sucrose is about 4.6% (w/v). In another embodiment, the concentration of sucrose is about 4.7% (w/v). In another embodiment, the concentration of sucrose is about 4.8% (w/v). In another embodiment, the concentration of sucrose is about 4.9% (w/v). In another embodiment, the concentration of sucrose is about 5.0% (w/v). In another embodiment, the concentration of sucrose is about 5.1% (w/v). In another embodiment, the concentration of sucrose is about 5.2% (w/v). In another embodiment, the concentration of sucrose is about 5.3% (w/v). In another embodiment, the concentration of sucrose is about 5.4% (w/v). In another embodiment, the concentration of sucrose is about 5.5% (w/v). In another embodiment, the concentration of sucrose is about 5.6% (w/v). In another embodiment, the concentration of sucrose is about 5.7% (w/v). In another embodiment, the concentration of sucrose is about 5.8% (w/v). In another embodiment, the concentration of sucrose is about 5.9% (w/v). In another embodiment, the concentration of sucrose is about 6.0% (w/v). In another embodiment, the concentration of sucrose is about 6.1% (w/v). In another embodiment, the concentration of sucrose is about 6.2% (w/v). In another embodiment, the concentration of sucrose is about 6.3% (w/v). In another embodiment, the concentration of sucrose is about 6.4% (w/v). In another embodiment, the concentration of sucrose is about 6.5% (w/v).

In certain embodiments, the molarity of the sucrose is from 50 to 300 mM. In other embodiments, the molarity of the sucrose is from 75 to 250 mM. In some embodiments, the molarity of the sucrose is from 100 to 200 mM. In other embodiments, the molarity of the sucrose is from 130 to 150 mM. In some embodiments, the molarity of the sucrose is from 135 to 150 mM. In certain embodiments, the molarity of the sucrose is about 135 mM. In certain embodiments, the molarity of the sucrose is about 136 mM. In certain embodiments, the molarity of the sucrose is about 137 mM. In certain embodiments, the molarity of the sucrose is about 138 mM. In certain embodiments, the molarity of the sucrose is about 139 mM. In certain embodiments, the molarity of the sucrose is about 140 mM. In certain embodiments, the molarity of the sucrose is about 141 mM. In certain embodiments, the molarity of the sucrose is about 142 mM. In certain embodiments, the molarity of the sucrose is about 143 mM. In certain embodiments, the molarity of the sucrose is about 144 mM. In certain embodiments, the molarity of the sucrose is about 145 mM. In certain embodiments, the molarity of the sucrose is about 146 mM. In certain embodiments, the molarity of the sucrose is about 150 mM. In certain embodiments, the molarity of the sucrose is about 151 mM. In certain embodiments, the molarity of the sucrose is about 151 mM. In certain embodiments, the molarity of the sucrose is about 152 mM. In certain embodiments, the molarity of the sucrose is about 153 mM. In certain embodiments, the molarity of the sucrose is about 154 mM. In certain embodiments, the molarity of the sucrose is about 155 mM.

In some embodiments, the pharmaceutical composition provided herein comprises HCl. In other embodiments, the pharmaceutical composition provided herein comprises succinic acid.

In some embodiments, the pharmaceutical composition provided herein has a pH in a range of 5.5 to 6.5. In other embodiments, the pharmaceutical composition provided herein has a pH in a range of 5.7 to 6.3. In some embodiments, the pharmaceutical composition provided herein has a pH of about 5.7. In some embodiments, the pharmaceutical composition provided herein has a pH of about 5.8. In some embodiments, the pharmaceutical composition provided herein has a pH of about 5.9. In some embodiments, the pharmaceutical composition provided herein has a pH of about 6.0. In some embodiments, the pharmaceutical composition provided herein has a pH of about 6.1. In some embodiments, the pharmaceutical composition provided herein has a pH of about 6.2. In some embodiments, the pharmaceutical composition provided herein has a pH of about 6.3.

In some embodiments, the pH is taken at room temperature. In other embodiments, the pH is taken at 15° C. to 27° C. In yet other embodiments, the pH is taken at 4° C. In yet other embodiments, the pH is taken at 25° C.

In some embodiments, the pH is adjusted by HCl. In some embodiments, the pharmaceutical composition comprises HCl, and the pharmaceutical composition has a pH in a range of 5.5 to 6.5 at room temperature. In some embodiments, the pharmaceutical composition comprises HCl, and the pharmaceutical composition has a pH in a range of 5.7 to 6.3 at room temperature. In some more specific embodiments, the pharmaceutical composition comprises HCl, and the pharmaceutical composition has a pH of about of 5.7 at room temperature. In some more specific embodiments, the pharmaceutical composition comprises HCl, and the pharmaceutical composition has a pH of about of 5.8 at room temperature. In some more specific embodiments, the pharmaceutical composition comprises HCl, and the pharmaceutical composition has a pH of about of 5.9 at room temperature. In some more specific embodiments, the pharmaceutical composition comprises HCl, and the pharmaceutical composition has a pH of about of 6.0 at room temperature. In some more specific embodiments, the pharmaceutical composition comprises HCl, and the pharmaceutical composition has a pH of about of 6.1 at room temperature. In some more specific embodiments, the pharmaceutical composition comprises HCl, and the pharmaceutical composition has a pH of about of 6.2 at room temperature. In some more specific embodiments, the pharmaceutical composition comprises HCl, and the pharmaceutical composition has a pH of about of 6.3 at room temperature.

In some embodiments, the pharmaceutical composition comprises HCl, and the pharmaceutical composition has a pH in a range of 5.5 to 6.5 at 15° C. to 27° C. In some embodiments, the pharmaceutical composition comprises HCl, and the pharmaceutical composition has a pH in a range of 5.7 to 6.3 at 15° C. to 27° C. In some more specific embodiments, the pharmaceutical composition comprises HCl, and the pharmaceutical composition has a pH of about of 5.7 at 15° C. to 27° C. In some more specific embodiments, the pharmaceutical composition comprises HCl, and the pharmaceutical composition has a pH of about of 5.8 at 15° C. to 27° C. In some more specific embodiments, the pharmaceutical composition comprises HCl, and the pharmaceutical composition has a pH of about of 5.9 at 15° C. to 27° C. In some more specific embodiments, the pharmaceutical composition comprises HCl, and the pharmaceutical composition has a pH of about of 6.0 at 15° C. to 27° C. In some more specific embodiments, the pharmaceutical composition comprises HCl, and the pharmaceutical composition has a pH of about of 6.1 at 15° C. to 27° C. In some more specific embodiments, the pharmaceutical composition comprises HCl, and the pharmaceutical composition has a pH of about of 6.2 at 15° C. to 27° C. In some more specific embodiments, the pharmaceutical composition comprises HCl, and the pharmaceutical composition has a pH of about of 6.3 at 15° C. to 27° C.

In some embodiments, the pH is adjusted by succinic acid. In some embodiments, the pharmaceutical composition comprises succinic acid, and the pharmaceutical composition has a pH in a range of 5.5 to 6.5 at room temperature. In some embodiments, the pharmaceutical composition comprises succinic acid, and the pharmaceutical composition has a pH in a range of 5.7 to 6.3 at room temperature. In some more specific embodiments, the pharmaceutical composition comprises succinic acid, and the pharmaceutical composition has a pH of about of 5.7 at room temperature. In some more specific embodiments, the pharmaceutical composition comprises succinic acid, and the pharmaceutical composition has a pH of about of 5.8 at room temperature. In some more specific embodiments, the pharmaceutical composition comprises succinic acid, and the pharmaceutical composition has a pH of about of 5.9 at room temperature. In some more specific embodiments, the pharmaceutical composition comprises succinic acid, and the pharmaceutical composition has a pH of about of 6.0 at room temperature. In some more specific embodiments, the pharmaceutical composition comprises succinic acid, and the pharmaceutical composition has a pH of about of 6.1 at room temperature. In some more specific embodiments, the pharmaceutical composition comprises succinic acid, and the pharmaceutical composition has a pH of about of 6.2 at room temperature. In some more specific embodiments, the pharmaceutical composition comprises succinic acid, and the pharmaceutical composition has a pH of about of 6.3 at room temperature.

In some embodiments, the pharmaceutical composition comprises succinic acid, and the pharmaceutical composition has a pH in a range of 5.5 to 6.5 at 15° C. to 27° C. In some embodiments, the pharmaceutical composition comprises succinic acid, and the pharmaceutical composition has a pH in a range of 5.7 to 6.3 at 15° C. to 27° C. In some more specific embodiments, the pharmaceutical composition comprises succinic acid, and the pharmaceutical composition has a pH of about of 5.7 at 15° C. to 27° C. In some more specific embodiments, the pharmaceutical composition comprises succinic acid, and the pharmaceutical composition has a pH of about of 5.8 at 15° C. to 27° C. In some more specific embodiments, the pharmaceutical composition comprises succinic acid, and the pharmaceutical composition has a pH of about of 5.9 at 15° C. to 27° C. In some more specific embodiments, the pharmaceutical composition comprises succinic acid, and the pharmaceutical composition has a pH of about of 6.0 at 15° C. to 27° C. In some more specific embodiments, the pharmaceutical composition comprises succinic acid, and the pharmaceutical composition has a pH of about of 6.1 at 15° C. to 27° C. In some more specific embodiments, the pharmaceutical composition comprises succinic acid, and the pharmaceutical composition has a pH of about of 6.2 at 15° C. to 27° C. In some more specific embodiments, the pharmaceutical composition comprises succinic acid, and the pharmaceutical composition has a pH of about of 6.3 at 15° C. to 27° C.

In some specific embodiments, the pharmaceutical composition provided herein comprises about 20 mM L-histidine, about 0.02% (w/v) TWEEN-20, and at least one of about 5.5% (w/v) trehalose dihydrate or about 5% (w/v) sucrose. In some embodiments, the pharmaceutical composition provided herein further comprises HCl or succinic acid. In some embodiments, the pH is about 6.0 at room temperature. In some embodiments, the pH is about 6.0 at 25° C.

In some specific embodiments, the pharmaceutical composition provided herein comprises about 20 mM L-histidine, about 0.02% (w/v) TWEEN-20, about 5.5% (w/v) trehalose dihydrate and HCl. In some embodiments, the pH is about 6.0 at room temperature. In some embodiments, the pH is about 6.0 at 25° C.

In some specific embodiments, the pharmaceutical composition provided herein comprises about 20 mM L-histidine, about 0.02% (w/v) TWEEN-20, about 5% (w/v) sucrose and HCl. In some embodiments, the pH is about 6.0 at room temperature. In some embodiments, the pH is about 6.0 at 25° C.

In other specific embodiments, the pharmaceutical composition provided herein comprises about 20 mM L-histidine, about 0.02% (w/v) TWEEN-20, about 5.5% (w/v) trehalose dihydrate and succinic acid. In some embodiments, the pH is about 6.0 at room temperature. In some embodiments, the pH is about 6.0 at 25° C.

In some specific embodiments, the pharmaceutical composition provided herein comprises about 20 mM L-histidine, about 0.02% (w/v) TWEEN-20, about 5% (w/v) sucrose and succinic acid. In some embodiments, the pH is about 6.0 at room temperature. In some embodiments, the pH is about 6.0 at 25° C.

In a specific embodiment, provided herein comprises
(a) an antibody drug conjugate comprising the following structure:

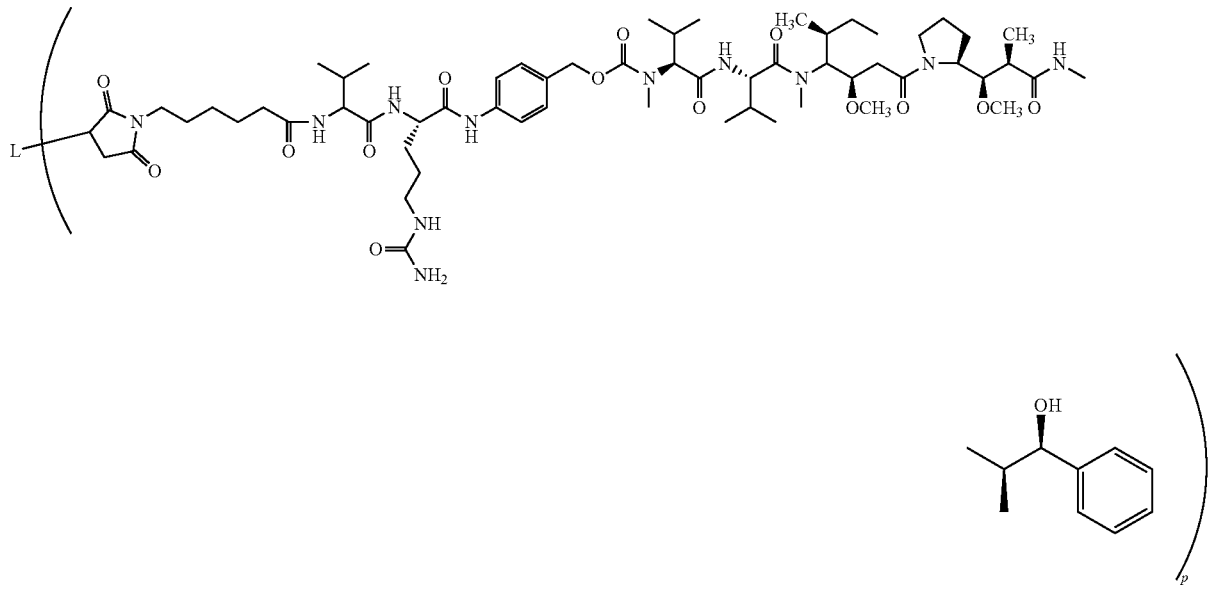

wherein L- represents the antibody or antigen binding fragment thereof and p is from 1 to 10; and
(b) a pharmaceutically acceptable excipient comprising about 20 mM L-histidine, about 0.02% (w/v) TWEEN-20, about 5.5% (w/v) trehalose dihydrate, and HCl, wherein the antibody drug conjugate is at the concentration of about 10 mg/mL, and wherein the pH is about 6.0 at 25° C.

In another specific embodiment, the pharmaceutical composition provided herein comprises:
(a) an antibody drug conjugate comprising the following structure:

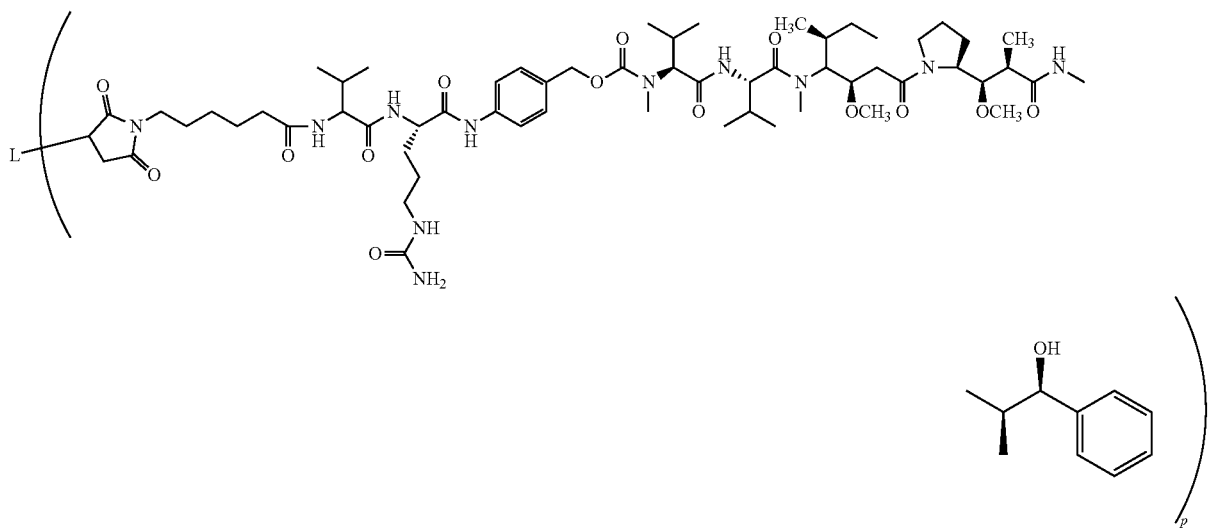

wherein L- represents the antibody or antigen binding fragment thereof and p is from 1 to 10; and (b) a pharmaceutically acceptable excipient comprising about 20 mM L-histidine, about 0.02% (w/v) TWEEN-20, about 5.5% (w/v) trehalose dihydrate, and succinic acid, wherein the antibody drug conjugate is at the concentration of about 10 mg/mL, and wherein the pH is about 6.0 at 25° C.

In yet another specific embodiment, the pharmaceutical composition provided herein comprises:

(a) an antibody drug conjugate comprising the following structure:

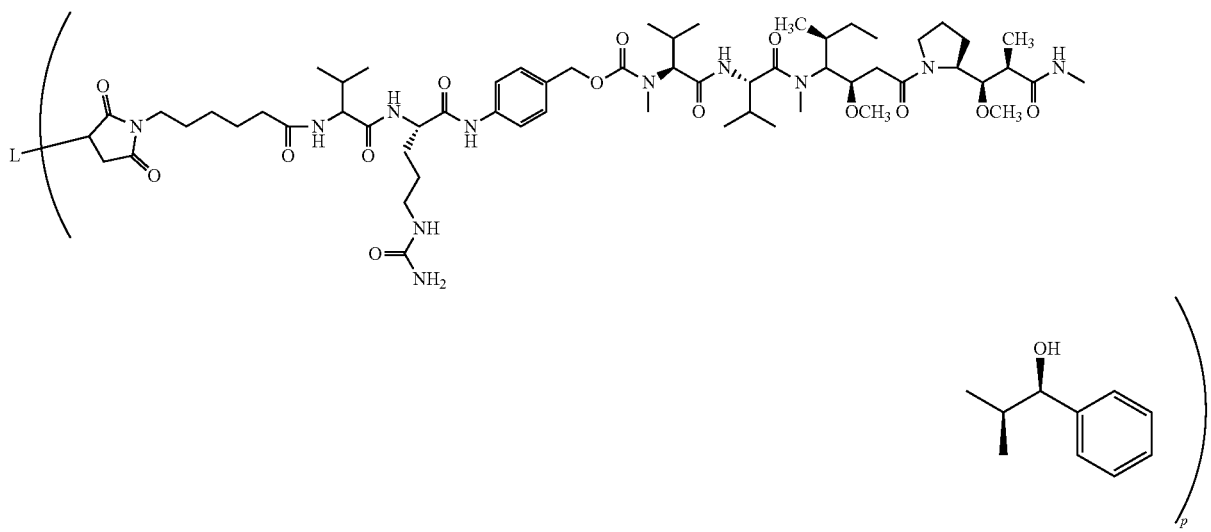

wherein L- represents the antibody or antigen binding fragment thereof and p is from 1 to 10; and (b) a pharmaceutically acceptable excipient comprising about 20 mM L-histidine, about 0.02% (w/v) TWEEN-20, about 5.0% (w/v) sucrose, and HCl, wherein the antibody drug conjugate is at the concentration of about 10 mg/mL, and wherein the pH is about 6.0 at 25° C.

Although certain numbers (and numerical ranges thereof) are provided, it is understood that, in certain embodiments, numerical values within, e.g., 2%, 5%, 10%, 15% or 20% of said numbers (or numerical ranges) are also contemplated. Other exemplary pharmaceutical compositions are provided in the Experimental section below.

A primary solvent in a vehicle may be either aqueous or non-aqueous in nature. In addition, the vehicle may contain other pharmaceutically acceptable excipients for modifying or maintaining the pH, osmolarity, viscosity, sterility or stability of the pharmaceutical composition. In certain embodiments, the pharmaceutically acceptable vehicle is an aqueous buffer. In other embodiments, a vehicle comprises, for example, sodium chloride and/or sodium citrate.

Pharmaceutical compositions provided herein may contain still other pharmaceutically acceptable formulation agents for modifying or maintaining the rate of release of an antibody drug conjugate and/or an additional agent, as described herein. Such formulation agents include those substances known to artisans skilled in preparing sustained-release formulations. For further reference pertaining to pharmaceutically and physiologically acceptable formulation agents, see, for example, *Remington's Pharmaceutical Sciences,* 18th Ed. (1990, Mack Publishing Co., Easton, Pa. 18042) pages 1435-1712, *The Merck Index,* 12th Ed. (1996, Merck Publishing Group, Whitehouse, NJ); and *Pharmaceutical Principles of Solid Dosage Forms* (1993, Technomic Publishing Co., Inc., Lancaster, Pa.). Additional pharmaceutical compositions appropriate for administration are known in the art and are applicable in the methods and compositions provided herein.

In some embodiments, the pharmaceutical composition provided herein is in a liquid form. In other embodiments, the pharmaceutical composition provided herein is lyophilized.

A pharmaceutical composition may be stored in a sterile vial as a solution, suspension, gel, emulsion, solid, or dihydrated or lyophilized powder. Such compositions may be stored either in a ready to use form, a lyophilized form requiring reconstitution prior to use, a liquid form requiring dilution prior to use, or other acceptable form. In some embodiments, a pharmaceutical composition is provided in a single-use container (e.g., a single-use vial, ampoule, syringe, or autoinjector (similar to, e.g., an EpiPen®)), whereas a multi-use container (e.g., a multi-use vial) is provided in other embodiments. Any drug delivery apparatus may be used to deliver peptides and the other agents described herein, including implants (e.g., implantable pumps) and catheter systems, both of which are known to the skilled artisan. Depot injections, which are generally administered subcutaneously or intramuscularly, may also be utilized to release peptides and/or other agents described herein over a defined period of time. Depot injections are usually either solid- or oil-based and generally comprise at least one of the formulation components set forth herein. The skilled artisan is familiar with possible formulations and uses of depot injections. In certain embodiments, the use of Nano Precision Medical's depot delivery technology (Nano Precision Medical; Emeryville, CA) is contemplated. The technology utilizes a titania nanotube membrane that produces zero-order release rates of macromolecules, such as protein and peptide therapeutics. The biocompatible membrane is housed in a small, subcutaneous implant that provides long-term (e.g., up to one year), constant-rate delivery of therapeutic macromolecules.

A pharmaceutical composition can be formulated to be compatible with its intended route of administration. Thus, pharmaceutical compositions include excipients suitable for administration by routes including parenteral (e.g., subcutaneous (s.c.), intravenous, intramuscular, or intraperitoneal), intradermal, oral (e.g., ingestion), inhalation, intracavity, intracranial, and transdermal (topical). Other exemplary routes of administration are set forth herein.

Pharmaceutical compositions may be in the form of a sterile injectable aqueous or oleagenous suspension. This suspension may be formulated using suitable dispersing or wetting agents and suspending agents disclosed herein or known to the skilled artisan. The sterile injectable preparation may also be a sterile injectable solution or suspension in a non-toxic parenterally-acceptable diluent or solvent, for example, as a solution in 1,3-butane diol. Acceptable diluents, solvents and dispersion media that may be employed include water, Ringer's solution, isotonic sodium chloride solution, Cremophor EL™ (BASF, Parsippany, NJ) or phosphate buffered saline (PBS), ethanol, polyol (e.g., glycerol, propylene glycol, and liquid polyethylene glycol), and suitable mixtures thereof. In addition, sterile, fixed oils are conventionally employed as a solvent or suspending medium. For this purpose any bland fixed oil may be employed, including synthetic mono- or diglycerides. Moreover, fatty acids such as oleic acid find use in the preparation of injectables. Prolonged absorption of particular injectable formulations can be achieved by including an agent that delays absorption (e.g., aluminum monostearate or gelatin).

In one embodiment, the pharmaceutical compositions provided herein may be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, and subcutaneous administration.

In one embodiment, the pharmaceutical compositions provided herein may be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, e.g., Remington, *The Science and Practice of Pharmacy,* supra).

In one embodiment, the pharmaceutical compositions intended for parenteral administration may include one or more pharmaceutically acceptable excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

In one embodiment, suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

In one embodiment, suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcellulose, hydroxypropyl methylcellulose, and polyvinylpyrrolidone. Suitable emulsifying agents include those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, KS).

In one embodiment, the pharmaceutical compositions provided herein may be formulated for single or multiple dosage administration. The single dosage formulations are packaged in an ampoule, a vial, or a syringe. The multiple dosage parenteral formulations may contain an antimicrobial agent at bacteriostatic or fungistatic concentrations. All parenteral formulations must be sterile, as known and practiced in the art.

In one embodiment, the pharmaceutical compositions are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

In one embodiment, the pharmaceutical compositions provided herein may be formulated as immediate or modified release dosage forms, including delayed-, sustained, pulsed-, controlled, targeted-, and programmed-release forms.

In one embodiment, the pharmaceutical compositions may be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

In one embodiment, suitable inner matrixes include polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

In one embodiment, suitable outer polymeric membranes include polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyloxyethanol copolymer, and ethylene/vinyl acetate/vinyl alcohol terpolymer.

Aqueous suspensions contain the active materials in admixture with excipients suitable for the manufacture thereof. Such excipients are suspending agents, for example sodium carboxymethylcellulose, methylcellulose, hydroxypropylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxy-ethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives.

Oily suspensions may be formulated by suspending the active ingredient in a vegetable oil, for example *arachis* oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation.

Dispersible powders and granules suitable for preparation of an aqueous suspension by addition of water provide the active ingredient in admixture with a dispersing or wetting agent, suspending agent and one or more preservatives. Suitable dispersing or wetting agents and suspending agents are exemplified herein.

Pharmaceutical compositions provided herein may also be in the form of oil-in-water emulsions. The oily phase may be a vegetable oil, for example olive oil or *arachis* oil, or a mineral oil, for example, liquid paraffin, or mixtures of these. Suitable emulsifying agents may be naturally-occurring gums, for example, gum acacia or gum tragacanth; naturally-occurring phosphatides, for example, soy bean, lecithin, and esters or partial esters derived from fatty acids; hexitol anhydrides, for example, sorbitan monooleate; and condensation products of partial esters with ethylene oxide, for example, polyoxyethylene sorbitan monooleate.

Pharmaceutical compositions can also include excipients to protect the composition against rapid degradation or elimination from the body, such as a controlled release formulation, including implants, liposomes, hydrogels, prodrugs and microencapsulated delivery systems. For example, a time delay material such as glyceryl monostearate or glyceryl stearate alone, or in combination with a wax, may be employed. Prolonged absorption of injectable pharmaceutical compositions can be achieved by including an agent that delays absorption, for example, aluminum monostearate or gelatin. Prevention of the action of microorganisms can be achieved by various antibacterial and antifungal agents, for example, parabens, chlorobutanol, phenol, ascorbic acid, thimerosal, and the like.

The pharmaceutical composition provided herein may be stored at −80° C., 4° C., 25° C. or 37° C.

A lyophilized composition can be made by freeze-drying the liquid pharmaceutical composition provided herein. In a specific embodiment, the pharmaceutical composition provided here is a lyophilized pharmaceutical composition. In some embodiments, the pharmaceutical formulations are lyophilized powders, which can be reconstituted for administration as solutions, emulsions and other mixtures. They may also be reconstituted and formulated as solids or gels.

In some embodiments, preparation of the lyophilized formulation provided herein involves batching of the formulated bulk solution for lyophilization, aseptic filtration, filling in vials, freezing vials in a freeze-dryer chamber, followed by lyophilization, stoppering and capping.

A lyophilizer can be used in preparing the lyophilized formulation. For example, a VirTis Genesis Model EL pilot unit can be employed. The unit incorporates a chamber with three working shelves (to a total usable shelf area of ca 0.4 square meters), an external condenser, and a mechanical vacuum pumping system. Cascaded mechanical refrigeration allows the shelves to be cooled to −70° C. or lower, and the external condenser to −90° C. or lower. Shelf temperature and chamber pressure were controlled automatically to +/−0.5° C. and +/−2 microns (milliTorr), respectively. The unit was equipped with a capacitance manometer vacuum gauge, a Pirani vacuum gauge, a pressure transducer (to measure from 0 to 1 atmosphere), and a relative humidity sensor.

The lyophilized powder can be prepared by dissolving an antibody drug conjugate provided herein, or a pharmaceutically acceptable derivative thereof, in a suitable solvent. In some embodiments, the lyophilized powder is sterile. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the antibody drug conjugate. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable excipient. Such amount can be empirically determined and adjusted according to specific needs.

An exemplary reconstitution procedure is illustrated as follows: (1) fit the 5 mL or 3 mL syringe with a with a 18 or 20 Gauge needle and filled the syringe with water of the grade Water for Injection (WFI); (2) measure appropriate amount of WFI using the syringe graduations, ensuring that the syringe was free of air bubbles; (3) inserted the needle through the rubber stopper; (4) dispense the entire contents of the syringe into the container down the vial wall, removed the syringe and needle and put into the sharp container; (4) swirl the vial continuously to carefully solubilize the entire vial contents until fully reconstituted (e.g., about 20-40 seconds) and minimize excessive agitation of the protein solution that could result in foaming.

5.3 Anti-191P4D12 Antibody Drug Conjugate

The pharmaceutical compositions, formulations and dosage forms provided herein comprise anti-191P4D12 antibody drug conjugates. The anti-191P4D12 antibody drug conjugate provided herein comprises an antibody or antigen binding fragment thereof that binds to 191P4D12 conjugated to one or more units of cytotoxic agents (or drug units). The cytotoxic agents (or drug units) can be covalently linked directly or via a linker unit (LU).

In some embodiments, the antibody drug conjugate compound has the following formula:

or a pharmaceutically acceptable salt or solvate thereof; wherein:

L is the antibody unit, e.g., the anti-191P4D12 antibody or an antigen binding fragment thereof as provided in Section 5.3.1 below, and (LU-D) is a linker unit-drug unit moiety, wherein:
LU— is a linker unit, and
D is a drug unit having cytostatic or cytotoxic activity against a target cell; and
p is an integer from 1 to 20.

In some embodiments, p ranges from 1 to 10, 1 to 9, 1 to 8, 1 to 7, 1 to 6, 1 to 5, 1 to 4, 1 to 3, or 1 to 2. In some embodiments, p ranges from 2 to 10, 2 to 9, 2 to 8, 2 to 7, 2 to 6, 2 to 5, 2 to 4 or 2 to 3. In other embodiments, p is about 1. In other embodiments, p is about 2. In other embodiments, p is about 3. In other embodiments, p is about 4. In other embodiments, p is about 5. In other embodiments, p is about 6. In other embodiments, p is about 7. In other embodiments, p is about 8. In other embodiments, p is about 9. In other embodiments, p is about 10.

In some embodiments, the antibody drug conjugate compound has the following formula:

or a pharmaceutically acceptable salt or solvate thereof, wherein:

L is the Antibody unit, e.g., the anti-191P4D12 antibody or an antigen binding fragment thereof as provided in Section 5.3.1 below; and -$A_a$-$W_w$—$Y_y$— is a linker unit (LU), wherein:
-A- is a stretcher unit,
a is 0 or 1,
each —W— is independently an amino acid unit,
w is an integer ranging from 0 to 12,
—Y— is a self-immolative spacer unit,
y is 0, 1 or 2;
D is a drug units having cytostatic or cytotoxic activity against the target cell; and
p is an integer from 1 to 20.

In some embodiments, a is 0 or 1, w is 0 or 1, and y is 0, 1 or 2. In some embodiments, a is 0 or 1, w is 0 or 1, and y is 0 or 1. In some embodiments, p ranges from 1 to 10, 1 to 9, 1 to 8, 1 to 7, 1 to 6, 1 to 5, 1 to 4, 1 to 3, or 1 to 2. In some embodiments, p ranges from 2 to 8, 2 to 7, 2 to 6, 2 to 5, 2 to 4 or 2 to 3. In other embodiments, p is 1, 2, 3, 4, 5 or 6. In some embodiments, p is 2 or 4. In some embodiments, when w is not zero, y is 1 or 2. In some embodiments, when w is 1 to 12, y is 1 or 2. In some embodiments, w is 2 to 12 and y is 1 or 2. In some embodiments, a is 1 and w and y are 0.

For compositions comprising a plurality antibodies or antigen binding fragments thereof, the drug loading is represented by p, the average number of drug molecules per antibody unit. Drug loading may range from 1 to 20 drugs (D) per antibody. The average number of drugs per antibody in preparation of conjugation reactions may be characterized by conventional means such as mass spectroscopy, ELISA assay, and HPLC. The quantitative distribution of antibody drug conjugates in terms of p may also be determined. In some instances, separation, purification, and characterization of homogeneous antibody drug conjugates where p is a certain value from antibody drug conjugates with other drug loadings may be achieved by means such as reverse phase HPLC or electrophoresis. In exemplary embodiments, p is from 2 to 8.

5.3.1 Anti-191P4D12 Antibodies or Antigen Binding Fragments

Figure 5A:
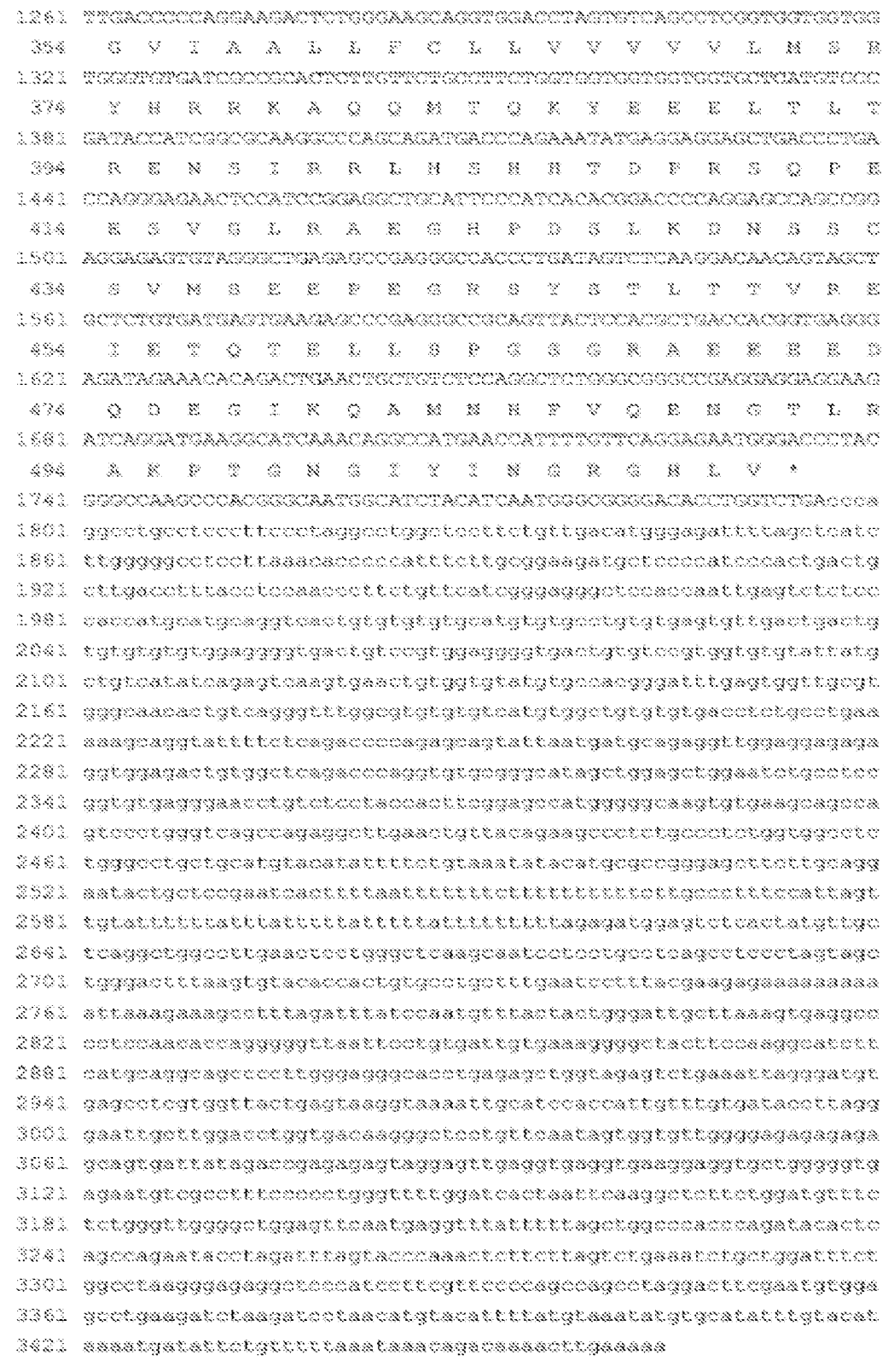

In one embodiment, the antibody or antigen binding fragment thereof that binds to 191P4D12-related proteins is an antibody or antigen binding fragment that specifically binds to 191P4D12 protein comprising amino acid sequence of SEQ ID NO:2 (see FIG. 5A). The corresponding cDNA encoding the 191P4D12 protein has a sequence of SEQ ID NO:1 (see FIG. 5A).

The antibody that specifically binds to 191P4D12 protein comprising amino acid sequence of SEQ ID NO:2 includes antibodies that can bind to other 191P4D12-related proteins. For example, antibodies that bind 191P4D12 protein comprising amino acid sequence of SEQ ID NO:2 can bind 191P4D12-related proteins such as 191P4D12 variants and the homologs or analogs thereof.

In some embodiments, the anti-191P4D12 antibody provided herein is a monoclonal antibody.

In some embodiments, the antibody comprises a heavy chain comprising an amino acid sequence of SEQ ID NO:4 (cDNA sequence of SEQ ID NO:3), and/or a light chain comprising an amino acid sequence of SEQ ID NO: 6 (cDNA sequence of SEQ ID NO:5), as shown in FIG. 5B.

In some embodiments, the anti-191P4D12 antibody or antigen binding fragment thereof comprises a heavy chain variable region comprising complementarity determining regions (CDRs) comprising the amino acid sequences of the CDRs of the heavy chain variable region set forth in SEQ ID NO:7 and a light chain variable region comprising CDRs comprising the amino acid sequences of the CDRs of the light chain variable region set forth in SEQ ID NO:8. SEQ ID NO:7 and SEQ ID NO:8 are as shown in FIG. 5C and listed below:

```
                                               SEQ ID NO: 7
MELGLCWVFLVAILEGVQCEVQLVESGGGLVQPGGSLRLSCAASGFTFSS

YNMNWVRQAPGKGLEWVSYISSSSSTIYYADSVKGRFTISRDNAKNSLSL

QMNSLRDEDTAVYYCARAYYYGMDVWGQGTTVTVSSASTKGPSVFPLAPS

SKSTSGGTAALGCLVKDYFPEPVTVSWNSGALTSGVHTFPAVLQSSGLYS

LSSVVTVPSSSLGTQTYICNVNHKPSNTKVDKRVEPKSCDKTHTCPPCPA

PELLGGPSVFLFPPKPKDTLMISRTPEVTCVVVDVSHEDPEVKFNWYVDG

VEVHNAKTKPREEQYNSTYRVVSVLTVLHQDWLNGKEYKCKVSNKALPAP

IEKTISKAKGQPREPQVYTLPPSREEMTKNQVSLTCLVKGFYPSDIAVEW

ESNGQPENNYKTTPPVLDSDGSFFLYSKLTVDKSRWQQGNVFSCSVMHEA

LHNHYTQKSLSLSPGK

SEQ ID NO: 8
MDMRVPAQLLGLLLLWFPGSRCDIQMTQSPSSVSASVGDRVTITCRASQG

ISGWLAWYQQKPGKAPKFLIYAASTLQSGVPSRFSGSGSGTDFTLTISSL

QPEDFATYYCQQANSFPPTFGGGTKVEIKRTVAAPSVFIFPPSDEQLKSG

TASVVCLLNNFYPREAKVQWKVDNALQSGNSQESVTEQDSKDSTYSLSST

LTLSKADYEKHKVYACEVTHQGLSSPVTKSFNRGEC
```

In some embodiments, the anti-191P4D12 antibody or antigen binding fragment thereof comprises a heavy chain variable region comprising the amino acid sequences of the heavy chain variable region set forth in SEQ ID NO:22 (which is the amino acid sequence ranging from the 20th amino acid (glutamic acid) to the 136th amino acid (serine) of SEQ ID NO:7) and a light chain variable region comprising the amino acid sequences of the light chain variable region set forth in SEQ ID NO:23 (which is the amino acid sequence ranging from the 23rd amino acid (aspartic acid) to the 130th amino acid (arginine) of SEQ ID NO:8). In other embodiments, the anti-191P4D12 antibody or antigen binding fragment thereof comprises a heavy chain variable region consisting of the amino acid sequences of the heavy chain variable region set forth in SEQ ID NO:22 (which is the amino acid sequence ranging from the 20th amino acid (glutamic acid) to the 136th amino acid (serine) of SEQ ID NO:7) and a light chain variable region consisting of the amino acid sequences of the light chain variable region set forth in SEQ ID NO:23 (which is the amino acid sequence ranging from the 23rd amino acid (aspartic acid) to the 130th amino acid (arginine) of SEQ ID NO:8). SEQ ID NO: 22 and SEQ ID NO:23 are listed below:

```
                                              SEQ ID NO: 22
EVQLVESGGGLVQPGGSLRLSCAASGFTFSSSSSYNMNWVRQAPGKGLEW

VSYISSTIYYADSVKGRFTISRDNAKNSLSLQMNSLRDEDTAVYYCARAY

YYGMDVWGQGTTVTVSS

SEQ ID NO: 23
DIQMTQSPSSVSASVGDRVTITCRASQGISGWLAWYQQKPGKAPKFLIYA

ASTLQSGVPSRFSGSGSGTDFTLTISSLQPEDFATYYCQQANSFPPTFGG

GTKVEIKR
```

CDR sequences can be determined according to well-known numbering systems. As described above, CDR regions are well-known to those skilled in the art and have been defined by well-known numbering systems. For example, the Kabat Complementarity Determining Regions (CDRs) are based on sequence variability and are the most commonly used (see, e.g., Kabat et al., supra). Chothia refers instead to the location of the structural loops (see, e.g., Chothia and Lesk, 1987, J. Mol. Biol. 196:901-17). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software (see, e.g., *Antibody Engineering* Vol. 2 (Kontermann and Dübel eds., 2d ed. 2010)). The "contact" hypervariable regions are based on an analysis of the available complex crystal structures. Another universal numbering system that has been developed and widely adopted is ImMunoGeneTics (IMGT) Information System® (Lafranc et al., 2003, Dev. Comp. Immunol. 27(1):55-77). IMGT is an integrated information system specializing in immunoglobulins (IG), T-cell receptors (TCR), and major histocompatibility complex (MHC) of human and other vertebrates. Herein, the CDRs are referred to in terms of both the amino acid sequence and the location within the light or heavy chain. As the "location" of the CDRs within the structure of the immunoglobulin variable domain is conserved between species and present in structures called loops, by using numbering systems that align variable domain sequences according to structural features, CDR and framework residues are readily identified. This information can be used in grafting and replacement of CDR residues from immunoglobulins of one species into an acceptor framework from, typically, a human antibody. An additional numbering system (AHon) has been developed by Honegger and Pluckthun, 2001, J. Mol. Biol. 309: 657-70. Correspondence between the numbering system, including, for example, the Kabat numbering and the IMGT unique numbering system, is well-known to one skilled in the art (see, e.g., Kabat, supra; Chothia and Lesk, supra; Martin, supra; Lefranc et al., supra). The residues from each of these hypervariable regions or CDRs are noted in Table 30 above.

In some embodiments, the anti-191P4D12 antibody or antigen binding fragment thereof comprises a heavy chain variable region comprising complementarity determining regions (CDRs) comprising the amino acid sequences of the CDRs of the heavy chain variable region set forth in SEQ ID NO:7 according to Kabat numbering and a light chain variable region comprising CDRs comprising the amino acid sequences of the CDRs of the light chain variable region set forth in SEQ ID NO:8 according to Kabat numbering.

In some embodiments, the anti-191P4D12 antibody or antigen binding fragment thereof comprises a heavy chain variable region comprising complementarity determining regions (CDRs) comprising the amino acid sequences of the CDRs of the heavy chain variable region set forth in SEQ ID NO:7 according to AbM numbering and a light chain variable region comprising CDRs comprising the amino acid sequences of the CDRs of the light chain variable region set forth in SEQ ID NO:8 according to AbM numbering.

In other embodiments, the anti-191P4D12 antibody or antigen binding fragment thereof comprises a heavy chain variable region comprising complementarity determining regions (CDRs) comprising the amino acid sequences of the CDRs of the heavy chain variable region set forth in SEQ ID NO:7 according to Chothia numbering and a light chain variable region comprising CDRs comprising the amino acid sequences of the CDRs of the light chain variable region set forth in SEQ ID NO:8 according to Chothia numbering.

In other embodiments, the anti-191P4D12 antibody or antigen binding fragment thereof comprises a heavy chain variable region comprising complementarity determining regions (CDRs) comprising the amino acid sequences of the CDRs of the heavy chain variable region set forth in SEQ ID NO:7 according to Contact numbering and a light chain variable region comprising CDRs comprising the amino acid sequences of the CDRs of the light chain variable region set forth in SEQ ID NO:8 according to Contact numbering.

In yet other embodiments, the anti-191P4D12 antibody or antigen binding fragment thereof comprises a heavy chain variable region comprising complementarity determining regions (CDRs) comprising the amino acid sequences of the CDRs of the heavy chain variable region set forth in SEQ ID NO:7 according to IMGT numbering and a light chain variable region comprising CDRs comprising the amino acid sequences of the CDRs of the light chain variable region set forth in SEQ ID NO:8 according to IMGT numbering.

As described above, the CDR sequences according to different numbering systems can be readily determined, e.g., using online tools such as the one provided by Antigen receptor Numbering And Receptor Classification (AN-ARCI). For example, the heavy chain CDR sequences within SEQ ID NO:7, and the light chain CDR sequences within SEQ ID NO:8 according to Kabat numbering as determined by ANARCI are listed in Table 31 below.

TABLE 31

|      | VH of SEQ ID NO: 7 | VL of SEQ ID NO: 8 |
|------|---------------------|---------------------|
| CDR1 | SYNMN (SEQ ID NO: 9) | RASQGISGWLA (SEQ ID NO: 12) |

TABLE 31-continued

|      | VH of SEQ ID NO: 7 | VL of SEQ ID NO: 8 |
|------|---------------------|---------------------|
| CDR2 | YISSSSSTIYYADSVKG (SEQ ID NO: 10) | AASTLQS (SEQ ID NO: 13) |
| CDR3 | AYYYGMDV (SEQ ID NO: 11) | QQANSFPPT (SEQ ID NO: 14) |

For another example, the heavy chain CDR sequences within SEQ ID NO:22, and the light chain CDR sequences within SEQ ID NO:23 according to IMGT numbering as determined by ANARCI are listed in Table 32 below.

TABLE 32

|      | VH of SEQ ID NO: 7 | VL of SEQ ID NO: 8 |
|------|---------------------|---------------------|
| CDR1 | GFTFSSYN (SEQ ID NO: 16) | QGISGW (SEQ ID NO: 19) |
| CDR2 | ISSSSTI (SEQ ID NO: 17) | AAS (SEQ ID NO: 20) |
| CDR3 | ARAYYYGMDV (SEQ ID NO: 18) | QQANSFPPT (SEQ ID NO: 21) |

In some embodiments, the antibody or antigen binding fragment thereof comprises CDR H1 comprising an amino acid sequence of SEQ ID NO:9, CDR H2 comprising an amino acid sequence of SEQ ID NO:10, CDR H3 comprising an amino acid sequence of SEQ ID NO:11, CDR L1 comprising an amino acid sequence of SEQ ID NO: 12, CDR L2 comprising an amino acid sequence of SEQ ID NO: 13, and CDR L3 comprising an amino acid sequence of SEQ ID NO: 14.

In some embodiments, the antibody or antigen binding fragment thereof comprises a heavy chain variable region comprising the amino acid sequence ranging from the 20th amino acid (glutamic acid) to the 136th amino acid (serine) of SEQ ID NO:7 and a light chain variable region comprising the amino acid sequence ranging from the 23rd amino acid (aspartic acid) to the 130th amino acid (arginine) of SEQ ID NO:8.

In some embodiments, the antibody comprises a heavy chain comprising the amino acid sequence ranging from the 20th amino acid (glutamic acid) to the 466th amino acid (lysine) of SEQ ID NO:7 and a light chain comprising the amino acid sequence ranging from the 23rd amino acid (aspartic acid) to the 236th amino acid (cysteine) of SEQ ID NO:8.

In some embodiments, amino acid sequence modification(s) of antibodies described herein are contemplated. For example, it may be desirable to optimize the binding affinity and/or other biological properties of the antibody, including but not limited to specificity, thermostability, expression level, effector functions, glycosylation, reduced immunogenicity, or solubility. Thus, in addition to the antibodies described herein, it is contemplated that antibody variants can be prepared. For example, antibody variants can be prepared by introducing appropriate nucleotide changes into the encoding DNA, and/or by synthesis of the desired antibody or polypeptide. Those skilled in the art who appreciate that amino acid changes may alter post-translational processes of the antibody, such as changing the number or position of glycosylation sites or altering the membrane anchoring characteristics.

In some embodiments, the antibodies provided herein are chemically modified, for example, by the covalent attachment of any type of molecule to the antibody. The antibody derivatives may include antibodies that have been chemically modified, for example, by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to, specific chemical cleavage, acetylation, formulation, metabolic synthesis of tunicamycin, etc. Additionally, the antibody may contain one or more non-classical amino acids.

Variations may be a substitution, deletion, or insertion of one or more codons encoding the single domain antibody or polypeptide that results in a change in the amino acid sequence as compared with the original antibody or polypeptide. Amino acid substitutions can be the result of replacing one amino acid with another amino acid comprising similar structural and/or chemical properties, such as the replacement of a leucine with a serine, e.g., conservative amino acid replacements. Standard techniques known to those of skill in the art can be used to introduce mutations in the nucleotide sequence encoding a molecule provided herein, including, for example, site-directed mutagenesis and PCR-mediated mutagenesis which results in amino acid substitutions. Insertions or deletions may optionally be in the range of about 1 to 5 amino acids. In certain embodiments, the substitution, deletion, or insertion includes fewer than 25 amino acid substitutions, fewer than 20 amino acid substitutions, fewer than 15 amino acid substitutions, fewer than 10 amino acid substitutions, fewer than 5 amino acid substitutions, fewer than 4 amino acid substitutions, fewer than 3 amino acid substitutions, or fewer than 2 amino acid substitutions relative to the original molecule. In a specific embodiment, the substitution is a conservative amino acid substitution made at one or more predicted non-essential amino acid residues. The variation allowed may be determined by systematically making insertions, deletions, or substitutions of amino acids in the sequence and testing the resulting variants for activity exhibited by the parental antibodies.

Amino acid sequence insertions include amino- and/or carboxyl-terminal fusions ranging in length from one residue to polypeptides containing multiple residues, as well as intrasequence insertions of single or multiple amino acid residues. Examples of terminal insertions include an antibody with an N-terminal methionyl residue.

Antibodies generated by conservative amino acid substitutions are included in the present disclosure. In a conservative amino acid substitution, an amino acid residue is replaced with an amino acid residue comprising a side chain with a similar charge. As described above, families of amino acid residues comprising side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity.

Following mutagenesis, the encoded protein can be expressed and the activity of the protein can be determined conservative (e.g., within an amino acid group with similar properties and/or side chains) substitutions may be made, so as to maintain or not significantly change the properties.

Amino acids may be grouped according to similarities in the properties of their side chains (see, e.g., Lehninger, *Biochemistry* 73-75 (2d ed. 1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); and (4) basic: Lys (K), Arg (R), His(H). Alternatively, naturally occurring residues may be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; and (6) aromatic: Trp, Tyr, Phe.

For example, any cysteine residue not involved in maintaining the proper conformation of the antibody also may be substituted, for example, with another amino acid, such as alanine or serine, to improve the oxidative stability of the molecule and to prevent aberrant crosslinking.

The variations can be made using methods known in the art such as oligonucleotide-mediated (site-directed) mutagenesis, alanine scanning, and PCR mutagenesis. Site-directed mutagenesis (see, e.g., Carter, 1986, Biochem J. 237:1-7; and Zoller et al., 1982, Nucl. Acids Res. 10:6487-500), cassette mutagenesis (see, e.g., Wells et al., 1985, Gene 34:315-23), or other known techniques can be performed on the cloned DNA to produce the anti-anti-MSLN antibody variant DNA.

Covalent modifications of antibodies are included within the scope of the present disclosure. Covalent modifications include reacting targeted amino acid residues of an antibody with an organic derivatizing agent that is capable of reacting with selected side chains or the N- or C-terminal residues of the antibody. Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains (see, e.g., Creighton, *Proteins: Structure and Molecular Properties* 79-86 (1983)), acetylation of the N-terminal amine, and amidation of any C-terminal carboxyl group.

Other types of covalent modification of the antibody included within the scope of this present disclosure include altering the native glycosylation pattern of the antibody or polypeptide (see, e.g., Beck et al., 2008, Curr. Pharm. Biotechnol. 9:482-501; and Walsh, 2010, Drug Discov. Today 15:773-80), and linking the antibody to one of a variety of nonproteinaceous polymers, e.g., polyethylene glycol (PEG), polypropylene glycol, or polyoxyalkylenes, in the manner set forth, for example, in U.S. Pat. Nos. 4,640, 835; 4,496,689; 4,301,144; 4,670,417; 4,791,192; or 4,179, 337.

In some embodiments, the antibody or antigen binding fragment provided herein comprises a heavy chain having more than 70% homologous to the heavy chain as set forth in SEQ ID NO: 7. In some embodiments, the antibody or antigen binding fragment provided herein comprises a heavy chain having more than 75% homologous to the heavy chain as set forth in SEQ ID NO:7. In some embodiments, the antibody or antigen binding fragment provided herein comprises a heavy chain having more than 80% homologous to the heavy chain as set forth in SEQ ID NO:7. In some embodiments, the antibody or antigen binding fragment provided herein comprises a heavy chain having more than 85% homologous to the heavy chain as set forth in SEQ ID NO:7. In some embodiments, the antibody or antigen binding fragment provided herein comprises a heavy chain having more than 90% homologous to the heavy chain as set forth in SEQ ID NO:7. In some embodiments, the antibody or antigen binding fragment provided herein comprises a heavy chain having more than 95% homologous to the heavy chain as set forth in SEQ ID NO:7.

In some embodiments, the antibody or antigen binding fragment provided herein comprises a light chain having more than 70% homologous to the light chain as set forth in SEQ ID NO:8. In some embodiments, the antibody or antigen binding fragment provided herein comprises a light chain having more than 75% homologous to the light chain as set forth in SEQ ID NO:8. In some embodiments, the antibody or antigen binding fragment provided herein comprises a light chain having more than 80% homologous to the light chain as set forth in SEQ ID NO:8. In some embodiments, the antibody or antigen binding fragment provided herein comprises a light chain having more than 85% homologous to the light chain as set forth in SEQ ID NO:8. In some embodiments, the antibody or antigen binding fragment provided herein comprises a light chain having more than 90% homologous to the light chain as set forth in SEQ ID NO:8. In some embodiments, the antibody or antigen binding fragment provided herein comprises a light chain having more than 95% homologous to the light chain as set forth in SEQ ID NO:8.

In some embodiments, the anti-191P4D12 antibody provided herein comprises heavy and light chain CDR regions of an antibody designated Ha22-2(2,4)6.1 produced by a hybridoma deposited under the American Type Culture Collection (ATCC) Accession NO: PTA-11267, or heavy and light chain CDR regions comprising amino acid sequences that are homologous to the amino acid sequences of the heavy and light chain CDR regions of Ha22-2(2,4)6.1, and wherein the antibodies retain the desired functional properties of the anti-191P4D12 antibody designated Ha22-2(2,4)6.1 produced by a hybridoma deposited under the American Type Culture Collection (ATCC) Accession NO: PTA-11267.

In some embodiments, the antibody or antigen binding fragment thereof provided herein comprises a humanized heavy chain variable region and a humanized light chain variable region, wherein:
 (a) the heavy chain variable region comprises CDRs comprising the amino acid sequences of the heavy chain variable region CDRs set forth in the antibody produced by a hybridoma deposited under the American Type Culture Collection (ATCC) Accession NO: PTA-11267;
 (b) the light chain variable region comprises CDRs comprising the amino acid sequences of the light chain variable region CDRs set forth in the antibody produced by a hybridoma deposited under the American Type Culture Collection (ATCC) Accession NO: PTA-11267.

In some embodiments, the anti-191P4D12 antibody provided herein comprises heavy and light chain variable regions of an antibody designated Ha22-2(2,4)6.1 produced by a hybridoma deposited under the American Type Culture Collection (ATCC) Accession NO: PTA-11267 (See, FIG. 3), or heavy and light variable regions comprising amino acid sequences that are homologous to the amino acid sequences of the heavy and light chain variable regions of Ha22-2(2,4)6.1, and wherein the antibodies retain the desired functional properties of the anti-191P4D12 antibody provided herein. As the constant region of the antibody of the invention, any subclass of constant region can be chosen. In one embodiment, human IgG1 constant region as the heavy chain constant region and human Ig kappa constant region as the light chain constant region can be used.

In some embodiments, the anti-191P4D12 antibody provided herein comprises heavy and light chains of an antibody designated Ha22-2(2,4)6.1 produced by a hybridoma deposited under the American Type Culture Collection (ATCC) Accession NO: PTA-11267 (See, FIG. 3), or heavy and light chains comprising amino acid sequences that are homologous to the amino acid sequences of the heavy and light chains of Ha22-2(2,4)6.1, and wherein the antibodies retain the desired functional properties of the anti-191P4D12 antibody provided herein.

In some embodiments, the antibody or antigen binding fragment thereof provided herein comprises a heavy chain variable region and a light chain variable region, wherein:
 (a) the heavy chain variable region comprises an amino acid sequence that is at least 80% homologous to the heavy chain variable region amino acid sequence of the antibody produced by a hybridoma deposited under the American Type Culture Collection (ATCC) Accession NO: PTA-11267; and
 (b) the light chain variable region comprises an amino acid sequence that is at least 80% homologous to the light chain variable region amino acid sequence of the antibody produced by a hybridoma deposited under the American Type Culture Collection (ATCC) Accession NO: PTA-11267.

In some embodiments, the heavy chain variable region comprises an amino acid sequence that is at least 85% homologous to the heavy chain variable region amino acid sequence of the antibody produced by a hybridoma deposited under the American Type Culture Collection (ATCC) Accession NO: PTA-11267. In other embodiments, the heavy chain variable region comprises an amino acid sequence that is at least 90% homologous to the heavy chain variable region amino acid sequence of the antibody produced by a hybridoma deposited under the American Type Culture Collection (ATCC) Accession NO: PTA-11267. In yet other embodiments, the heavy chain variable region comprises an amino acid sequence that is at least 95% homologous to the heavy chain variable region amino acid sequence of the antibody produced by a hybridoma deposited under the American Type Culture Collection (ATCC) Accession NO: PTA-11267. In other embodiments, the heavy chain variable region may be 85%, 86%, 87%, 88%, 89%, 90%, 91%, 92%, 93%, 94%, 95%, 96%, 97%, 98% or 99% homologous to the heavy chain variable region amino acid sequence of the antibody produced by a hybridoma deposited under the American Type Culture Collection (ATCC) Accession NO: PTA-11267.

In some embodiments, the light chain variable region comprises an amino acid sequence that is at least 85% homologous to the light chain variable region amino acid sequence of the antibody produced by a hybridoma deposited under the American Type Culture Collection (ATCC) Accession NO: PTA-11267. In other embodiments, the light chain variable region comprises an amino acid sequence that is at least 90% homologous to the light chain variable region amino acid sequence of the antibody produced by a hybridoma deposited under the American Type Culture Collection (ATCC) Accession NO: PTA-11267. In yet other embodiments, the light chain variable region comprises an amino acid sequence that is at least 95% homologous to the light chain variable region amino acid sequence of the antibody produced by a hybridoma deposited under the American Type Culture Collection (ATCC) Accession NO: PTA-11267. In other embodiments, the light chain variable region may be 85%, 86%, 87%, 88%, 89%, 90%, 91%, 92%, 93%, 94%, 95%, 96%, 97%, 98% or 99% homologous to the light chain variable region amino acid sequence of the antibody produced by a hybridoma deposited under the American Type Culture Collection (ATCC) Accession NO: PTA-11267.

In other embodiments, the antibody or antigen binding fragment thereof provided herein comprises a heavy chain and a light chain, wherein:
 (a) the heavy chain comprises an amino acid sequence that is at least 80% homologous to the heavy chain amino acid sequence of the antibody produced by a hybridoma deposited under the American Type Culture Collection (ATCC) Accession NO: PTA-11267; and
 (b) the light chain comprises an amino acid sequence that is at least 80% homologous to the light chain amino acid sequence of the antibody produced by a hybridoma deposited under the American Type Culture Collection (ATCC) Accession NO: PTA-11267.

In some embodiments, the heavy chain comprises an amino acid sequence that is at least 85% homologous to the heavy chain amino acid sequence of the antibody produced by a hybridoma deposited under the American Type Culture Collection (ATCC) Accession NO: PTA-11267. In other embodiments, the heavy chain comprises an amino acid sequence that is at least 90% homologous to the heavy chain amino acid sequence of the antibody produced by a hybridoma deposited under the American Type Culture Collection (ATCC) Accession NO: PTA-11267. In yet other embodiments, the heavy chain comprises an amino acid sequence that is at least 95% homologous to the heavy chain amino acid sequence of the antibody produced by a hybridoma deposited under the American Type Culture Collection (ATCC) Accession NO: PTA-11267. In other embodiments, the heavy chain may be 85%, 86%, 87%, 88%, 89%, 90%, 91%, 92%, 93%, 94%, 95%, 96%, 97%, 98% or 99% homologous to the heavy chain amino acid sequence of the antibody produced by a hybridoma deposited under the American Type Culture Collection (ATCC) Accession NO: PTA-11267.

In some embodiments, the light chain comprises an amino acid sequence that is at least 85% homologous to the light chain amino acid sequence of the antibody produced by a hybridoma deposited under the American Type Culture Collection (ATCC) Accession NO: PTA-11267. In other embodiments, the light chain comprises an amino acid sequence that is at least 90% homologous to the light chain amino acid sequence of the antibody produced by a hybridoma deposited under the American Type Culture Collection (ATCC) Accession NO: PTA-11267. In yet other embodiments, the light chain comprises an amino acid sequence that is at least 95% homologous to the light chain amino acid sequence of the antibody produced by a hybridoma deposited under the American Type Culture Collection (ATCC) Accession NO: PTA-11267. In other embodiments, the light chain may be 85%, 86%, 87%, 88%, 89%, 90%, 91%, 92%, 93%, 94%, 95%, 96%, 97%, 98% or 99% homologous to the light chain amino acid sequence of the antibody produced by a hybridoma deposited under the American Type Culture Collection (ATCC) Accession NO: PTA-11267.

Engineered antibodies provided herein include those in which modifications have been made to framework residues within VH and/or VL (e.g. to improve the properties of the antibody). Typically, such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis or PCR-mediated mutagenesis (e.g., "backmutated" from leucine to methionine). Such "backmutated" antibodies are also intended to be encompassed by the invention.

Another type of framework modification involves mutating one or more residues within the framework region, or even within one or more CDR regions, to remove T-cell epitopes to thereby reduce the potential immunogenicity of the antibody. This approach is also referred to as "deimmunization" and is described in further detail in U.S. Patent Publication No. 2003/0153043 by Carr et al.

In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an anti-191P4D12 antibody provided herein may be chemically modified (e.g., one or more chemical moieties can be attached to the antibody) or be modified to alter its glycosylation, again to alter one or more functional properties of the antibody. Each of these embodiments is described in further detail below.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the anti-191P4D12 antibody.

In another embodiment, the Fc hinge region of an antibody is mutated to decrease the biological half-life of the anti-191P4D12 antibody. More specifically, one or more amino acid mutations are introduced into the CH2-CH3 domain interface region of the Fc-hinge fragment such that the antibody has impaired Staphylococcal protein A (SpA) binding relative to native Fc-hinge domain SpA binding. This approach is described in further detail in U.S. Pat. No. 6,165,745 by Ward et al.

In another embodiment, the anti-191P4D12 antibody is modified to increase its biological half-life. Various approaches are possible. For example, mutations can be introduced as described in U.S. Pat. No. 6,277,375 to Ward. Alternatively, to increase the biological half-life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector function(s) of the antibody. For example, one or more amino acids selected from amino acid specific residues can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

Reactivity of the anti-191P4D12 antibodies with a 191P4D12-related protein can be established by a number of well-known means, including Western blot, immunoprecipitation, ELISA, and FACS analyses using, as appropriate, 191P4D12-related proteins, 191P4D12-expressing cells or extracts thereof. A 191P4D12 antibody or fragment thereof can be labeled with a detectable marker or conjugated to a second molecule. Suitable detectable markers include, but are not limited to, a radioisotope, a fluorescent compound, a bioluminescent compound, chemiluminescent compound, a metal chelator or an enzyme. Further, bi-specific antibodies specific for two or more 191P4D12 epitopes are generated using methods generally known in the art. Homodimeric antibodies can also be generated by cross-linking techniques known in the art (e.g., Wolff et al., Cancer Res. 53: 2560-2565).

In yet another specific embodiment, the anti-191P4D12 antibody provided herein is an antibody comprising heavy and light chain of an antibody designated Ha22-2(2,4)6.1. The heavy chain of Ha22-2(2,4)6.1 consists of the amino acid sequence ranging from $20^{th}$ E residue to the $466^{th}$ K residue of SEQ ID NO:7 and the light chain of Ha22-2(2, 4)6.1 consists of amino acid sequence ranging from $23^{rd}$ D residue to the $236^{th}$ C residue of SEQ ID NO:8 sequence.

The hybridoma producing the antibody designated Ha22-2(2,4)6.1 was sent (via Federal Express) to the American Type Culture Collection (ATCC), P.O. Box 1549, Manassas, VA 20108 on 18 Aug. 2010 and assigned Accession number PTA-11267.

5.3.2 Cytotoxic Agents (Drug Units)

In some embodiments, the ADC comprises an antibody or antigen binding fragment thereof conjugated to dolastatins or dolastatin peptidic analogs and derivatives, the auristatins (U.S. Pat. Nos. 5,635,483; 5,780,588). Dolastatins and auristatins have been shown to interfere with microtubule dynamics, GTP hydrolysis, and nuclear and cellular division (Woyke et al (2001) Antimicrob. Agents and Chemother. 45(12):3580-3584) and have anticancer (U.S. Pat. No. 5,663,149) and antifungal activity (Pettit et al (1998) Antimicrob. Agents Chemother. 42:2961-2965). The dolastatin or auristatin drug unit may be attached to the antibody through the N (amino) terminus or the C (carboxyl) terminus of the peptidic drug unit (WO 02/088172).

Exemplary auristatin embodiments include the N-terminus linked monomethylauristatin drug units DE and DF, disclosed in "Senter et al, Proceedings of the American Association for Cancer Research, Volume 45, Abstract Number 623, presented Mar. 28, 2004 and described in United States Patent Publication No. 2005/0238649, the disclosure of which is expressly incorporated by reference in its entirety.

In some embodiments, the auristatin is MMAE (wherein the wavy line indicates the covalent attachment to a linker of an antibody drug conjugate).

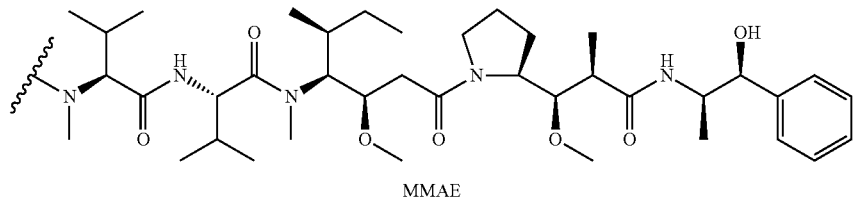 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@H](C)[C@@H](O)c1ccccc1)OC)C(C)C)C(C)C]

MMAE

In some embodiments, an exemplary embodiment comprising MMAE and a linker component (described further herein) has the following structure (wherein L presents the antibody and p ranges from 1 to 12):

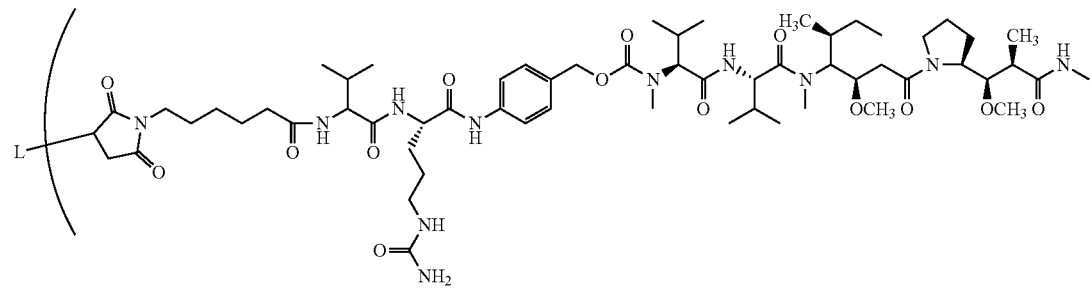

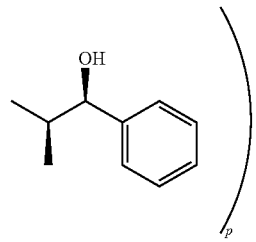

Typically, peptide-based drug units can be prepared by forming a peptide bond between two or more amino acids and/or peptide fragments. Such peptide bonds can be prepared, for example, according to the liquid phase synthesis method (see E. Schröder and K. Lake, "The Peptides", volume 1, pp 76-136, 1965, Academic Press) that is well-known in the field of peptide chemistry. The auristatin/dolastatin drug units may be prepared according to the methods of: U.S. Pat. Nos. 5,635,483; 5,780,588; Pettit et al (1989) J. Am. Chem. Soc. 111:5463-5465; Pettit et al (1998) Anti-Cancer Drug Design 13:243-277; Pettit, G. R., et al. Synthesis, 1996, 719-725; Pettit et al (1996) J. Chem. Soc. Perkin Trans. 1 5:859-863; and Doronina (2003) Nat Biotechnol 21(7):778-784.

5.3.3 Linkers

Typically, the antibody drug conjugates comprise a linker unit between the drug unit (e.g., MMAE) and the antibody unit (e.g., the anti-191P4D12 antibody or antigen binding fragment thereof). In some embodiments, the linker is cleavable under intracellular conditions, such that cleavage of the linker releases the drug unit from the antibody in the intracellular environment. In yet other embodiments, the linker unit is not cleavable and the drug is released, for example, by antibody degradation.

In some embodiments, the linker is cleavable by a cleaving agent that is present in the intracellular environment (e.g., within a lysosome or endosome or caveolae). The linker can be, e.g., a peptidyl linker that is cleaved by an intracellular peptidase or protease enzyme, including, but not limited to, a lysosomal or endosomal protease. In some embodiments, the peptidyl linker is at least two amino acids long or at least three amino acids long. Cleaving agents can include cathepsins B and D and plasmin, all of which are known to hydrolyze dipeptide drug derivatives resulting in the release of active drug inside target cells (see, e.g., Dubowchik and Walker, 1999, Pharm. Therapeutics 83:67-123). Most typical are peptidyl linkers that are cleavable by enzymes that are present in 191P4D12-expressing cells. For example, a peptidyl linker that is cleavable by the thiol-dependent protease cathepsin-B, which is highly expressed in cancerous tissue, can be used (e.g., a Phe-Leu or a Gly-Phe-Leu-Gly linker (SEQ ID NO:15)). Other examples of such linkers are described, e.g., in U.S. Pat. No. 6,214,345, incorporated herein by reference in its entirety and for all purposes. In a specific embodiment, the peptidyl linker cleavable by an intracellular protease is a Val-Cit linker or a Phe-Lys linker (see, e.g., U.S. Pat. No. 6,214,345, which describes the synthesis of doxorubicin with the Val-Cit linker). One advantage of using intracellular proteolytic release of the therapeutic agent is that the agent is typically attenuated when conjugated and the serum stabilities of the conjugates are typically high.

In other embodiments, the cleavable linker is pH-sensitive, i.e., sensitive to hydrolysis at certain pH values. Typically, the pH-sensitive linker hydrolyzable under acidic conditions. For example, an acid-labile linker that is hydrolyzable in the lysosome (e.g., a hydrazone, semicarbazone, thiosemicarbazone, cis-aconitic amide, orthoester, acetal, ketal, or the like) can be used. (See, e.g., U.S. Pat. Nos. 5,122,368; 5,824,805; 5,622,929; Dubowchik and Walker, 1999, Pharm. Therapeutics 83:67-123; Neville et al., 1989, Biol. Chem. 264:14653-14661.) Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, e.g., a thioether attached to the therapeutic agent via an acylhydrazone bond (see, e.g., U.S. Pat. No. 5,622,929).

In yet other embodiments, the linker is cleavable under reducing conditions (e.g., a disulfide linker). A variety of disulfide linkers are known in the art, including, for example, those that can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio) toluene), SPDB and SMPT. (See, e.g., Thorpe et al., 1987, Cancer Res. 47:5924-5931; Wawrzynczak et al., In *Immunoconjugates: Antibody Conjugates in Radioimagery and Therapy of Cancer* (C. W. Vogel ed., Oxford U. Press, 1987. See also U.S. Pat. No. 4,880,935.)

In yet other specific embodiments, the linker is a malonate linker (Johnson et al., 1995, Anticancer Res. 15:1387-93), a maleimidobenzoyl linker (Lau et al., 1995, Bioorg-Med-Chem. 3(10):1299-1304), or a 3'-N-amide analog (Lau et al., 1995, Bioorg-Med-Chem. 3(10):1305-12).

In yet other embodiments, the linker unit is not cleavable and the drug is released by antibody degradation. (See U.S. Publication No. 2005/0238649 incorporated by reference herein in its entirety and for all purposes).

Typically, the linker is not substantially sensitive to the extracellular environment. As used herein, "not substantially sensitive to the extracellular environment," in the context of a linker, means that no more than about 20%, typically no more than about 15%, more typically no more than about 10%, and even more typically no more than about 5%, no more than about 3%, or no more than about 1% of the linkers, in a sample of antibody drug conjugate, are cleaved when the antibody drug conjugate presents in an extracellular environment (e.g., in plasma). Whether a linker is not substantially sensitive to the extracellular environment can be determined, for example, by incubating with plasma the antibody-drug conjugate compound for a predetermined time period (e.g., 2, 4, 8, 16, or 24 hours) and then quantitating the amount of free drug present in the plasma.

In other non-mutually exclusive embodiments, the linker promotes cellular internalization. In certain embodiments, the linker promotes cellular internalization when conjugated to the therapeutic agent (i.e., in the milieu of the linker-therapeutic agent moiety of the antibody-drug conjugate compound as described herein). In yet other embodiments, the linker promotes cellular internalization when conjugated to both the auristatin compound and the anti-191P4D12 antibody or antigen binding fragment thereof.

A variety of exemplary linkers that can be used with the present compositions and methods are described in WO 2004-010957, U.S. Publication No. 2006/0074008, U.S. Publication No. 20050238649, and U.S. Publication No. 2006/0024317 (each of which is incorporated by reference herein in its entirety and for all purposes).

A "linker unit" (LU) is a bifunctional compound that can be used to link a drug unit and an antibody unit to form an antibody drug conjugate. In some embodiments, the linker unit has the formula:

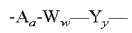

wherein: -A- is a stretcher unit,
a is 0 or 1,
each —W— is independently an amino acid unit,
w is an integer ranging from 0 to 12,
—Y— is a self-immolative spacer unit, and
y is 0, 1 or 2.

In some embodiments, a is 0 or 1, w is 0 or 1, and y is 0, 1 or 2. In some embodiments, a is 0 or 1, w is 0 or 1, and y is 0 or 1. In some embodiments, when w is 1 to 12, y is 1 or 2. In some embodiments, w is 2 to 12 and y is 1 or 2. In some embodiments, a is 1 and w and y are 0.

5.3.3.1 Stretcher Unit

The stretcher unit (A), when present, is capable of linking an antibody unit to an amino acid unit (—W—), if present, to a spacer unit (—Y—), if present; or to a drug unit (-D). Useful functional groups that can be present on an anti-191P4D12 antibody or an antigen binding fragment thereof (e.g. Ha22-2(2,4)6.1), either naturally or via chemical manipulation include, but are not limited to, sulfhydryl, amino, hydroxyl, the anomeric hydroxyl group of a carbohydrate, and carboxyl. Suitable functional groups are sulfhydryl and amino. In one example, sulfhydryl groups can be generated by reduction of the intramolecular disulfide bonds of an anti-191P4D12 antibody or an antigen binding fragment thereof. In another embodiment, sulfhydryl groups can be generated by reaction of an amino group of a lysine moiety of an anti-191P4D12 antibody or an antigen binding fragment with 2-iminothiolane (Traut's reagent) or other sulfhydryl generating reagents. In certain embodiments, the anti-191P4D12 antibody or antigen binding fragment thereof is a recombinant antibody and is engineered to carry one or more lysines. In certain other embodiments, the recombinant anti-191P4D12 antibody is engineered to carry additional sulfhydryl groups, e.g., additional cysteines.

In one embodiment, the stretcher unit forms a bond with a sulfur atom of the antibody unit. The sulfur atom can be derived from a sulfhydryl group of an antibody. Representative stretcher units of this embodiment are depicted within the square brackets of Formulas Ma and IIIb below, wherein L-, —W—, —Y—, -D, w and y are as defined above, and $R^{17}$ is selected from —$C_1$-$C_{10}$ alkylene-, $C_1$-$C_{10}$ alkenylene-, —$C_1$-$C_{10}$ alkynylene-, carbocyclo-, —O—($C_1$-$C_8$ alkylene)-, 0-($C_1$-$C_8$ alkenylene)-, —O—($C_1$-$C_8$ alkynylene)-, -arylene-, alkylene-arylene-, —$C_2$-$C_{10}$ alkenylene-arylene, —$C_2$-$C_{10}$ alkynylene-arylene, -arylene-$C_1$-$C_{10}$ alkylene-, -arylene-$C_2$-$C_{10}$ alkenylene-, -arylene-$C_2$-$C_{10}$ alkynylene-, —$C_1$-$C_{10}$ alkylene-(carbocyclo)-, —$C_2$-$C_{10}$ alkenylene-(carbocyclo)-, —$C_2$-$C_{10}$ alkynylene-(carbocyclo)-, -(carbocyclo)-$C_1$-$C_{10}$ alkylene-, -(carbocyclo)-$C_2$-$C_{10}$ alkenylene-, -(carbocyclo)-$C_2$-$C_{10}$ alkynylene, -heterocyclo-, alkylene-(heterocyclo)-, —$C_2$-$C_{10}$ alkenylene-(heterocyclo)-, —$C_2$-$C_{10}$ alkynylene-(heterocyclo)-, -(heterocyclo)-$C_1$-$C_{10}$ alkylene-, -(heterocyclo)-$C_2$-$C_{10}$ alkenylene-, -(heterocyclo)-$C_1$-$C_{10}$ alkynylene-, —(CH$_2$CH$_2$O)$_r$—, or —(CH$_2$CH$_2$O)$_r$—CH$_2$—, and r is an integer ranging from 1-10, wherein said alkyl, alkenyl, alkynyl, alkylene, alkenylene, alkynylene, aryl, carbocycle, carbocyclo, heterocyclo, and arylene radicals, whether alone or as part of another group, are optionally substituted. In some embodiments, said alkyl, alkenyl, alkynyl, alkylene, alkenylene, alkynylene, aryl, carbocycle, carbocyclo, heterocyclo, and arylene radicals, whether alone or as part of another group, are unsubstituted.

In some embodiments, $R^{17}$ is selected from —$C_1$-$C_{10}$ alkylene-, -carbocyclo-, —O—($C_1$-$C_8$ alkylene)-, -arylene-, —$C_1$-$C_{10}$ alkylene-arylene-, -arylene-$C_1$-$C_{10}$ alkylene-, alkylene-(carbocyclo)-, -(carbocyclo)-$C_1$-$C_{10}$ alkylene-, —$C_3$-$C_8$ heterocyclo-, —$C_1$-$C_{10}$ alkylene-(heterocyclo)-, -(heterocyclo)-$C_1$-$C_{10}$ alkylene-, —(CH$_2$CH$_2$O)$_r$—, and —(CH$_2$CH$_2$O)$_r$—CH$_2$—; and r is an integer ranging from 1-10, wherein said alkylene groups are unsubstituted and the remainder of the groups are optionally substituted.

It is to be understood from all the exemplary embodiments that even where not denoted expressly, 1 to 20 drug units can be linked to an antibody unit (p=1-20).

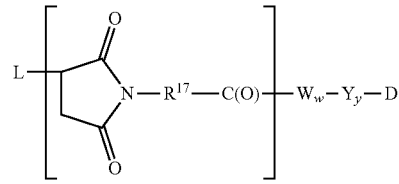

IIIa

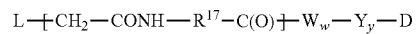

IIIb

An illustrative stretcher unit is that of Formula IIIa wherein $R^{17}$ is —(CH$_2$)$_5$—:

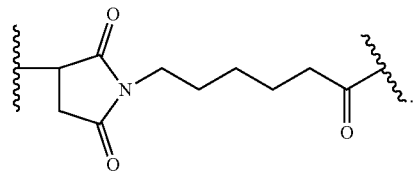 [SMILES: *C(=O)CCCCCN1C(=O)CC(*)C1=O]

Another illustrative stretcher unit is that of Formula IIIa wherein $R^{17}$ is —(CH$_2$CH$_2$O)$_r$—CH$_2$—; and r is 2:

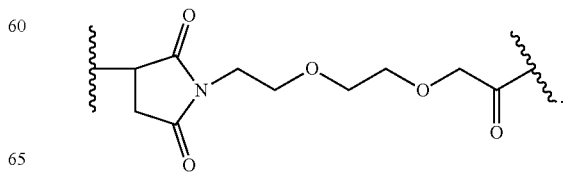

An illustrative Stretcher unit is that of Formula IIIa wherein $R^{17}$ is arylene- or arylene-$C_1$-$C_{10}$ alkylene-. In some embodiments, the aryl group is an unsubstituted phenyl group.

Still another illustrative stretcher unit is that of Formula IIIb wherein $R^{17}$ is —$(CH_2)_5$—:

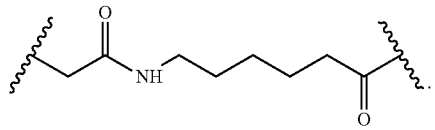 [SMILES: *CC(=O)NCCCCCC(*)=O]

In certain embodiments, the stretcher unit is linked to the antibody unit via a disulfide bond between a sulfur atom of the antibody unit and a sulfur atom of the stretcher unit. A representative stretcher unit of this embodiment is depicted within the square brackets of Formula IV, wherein $R^{17}$, L-, —W—, —Y—, -D, w and y are as defined above.

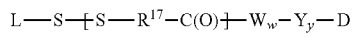
IV

It should be noted that throughout this application, the S moiety in the formula below refers to a sulfur atom of the antibody unit, unless otherwise indicated by context.

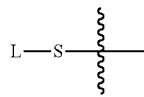

In certain of the structural descriptions of sulfur linked ADC herein the antibody is represented as "L". It could also be indicated as "Ab-S". The inclusion of "S" merely indicated the sulfur-linkage feature, and does not indicate that a particular sulfur atom bears multiple linker-drug moieties. The left parentheses of the structures using the "Ab-S" description may also be placed to the left of the sulfur atom, between Ab and S, which would be an equivalent description of the ADC of the invention described throughout herein.

In yet other embodiments, the stretcher contains a reactive site that can form a bond with a primary or secondary amino group of an antibody unit. Examples of these reactive sites include, but are not limited to, activated esters such as succinimide esters, 4 nitrophenyl esters, pentafluorophenyl esters, tetrafluorophenyl esters, anhydrides, acid chlorides, sulfonyl chlorides, isocyanates and isothiocyanates. Representative stretcher units of this embodiment are depicted within the square brackets of Formulas Va and Vb, wherein —$R^{17}$—, L-, —W—, —Y—, -D, w and y are as defined above;

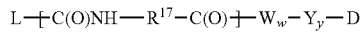
Va

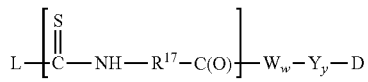
Vb

In some embodiments, the stretcher contains a reactive site that is reactive to a modified carbohydrate's (—CHO) group that can be present on an antibody unit. For example, a carbohydrate can be mildly oxidized using a reagent such as sodium periodate and the resulting (—CHO) unit of the oxidized carbohydrate can be condensed with a Stretcher that contains a functionality such as a hydrazide, an oxime, a primary or secondary amine, a hydrazine, a thiosemicarbazone, a hydrazine carboxylate, and an arylhydrazide such as those described by Kaneko et al., 1991, *Bioconjugate Chem.* 2:133-41. Representative stretcher units of this embodiment are depicted within the square brackets of Formulas VIa, VIb, and VIc, wherein —$R^{17}$—, L-, —W—, —Y—, -D, w and y are as defined as above.

VIa

VIb

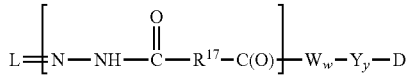
VIc

5.3.3.2 Amino Acid Unit

The amino acid unit (—W—), when present, links the stretcher unit to the spacer unit if the spacer unit is present, links the stretcher unit to the drug unit if the spacer unit is absent, and links the antibody unit to the drug unit if the stretcher unit and spacer unit are absent.

$W_w$— can be, for example, a monopeptide, dipeptide, tripeptide, tetrapeptide, pentapeptide, hexapeptide, heptapeptide, octapeptide, nonapeptide, decapeptide, undecapeptide or dodecapeptide unit. Each —W— unit independently has the formula denoted below in the square brackets, and w is an integer ranging from 0 to 12:

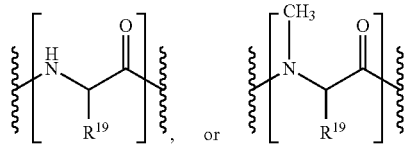

wherein $R^{19}$ is hydrogen, methyl, isopropyl, isobutyl, sec-butyl, benzyl, p-hydroxybenzyl, —$CH_2OH$, —$CH(OH)CH_3$, —$CH_2CH_2SCH_3$, —$CH_2CONH_2$, —$CH_2COOH$, —$CH_2CH_2CONH_2$, —$CH_2CH_2COOH$, —$(CH_2)_3NHC(=NH)NH_2$, —$(CH_2)_3NH_2$, —$(CH_2)_3NHCOCH_3$, —$(CH_2)_3NHCHO$, —$(CH_2)_4NHC(=NH)NH_2$, —$(CH_2)_4NH_2$, —$(CH_2)_4NHCOCH_3$, —$(CH_2)_4NHCHO$, —$(CH_2)_3NHCONH_2$, —$(CH_2)_4NHCONH_2$, —$CH_2CH_2CH(OH)CH_2NH_2$, 2-pyridylmethyl-, 3-pyridylmethyl-, 4-pyridylmethyl-, phenyl, cyclohexyl,

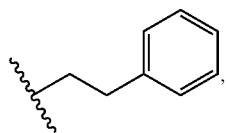
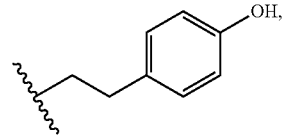

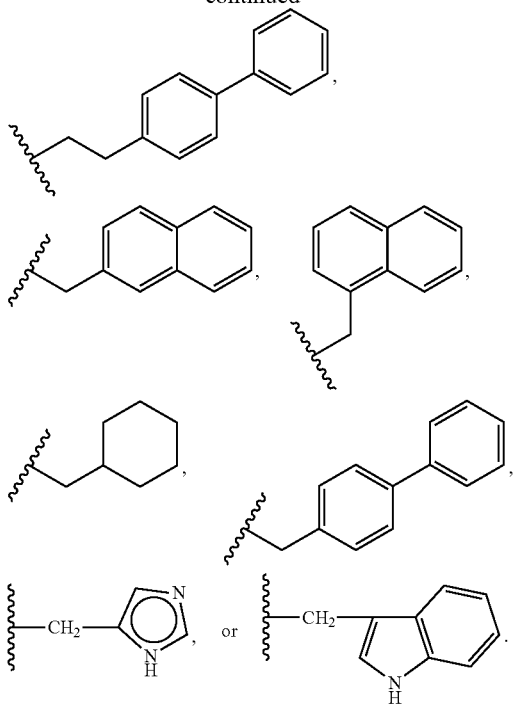

In some embodiments, the amino acid unit can be enzymatically cleaved by one or more enzymes, including a cancer or tumor-associated protease, to liberate the drug unit (-D), which in one embodiment is protonated in vivo upon release to provide a drug (D).

In certain embodiments, the amino acid unit comprises natural amino acids. In other embodiments, the amino acid unit comprises non-natural amino acids. Illustrative Ww units are represented by Formulas VII-IX below:

VII

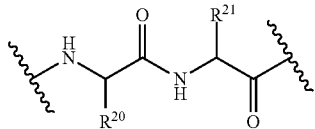

wherein $R^{20}$ and $R^{21}$ are as follows:

| $R^{20}$ | $R^{21}$ |
|---|---|
| Benzyl | $(CH_2)_4NH_2$; |
| methyl | $(CH_2)_4NH_2$; |
| isopropyl | $(CH_2)_4NH_2$; |
| isopropyl | $(CH_2)_3NHCONH_2$; |
| benzyl | $(CH_2)_3NHCONH_2$; |
| isobutyl | $(CH_2)_3NHCONH_2$; |
| sec-butyl | $(CH_2)_3NHCONH_2$; |
| —CH₂—(indole) | $(CH_2)_3NHCONH_2$; |
| benzyl | methyl; |
| benzyl | $(CH_2)_3NHC(=NH)NH_2$; |

VIII

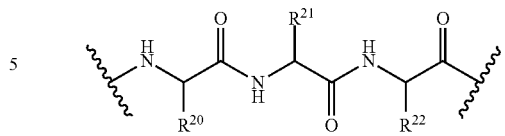

wherein $R^{20}$, $R^{21}$ and $R^{22}$ are as follows:

| $R^{20}$ | $R^{21}$ | $R^{22}$ |
|---|---|---|
| benzyl | benzyl | $(CH_2)_4NH_2$; |
| isopropyl | benzyl | $(CH_2)_4NH_2$; and |
| H | benzyl | $(CH_2)_4NH_2$; |

IX

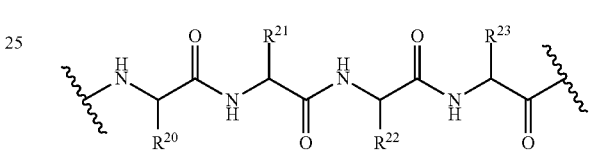

wherein $R^{20}$, $R^{21}$, $R^{22}$ and $R^{23}$ are as follows:

| $R^{20}$ | $R^{21}$ | $R^{22}$ | $R^{23}$ |
|---|---|---|---|
| H | benzyl | isobutyl | H; and |
| methyl | isobutyl | methyl | isobutyl. |

Exemplary amino acid units include, but are not limited to, units of Formula VII above where: $R^{20}$ is benzyl and $R^{21}$ is (CH₂)₄NH₂; $R^{20}$ is isopropyl and $R^{21}$ is —(CH₂)₄NH₂; or $R^{20}$ is isopropyl and $R^{21}$ is —(CH₂)₃NHCONH₂.

Another exemplary amino acid unit is a unit of Formula VIII wherein $R^{20}$ is benzyl, $R^{21}$ is benzyl, and $R^{22}$ is —(CH₂)₄NH₂.

Useful —W_w— units can be designed and optimized in their selectivity for enzymatic cleavage by a particular enzyme, for example, a tumor-associated protease. In one embodiment, a —W_w— unit is that whose cleavage is catalyzed by cathepsin B, C and D, or a plasmin protease.

In one embodiment, —W_w— is a dipeptide, tripeptide, tetrapeptide or pentapeptide. When $R^{19}$, $R^{20}$, $R^{21}$, $R^{22}$ or $R^{23}$ is other than hydrogen, the carbon atom to which $R^{19}$, $R^{20}$, $R^{21}$, $R^{22}$ or $R^{23}$ is attached is chiral.

Each carbon atom to which $R^{19}$, $R^{20}$, $R^{21}$, $R^{22}$ or $R^{23}$ is attached is independently in the (S) or (R) configuration.

In one specific embodiment, the amino acid unit is valine-citrulline (vc or Val-Cit). In another specific embodiment, the amino acid unit is phenylalanine-lysine (i.e., fk). In yet another specific embodiment, the amino acid unit is N-methylvaline-citrulline. In yet another specific embodiment, the amino acid unit is 5-aminovaleric acid, homo phenylalanine lysine, tetraisoquinolinecarboxylate lysine, cyclohexylalanine lysine, isonipecotic acid lysine, beta-alanine lysine, glycine serine valine glutamine and isonipecotic acid.

5.3.3.3 Spacer Unit

The spacer unit (—Y—), when present, links an amino acid unit to the drug unit when an amino acid unit is present. Alternately, the spacer unit links the stretcher unit to the drug unit when the amino acid unit is absent. The spacer unit also links the drug unit to the antibody unit when both the amino acid unit and stretcher unit are absent.

Spacer units are of two general types: non self-immolative or self-immolative. A non self-immolative spacer unit is one in which part or all of the spacer unit remains bound to the drug unit after cleavage, particularly enzymatic, of an amino acid unit from the antibody drug conjugate. Examples of a non self-immolative spacer unit include, but are not limited to a (glycine-glycine) spacer unit and a glycine spacer unit (both depicted in Scheme 1) (infra). When a conjugate containing a glycine-glycine spacer unit or a glycine Spacer unit undergoes enzymatic cleavage via an enzyme (e.g., a tumor-cell associated-protease, a cancer-cell-associated protease or a lymphocyte-associated protease), a glycine-glycine-drug unit or a glycine-drug unit is cleaved from L-Aa-Ww-. In one embodiment, an independent hydrolysis reaction takes place within the target cell, cleaving the glycine-drug unit bond and liberating the drug.

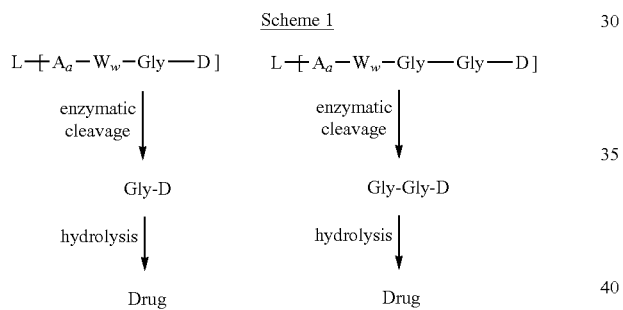

Scheme 1

In some embodiments, a non self-immolative spacer unit (—Y—) is -Gly-. In some embodiments, a non self-immolative spacer unit (—Y—) is -Gly-Gly-.

In one embodiment, the spacer unit is absent (—$Y_y$— where y=0).

Alternatively, an antibody drug conjugate containing a self-immolative spacer unit can release -D. As used herein, the term "self-immolative spacer" refers to a bifunctional chemical moiety that is capable of covalently linking together two spaced chemical moieties into a stable tripartite molecule. It will spontaneously separate from the second chemical moiety if its bond to the first moiety is cleaved.

In some embodiments, —$Y_y$— is a p-aminobenzyl alcohol (PAB) unit (see Schemes 2 and 3) whose phenylene portion is substituted with $Q_m$ wherein Q is —$C_1$-$C_8$ alkyl, —$C_1$-$C_8$ alkenyl, —$C_1$-$C_8$ alkynyl, —O—($C_1$-$C_8$ alkyl), —O—($C_1$-$C_8$ alkenyl), —O—($C_1$-$C_8$ alkynyl), -halogen, -nitro or -cyano; and m is an integer ranging from 0-4. The alkyl, alkenyl and alkynyl groups, whether alone or as part of another group, can be optionally substituted.

In some embodiments, —Y— is a PAB group that is linked to —$W_w$— via the amino nitrogen atom of the PAB group, and connected directly to -D via a carbonate, carbamate or ether group. Without being bound by any particular theory or mechanism, Scheme 2 depicts a possible mechanism of Drug release of a PAB group which is attached directly to -D via a carbamate or carbonate group as described by Toki et al., 2002, *J. Org. Chem.* 67:1866-1872.

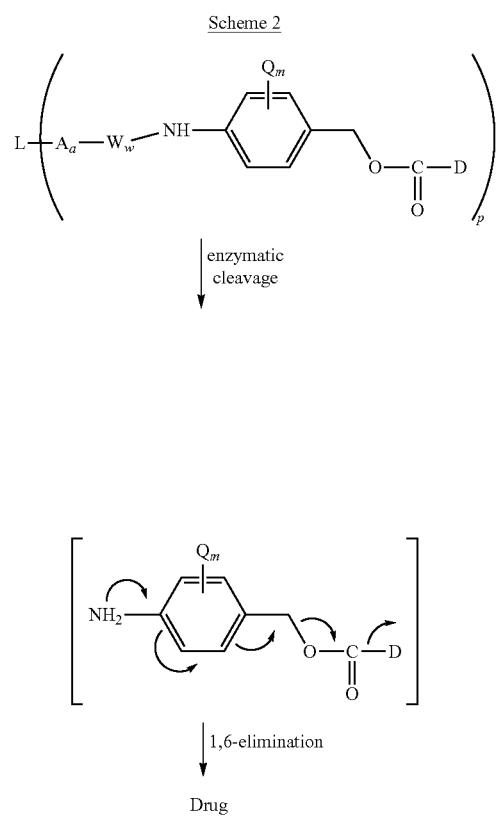

Scheme 2

In Scheme 2, Q is —$C_1$-$C_8$ alkyl, —$C_1$-$C_8$ alkenyl, —$C_1$-$C_8$ alkynyl, —O—($C_1$-$C_8$ alkyl), —O—($C_1$-$C_8$ alkenyl), —O—($C_1$-$C_8$ alkynyl), -halogen, -nitro or -cyano; m is an integer ranging from 0-4; and p ranges from 1 to about 20. The alkyl, alkenyl and alkynyl groups, whether alone or as part of another group, can be optionally substituted.

Without being bound by any particular theory or mechanism, Scheme 3 depicts a possible mechanism of drug release of a PAB group which is attached directly to -D via an ether or amine linkage, wherein D includes the oxygen or nitrogen group that is part of the drug unit.

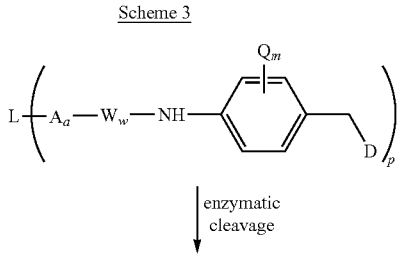

Scheme 3

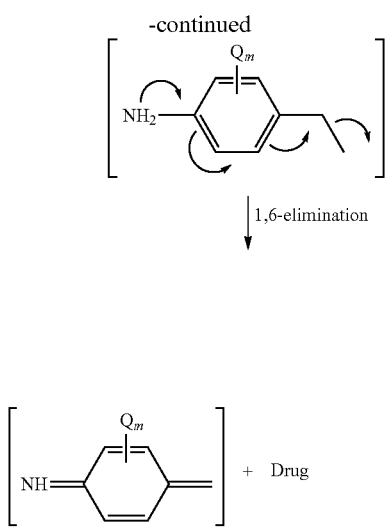

1,6-elimination

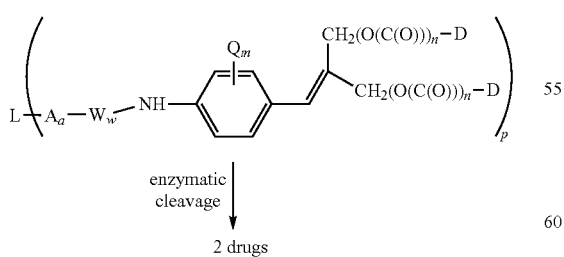
+ Drug

In Scheme 3, Q is —$C_1$-$C_8$ alkyl, —$C_1$-$C_8$ alkenyl, —$C_1$-$C_8$ alkynyl, —O—($C_1$-$C_8$ alkyl), —O—($C_1$-$C_8$ alkenyl), —O—($C_1$-$C_8$ alkynyl), -halogen, -nitro or -cyano; m is an integer ranging from 0-4; and p ranges from 1 to about 20. The alkyl, alkenyl and alkynyl groups, whether alone or as part of another group, can be optionally substituted.

Other examples of self-immolative spacers include, but are not limited to, aromatic compounds that are electronically similar to the PAB group such as 2-aminoimidazol-5-methanol derivatives (Hay et al., 1999, *Bioorg. Med. Chem. Lett.* 9:2237) and ortho or para-aminobenzylacetals. Spacers can be used that undergo cyclization upon amide bond hydrolysis, such as substituted and unsubstituted 4-aminobutyric acid amides (Rodrigues et al., 1995, *Chemistry Biology* 2:223), appropriately substituted bicyclo[2.2.1] and bicyclo[2.2.2] ring systems (Storm et al., 1972, *J. Amer. Chem. Soc.* 94:5815) and 2-aminophenylpropionic acid amides (Amsberry et al., 1990, *J. Org. Chem.* 55:5867). Elimination of amine-containing drugs that are substituted at the α-position of glycine (Kingsbury et al., 1984, 1 Med Chem. 27:1447) are also examples of self-immolative spacers.

In one embodiment, the spacer unit is a branched bis (hydroxymethyl)-styrene (BHMS) unit as depicted in Scheme 4, which can be used to incorporate and release multiple drugs.

Scheme 4

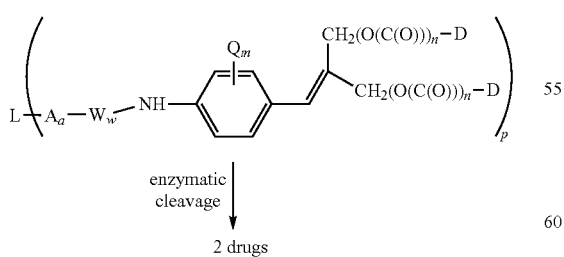

enzymatic cleavage 2 drugs

In Scheme 4, Q is —$C_1$-$C_8$ alkyl, —$C_1$-$C_8$ alkenyl, —$C_1$-$C_8$ alkynyl, —O—($C_1$-$C_8$ alkyl), —O—($C_1$-$C_8$ alkenyl), —O—($C_1$-$C_8$ alkynyl), -halogen, -nitro or -cyano; m is an integer ranging from 0-4; n is 0 or 1; and p ranges ranging from 1 to about 20. The alkyl, alkenyl and alkynyl groups, whether alone or as part of another group, can be optionally substituted.

In some embodiments, the -D units are the same. In yet another embodiment, the -D moieties are different.

In one aspect, spacer units (—$Y_y$—) are represented by Formulas X-XII:

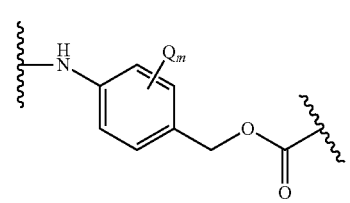

wherein Q is —$C_1$-$C_8$ alkyl, —$C_1$-$C_8$ alkenyl, —$C_1$-$C_8$ alkynyl, —O—($C_1$-$C_8$ alkyl), —O—($C_1$-$C_8$ alkenyl), —O—($C_1$-$C_8$ alkynyl), -halogen, -nitro or -cyano; and m is an integer ranging from 0-4. The alkyl, alkenyl and alkynyl groups, whether alone or as part of another group, can be optionally substituted.

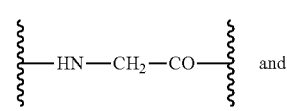

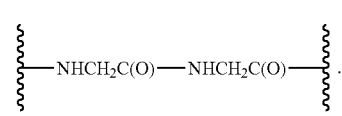

Embodiments of the Formula I and II comprising antibody-drug conjugate compounds can include:

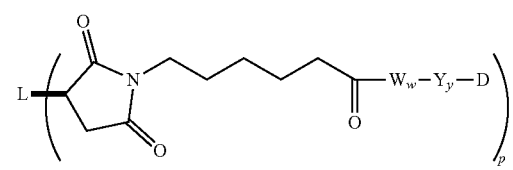

wherein w and y are each 0, 1 or 2, and,

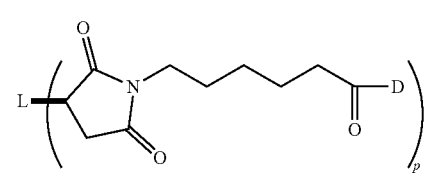

wherein w and y are each 0,

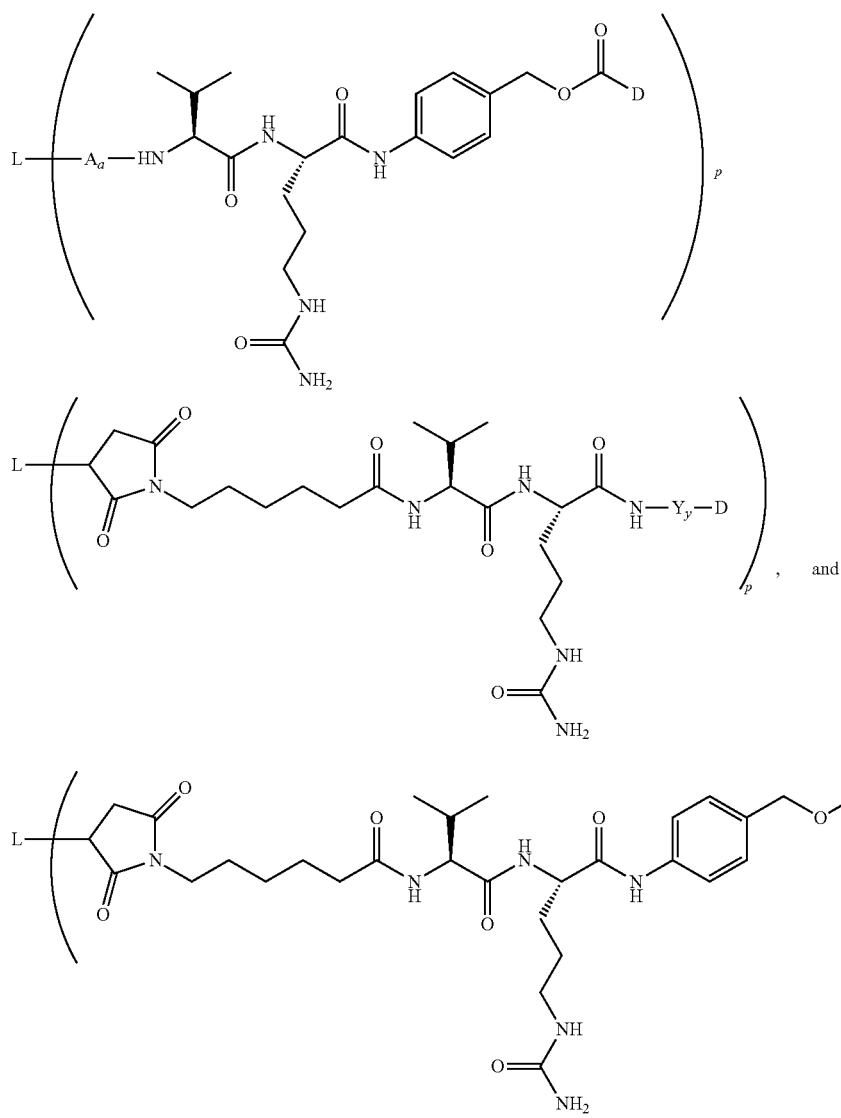

5.3.3.4 Drug Loading

Drug loading is represented by p and is the average number of drug units per antibody in a molecule. Drug loading may range from 1 to 20 drug units (D) per antibody. The ADCs provided herein include collections of antibodies or antigen binding fragments conjugated with a range of drug units, e.g., from 1 to 20. The average number of drug units per antibody in preparations of ADC from conjugation reactions may be characterized by conventional means such as mass spectroscopy and, ELISA assay. The quantitative distribution of ADC in terms of p may also be determined. In some instances, separation, purification, and characterization of homogeneous ADC where p is a certain value from ADC with other drug loadings may be achieved by means such as electrophoresis.

In certain embodiments, the drug loading for an ADC provided herein ranges from 1 to 20. In certain embodiments, the drug loading for an ADC provided herein ranges from 1 to 18. In certain embodiments, the drug loading for an ADC provided herein ranges from 1 to 15. In certain embodiments, the drug loading for an ADC provided herein ranges from 1 to 12. In certain embodiments, the drug loading for an ADC provided herein ranges from 1 to 10. In certain embodiments, the drug loading for an ADC provided herein ranges from 1 to 9. In certain embodiments, the drug loading for an ADC provided herein ranges from 1 to 8. In certain embodiments, the drug loading for an ADC provided herein ranges from 1 to 7. In certain embodiments, the drug loading for an ADC provided herein ranges from 1 to 6. In certain embodiments, the drug loading for an ADC provided herein ranges from 1 to 5. In certain embodiments, the drug loading for an ADC provided herein ranges from 1 to 4. In certain embodiments, the drug loading for an ADC provided herein ranges from 1 to 3. In certain embodiments, the drug loading for an ADC provided herein ranges from 2 to 12. In certain embodiments, the drug loading for an ADC provided herein ranges from 2 to 10. In certain embodiments, the drug loading for an ADC provided herein ranges from 2 to 9. In certain embodiments, the drug loading for an ADC provided herein ranges from 2 to 8. In certain embodiments, the drug loading for an ADC provided herein ranges from 2 to 7. In certain embodiments, the drug loading for an ADC provided herein ranges from 2 to 6. In certain embodiments, the drug loading for an ADC provided herein ranges from 2 to 5.

In certain embodiments, the drug loading for an ADC provided herein ranges from 1 to about 8; from about 2 to about 6; from about 3 to about 5; from about 3 to about 4; from about 3.1 to about 3.9; from about 3.2 to about 3.8; from about 3.2 to about 3.7; from about 3.2 to about 3.6; from about 3.3 to about 3.8; or from about 3.3 to about 3.7.

In certain embodiments, fewer than the theoretical maximum of drug units are conjugated to an antibody during a conjugation reaction. An antibody may contain, for example, lysine residues that do not react with the drug-linker intermediate or linker reagent. Generally, antibodies do not contain many free and reactive cysteine thiol groups which may be linked to a drug unit; indeed most cysteine thiol residues in antibodies exist as disulfide bridges. In certain embodiments, an antibody may be reduced with a reducing agent such as dithiothreitol (DTT) or tricarbonylethylphosphine (TCEP), under partial or total reducing conditions, to generate reactive cysteine thiol groups. In certain embodiments, an antibody is subjected to denaturing conditions to reveal reactive nucleophilic groups such as lysine or cysteine. In some embodiments, the linker unit or a drug unit is conjugated via a lysine residue on the antibody unit. In some embodiments, the linker unit or a drug unit is conjugated via a cysteine residue on the antibody unit.

In some embodiments, the amino acid that attaches to a linker unit or a drug unit is in the heavy chain of an antibody or antigen binding fragment thereof. In some embodiments, the amino acid that attaches to a linker unit or a drug unit is in the light chain of an antibody or antigen binding fragment thereof. In some embodiments, the amino acid that attaches to a linker unit or a drug unit is in the hinge region of an antibody or antigen binding fragment thereof. In some embodiments, the amino acid that attaches to a linker unit or a drug unit is in the Fc region of an antibody or antigen binding fragment thereof. In other embodiments, the amino acid that attaches to a linker unit or a drug unit is in the constant region (e.g., $CH_1$, $CH_2$, or $CH_3$ of a heavy chain, or $CH_1$ of a light chain) of an antibody or antigen binding fragment thereof. In yet other embodiments, the amino acid that attaches to a linker unit or a drug unit is in the VH framework regions of an antibody or antigen binding fragment thereof. In yet other embodiments, the amino acid that attaches to a linker unit or a drug unit is in the VL framework regions of an antibody or antigen binding fragment thereof.

The loading (drug/antibody ratio) of an ADC may be controlled in different ways, e.g., by: (i) limiting the molar excess of drug-linker intermediate or linker reagent relative to antibody, (ii) limiting the conjugation reaction time or temperature, (iii) partial or limiting reductive conditions for cysteine thiol modification, (iv) engineering by recombinant techniques the amino acid sequence of the antibody such that the number and position of cysteine residues is modified for control of the number and/or position of linker-drug attachments (such as thioMab or thioFab prepared as disclosed herein and in WO2006/034488 (herein incorporated by reference in its entirety)).

It is to be understood that where more than one nucleophilic group reacts with a drug-linker intermediate or linker reagent followed by drug unit reagent, then the resulting product is a mixture of ADC compounds with a distribution of one or more drug unit attached to an antibody unit. The average number of drugs per antibody may be calculated from the mixture by a dual ELISA antibody assay, which is specific for antibody and specific for the drug. Individual ADC molecules may be identified in the mixture by mass spectroscopy and separated by HPLC, e.g. hydrophobic interaction chromatography (see, e.g., Hamblett, K. J., et al. "Effect of drug loading on the pharmacology, pharmacokinetics, and toxicity of an anti-CD30 antibody-drug conjugate," Abstract No. 624, American Association for Cancer Research, 2004 Annual Meeting, Mar. 27-31, 2004, Proceedings of the AACR, Volume 45, March 2004; Alley, S. C., et al. "Controlling the location of drug attachment in antibody-drug conjugates," Abstract No. 627, American Association for Cancer Research, 2004 Annual Meeting, Mar. 27-31, 2004, Proceedings of the AACR, Volume 45, March 2004). In certain embodiments, a homogeneous ADC with a single loading value may be isolated from the conjugation mixture by electrophoresis or chromatography.

5.3.3 Preparation of the Antibody Drug Conjugates

The generation of antibody drug conjugates provided herein can be accomplished by any technique known to the skilled artisan. Briefly, the antibody drug conjugates comprise an anti-191P4D12 antibody or antigen binding fragment thereof as the antibody unit, a drug, and optionally a linker that joins the drug and the binding agent. In some embodiments, the antibody is anti-191P4D12 antibody comprising the CDR regions of an antibody designated Ha22-2 (2,4)6.1 described above. In a specific embodiment, the antibody is anti-191P4D12 antibody comprising heavy and light chain variable regions of an antibody designated Ha22-2(2,4)6.1 described above. In a specific embodiment, the antibody is anti-191P4D12 antibody comprising heavy and light chain of an antibody designated Ha22-2(2,4)6.1 described above.

A number of different reactions are available for covalent attachment of drugs and/or linkers to binding agents. This is often accomplished by reaction of the amino acid residues of the binding agent, e.g., antibody molecule, including the amine groups of lysine, the free carboxylic acid groups of glutamic and aspartic acid, the sulfhydryl groups of cysteine and the various moieties of the aromatic amino acids. One of the most commonly used non-specific methods of covalent attachment is the carbodiimide reaction to link a carboxy (or amino) group of a compound to amino (or carboxy) groups of the antibody. Additionally, bifunctional agents such as dialdehydes or imidoesters have been used to link the amino group of a compound to amino groups of an antibody molecule. Also available for attachment of drugs to binding agents is the Schiff base reaction. This method involves the periodate oxidation of a drug that contains glycol or hydroxy groups, thus forming an aldehyde which is then reacted with the binding agent. Attachment occurs via formation of a Schiff base with amino groups of the binding agent. Isothiocyanates can also be used as coupling agents for covalently attaching drugs to binding agents. Other techniques are known to the skilled artisan and within the scope of the present invention.

In certain embodiments, an intermediate, which is the precursor of the linker, is reacted with the drug under appropriate conditions. In certain embodiments, reactive groups are used on the drug and/or the intermediate. The product of the reaction between the drug and the intermediate, or the derivatized drug, is subsequently reacted with the anti-191P4D12 antibody under appropriate conditions.

Each of the particular units of the antibody drug conjugates is described in more detail herein. The synthesis and structure of exemplary linker units, stretcher units, amino acid units, self-immolative spacer unit, and drug units are also described in U.S. Patent Application Publication Nos. 2003-0083263, 2005-0238649 and 2005-0009751, each of which is incorporated herein by reference in its entirety and for all purposes.

An exemplary method for generating the antibody drug conjugates provided herein is described briefly below.

The Ha22-2(2,4)6.1 antibody is conjugated to an auristatin derivative MMAE using a vc (Val-Cit) linker described herein to create the antibody drug conjugate (ADC) (designated as AGS-22M6E) using the following protocols. The conjugation of the vc (Val-Cit) linker to the MMAE (Seattle Genetics, Inc., Seattle, WA) was completed using the general method set forth in Scheme 5 below to create the cytotoxic vcMMAE (see, U.S. Pat. No. 7,659,241).

Scheme 5 General Method for Synthesis of vcMMAE

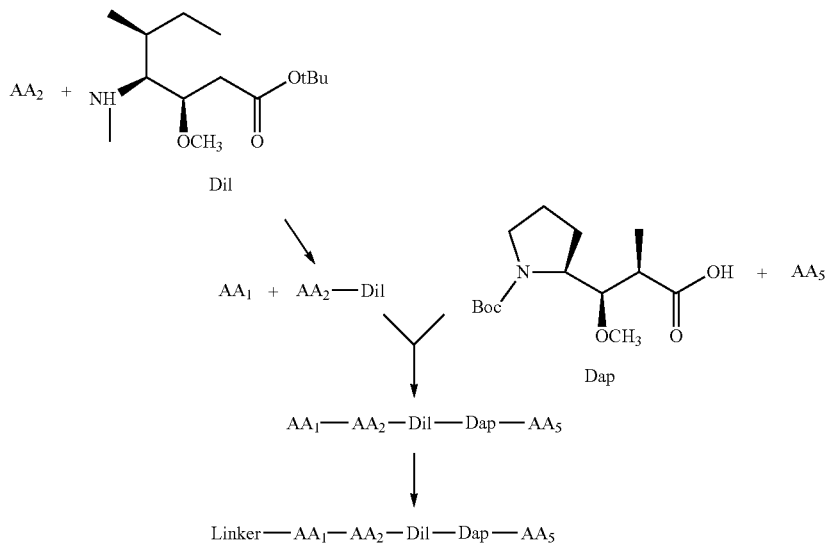

Where:
  AA1=Amino Acid 1
  AA2=Amino Acid 2
  AA5=Amino Acid 5
  DIL=Dolaisoleuine
  DAP=Dolaproine
  Linker=Val-Cit (vc)

Next, the antibody drug conjugate AGS-22M6E was made using the following protocols.

Briefly, a 15 mg/mL solution of the Ha22-2(2,4)6.1 antibody in 10 mM acetate at pH 5.0, 1% sorbitol, 3% L-arginine is added with a 20% volume of 0.1 M TrisCl at pH 8.4, 25 mM EDTA and 750 mM NaCl to adjust the pH of the solution to 7.5, 5 mM EDTA and 150 mM sodium chloride. The antibody is then partially reduced by adding 2.3 molar equivalents of TCEP (relative to moles of MAb) and then stirred at 37° C. for 2 hours. The partially reduced antibody solution is then cooled to 5° C. and 4.4 molar equivalents of vcMMAE (relative to moles of antibody) are added as a 6% (v/v) solution of DMSO. The mixture is stirred for 60 minutes at 5° C., then for 15 additional minutes following the addition of 1 molar equivalents of N-acetylcysteine relative to vcMMAE. Excess quenched vcMMAE and other reaction components are removed by ultrafiltration/diafiltration of the antibody drug conjugate (ADC) with 10 volumes of 20 mM histidine, pH 6.0.

The resulting antibody drug conjugate AGS-22M6E has the following formula:

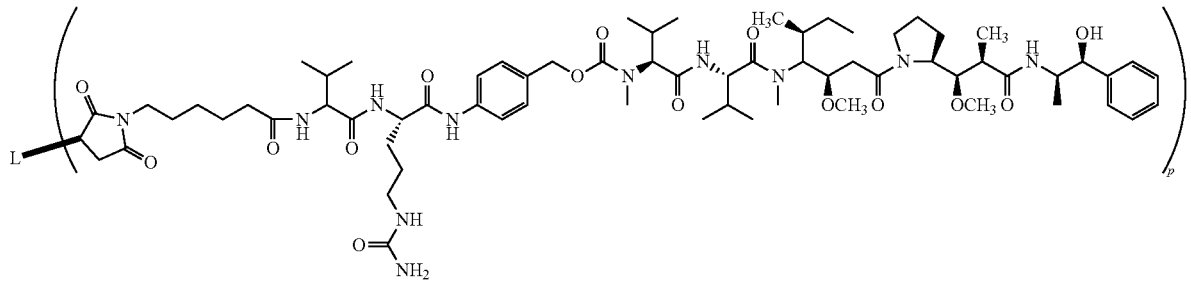

wherein L is Ha22-2(2,4)6.1 and p is from 1 to 20.

5.4 Methods of Using the Pharmaceutical Compositions

In one aspect, provided herein is a method of preventing or treating a disease or disorder in a subject comprising administering to the subject an effective amount of the pharmaceutical composition provided herein. In some embodiments, the subject is a human subject.

In some embodiments, the disease or disorder is cancer. In some embodiments, the cancer has tumor cells expressing 191P4D12. In some embodiments, the cancer is a solid tumor. In some embodiments, the cancer is colon cancer, pancreatic cancer, ovarian cancer, lung cancer, bladder cancer, breast cancer, esophageal cancer, head cancer, or neck cancer. In some embodiments, the cancer is colon cancer. In some embodiments, the cancer is pancreatic cancer. In some embodiments, the cancer is ovarian cancer. In some embodiments, the cancer is lung cancer. In some embodiments, the lung cancer is non-small cell lung cancer. In some embodiments, the cancer is bladder cancer. In some embodiments, the cancer is advanced bladder cancer. In some embodiments, the cancer is metastatic bladder cancer. In some embodiments, the cancer is urothelial cancer. In some embodiments, the cancer is advanced urothelial cancer. In some embodiments, the cancer is breast cancer. In some embodiments, the cancer is esophageal cancer. In some embodiments, the cancer is head cancer. In some embodiments, the cancer is neck cancer. In some embodiments, the cancer is advanced or metastatic cancer.

In some embodiments, treatment with the pharmaceutical composition provided herein is indicated for subjects who have received one or more rounds of chemotherapy. Alternatively, the pharmaceutical composition provided herein is combined with a chemotherapeutic or radiation regimen for subjects who have not received chemotherapeutic treatment. Additionally, in some embodiments, use of the pharmaceutical composition provided herein can enable the use of reduced dosages of concomitant chemotherapy, particularly for subjects who do not tolerate the toxicity of the chemotherapeutic agent very well. In some embodiments, the pharmaceutical composition disclosed herein is administered to patients with metastatic urothelial cancer who have shown disease progression or relapse during or after treatment with an immune checkpoint inhibitor.

Methods of administering the pharmaceutical composition provided herein include, but are not limited to, parenteral administration (e.g., intradermal, intramuscular, intraperitoneal, intravenous and subcutaneous), epidural, and mucosal (e.g., intranasal and oral routes). In a specific embodiment, the pharmaceutical composition provided herein is administered intranasally, intramuscularly, intravenously, or subcutaneously. The pharmaceutical composition provided herein may be administered by any convenient route, for example by infusion or bolus injection, by absorption through epithelial or mucocutaneous linings (e.g., oral mucosa, intranasal mucosa, rectal and intestinal mucosa, etc.) and may be administered together with other biologically active agents. Administration can be systemic or local. In addition, pulmonary administration can also be employed, e.g., by use of an inhaler or nebulizer, and formulation with an aerosolizing agent. See, e.g., U.S. Pat. Nos. 6,019,968, 5,985,320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entirety.

In a specific embodiment, it may be desirable to administer the pharmaceutical composition provided herein locally to the area in need of treatment. This may be achieved by, for example, and not by way of limitation, local infusion, by topical administration (e.g., by intranasal spray), by injection, or by means of an implant, said implant being of a porous, non-porous, or gelatinous material, including membranes, such as sialastic membranes, or fibers. In some embodiments, when administering the pharmaceutical composition provided herein, care must be taken to use materials to which the antibody drug conjugate provided herein does not absorb.

In another embodiment, the pharmaceutical composition provided herein can be delivered in a vesicle, in particular a liposome (see Langer, 1990, Science 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

In another embodiment, the pharmaceutical composition provided herein can be delivered in a controlled release or sustained release system. In one embodiment, a pump may be used to achieve controlled or sustained release (see Langer, supra; Sefton, 1987, CRC Crit. Ref. Biomed. Eng. 14:20; Buchwald et al., 1980, Surgery 88:507; Saudek et al., 1989, N. Engl. J. Med. 321:574). In another embodiment, polymeric materials can be used to achieve controlled or sustained release of a prophylactic or therapeutic agent (e.g., an antibody drug conjugate provided herein) or a pharmaceutical composition provided herein (see e.g., Medical Applications of Controlled Release, Langer and Wise (eds.), CRC Pres., Boca Raton, Florida (1974); Controlled Drug Bioavailability, Drug Product Design and Performance, Smolen and Ball (eds.), Wiley, New York (1984); Ranger and Peppas, 1983, J., Macromol. Sci. Rev. Macromol. Chem. 23:61; see also Levy et al., 1985, Science 228:190; During et al., 1989, Ann. Neurol. 25:351; Howard et al., 1989, J. Neurosurg. 7 1:105); U.S. Pat. Nos. 5,679,377; 5,916,597; 5,912,015; 5,989,463; 5,128,326; PCT Publication No. WO 99/15154; and PCT Publication No. WO 99/20253. Examples of polymers used in sustained release formulations include, but are not limited to, poly(-hydroxy ethyl methacrylate), poly(methyl methacrylate), poly (acrylic acid), poly(ethylene-co-vinyl acetate), poly(methacrylic acid), polyglycolides (PLG), polyanhydrides, poly (N-vinyl pyrrolidone), poly(vinyl alcohol), polyacrylamide, poly(ethylene glycol), polylactides (PLA), poly(lactide-co-glycolides) (PLGA), and polyorthoesters. In an embodiment, the polymer used in a sustained release formulation is inert, free of leachable impurities, stable on storage, sterile, and biodegradable. In yet another embodiment, a controlled or sustained release system can be placed in proximity of the therapeutic target, i.e., the nasal passages or lungs, thus requiring only a fraction of the systemic dose (see, e.g., Goodson, in Medical Applications of Controlled Release, supra, vol. 2, pp. 115-138 (1984)). Controlled release systems are discussed in the review by Langer (1990, Science 249:1527-1533). Any technique known to one of skill in the art can be used to produce sustained release formulations comprising the antibody drug conjugate or pharmaceutical composition provided herein. See, e.g., U.S. Pat. No. 4,526,938, PCT publication WO 91/05548, PCT publication WO 96/20698, Ning et al., 1996, "Intratumoral Radioimmunotherapy of a Human Colon Cancer Xenograft Using a Sustained-Release Gel," Radiotherapy & Oncology 39:179-189, Song et al., 1995, "Antibody Mediated Lung Targeting of Long-Circulating Emulsions," PDA Journal of Pharmaceutical Science & Technology 50:372-397, Cleek et al., 1997, "Biodegradable Polymeric Carriers for a bFGF Antibody for Cardiovascular Application," Pro. Int'l. Symp. Control. Rel. Bioact. Mater. 24:853-854, and Lam et al., 1997, "Microencapsulation of Recombinant Humanized Monoclonal Antibody for Local Delivery," Proc. Int'l. Symp. Control Rel. Bioact. Mater. 24:759-760, each of which is incorporated herein by reference in their entirety.

The amount of the pharmaceutical composition provided herein that will be effective in the prevention and/or treatment of a cancer can be determined by standard clinical techniques. In addition, in vitro assays may optionally be employed to help identify optimal dosage ranges. The precise dose to be employed will also depend on the route of administration, and the seriousness of a disease or disorder, and should be decided according to the judgment of the practitioner and each subject's circumstances. Effective doses may be extrapolated from dose-response curves derived from in vitro or animal model test systems.

In certain embodiments, therapeutic methods provided herein contemplate the administration of a single ADC as well as combinations, or cocktails, of different ADCs comprising different anti-191P4D12 antibodies or different drug units. In some embodiments, such methods have certain advantages because, e.g., they contain ADCs that target different epitopes, exploit different effector mechanisms or combine directly cytotoxic antibodies with antibodies that rely on immune effector functionality. Such methods can exhibit synergistic therapeutic effects. In addition, the pharmaceutical composition provided herein can be administered concomitantly with other therapeutic modalities, including but not limited to various chemotherapeutic and biologic agents, androgen-blockers, immune modulators (e.g., IL-2, GM-CSF), surgery or radiation.

In one embodiment, there is synergy when tumors, including human tumors, are treated with the pharmaceutical composition provided herein in conjunction with chemotherapeutic agents or radiation or combinations thereof.

The method for inhibiting growth of tumor cells using the pharmaceutical composition provided herein and a combination of chemotherapy or radiation or both comprises administering the present pharmaceutical composition before, during, or after commencing chemotherapy or radiation therapy, as well as any combination thereof (i.e. before and during, before and after, during and after, or before, during, and after commencing the chemotherapy and/or radiation therapy). Depending on the treatment protocol and the specific patient needs, the method is performed in a manner that will provide the most efficacious treatment and ultimately prolong the life of the patient.

The administration of chemotherapeutic agents can be accomplished in a variety of ways including systemically by the parenteral and enteral routes. In one embodiment, the chemotherapeutic agent is administered separately. Particular examples of chemotherapeutic agents or chemotherapy include cisplatin, dacarbazine (DTIC), dactinomycin, mechlorethamine (nitrogen mustard), streptozocin, cyclophosphamide, carmustine (BCNU), lomustine (CCNU), doxorubicin (adriamycin), daunorubicin, procarbazine, mitomycin, cytarabine, etoposide, methotrexate, 5-fluorouracil, vinblastine, vincristine, bleomycin, paclitaxel (taxol), docetaxel (taxotere), aldesleukin, asparaginase, busulfan, carboplatin, cladribine, dacarbazine, floxuridine, fludarabine, hydroxyurea, ifosfamide, interferon alpha, leuprolide, megestrol, melphalan, mercaptopurine, plicamycin, mitotane, pegaspargase, pentostatin, pipobroman, plicamycin, streptozocin, tamoxifen, teniposide, testolactone, thioguanine, thiotepa, uracil mustard, vinorelbine, gemcitabine, chlorambucil, taxol and combinations thereof.

The source of radiation, used in combination with the pharmaceutical composition provided herein, can be either external or internal to the patient being treated. When the source is external to the patient, the therapy is known as external beam radiation therapy (EBRT). When the source of radiation is internal to the patient, the treatment is called brachytherapy (BT).

The above described therapeutic regimens may be further combined with additional cancer treating agents and/or regimes, for example additional chemotherapy, cancer vaccines, signal transduction inhibitors, agents useful in treating abnormal cell growth or cancer, antibodies (e.g. Anti-CTLA-4 antibodies as described in WO/2005/092380 (Pfizer)) or other ligands that inhibit tumor growth by binding to IGF-1R, and cytokines.

When the mammal is subjected to additional chemotherapy, chemotherapeutic agents described above may be used. Additionally, growth factor inhibitors, biological response modifiers, anti-hormonal therapy, selective estrogen receptor modulators (SERMs), angiogenesis inhibitors, and anti-androgens may be used. For example, anti-hormones, for example anti-estrogens such as Nolvadex (tamoxifen) or, anti-androgens such as Casodex (4'-cyano-3-(4-fluorophenylsulphonyl)-2-hydroxy-2-methyl-3-'-(trifluoromethyl)propionanilide) may be used.

In some embodiments, the pharmaceutical provided herein in used in combination with a second therapeutic agent, e.g., for treating a cancer.

In some embodiments, the second therapeutic agent is an immune checkpoint inhibitor. As used herein, the term "immune checkpoint inhibitor" or "checkpoint inhibitor" refers to molecules that totally or partially reduce, inhibit, interfere with or modulate one or more checkpoint proteins. Without being limited by a particular theory, checkpoint proteins regulate T-cell activation or function. Numerous checkpoint proteins are known, such as CTLA-4 and its ligands CD80 and CD86; and PD-1 with its ligands PD-L1 and PD-L2 (Pardoll, Nature Reviews Cancer, 2012, 12, 252-264). These proteins appear responsible for co-stimulatory or inhibitory interactions of T-cell responses. Immune checkpoint proteins appear to regulate and maintain self-tolerance and the duration and amplitude of physiological immune responses. Immune checkpoint inhibitors include antibodies or are derived from antibodies.

In one embodiment, the checkpoint inhibitor is a CTLA-4 inhibitor. In one embodiment, the CTLA-4 inhibitor is an anti-CTLA-4 antibody. Examples of anti-CTLA-4 antibodies include, but are not limited to, those described in U.S. Pat. Nos. 5,811,097; 5,811,097; 5,855,887; 6,051,227; 6,207,157; 6,682,736; 6,984,720; and 7,605,238, all of which are incorporated herein in their entireties. In one embodiment, the anti-CTLA-4 antibody is tremelimumab (also known as ticilimumab or CP-675,206). In another embodiment, the anti-CTLA-4 antibody is ipilimumab (also known as MDX-010 or MDX-101). Ipilimumab is a fully human monoclonal IgG antibody that binds to CTLA-4. Ipilimumab is marketed under the trade name Yervoy™.

In one embodiment, the checkpoint inhibitor is a PD-1/PD-L1 inhibitor. Examples of PD-1/PD-L1 inhibitors include, but are not limited to, those described in U.S. Pat. Nos. 7,488,802; 7,943,743; 8,008,449; 8,168,757; 8,217, 149, and PCT Patent Application Publication Nos. WO2003042402, WO2008156712, WO2010089411, WO2010036959, WO2011066342, WO2011159877, WO2011082400, and WO2011161699, all of which are incorporated herein in their entireties.

In one embodiment, the checkpoint inhibitor is a PD-1 inhibitor. In one embodiment, the PD-1 inhibitor is an anti-PD-1 antibody. In one embodiment, the anti-PD-1 antibody is BGB-A317, nivolumab (also known as ONO-4538, BMS-936558, or MDX1106) or pembrolizumab (also known as MK-3475, SCH 900475, or lambrolizumab). In one embodiment, the anti-PD-1 antibody is nivolumab. Nivolumab is a human IgG4 anti-PD-1 monoclonal antibody, and is marketed under the trade name Opdivo™. In another embodiment, the anti-PD-1 antibody is pembrolizumab. Pembrolizumab is a humanized monoclonal IgG4 antibody and is marketed under the trade name Keytruda™. In yet another embodiment, the anti-PD-1 antibody is CT-011, a humanized antibody. CT-011 administered alone has failed to show response in treating acute myeloid leukemia (AML) at relapse. In yet another embodiment, the anti-PD-1 antibody is AMP-224, a fusion protein. In another embodiment, the PD-1 antibody is BGB-A317. BGB-A317 is a monoclonal antibody in which the ability to bind Fc gamma receptor I is specifically engineered out, and which has a unique binding signature to PD-1 with high affinity and superior target specificity.

In one embodiment, the checkpoint inhibitor is a PD-L1 inhibitor. In one embodiment, the PD-L1 inhibitor is an anti-PD-L1 antibody. In one embodiment, the anti-PD-L1 antibody is MEDI4736 (durvalumab). In another embodiment, the anti-PD-L1 antibody is BMS-936559 (also known as MDX-1105-01). In yet another embodiment, the PD-L1 inhibitor is atezolizumab (also known as MPDL3280A, and Tecentriq®).

In one embodiment, the checkpoint inhibitor is a PD-L2 inhibitor. In one embodiment, the PD-L2 inhibitor is an anti-PD-L2 antibody. In one embodiment, the anti-PD-L2 antibody is rHIgM12B7A.

In one embodiment, the checkpoint inhibitor is a lymphocyte activation gene-3 (LAG-3) inhibitor. In one embodiment, the LAG-3 inhibitor is IMP321, a soluble Ig fusion protein (Brignone et al., *J. Immunol.*, 2007, 179, 4202-4211). In another embodiment, the LAG-3 inhibitor is BMS-986016.

In one embodiment, the checkpoint inhibitors is a B7 inhibitor. In one embodiment, the B7 inhibitor is a B7-H3 inhibitor or a B7-H4 inhibitor. In one embodiment, the B7-H3 inhibitor is MGA271, an anti-B7-H3 antibody (Loo et al., *Clin. Cancer Res.*, 2012, 3834).

In one embodiment, the checkpoint inhibitors is a TIM3 (T-cell immunoglobulin domain and mucin domain 3) inhibitor (Fourcade et al., *J. Exp. Med.*, 2010, 207, 2175-86; Sakuishi et al., *J. Exp. Med.*, 2010, 207, 2187-94).

In one embodiment, the checkpoint inhibitor is an OX40 (CD134) agonist. In one embodiment, the checkpoint inhibitor is an anti-OX40 antibody. In one embodiment, the anti-OX40 antibody is anti-OX-40. In another embodiment, the anti-OX40 antibody is MEDI6469.

In one embodiment, the checkpoint inhibitor is a GITR agonist. In one embodiment, the checkpoint inhibitor is an anti-GITR antibody. In one embodiment, the anti-GITR antibody is TRX518.

In one embodiment, the checkpoint inhibitor is a CD137 agonist. In one embodiment, the checkpoint inhibitor is an anti-CD137 antibody. In one embodiment, the anti-CD137 antibody is urelumab. In another embodiment, the anti-CD137 antibody is PF-05082566.

In one embodiment, the checkpoint inhibitor is a CD40 agonist. In one embodiment, the checkpoint inhibitor is an anti-CD40 antibody. In one embodiment, the anti-CD40 antibody is CF-870,893.

In one embodiment, the checkpoint inhibitor is recombinant human interleukin-15 (rhIL-15).

In one embodiment, the checkpoint inhibitor is an IDO inhibitor. In one embodiment, the IDO inhibitor is INCB024360. In another embodiment, the IDO inhibitor is indoximod.

In certain embodiments, the combination therapies provided herein include two or more of the checkpoint inhibitors described herein (including checkpoint inhibitors of the same or different class). Moreover, the combination therapies described herein can be used in combination with one or more second active agents as described herein where appropriate for treating diseases described herein and understood in the art.

In some embodiments, the checkpoint inhibitor is administered prior to the administration of the present pharmaceutical composition. In other embodiments, the checkpoint inhibitor is administered simultaneously (e.g., in the same dosing period) with the pharmaceutical composition provided herein. In yet other embodiments, the checkpoint inhibitor is administered after the administration of the pharmaceutical composition provided herein.

In some embodiments, the amount of the checkpoint inhibitor can be determined by standard clinical techniques.

A dosage of the checkpoint inhibitor results in a serum titer of from about 0.1 µg/ml to about 450 µg/ml, and in some embodiments at least 0.1 µg/ml, at least 0.2 µg/ml, at least 0.4 µg/ml, at least 0.5 µg/ml, at least 0.6 µg/ml, at least 0.8 µg/ml, at least 1 µg/ml, at least 1.5 µg/ml, such as at least 2 µg/ml, at least 5 µg/ml, at least 10 µg/ml, at least 15 µg/ml, at least 20 µg/ml, at least 25 µg/ml, at least 30 µg/ml, at least 35 µg/ml, at least 40 µg/ml, at least 50 µg/ml, at least 75 µg/ml, at least 100 µg/ml, at least 125 µg/ml, at least 150 µg/ml, at least 200 µg/ml, at least 250 µg/ml, at least 300 µg/ml, at least 350 µg/ml, at least 400 µg/ml, or at least 450 µg/ml can be administered to a human for the prevention and/or treatment of a cancer. It is to be understood that the precise dose of the checkpoint inhibitor to be employed will also depend on the route of administration, and the seriousness of a cancer in a subject, and should be decided according to the judgment of the practitioner and each patient's circumstances.

In some embodiments, the dosage of the checkpoint inhibitor (e.g., a PD-1 inhibitor or a PD-L1 inhibitor) administered to a patient is typically 0.1 mg/kg to 100 mg/kg of the subject's body weight. In some embodiments, the dosage administered to the patient is about 1 mg/kg to about 75 mg/kg of the subject's body weight. In some embodiments, the dosage administered to a patient is between 1 mg/kg and 20 mg/kg of the subject's body weight, such as 1 mg/kg to 5 mg/kg of the subject's body weight. In some embodiments, dosage administered to a patient is about 1 mg/kg of the subject's body weight. In some embodiments, dosage administered to a patient is about 1.5 mg/kg of the subject's body weight. In some embodiments, dosage administered to a patient is about 2 mg/kg of the subject's body weight. In some embodiments, dosage administered to a patient is about 2.5 mg/kg of the subject's body weight. In some embodiments, dosage administered to a patient is about 3 mg/kg of the subject's body weight. In some embodiments, dosage administered to a patient is about 3.5 mg/kg of the subject's body weight. In some embodiments, dosage administered to a patient is about 4 mg/kg of the subject's body weight. In some embodiments, dosage administered to a patient is about 4.5 mg/kg of the subject's body weight. In some embodiments, dosage administered to a patient is about 5 mg/kg of the subject's body weight. In some embodiments, dosage administered to a patient is about 5.5 mg/kg of the subject's body weight. In some embodiments, dosage administered to a patient is about 6 mg/kg of the subject's body weight. In some embodiments, dosage administered to a patient is about 6.5 mg/kg of the subject's body weight. In some embodiments, dosage administered to a patient is about 7 mg/kg of the subject's body weight. In some embodiments, dosage administered to a patient is about 7.5 mg/kg of the subject's body weight. In some embodiments, dosage administered to a patient is about 8 mg/kg of the subject's body weight. In some embodiments, dosage administered to a patient is about 8.5 mg/kg of the subject's body weight. In some embodiments, dosage administered to a patient is about 9.0 mg/kg of the subject's body weight. In some embodiments, dosage administered to a patient is about 10.0 mg/kg of the subject's body weight. In some embodiments, dosage administered to a patient is about 15.0 mg/kg of the subject's body weight. In some embodiments, dosage administered to a patient is about 20.0 mg/kg of the subject's body weight.

In some embodiments, the pharmaceutical composition provided herein is supplied as a dry sterilized lyophilized powder or water free concentrate in a hermetically sealed container and can be reconstituted, e.g., with water or saline to the appropriate concentration for administration to a subject. In certain embodiments, the antibody drug conjugate is supplied as a dry sterile lyophilized powder in a hermetically sealed container at a unit dosage of at least 0.1 mg, at least 0.5 mg, at least 1 mg, at least 2 mg, or at least 3 mg, such as at least 5 mg, at least 10 mg, at least 15 mg, at least 25 mg, at least 30 mg, at least 35 mg, at least 45 mg, at least 50 mg, at least 60 mg, at least 75 mg, at least 80 mg, at least 85 mg, at least 90 mg, at least 95 mg, or at least 100 mg. The lyophilized antibody drug conjugate can be stored at between 2 and 8° C. in its original container and the antibody drug conjugate can be administered within 12 hours, such as within 6 hours, within 5 hours, within 3 hours, or within 1 hour after being reconstituted. In an alternative embodiment, the pharmaceutical composition comprising the antibody drug conjugate provided herein is supplied in liquid form in a hermetically sealed container indicating the quantity and concentration of the antibody drug conjugate. In certain embodiments, the liquid form of the antibody drug conjugate is supplied in a hermetically sealed container at least 0.1 mg/ml, at least 0.5 mg/ml, or at least 1 mg/ml, and such as at least 5 mg/ml, at least 10 mg/ml, at least 15 mg/ml, at least 25 mg/ml, at least 30 mg/ml, at least 40 mg/ml, at least 50 mg/ml, at least 60 mg/ml, at least 70 mg/ml, at least 80 mg/ml, at least 90 mg/ml, or at least 100 mg/ml.

In some embodiments, the amount of a prophylactic or therapeutic agent (e.g., an antibody drug conjugate provided herein), or a pharmaceutical composition provided herein that will be effective in the prevention and/or treatment of a cancer can be determined by standard clinical techniques.

Accordingly, a dosage of an antibody drug conjugate in the pharmaceutical composition that results in a serum titer of from about 0.1 µg/ml to about 450 µg/ml, and in some embodiments at least 0.1 µg/ml, at least 0.2 µg/ml, at least 0.4 µg/ml, at least 0.5 µg/ml, at least 0.6 µg/ml, at least 0.8 µg/ml, at least 1 µg/ml, at least 1.5 µg/ml, such as at least 2 µg/ml, at least 5 µg/ml, at least 10 µg/ml, at least 15 µg/ml, at least 20 µg/ml, at least 25 µg/ml, at least 30 µg/ml, at least 35 µg/ml, at least 40 µg/ml, at least 50 µg/ml, at least 75 µg/ml, at least 100 µg/ml, at least 125 µg/ml, at least 150 µg/ml, at least 200 µg/ml, at least 250 µg/ml, at least 300 µg/ml, at least 350 µg/ml, at least 400 µg/ml, or at least 450 µg/ml can be administered to a human for the prevention and/or treatment of a cancer. It is to be understood that the precise dose to be employed in the formulation will also depend on the route of administration, and the seriousness of a cancer in a subject, and should be decided according to the judgment of the practitioner and each patient's circumstances.

Effective doses may be extrapolated from dose-response curves derived from in vitro or animal model test systems.

For the pharmaceutical composition comprising the antibody drug conjugate provided herein, the dosage of the antibody drug conjugate administered to a patient is typically 0.1 mg/kg to 100 mg/kg of the subject's body weight. In some embodiments, the dosage administered to the patient is about 1 mg/kg to about 75 mg/kg of the subject's body weight. In some embodiments, the dosage administered to a patient is between 1 mg/kg and 20 mg/kg of the subject's body weight, such as 1 mg/kg to 5 mg/kg of the subject's body weight. In some embodiments, dosage administered to a patient is about 1 mg/kg of the subject's body weight. In some embodiments, dosage administered to a patient is about 1.25 mg/kg of the subject's body weight. In some embodiments, dosage administered to a patient is about 1.5 mg/kg of the subject's body weight. In some embodiments, dosage administered to a patient is about 2 mg/kg of the subject's body weight. In some embodiments, dosage administered to a patient is about 2.5 mg/kg of the subject's body weight. In some embodiments, dosage administered to a patient is about 3 mg/kg of the subject's body weight. In some embodiments, dosage administered to a patient is about 3.5 mg/kg of the subject's body weight. In some embodiments, dosage administered to a patient is about 4 mg/kg of the subject's body weight. In some embodiments, dosage administered to a patient is about 4.5 mg/kg of the subject's body weight. In some embodiments, dosage administered to a patient is about 5 mg/kg of the subject's body weight. In some embodiments, dosage administered to a patient is about 5.5 mg/kg of the subject's body weight. In some embodiments, dosage administered to a patient is about 6 mg/kg of the subject's body weight. In some embodiments, dosage administered to a patient is about 6.5 mg/kg of the subject's body weight. In some embodiments, dosage administered to a patient is about 7 mg/kg of the subject's body weight. In some embodiments, dosage administered to a patient is about 7.5 mg/kg of the subject's body weight. In some embodiments, dosage administered to a patient is about 8 mg/kg of the subject's body weight. In some embodiments, dosage administered to a patient is about 8.5 mg/kg of the subject's body weight.

In some embodiments, the antibody drug conjugate formulated in the pharmaceutical composition provided herein is administered based on the patient's actual body weight at baseline and doses will not change unless the patient's weight changes by >10% from baseline of the previous cycle, or the dose adjustment criteria is met. In some embodiments, actual weight will be used except for patients weighing greater than 100 kg, in such cases, the dose will be calculated based on a weight of 100 kg. In some embodiments, the maximum doses are 100 mg for patients receiving the 1.00 mg/kg dose level and 125 mg for patients receiving the 1.25 mg/kg dose level.

In one embodiment, approximately 100 mg/kg or less, approximately 75 mg/kg or less, approximately 50 mg/kg or less, approximately 25 mg/kg or less, approximately 10 mg/kg or less, approximately 5 mg/kg or less, approximately 1 mg/kg or less, approximately 0.5 mg/kg or less, or approximately 0.1 mg/kg or less of an antibody drug conjugate formulated in the present pharmaceutical composition is administered 5 times, 4 times, 3 times, 2 times or 1 time to treat a cancer. In some embodiments, the pharmaceutical composition comprising the antibody drug conjugate provided herein is administered about 1-12 times, wherein the doses may be administered as necessary, e.g., weekly, biweekly, monthly, bimonthly, trimonthly, etc., as determined by a physician. In some embodiments, a lower dose (e.g., 0.1-15 mg/kg) can be administered more frequently (e.g., 3-6 times). In other embodiments, a higher dose (e.g., 25-100 mg/kg) can be administered less frequently (e.g., 1-3 times).

In some embodiments, a single dose of an antibody drug conjugate formulated in the pharmaceutical composition provided herein is administered to a patient to prevent and/or treat a cancer 1, 2, 3, 4, 5, 6, 7, 8, 9, 10, 11, 12, 13, 14, 15, 16, 17, 18, 19, 20, 21, 22, 23, 24, 25, or 26 times for every two-week cycle (e.g., about 14 day) over a time period (e.g., a year), wherein the dose is selected from the group consisting of about 0.1 mg/kg, about 0.5 mg/kg, about 1 mg/kg, about 1.25 mg/kg, about 1.5 mg/kg, about 2 mg/kg, about 2.5 mg/kg, about 3 mg/kg, about 4 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, about 100 mg/kg, or a combination thereof (i.e., each dose monthly dose may or may not be identical).

In some embodiments, a single dose of an antibody drug conjugate formulated in the pharmaceutical composition provided herein is administered to a patient to prevent and/or treat a cancer 1, 2, 3, 4, 5, 6, 7, 8, 9, 10, 11, 12, 13, 14, 15, 16, 17, 18, 19, 20, 21, 22, 23, 24, 25, or 26 times for every three-week cycle (e.g., about 21 day) over a time period (e.g., a year), wherein the dose is selected from the group consisting of about 0.1 mg/kg, about 0.5 mg/kg, about 1 mg/kg, about 1.25 mg/kg, about 1.5 mg/kg, about 2 mg/kg, about 2.5 mg/kg, about 3 mg/kg, about 4 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, about 100 mg/kg, or a combination thereof (i.e., each dose monthly dose may or may not be identical).

In some embodiments, a single dose of an antibody drug conjugate formulated in the pharmaceutical composition provided herein is administered to a patient to prevent and/or treat a cancer 1, 2, 3, 4, 5, 6, 7, 8, 9, 10, 11, 12, 13, 14, 15, 16, 17, 18, 19, 20, 21, 22, 23, 24, 25, or 26 times for every four-week cycle (e.g., about 28 day) over a time period (e.g., a year), wherein the dose is selected from the group consisting of about 0.1 mg/kg, about 0.5 mg/kg, about 1 mg/kg, about 1.25 mg/kg, about 1.5 mg/kg, about 2 mg/kg, about 2.5 mg/kg, about 3 mg/kg, about 4 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, about 100 mg/kg, or a combination thereof (i.e., each dose monthly dose may or may not be identical).

In another embodiment, a single dose of an antibody drug conjugate formulated in the pharmaceutical composition provided herein is administered to patient to prevent and/or treat a cancer 1, 2, 3, 4, 5, 6, 7, 8, 9, 10, 11, or 12 times at about monthly (e.g., about 30 day) intervals over a time period (e.g., a year), wherein the dose is selected from the group consisting of about 0.1 mg/kg, about 0.5 mg/kg, about 1 mg/kg, about 1.25 mg/kg, about 1.5 mg/kg, about 2 mg/kg, about 2.5 mg/kg, about 3 mg/kg, about 4 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, about 100 mg/kg, or a combination thereof (i.e., each dose monthly dose may or may not be identical).

In another embodiment, a single dose of an antibody drug conjugate formulated in the pharmaceutical composition provided herein is administered to patient to prevent and/or treat a cancer 1, 2, 3, 4, 5, or 6 times at about bi-monthly (e.g., about 60 day) intervals over a time period (e.g., a year), wherein the dose is selected from the group consisting of about 0.1 mg/kg, about 0.5 mg/kg, about 1 mg/kg, about 1.25 mg/kg, about 1.5 mg/kg, about 2 mg/kg, about 2.5 mg/kg, about 3 mg/kg, about 4 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, about 100 mg/kg, or a combination thereof (i.e., each dose monthly dose may or may not be identical).

In yet another embodiment, a single dose of an antibody drug conjugate formulated in the pharmaceutical composition provided herein is administered to patient to prevent and/or treat a cancer 1, 2, 3 or 4 times at about tri-monthly (e.g., about 120 day) intervals over a time period (e.g., a year), wherein the dose is selected from the group consisting of about 0.1 mg/kg, about 0.5 mg/kg, about 1 mg/kg, about 1.25 mg/kg, about 1.5 mg/kg, about 2 mg/kg, about 2.5 mg/kg, about 3 mg/kg, about 4 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, about 100 mg/kg, or a combination thereof (i.e., each dose monthly dose may or may not be identical).

In certain embodiments, the route of administration for a dose of an antibody drug conjugate formulated in the pharmaceutical composition provided herein to a patient is intranasal, intramuscular, intravenous, or a combination thereof, but other routes described herein are also acceptable. Each dose may or may not be administered by an identical route of administration. In some embodiments, an antibody drug conjugate formulated in the pharmaceutical composition provided herein may be administered via multiple routes of administration simultaneously or subsequently to other doses of one or more additional therapeutic agents.

In some more specific embodiments, the antibody drug conjugate formulated in the pharmaceutical composition provided herein is administered at a dose of about 1 mg/kg, about 1.25 mg/kg, or about 1.5 mg/kg of the subject's body weight by an intravenous (IV) injection or infusion.

In some more specific embodiments, the antibody drug conjugate formulated in the pharmaceutical composition provided herein is administered at a dose of about 1 mg/kg, 1.25 mg/kg, or about 1.5 mg/kg of the subject's body weight by an intravenous (IV) injection or infusion over about 30 minutes twice every three-week cycle. In some embodiments, the antibody drug conjugate formulated in the pharmaceutical composition is administered by an intravenous (IV) injection or infusion over about 30 minutes on Days 1 and 8 of every three-week cycle. In some embodiments, the method further comprises administering an immune checkpoint inhibitor by an intravenous (IV) injection or infusion one or more times in each three-week cycle. In some embodiments, the method further comprises administering an immune checkpoint inhibitor by an intravenous (IV) injection or infusion on Day 1 of every three-week cycle. In some embodiments, the immune checkpoint inhibitor is pembrolizumab, and wherein pembrolizumab is administered at amount of about 200 mg over about 30 minutes. In other embodiments, the immune checkpoint inhibitor is atezolizumab, and wherein atezolizumab is administered at amount of about 1200 mg over about 60 minutes or 30 minutes. In some embodiments, the antibody drug conjugate is administered to patients with urothelial cancer who have shown disease progression or relapse during or after treatment with an immune checkpoint inhibitor. In some embodiments, the antibody drug conjugate is administered to patients with metastatic urothelial cancer who have shown disease progression or relapse during or after treatment with an immune checkpoint inhibitor.

In other more specific embodiments, the antibody drug conjugate formulated in the pharmaceutical composition provided herein is administered at a dose of about 1 mg/kg, 1.25 mg/kg, or about 1.5 mg/kg of the subject's body weight by an intravenous (IV) injection or infusion over about 30 minutes three times every four-week cycle. In some embodiments, the antibody drug conjugate formulated in the pharmaceutical composition is administered by an intravenous (IV) injection or infusion over about 30 minutes on Days 1, 8 and 15 of every four-week cycle. In some embodiments, the method further comprises administering an immune checkpoint inhibitor by an intravenous (IV) injection or infusion one or more times in each four-week cycle. In some embodiments, the immune checkpoint inhibitor is pembrolizumab. In other embodiments, the immune checkpoint inhibitor is atezolizumab. In some embodiments, the antibody drug conjugate is administered to patients with urothelial cancer who have shown disease progression or relapse during or after treatment with an immune checkpoint inhibitor. In some embodiments, the antibody drug conjugate is administered to patients with metastatic urothelial cancer who have shown disease progression or relapse during or after treatment with an immune checkpoint inhibitor.

For the sake of conciseness, certain abbreviations are used herein. One example is the single letter abbreviation to represent amino acid residues. The amino acids and their corresponding three letter and single letter abbreviations are as follows:

| | | |
|---|---|---|
| alanine | Ala | (A) |
| arginine | Arg | (R) |
| asparagine | Asn | (N) |
| aspartic acid | Asp | (D) |
| cysteine | Cys | (C) |
| glutamic acid | Glu | (E) |
| glutamine | Gln | (Q) |
| glycine | Gly | (G) |
| histidine | His | (H) |
| isoleucine | Ile | (I) |

-continued

| | | |
|---|---|---|
| leucine | Leu | (L) |
| lysine | Lys | (K) |
| methionine | Met | (M) |
| phenylalanine | Phe | (F) |
| proline | Pro | (P) |
| serine | Ser | (S) |
| threonine | Thr | (T) |
| tryptophan | Trp | (W) |
| tyrosine | Tyr | (Y) |
| valine | Val | (V) |

The invention is generally disclosed herein using affirmative language to describe the numerous embodiments. The invention also specifically includes embodiments in which particular subject matter is excluded, in full or in part, such as substances or materials, method steps and conditions, protocols, procedures, assays or analysis. Thus, even though the invention is generally not expressed herein in terms of what the invention does not include, aspects that are not expressly included in the invention are nevertheless disclosed herein.

Particular embodiments of this invention are described herein, including the best mode known to the inventors for carrying out the invention. Upon reading the foregoing description, variations of the disclosed embodiments may become apparent to individuals working in the art, and it is expected that those skilled artisans may employ such variations as appropriate. Accordingly, it is intended that the invention be practiced otherwise than as specifically described herein, and that the invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All publications, patent applications, accession numbers, and other references cited in this specification are herein incorporated by reference in its entirety as if each individual publication or patent application were specifically and individually indicated to be incorporated by reference. The publications discussed herein are provided solely for their disclosure prior to the filing date of the present application. Nothing herein is to be construed as an admission that the present invention is not entitled to antedate such publication by virtue of prior invention. Further, the dates of publication provided can be different from the actual publication dates which can need to be independently confirmed.

A number of embodiments of the invention have been described. Nevertheless, it will be understood that various modifications may be made without departing from the spirit and scope of the invention. Accordingly, the descriptions in the Experimental section are intended to illustrate but not limit the scope of invention described in the claims.

6. EXAMPLES

The following is a description of various methods and materials used in the studies, and are put forth so as to provide those of ordinary skill in the art with a complete disclosure and description of how to make and use the present invention, and are not intended to limit the scope of what the inventors regard as their invention nor are they intended to represent that the experiments below were performed and are all of the experiments that may be performed. It is to be understood that exemplary descriptions written in the present tense were not necessarily performed, but rather that the descriptions can be performed to generate the data and the like associated with the teachings of the present invention. Efforts have been made to ensure accuracy with respect to numbers used (e.g., amounts, temperature, etc.), but some experimental errors and deviations should be accounted for.

6.1 Example 1—pH and Buffer Screen

AGS-22M6E was formulated at 10 mg/mL in fourteen candidate buffers (all at 20 mM, as detailed in Table 1 below). Formulations using 20 mM sodium citrate buffer titrated to pH 5.2 and 5.7 with citric acid, and 20 mM Histidine buffer titrated to pH 5.5, 6.0 and 6.5 with HCl were evaluated. In addition, three different anions were evaluated in the histidine buffer systems—chloride, phosphate and succinate. The liquid formulations were subjected to 40° C. storage temperature condition for 2 weeks, room temperature (RT) agitation for 24 hours, and freeze-thaw cycles (freezing at −70° C. and thawing at 20° C.-25° C. for 1, 3 and 10 cycles).

TABLE 1

| Formulation # | Buffer | pH | Trehalose Dihydrate (%) | Sucrose (%) | Tween 20 Conc. (w/v %) |
|---|---|---|---|---|---|
| F1 | 20 mM sodium citrate/citric acid | 5.2 | 5.5 | 0 | 0.02 |
| F2 |  | 5.7 |  |  |  |
| F3 | 20 mM histidine/ HCl | 5.5 |  |  |  |
| F4 |  | 6 |  |  |  |
| F5 |  | 6.5 |  |  |  |
| F6 | 20 mM sodium citrate/citric acid | 5.2 | 0 | 5 |  |
| F7 |  | 5.7 |  |  |  |
| F8 | 20 mM histidine/ HCl | 5.5 |  |  |  |
| F9 |  | 6 |  |  |  |
| F10 |  | 6.5 |  |  |  |
| F11 | 20 mM histidine/ Phosphoric acid | 5.5 | 5.5 | 0 |  |
| F12 |  | 6 |  |  |  |
| F13 | 20 mM histidine/ Succinic acid | 5.5 |  |  |  |
| F14 |  | 6 |  |  |  |

Note:
5% sucrose (m. wt. 342) = 146 mM; 5.5% trehalose dihydrate (m. wt. 378) = 146 mM.

Formulation preparation and study design are described in more detail below.

Protein Product Used for Formulation Study

Four tubes each containing about 50 ml of AGS-22M6E (Lot #AGS22 M6-VCE-02), totaling about 2.5 grams were received frozen. AGS-22M6E was at 12.5 mg/mL in 20 mM histidine pH 6.0 buffer containing 5% sucrose and 0.02% polysorbate-20. The material was stored at −70° C. until used.

Preparation of Formulation Buffers

Stock solutions including citric acid (0.1 M), sodium citrate (0.1 M) and L-histidine (0.2 M), succinic acid (0.25 M), trehalose Dihydrate (40%), sucrose (40%), hydrochloric Acid (2 M) and phosphoric Acid (2 M) were prepared according to Table 2 below:

TABLE 2

| Stocks | MW (g/mol) | Desired Concentration (mol/L) | Volume (L) | Mass Required (g) |
|---|---|---|---|---|
| Citric Acid Monohydrate | 210.14 | 0.1 | 1.0 | 21.01 |
| Sodium Citrate Dihydrate | 294.1 | 0.1 | 2.0 | 58.82 |
| L-Histidine | 155.15 | 0.2 | 1.5 | 46.55 |
| Trehalose Dihydrate | 378.33 | 40% | 1.5 | 600.00 |
| Sucrose | 342.30 | 40% | 1.0 | 400.00 |
| Succinic Acid | 118.09 | 0.25 | 0.8 | 23.62 |

| Stocks | Initial Conc (M) | Final Conc (M) | Final Volume (mL) | To measure out | |
|---|---|---|---|---|---|
|  |  |  |  | Concentrated Acid (mL) | Water (mL) |
| Hydrochloric Acid | 12.1 | 2.0 | 500 | 82.6 | 417.4 |
| Phosphoric Acid | 14.8 | 2.0 | 500 | 67.6 | 432.4 |

Reagents were weighed out according to the table above. Appropriate volume of Milli-Q water was added to dissolve the reagents. The solutions were filtered through 0.22 um filters.

Preparation of Formulation Buffers for Dialysis 1.0 L of each formulation was prepared for dialysis and placebo vialing according to Table 3 below:

TABLE 3

| Formulation # | pH | 0.1M Citric Acid Monohydrate (mL) | 0.1M Sodium Citrate dihydrate (mL) | 0.2M L-Histidine (mL) | 40% Trehalose Dihydrate (mL) | 40% Sucrose (mL) | Water (mL) | pH Adjustment with | Total volume (mL) |
|---|---|---|---|---|---|---|---|---|---|
| F1 | 5.2 | 61 | 139 |  | 137.5 |  | 662.5 |  | 1000 |
| F2 | 5.7 | 37 | 163 |  | 137.5 |  | 662.5 |  | 1000 |
| F3 | 5.5 |  |  | 100 | 137.5 |  | 762.5 | 2M HCl | 1000 |
| F4 | 6.0 |  |  | 100 | 137.5 |  | 762.5 | 2M HCl | 1000 |
| F5 | 6.5 |  |  | 100 | 137.5 |  | 762.5 | 2M HCl | 1000 |
| F6 | 5.2 | 61 | 139 |  |  | 125 | 675 |  | 1000 |
| F7 | 5.7 | 37 | 163 |  |  | 125 | 675 |  | 1000 |
| F8 | 5.5 |  |  | 100 |  | 125 | 775 | 2M HCl | 1000 |
| F9 | 6.0 |  |  | 100 |  | 125 | 775 | 2M HCl | 1000 |
| F10 | 6.5 |  |  | 100 |  | 125 | 775 | 2M HCl | 1000 |
| F11 | 5.5 |  |  | 100 | 137.5 |  | 762.5 | 2M Phosphoric Acid | 1000 |
| F12 | 6.0 |  |  | 100 | 137.5 |  | 762.5 | 2M Phosphoric Acid | 1000 |
| F13 | 5.5 |  |  | 100 | 137.5 |  | 762.5 | 0.25M Succinic Acid | 1000 |

TABLE 3-continued

| Formulation # | pH | 0.1M Citric Acid Monohydrate (mL) | 0.1M Sodium Citrate dihydrate (mL) | 0.2M L-Histidine (mL) | 40% Trehalose Dihydrate (mL) | 40% Sucrose (mL) | Water (mL) | pH Adjustment with | Total volume (mL) |
|---|---|---|---|---|---|---|---|---|---|
| F14 | 5.5 | | | 100 | 137.5 | | 762.5 | 0.25M Succinic Acid | 1000 | pH was adjusted with appropriate acid to the target pH ±0.1. The buffers were stored at 4° C. until used.

Formulation Preparation 4 tubes each containing 50 ml AGS-22M6E (Lot #AGS22 M6-VCE-02) were thawed in a room temperature water bath, then combined in a 250 ml bottle. 11 ml was allocated for each formulation and was added to dialysis cassettes. Cassettes were placed in beakers containing ~40 fold excess of formulation buffer and stirred overnight at 2-8° C. Buffer was discarded and fresh buffer was added and stirred overnight at 2-8° C. Material was removed from cassettes and transferred to 50 ml tubes, the concentrations were determined and the volumes were adjusted with corresponding formulation buffer so that the final concentration was 10 mg/ml. Placebos were the corresponding buffers used for formulating the product.

Formulation Vialing and Stoppering

Sterile filtration and filling were performed in a Baker SG600 laminar airflow hood. Formulations and placebos were sterile-filtered using aseptic technique (Millipore Millex-GV 0.22 μm PVDF syringe filters, #SLGV033RS). Sterile stoppered vials (Hollister-Stier 2-ml sterile stoppered vials, #7505ZA) were decrimped in the hood, and the stoppers were removed using aseptic technique. Vials were filled with 1.0 ml of formulated product or placebo, and then restoppered.

Material Requirements and Sample Map

Material requirements and sample map are as follows:

TABLE 4

| Concentration (mg/mL) | Condition | # of Vials | Fill Volume | Total Fill volume | Total Protein (mg) | Total ml per formulation | Total mg per formulation |
|---|---|---|---|---|---|---|---|
| 10 | 40° C. | 5 | 1 | 5.0 | 50 | | |
| 10 | 1 cycleFz/Th at −70° C./25° C. | 1 | 1 | 1.0 | 10 | | |
| 10 | 3 cycleFz/Th at −70° C./25° C. | 1 | 1 | 1.0 | 10 | | |
| 10 | 10 cycleFz/Th at −70° C. | 1 | 1 | 1.0 | 10 | | |
| 10 | Tween 20 Assay | 1 | 1 | 1.0 | 10 | | |
| 10 | RT Shake for 24hrs | 1 | 1 | 1.0 | 10 | 10 | 100 |

| # of Prot Concs to Test | # of Buffers to Test | Total # Vials | Total Fill Volume (mL) | Protein In Vials (mg) | Protein required (mg) | | |
|---|---|---|---|---|---|---|---|
| 1 | 14 | 140 | 140.0 | 1400 | 1680 | Total Sample Number: 112 | |

| | | Days at Storage Condition | | | |
|---|---|---|---|---|---|
| Condition | | 0 | 3 | 7 | 14 |
| 40° C. | | X | X | X | X |
| 1 cycleFz/Th at −70 < C/25 < C | | | X | | |
| 3 cycleFz/Th at −70 < C/25 < C | | | | X | |
| 10 cycleFz/Th at −70 < C/25 < C | | | | | X |
| RT Shake for 24 hrs | | X | | | |

Time Point and Assays

Time point and assays are as in Table 5 below.

TABLE 5

| Analytical Assay | T = 0 13 Apr. 2010 | T = 3 d 16 Apr. 2010 | T = 7 d 20 Apr. 2010 | T = 14 d Apr. 27, 2010 | 1 X Fz/Th at −70° C./ 25° C. | 3 XFz/Th at −70° C./ 25° C. | 10 XFz/Th at −70° C./ 25° C. | RT Shake for 24 hrs |
|---|---|---|---|---|---|---|---|---|
| pH | X | X | | | | | | |
| Osmolality | X | X | | | | | | |
| Visual appearance | X | X | X | X | X | X | X | X |
| A280 | X | X | X | X | X | X | X | X |
| Turbidity | X | X | X | X | X | X | X | X |
| Non-reduced Reduced SDS-PAGE | X | X | X | X | X | X | X | X |

TABLE 5-continued

| Analytical Assay | T = 0 13 Apr. 2010 | T = 3 d 16 Apr. 2010 | T = 7 d 20 Apr. 2010 | T = 14 d Apr. 27, 2010 | 1 X Fz/Th at −70° C./ 25° C. | 3 XFz/Th at −70° C./ 25° C. | 10 XFz/Th at −70° C./ 25° C. | RT Shake for 24 hrs |
|---|---|---|---|---|---|---|---|---|
| SE-HPLC | X | X | X | X | X | X | X | X |
| RP-HPLC | X | | | X | | | | |
| Potency | | | | Provide samples for testing | | | | |

Liquid Formulation 40° C. Stability Study Design

Formulations and placebo vials were placed upright in an incubator set to 40° C. At each time point, one active and one placebo vial for each formulation were removed from the storage conditions according to the sample map. Samples were frozen at −70° C. and batch analyzed at the end of the study. Prior to analysis, samples were thawed at RT. Sets of 3 aliquots of each sample (70 uL aliquots for each sample) were frozen at −70° C. after filter through 0.22 um filter. After analytical testing, any remaining material was stored at 2-8° C. overnight, in case re-testing was needed. After all of the assays were complete, remaining materials were then stored at −70° C. Two frozen aliquots were used for cIEF and potency assays.

Freeze-Thaw (−70° C.) Stability Study Design

One vial for each formulation (1.0 mL fill) was placed upright in a −70° C. freezer for at least 4 hours, which allowed for freezing. For thawing, each vial was removed from storage and thawed at room temperature until ice was no longer observed, and then the vial was gently swirled. This constituted one complete freeze-thaw cycle. One, three and ten freeze-thaw cycles were completed for each tested formulation sample vial. Following the final freeze-thaw cycle, all samples were evaluated by analytical testing. Sets of 3 aliquots of each sample (70 uL aliquots for each sample) were frozen at −70° C. immediately. After analytical testing, any remaining material was stored at 2-8° C. overnight, in case re-testing was needed. After all of the assays were complete, the remaining materials were stored at −70° C. Two frozen aliquots were used for cIEF and potency assays.

Agitation Study Design

One vial for each formulation was secured upright in a standard freezer box. The box was then attached to an IKA-VIBRAMAX-VXR orbital shaker set at 500 rpm at room temperature for 24 hours. The samples were then removed and stored at −70° C. until analysis.

Formulation Standard 1.2 mL of AGS-22M6E (Lot #AGS22 M6-VCE-02) starting material (12.5 mg/mL in 20 mM Histidine pH 6.0 buffer containing 5% sucrose and 0.02% polysorbate-20) was taken and aliquoted at 200 ul/vial, then stored at −70° C. as formulation standard for this study.

Visual appearance, A280 (protein concentration and drug loading), A330 (turbidity), SE-HPLC, non-reduced and reduced SDS-PAGE, RP-HPLC-NPI. iCIEF and potency were used to evaluate the stability of AGS-22M6E Visual appearance: All samples showed no color, no cloudiness and no particulates over the course of the study. No particulates were seen even upon shaking.

A280 (protein concentration) analysis: The results of the A280 analysis are shown in Table 6 below.

TABLE 6

| | A280 Days at 40° C. | | | |
|---|---|---|---|---|
| Sample | 0 | 3 | 7 | 14 |
| F1 | 0.6549 | 0.6274 | 0.6805 | 0.6449 |
| F2 | 0.6818 | 0.7017 | 0.6929 | 0.6853 |

TABLE 6-continued

| F3 | 0.7069 | 0.6491 | 0.7130 | 0.6990 |
| F4 | 0.7056 | 0.7147 | 0.7106 | 0.7217 |
| F5 | 0.7123 | 0.6837 | 0.7138 | 0.7201 |
| F6 | 0.6616 | 0.6789 | 0.6935 | 0.6830 |
| F7 | 0.6594 | 0.6558 | 0.6672 | 0.6730 |
| F8 | 0.6986 | 0.6903 | 0.7037 | 0.7017 |
| F9 | 0.6834 | 0.7002 | 0.7063 | 0.7061 |
| F10 | 0.6888 | 0.6839 | 0.6937 | 0.7023 |
| F11 | 0.7032 | 0.7109 | 0.7074 | 0.6950 |
| F12 | 0.7040 | 0.6622 | 0.7088 | 0.7255 |
| F13 | 0.6736 | 0.6754 | 0.6874 | 0.6818 |
| F14 | 0.6944 | 0.6745 | 0.6878 | 0.7003 |

| | A280 | | | | |
|---|---|---|---|---|---|
| Sample | 0 | 1X FzTh | 3X FzTh | 10X FzTh | 24 hr Shake |
| F1 | 0.6549 | 0.6582 | 0.6951 | 0.65725 | 0.66017 |
| F2 | 0.6818 | 0.6809 | 0.6761 | 0.68321 | 0.67565 |
| F3 | 0.7069 | 0.6963 | 0.6958 | 0.69771 | 0.70847 |
| F4 | 0.7056 | 0.7048 | 0.6817 | 0.69875 | 0.68629 |
| F5 | 0.7123 | 0.7027 | 0.6961 | 0.70278 | 0.71533 |
| F6 | 0.6616 | 0.6651 | 0.6715 | 0.68515 | 0.66747 |
| F7 | 0.6594 | 0.6622 | 0.6585 | 0.63399 | 0.65046 |
| F8 | 0.6986 | 0.6969 | 0.7042 | 0.69579 | 0.69878 |
| F9 | 0.6834 | 0.6893 | 0.6876 | 0.67558 | 0.69247 |
| F10 | 0.6888 | 0.6862 | 0.6921 | 0.68071 | 0.68312 |
| F11 | 0.7032 | 0.6967 | 0.6905 | 0.68287 | 0.70169 |
| F12 | 0.7040 | 0.6892 | 0.7064 | 0.69924 | 0.68928 |
| F13 | 0.6736 | 0.6746 | 0.6745 | 0.65992 | 0.66715 |
| F14 | 0.6944 | 0.6831 | 0.7003 | 0.67608 | 0.68892 |

| | Concentration (mg/mL) Days at 40° C. | | | |
|---|---|---|---|---|
| Sample | 0 | 3 | 7 | 14 |
| F1 | 9.01 | 8.63 | 9.36 | 8.87 |
| F2 | 9.38 | 9.65 | 9.53 | 9.43 |
| F3 | 9.72 | 8.93 | 9.81 | 9.62 |
| F4 | 9.71 | 9.83 | 9.77 | 9.93 |
| F5 | 9.80 | 9.40 | 9.82 | 9.90 |
| F6 | 9.10 | 9.34 | 9.54 | 9.40 |
| F7 | 9.07 | 9.02 | 9.18 | 9.26 |
| F8 | 9.61 | 9.50 | 9.68 | 9.65 |
| F9 | 9.40 | 9.63 | 9.71 | 9.71 |
| F10 | 9.47 | 9.41 | 9.54 | 9.66 |
| F11 | 9.67 | 9.78 | 9.73 | 9.56 |
| F12 | 9.68 | 9.11 | 9.75 | 9.98 |
| F13 | 9.27 | 9.29 | 9.46 | 9.38 |
| F14 | 9.55 | 9.28 | 9.46 | 9.63 |

| | Concentration (mg/mL) | | | | |
|---|---|---|---|---|---|
| Sample | 0 | 1X FzTh | 3X FzTh | 10X | 24 hr Shake |
| F1 | 9.01 | 9.05 | 9.56 | 9.04 | 9.08 |
| F2 | 9.38 | 9.37 | 9.30 | 9.40 | 9.29 |
| F3 | 9.72 | 9.58 | 9.57 | 9.60 | 9.75 |
| F4 | 9.71 | 9.69 | 9.38 | 9.61 | 9.44 |
| F5 | 9.80 | 9.67 | 9.57 | 9.67 | 9.84 |
| F6 | 9.10 | 9.15 | 9.24 | 9.42 | 9.18 |
| F7 | 9.07 | 9.11 | 9.06 | 8.72 | 8.95 |
| F8 | 9.61 | 9.59 | 9.69 | 9.57 | 9.61 |

TABLE 6-continued

| | | | | | |
|---|---|---|---|---|---|
| F9  | 9.40 | 9.48 | 9.46 | 9.29 | 9.53 |
| F10 | 9.47 | 9.44 | 9.52 | 9.36 | 9.40 |
| F11 | 9.67 | 9.58 | 9.50 | 9.39 | 9.65 |
| F12 | 9.68 | 9.48 | 9.72 | 9.62 | 9.48 |
| F13 | 9.27 | 9.28 | 9.28 | 9.08 | 9.18 |
| F14 | 9.55 | 9.40 | 9.63 | 9.30 | 9.48 |

As shown, no changes of protein concentration were observed.

A330 (turbidity) analysis: The results of the A330 analysis are shown in Table 7 below.

TABLE 7

| | A330 Days at 40° C. | | | | |
|---|---|---|---|---|---|
| | 0 | 3 | 7 | 14 | |
| Sample | Placebo | Active | Active | Active | Placebo | Active |
| F1  | −0.0006 | 0.0591 | 0.1030 | 0.1053 | 0.0131 | 0.1223 |
| F2  | −0.0040 | 0.0727 | 0.0934 | 0.1067 | 0.0363 | 0.1070 |
| F3  | −0.0063 | 0.0585 | 0.0632 | 0.0715 | 0.0018 | 0.0736 |
| F4  | −0.0036 | 0.0601 | 0.0667 | 0.0730 | 0.0053 | 0.0757 |
| F5  | 0.0027 | 0.0659 | 0.0720 | 0.0917 | 0.0030 | 0.0823 |
| F6  | 0.0028 | 0.1018 | 0.0970 | 0.1196 | 0.0004 | 0.1269 |
| F7  | 0.0029 | 0.0705 | 0.0885 | 0.0925 | 0.0073 | 0.1031 |
| F8  | 0.0019 | 0.0620 | 0.0598 | 0.0801 | 0.0112 | 0.0860 |
| F9  | 0.0041 | 0.0681 | 0.0776 | 0.0982 | 0.0193 | 0.1046 |
| F10 | 0.0013 | 0.0628 | 0.0760 | 0.0905 | 0.0156 | 0.0886 |
| F11 | 0.0036 | 0.0773 | 0.0649 | 0.0722 | 0.0100 | 0.0782 |
| F12 | 0.0014 | 0.0652 | 0.0641 | 0.0861 | 0.0131 | 0.0796 |
| F13 | 0.0142 | 0.0655 | 0.0660 | 0.0708 | 0.0121 | 0.0936 |
| F14 | 0.0112 | 0.0659 | 0.0637 | 0.0701 | 0.0122 | 0.0857 |

TABLE 7-continued

| | A330 | | | | | |
|---|---|---|---|---|---|---|
| | 1X FzTh | 3X FzTh | 10X FzTh | | 24 hr Shake | |
| Sample | Active | Active | Placebo | Active | Placebo | Active |
| F1  | 0.0638 | 0.0787 | 0.0042  | 0.0755 | 0.0083  | 0.0698 |
| F2  | 0.0683 | 0.0757 | 0.0075  | 0.0774 | 0.0089  | 0.0719 |
| F3  | 0.0631 | 0.0645 | 0.0008  | 0.0620 | 0.0235  | 0.0669 |
| F4  | 0.0593 | 0.0908 | 0.0005  | 0.0600 | 0.0036  | 0.0577 |
| F5  | 0.0647 | 0.0598 | 0.0049  | 0.0685 | 0.0099  | 0.0615 |
| F6  | 0.0805 | 0.0796 | −0.0001 | 0.0728 | 0.0180  | 0.0737 |
| F7  | 0.0714 | 0.0777 | 0.0025  | 0.0745 | 0.0100  | 0.0695 |
| F8  | 0.0630 | 0.0750 | 0.0006  | 0.0696 | 0.0053  | 0.0568 |
| F9  | 0.0670 | 0.0737 | 0.0034  | 0.0715 | 0.0022  | 0.0692 |
| F10 | 0.0595 | 0.0750 | 0.0007  | 0.0752 | 0.0050  | 0.0676 |
| F11 | 0.0559 | 0.0763 | 0.0016  | 0.0694 | 0.0013  | 0.0629 |
| F12 | 0.0625 | 0.0679 | 0.0006  | 0.0695 | 0.0028  | 0.0695 |
| F13 | 0.0616 | 0.0701 | 0.0028  | 0.0820 | −0.0009 | 0.0759 |
| F14 | 0.0611 | 0.0745 | −0.0017 | 0.1033 | 0.0108  | 0.0972 |

As shown, formulations F1 and F6 exhibited the most significant increases in turbidity over time. At T=0, higher turbidity was noted for formulation F6 which was not observed in other formulations.

SDS-PAGE analysis: The results of the SDS-PAGE analysis are shown in FIGS. 1A, 1B, 1C, and 1D. Minor low molecular weight (LMW) bands (~35 kD) were observed by reduced SDS-PAGE in F1 and F6 after 14 days. In non-reduced SDS-PAGE analysis, F1, F2, F6 and F7 also demonstrated minor high molecular weight (HMW) bands (~200 kD) not previously present at T=0.

Figure 1E:
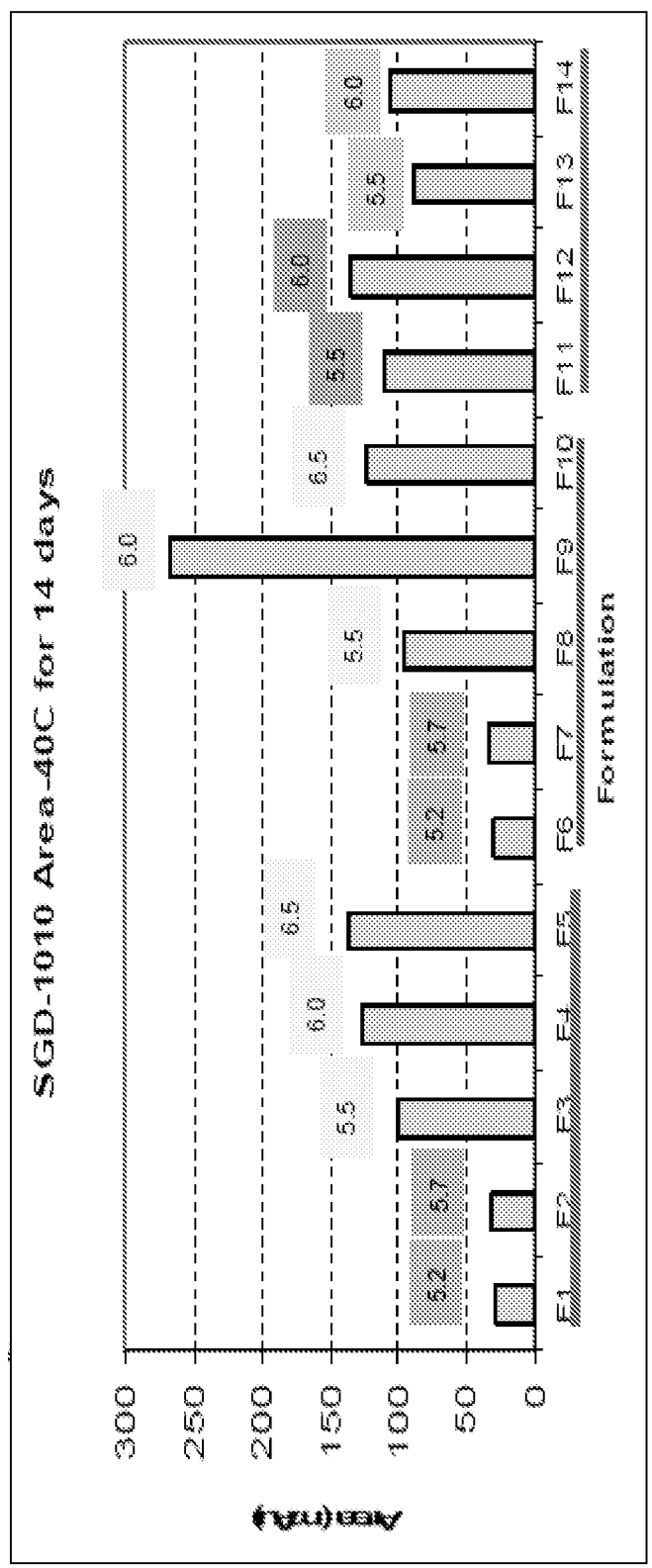

RP-HPLC analysis: Table 8 and FIG. 1E show the results of the RP-HPLC analysis. No free SGD1010 (trace cleavage of the drug MMAE) was detected by RP-HPLC at t=0 for any of the formulations, however after 14 days at 40° C., SGD1010 (ranging from 0.17-1.59 uM) was noted and was slightly faster at higher pH for the histidine than for the citrate formulations, with the histidine/succinic acid performing slightly better than the histidine/phosphoric and histidine/HCl.

TABLE 8

| Formulation # | Buffer | pH | Trehalose Dihydrate (%) | Sucrose (%) | Area | μM SGD1010 |
|---|---|---|---|---|---|---|
| F1  | 20 mM sodium citrate/citric acid | 5.2 | 5.5 | 0 | 0   | 0.00 |
|     |                                  |     |     |   | 28  | 0.17 |
| F2  |                                  | 5.7 |     |   | 0   | 0.00 |
|     |                                  |     |     |   | 31  | 0.18 |
| F3  | 20 mM histidine/HCl              | 5.5 |     |   | 0   | 0.00 |
|     |                                  |     |     |   | 101 | 0.60 |
| F4  |                                  | 6   |     |   | 0   | 0.00 |
|     |                                  |     |     |   | 127 | 0.76 |
| F5  |                                  | 6.5 |     |   | 0   | 0.00 |
|     |                                  |     |     |   | 136 | 0.81 |
| F6  | 20 mM sodium citrate/citric acid | 5.2 | 0   | 5 | 0   | 0.00 |
|     |                                  |     |     |   | 30  | 0.18 |
| F7  |                                  | 5.7 |     |   | 0   | 0.00 |
|     |                                  |     |     |   | 34  | 0.20 |
| F8  | 20 mM histidine/HCl              | 5.5 |     |   | 0   | 0.00 |
|     |                                  |     |     |   | 96  | 0.57 |
| F9  |                                  | 6   |     |   | 0   | 0.00 |
|     |                                  |     |     |   | 267 | 1.59 |
| F10 |                                  | 6.5 |     |   | 0   | 0.00 |
|     |                                  |     |     |   | 124 | 0.74 |
| F11 | 20 mM histidine/ Phosphoric acid | 5.5 | 5.5 | 0 | 0   | 0.00 |
|     |                                  |     |     |   | 111 | 0.66 |
| F12 |                                  | 6   |     |   | 0   | 0.00 |
|     |                                  |     |     |   | 135 | 0.80 |
| F13 | 20 mM histidine/ Succinic acid   | 5.5 |     |   | 0   | 0.00 |
|     |                                  |     |     |   | 89  | 0.53 |
| F14 |                                  | 6   |     |   | 0   | 0.00 |
|     |                                  |     |     |   | 106 | 0.63 |

Figure 1F:
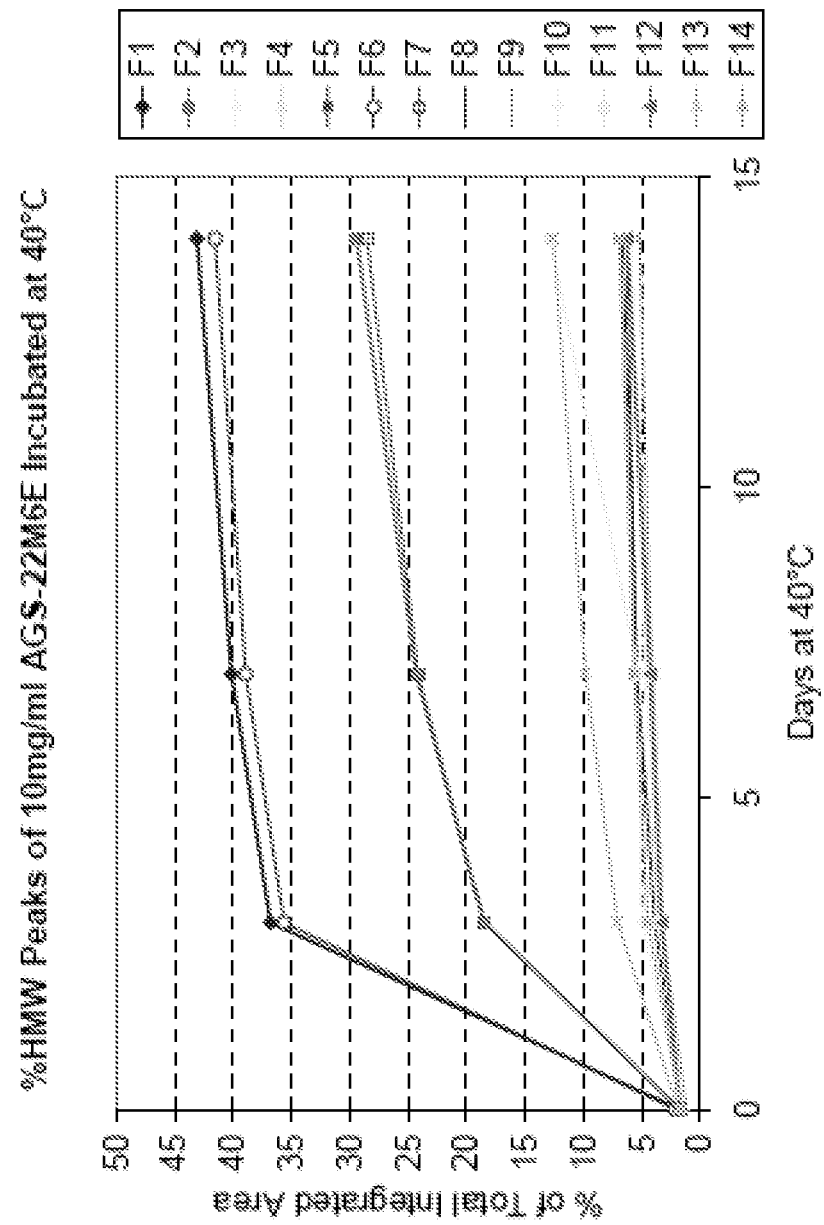
Figure 1G:
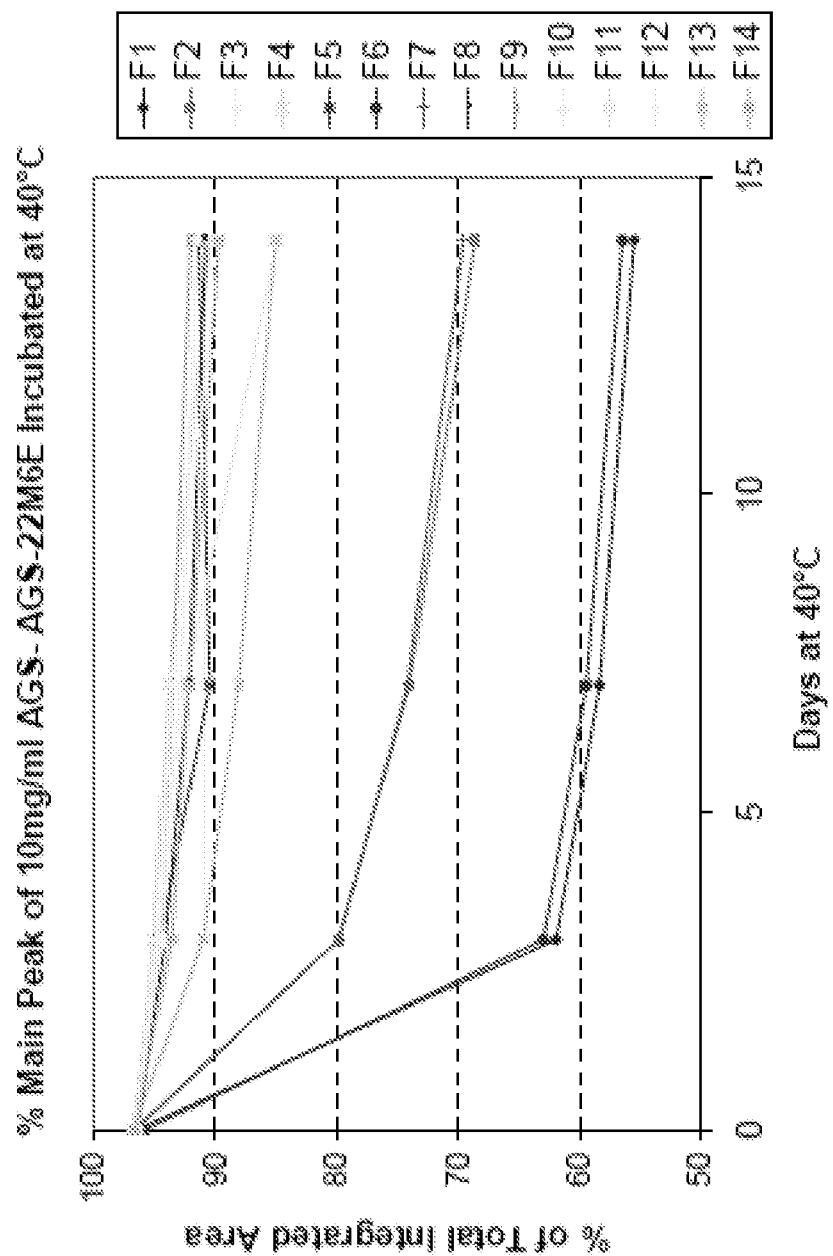
Figure 1H:
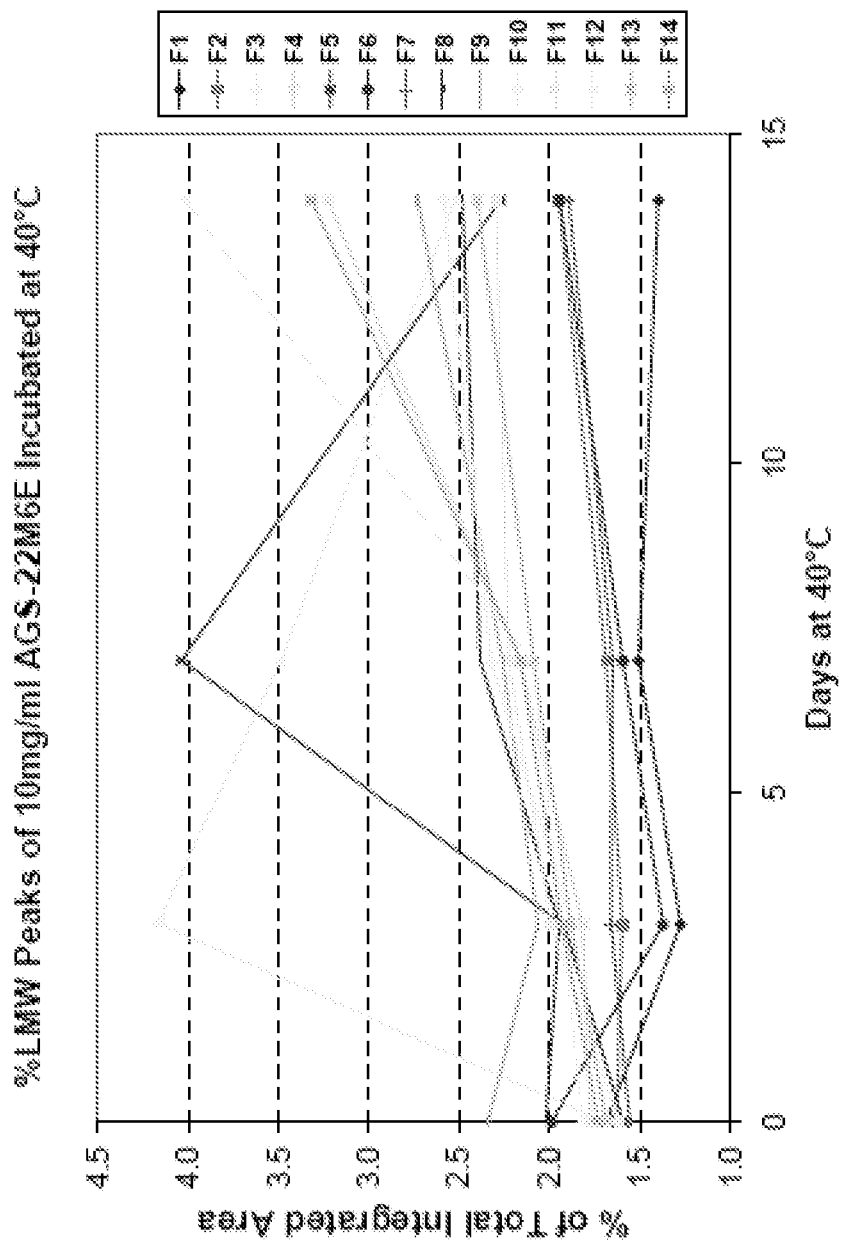

SE-HPLC analysis: As shown in Table 9 below and FIGS. 1F, 1G, and 1H, increasing levels of HMW aggregates were evident by SE-HPLC for all formulations at pH 5.2-5.7, with the citrate formulations showing more aggregates than histidine at corresponding pH. At similar pH, citrate showed more aggregates than histidine. Histidine formulations at pH 6.0 showed better stability than those at pH 5.5 and at pH 6.5. There was no difference observed between trehalose and sucrose.

TABLE 9

| Formulation | Days at 40° C. | Main Peak Retention Time | % of Total Intearated Area | | | Integrated Area | | | |
|---|---|---|---|---|---|---|---|---|---|
| | | | Pre Peaks | Main Peak | Post Peaks | Pre Peaks | Main Peak | Post Peaks | Total |
| 1 | 0 | 19.5 | 1.8 | 96.5 | 1.7 | 83 | 4500 | 79 | 4661 |
| | 3 | 19.5 | 36.8 | 61.9 | 1.3 | 1812 | 3050 | 63 | 4924 |
| | 7 | 19.6 | 40.1 | 58.3 | 1.5 | 1953 | 2839 | 73 | 4866 |
| | 14 | 19.6 | 43.1 | 55.5 | 1.4 | 2095 | 2696 | 68 | 4858 |
| 2 | 0 | 19.5 | 1.8 | 96.6 | 1.6 | 93 | 4936 | 83 | 5112 |
| | 3 | 19.6 | 18.5 | 79.9 | 1.6 | 889 | 3832 | 77 | 4797 |
| | 7 | 19.6 | 24.3 | 74.0 | 1.7 | 1299 | 3949 | 90 | 5338 |
| | 14 | 19.6 | 29.4 | 63.6 | 1.9 | 1442 | 3363 | 95 | 4901 |
| 3 | 0 | 19.5 | 1.6 | 96.7 | 1.7 | 82 | 5078 | 89 | 5249 |
| | 3 | 19 5 | 5.0 | 90.8 | 4.2 | 253 | 4603 | 211 | 5067 |
| | 7 | 19.5 | 5.5 | 91.0 | 3.5 | 268 | 4463 | 171 | 4903 |
| | 14 | 19.5 | 6.5 | 91.0 | 2.5 | 311 | 4333 | 120 | 4764 |
| 4 | 0 | 19.5 | 1.7 | 96.5 | 1.8 | 81 | 4636 | 85 | 4802 |
| | 3 | 19.5 | 3.1 | 95.1 | 1.8 | 149 | 4571 | 87 | 4808 |
| | 7 | 19.5 | 3.9 | 93.9 | 2.2 | 201 | 4797 | 110 | 5108 |
| | 14 | 19.5 | 6.3 | 90.5 | 3.2 | 314 | 4536 | 162 | 5012 |
| 5 | 0 | 19.5 | 1.6 | 96.8 | 1.6 | 85 | 4991 | 82 | 5158 |
| | 3 | 19.5 | 3.5 | 94.6 | 1.9 | 167 | 4534 | 92 | 4793 |
| | 7 | 19.5 | 5.5 | 90.5 | 4.0 | 282 | 4622 | 206 | 5109 |
| | 14 | 19.5 | 6.3 | 91.4 | 2.3 | 308 | 4430 | 110 | 4847 |
| 6 | 0 | 19.5 | 2.2 | 95.8 | 2.0 | 97 | 4242 | 88 | 4427 |
| | 3 | 19.6 | 35.6 | 63.0 | 1.4 | 1754 | 3100 | 68 | 4921 |
| | 7 | 19.6 | 38.9 | 59.5 | 1.6 | 1908 | 2915 | 78 | 4902 |
| | 14 | 19.6 | 41.6 | 58.5 | 1.9 | 2047 | 2783 | 96 | 4926 |
| 7 | 0 | 19.5 | 1.8 | 96.7 | 1.6 | 89 | 4867 | 78 | 5034 |
| | 3 | 19.6 | 18.6 | 79.8 | 1.7 | 906 | 3895 | 81 | 4882 |
| | 7 | 19.6 | 24.2 | 74.2 | 1.7 | 1145 | 3515 | 78 | 4739 |
| | 14 | 19.6 | 28.5 | 69.6 | 1.9 | 1360 | 3318 | 90 | 4768 |
| 8 | 0 | 19.5 | 1.6 | 96.4 | 2.0 | 82 | 4968 | 104 | 5154 |
| | 3 | 19.5 | 3.9 | 94.1 | 1.9 | 184 | 4421 | 91 | 4696 |
| | 7 | 19.5 | 5.4 | 92.2 | 2.4 | 259 | 4388 | 113 | 4760 |
| | 14 | 19.5 | 6.7 | 90.8 | 2.5 | 322 | 4343 | 119 | 4785 |
| 9 | 0 | 19.6 | 1.2 | 96.5 | 2.3 | 60 | 4987 | 121 | 5168 |
| | 3 | 19.5 | 3.3 | 94.6 | 2.1 | 158 | 4504 | 98 | 4760 |
| | 7 | 19.5 | 4.2 | 93.6 | 2.3 | 209 | 4659 | 113 | 4981 |
| | 14 | 19.5 | 5.2 | 92.1 | 2.7 | 249 | 4408 | 130 | 4787 |
| 10 | 0 | 19.5 | 1.6 | 98.7 | 1.7 | 82 | 4914 | 85 | 5081 |
| | 3 | 19.5 | 3.4 | 94.8 | 1.9 | 155 | 4387 | 87 | 4629 |
| | 7 | 19.5 | 4.8 | 92.9 | 2.3 | 229 | 4466 | 111 | 4807 |
| | 14 | 19.5 | 5.9 | 91.5 | 2.6 | 276 | 4312 | 122 | 4710 |
| 11 | 0 | 19.5 | 1.6 | 96.8 | 1.6 | 82 | 4989 | 83 | 5154 |
| | 3 | 19.5 | 3.6 | 94.4 | 2.0 | 168 | 4415 | 93 | 4676 |
| | 7 | 19.5 | 5.3 | 92.5 | 2.2 | 250 | 4400 | 106 | 4756 |
| | 14 | 19.5 | 12.9 | 84.8 | 2.3 | 625 | 4107 | 111 | 4843 |
| 12 | 0 | 19.6 | 1.7 | 96.4 | 1.8 | 97 | 5340 | 101 | 5538 |
| | 3 | 19.5 | 3.3 | 94.7 | 1.9 | 159 | 4504 | 92 | 4755 |
| | 7 | 19.5 | 4.3 | 93.6 | 2.1 | 214 | 4637 | 104 | 4955 |
| | 14 | 19.5 | 6.3 | 89.7 | 4.0 | 319 | 4538 | 204 | 5060 |
| 13 | 0 | 19.5 | 1.9 | 96.7 | 1.7 | 93 | 4806 | 84 | 4969 |
| | 3 | 19.5 | 7.1 | 91.0 | 1.9 | 326 | 4184 | 86 | 4596 |
| | 7 | 19.5 | 9.8 | 88.1 | 2.1 | 456 | 4083 | 97 | 4636 |
| | 14 | 19.5 | 12.6 | 85.0 | 2.4 | 598 | 4041 | 114 | 4753 |
| 14 | 0 | 19.5 | 1.6 | 96.6 | 1.7 | 82 | 4634 | 86 | 5002 |
| | 3 | 19.5 | 4.5 | 93.6 | 1.9 | 204 | 4265 | 88 | 4557 |
| | 7 | 19.5 | 5.7 | 92.2 | 2.2 | 267 | 4342 | 102 | 4711 |
| | 14 | 19.5 | 6.9 | 89.7 | 3.3 | 349 | 4503 | 167 | 5018 |

No significant changes were observed between any of the formulations, either after 24 hrs of shaking at room temperature or after one, three and ten freeze-thaw cycles, as demonstrated by A330, SDS-PAGE and SE-HPLC (data not shown here). This provided assurance that the formulation study samples could be pulled at different time points and stored at −70° C.

Based on the results obtained from this study, formulations F4, F9 and F14 were selected as optimal among the 14 formulations tested and were therefore chosen as the 3 formulations to be further evaluated in the subsequent studies.

6.2 Example 2—Bulk Drug Substance (BDS) Freeze-Thaw and Shake Study

The formulations F4, F9 and F14 were prepared as described in Section 6.1 above. Each of the formulations F4, F9, and F14 was subjected to 1, 3 and 10 cycles of freezing at both −20° C. and −70° C. followed by thawing at between 20° C.-25° C. The samples were analyzed by visual inspection, concentration (A280) measurement, turbidity (A330) measurement, SE-HPLC, SDS-PAGE (R & NR). For the 10 cycles of freeze-thaw study, samples were also analyzed by RP-HPLC NPI.

The material requirements and the sample map are shown in Table 10 below:

An agitation study at RT for 24 hrs was also performed on each formulation and all test samples were analyzed for visual, concentration (A280), Turbidity (A330), SE-HPLC and HIAC.

Selected samples from the above studies were also used for iCIEF and Potency studies.

Formulation vialing and stoppering, agitation study design, freeze-thaw study design, and formulation standard are as described below.

Formulation Vialing and Stoppering

Sterile filtration and filling were performed in a Baker SG600 laminar airflow hood. Formulations and placebos were sterile-filtered using aseptic technique (Millipore Millex-GV 0.22 μm PVDF syringe filters, #SLGV033RS). The filtered AGS-22M6E and filtered formulation buffers (placebo) were transferred to the sterile screw-cap polycarbonate bottles (Nalgene 5-ml, #3500-05) using a 5 mL electronic pipette with sterile tips.

Agitation Study Design

One vial per formulation was secured upright in a standard freezer box. The box was then attached to an IKA-VIBRAMAX-VXR orbital shaker set at 500 rpm at room temperature for 24 hours. Then the samples were removed and stored at 70° C. until analysis. Sets of 3 aliquots of each sample (70 uL aliquots for each sample) were frozen at −70° C. after filter through 0.22 um filter. After analytical testing, any remaining material was stored at 2-8° C. overnight, in case re-testing was needed. After all of the assays were

TABLE 10

| Concentration (mg/mL) | Condition | # of Vials | Fill Volume | Total Fill volume | Total Protein (mg) |
|---|---|---|---|---|---|
| 10 | T = 0 | 1 | 3.5 | 3.5 | 35 |
| 10 | 1 cycle Fz/Th at −20° C./25° C. | 1 | 1 | 1.0 | 10 |
| 10 | 3 cycle Fz/Th at −20° C./25° C. | 1 | 1 | 1.0 | 10 |
| 10 | 10 cycle Fz/Th at −20° C./25° C. | 1 | 1 | 1.0 | 10 |
| 10 | 1 cycle Fz/Th at −70° C./25° C. | 1 | 1 | 1.0 | 10 |
| 10 | 3 cycle Fz/Th at −70° C./25° C. | 1 | 1 | 1.0 | 10 |
| 10 | 10 cycle Fz/Th at −70° C./25° C. | 1 | 1 | 1.0 | 10 |
| 10 | Shake at RT for 24 hrs | 1 | 3.5 | 3.5 | 35 |

| # of Prot Concs to Test | # of Buffers to Test | Total # Vials | Total Fill Volume (mL) | Protein In Vials (mg) | Protein required (mg) |
|---|---|---|---|---|---|
| 1 | 3 | 24 | 39 | 390 | 468 |

Notes:
Vials: 5 mL sterile screw-cap polycarbonate bottles (Nalgene 5-ml, #3500-05)
BDS Fz/Th: 1 mL fill in 5 mL polycarbonate bottle.
BDS shaking: 3.5 mL fill in 5 mL polycarbonate bottle.

Table 11 below lists the assays and time points.

TABLE 11

| Analytical Assay | T = 0 | 1X Fz/Th at −70° C./ 25° C. | 3X Fz/Th at −70° C./ 25° C. | 10X Fz/Th at −70° C./ 25° C. | 1X Fz/Th at −20° C./ 25° C. | 3X Fz/Th at −20° C./ 25° C. | 10X Fz/Th at 20° C./ 25° C. | RT Shake for 24 hrs |
|---|---|---|---|---|---|---|---|---|
| pH | X | | | | | | | |
| Osmolality | X | | | | | | | |
| Visual appearance | X | X | X | X | X | X | X | X |
| A280 | X | X | X | X | X | X | X | X |
| Turbidity (A330) | X | X | X | X | X | X | X | X |
| Non-reduced SDS-PAGE | X | X | X | X | X | X | X | X |
| Reduced SDS-PAGE | X | X | X | X | X | X | X | X |
| SE-HPLC | X | X | X | X | X | X | X | X |
| RP-HPLC-NPI | X | X | X | X | X | X | X | X |
| HIAC | X | | | | | | | X |
| Potency &CIEF | | | | Provide samples for testing | | | | | complete, remaining materials were then stored at −70° C. Two frozen aliquots were used for cIEF and potency assays.

Freeze-Thaw (−70° C. and −20° C.) Stability Study Design 1 vial per formulation (1 ml fill in 5 mL polycarbonate bottle) was placed upright in a −70° C. and −20° C. freezer for at least 4 hours, which allowed for freezing. For thawing, each vial was removed from storage and thawed at room temperature (20-25° C.) until ice was no longer observed, then the vial was gently swirled. This constituted one complete freeze-thaw cycle. Ten freeze-thaw cycles were completed for each tested formulation sample vial. Following the final freeze-thaw cycle, all samples were evaluated by analytical testing. The samples were analyzed by the following methods: Visual appearance, A280/A248, Turbidity (A330), SE-HPLC, RP-HPLC-NPI and SDS-PAGE (R & NR). Sets of 3 aliquots of each sample (70 uL aliquots for each sample) were frozen at −70° C. after filter through 0.22 um filter. After analytical testing, any remaining material was stored at 2-8° C. overnight, in case re-testing was needed. After all of the assays were complete, remaining materials were then stored at −70° C. Two frozen aliquots were used for cIEF and potency assays.

Formulation Standard 15 mL of AGS-22M6E starting material at 12.8 mg/mL in 5.0% Sucrose, 0.02% Tween 20, pH 6.0 was taken and aliquoted at 500 ul/vial, then stored at −70° C. as formulation standard for this study.

Results

Visual appearance: Visual appearance for all samples were analyzed in this study and no particulates were seen, even upon shaking.

A280 and A330 analysis: A280 and A330 data for formulations subjected to different conditions in this study are summarized in Table 12 below. As shown, there was no change in protein concentration at any of the conditions of shaking or freeze-thaw. In addition, there was no increase in turbidity upon freeze-thaw or shaking.

TABLE 12

| Time Point | Formulation | Dilution Factor | A330 | A280 | A280 (with Placebo A280 subtracted) | Conc (mg/mL) | A330 Undiluted |
|---|---|---|---|---|---|---|---|
| T = 0, BDS | 4 | 20 | 0.012 | 0.741 | 0.728 | 10.01 | 0.083 |
| | 9 | 20 | 0.021 | 0.811 | 0.795 | 10.94 | 0.091 |
| | 14 | 20 | 0.004 | 0.820 | 0.789 | 10.86 | 0.103 |
| Shake | 4 | 20 | 0.011 | 0.749 | 0.736 | 10.12 | 0.089 |
| | 9 | 20 | 0.027 | 0.827 | 0.811 | 11.16 | 0.960 |
| | 14 | 20 | 0.001 | 0.820 | 0.789 | 10.86 | 0.107 |
| 1X −20 C. FzTh | 4 | 20 | 0.006 | 0.765 | 0.752 | 10.34 | 0.097 |
| | 9 | 20 | 0.026 | 0.812 | 0.796 | 10.96 | 0.098 |
| | 14 | 20 | 0.005 | 0.823 | 0.792 | 10.90 | 0.112 |
| 3X −20 C. FzTh | 4 | 20 | 0.003 | 0.779 | 0.766 | 10.54 | 0.096 |
| | 9 | 20 | 0.030 | 0.819 | 0.803 | 11.05 | 0.098 |
| | 14 | 20 | 0.003 | 0.821 | 0.790 | 10.87 | 0.108 |
| 10X −20 C. FzTh | 4 | 20 | 0.001 | 0.783 | 0.770 | 10.59 | 0.097 |
| | 9 | 20 | 0.031 | 0.822 | 0.806 | 11.08 | 0.109 |
| | 14 | 20 | 0.008 | 0.818 | 0.787 | 10.83 | 0.128 |
| 1X −70 C. FzTh | 4 | 20 | 0.002 | 0.780 | 0.767 | 10.55 | 0.114 |
| | 9 | 20 | 0.028 | 0.839 | 0.823 | 11.32 | 0.120 |
| | 14 | 20 | 0.001 | 0.816 | 0.785 | 10.80 | 0.108 |
| 3X −70 C. FzTh | 4 | 20 | 0.004 | 0.789 | 0.776 | 10.67 | 0.095 |
| | 9 | 20 | 0.031 | 0.846 | 0.830 | 11.42 | 0.097 |
| | 14 | 20 | 0.003 | 0.830 | 0.799 | 11.00 | 0.107 |
| 10X −70 C. FzTh | 4 | 20 | 0.006 | 0.797 | 0.784 | 10.78 | 0.091 |
| | 9 | 20 | 0.031 | 0.833 | 0.817 | 11.24 | 0.090 |
| | 14 | 20 | 0.002 | 0.827 | 0.796 | 10.95 | 0.093 |

Figure 2A:
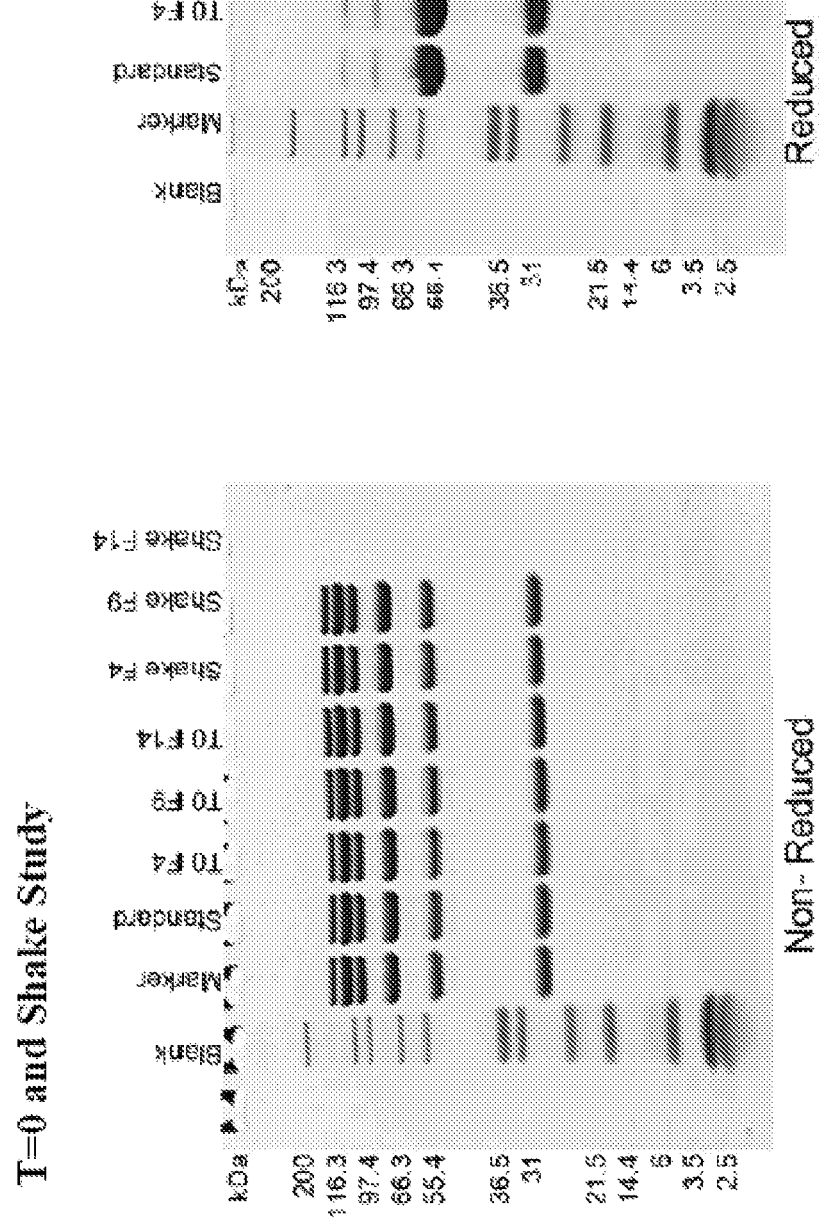
Figure 2B:
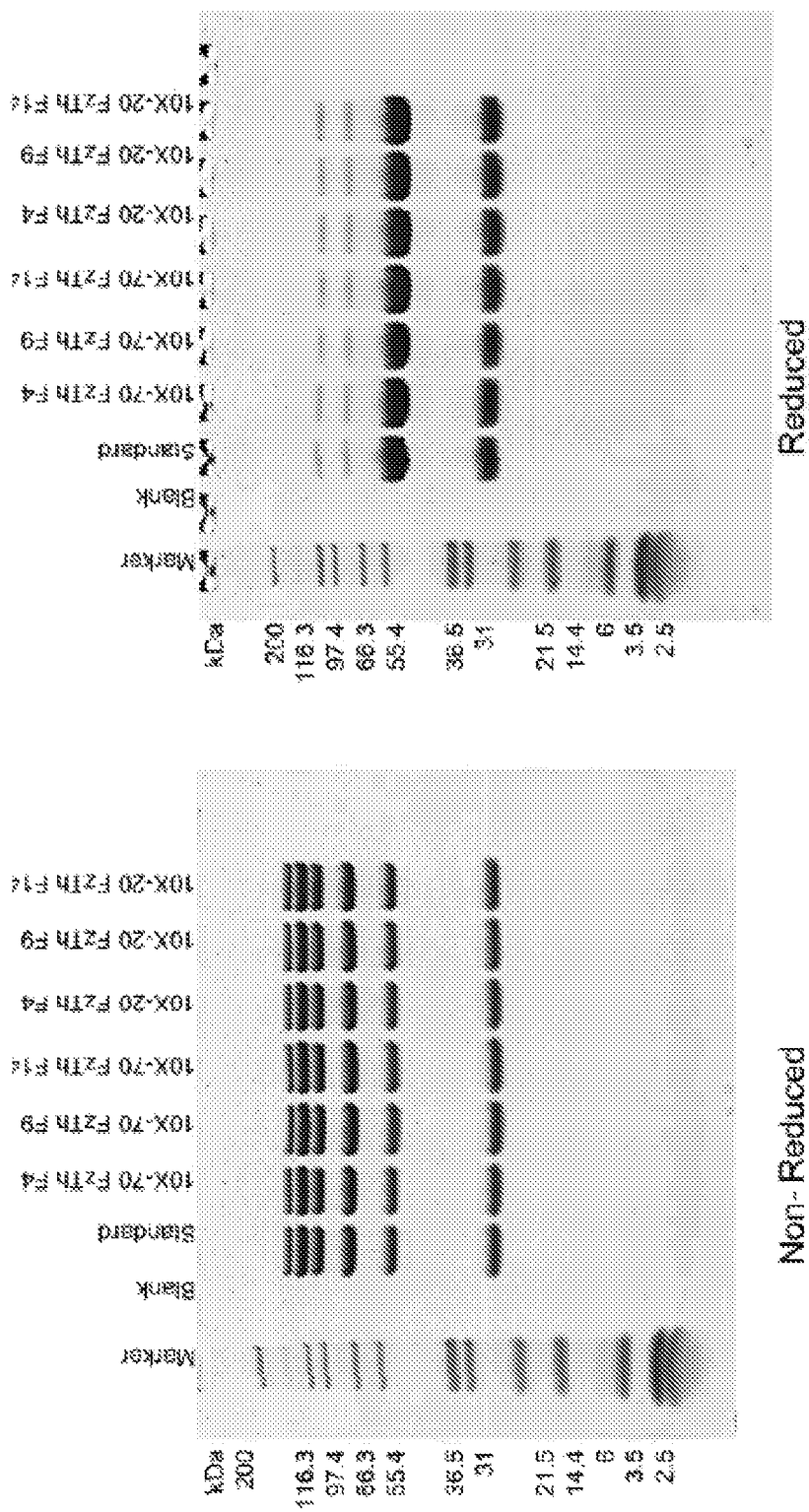
FIG. 2B depicts the SDS-PAGE results of the cycle freeze-thaw study for the formulations F4, F9, and F14.

SDS-PAGE analysis: SDS-PAGE analysis results are shown in FIGS. 2A and 2B. As shown, there are no changes seen by SDS-PAGE for the shake study samples and for the freeze-thaw samples. Both reduced and non-reduced gels are comparable to the formulation standard.

RP-HPLC analysis: For the 10-cycle freeze-thaw samples, RP-HPLC analysis was performed. No evidence of SGD1010 peak was seen in any formulation as analyzed by RP-HPLC (data not shown here).

SE-HPLC analysis: The results of the SE-HPLC analysis are summarized in Table 13 below. As shown, there were no differences observed between T0 and the shake samples or the freeze-thaw samples for any of the three formulations (F4, F9, and 14) or placebos.

TABLE 13

| Sample Name | Condition | % of Total Integrated Area | | | | Integrated Area | | | |
|---|---|---|---|---|---|---|---|---|---|
| | | Main Peak | | | | | | | |
| | | Retention Time | Pre Peaks | Main Peak | Post Peaks | Pre Peaks | Main Peak | Post Peaks | Total |
| F4, BDS | T0 | 19.6 | 1.3 | 95.7 | 3.0 | 66 | 4955 | 154 | 5175 |
| | Shaking for 24 hr RT | 19.5 | 1.2 | 96.2 | 2.6 | 64 | 4937 | 134 | 5134 |
| | 1 F/T –20° C. | 19.6 | 1.2 | 95.9 | 2.9 | 63 | 4913 | 150 | 5125 |
| | 3 F/T –20° C. | 19.5 | 1.2 | 96.1 | 2.7 | 63 | 4960 | 138 | 5161 |
| | 10 F/T –20° C. | 19.5 | 1.2 | 96.3 | 2.4 | 64 | 4935 | 125 | 5123 |
| | 1 F/T –70° C. | 19.6 | 1.2 | 96.0 | 2.7 | 63 | 4929 | 141 | 5132 |
| | 3 F/T –70° C. | 19.5 | 1.2 | 96.2 | 2.5 | 64 | 5006 | 132 | 5202 |
| | 10 F/T –70° C. | 19.6 | 1.3 | 95.9 | 2.8 | 68 | 4981 | 143 | 5192 |
| F9, BDS | T0 | 19.6 | 1.3 | 95.6 | 3.1 | 66 | 5002 | 164 | 5232 |
| | Shaking for 24 hr RT | 19.6 | 1.3 | 96.4 | 2.3 | 65 | 4980 | 120 | 5164 |
| | 1 F/T –20° C. | 19.5 | 1.3 | 95.8 | 2.9 | 71 | 5007 | 152 | 5229 |
| | 3 F/T –20° C. | 19.5 | 1.2 | 96.5 | 2.3 | 63 | 4997 | 119 | 5179 |
| | 10 F/T –20° C. | 19.6 | 1.2 | 96.1 | 2.7 | 64 | 4944 | 137 | 5145 |
| | 1 F/T –70° C. | 19.6 | 1.3 | 96.3 | 2.4 | 64 | 4918 | 125 | 5107 |
| | 3 F/T –70° C. | 19.5 | 1.2 | 96.3 | 2.5 | 63 | 4978 | 127 | 5168 |
| | 10 F/T –70° C. | 19.5 | 1.2 | 96.1 | 2.6 | 65 | 4996 | 136 | 5197 |
| F14, BDS | T0 | 19.6 | 1.3 | 95.7 | 3.0 | 72 | 5190 | 161 | 5423 |
| | Shaking for 24 hr RT | 19.6 | 1.3 | 96.1 | 2.6 | 67 | 5052 | 138 | 5256 |
| | 1 F/T –20° C. | 19.6 | 1.4 | 95.7 | 2.9 | 74 | 5090 | 154 | 5319 |
| | 3 F/T –20° C. | 19.5 | 1.2 | 96.1 | 2.7 | 65 | 5047 | 142 | 5254 |
| | 10 F/T –20° C. | 19.6 | 1.3 | 96.3 | 2.4 | 66 | 5028 | 127 | 5221 |
| | 1 F/T –70° C. | 19.6 | 1.2 | 96.4 | 2.4 | 66 | 5106 | 125 | 5297 |
| | 3 F/T –70° C. | 19.5 | 1.2 | 96.3 | 2.4 | 65 | 5075 | 129 | 5269 |
| | 10 F/T –70° C. | 19.6 | 1.3 | 95.5 | 3.2 | 71 | 5096 | 169 | 5336 |

The SEC profiles obtained for each of the BDS formulations, at each of the study conditions, were analyzed (data not shown here). There was no difference noted for any of the formulations at any condition, as compared to BDS at T=0.

Table 14 below summarizes the HIAC data for the BDS samples for each of the 3 formulations tested. Comparison of results for samples prior to and after shaking at RT for 24 hrs reveals that less than 100 particles were in the range between 10µ and 25 µm, with less than 2 particles being in the 25 µm range for all formulations.

Overall, results demonstrated that all three BDS formulations tested exhibit excellent stability under treatment of freeze-thaw cycling and agitation, and no changes were seen in any of the samples relative to T=0, by any of the analytical methods.

6.3 Example 3—Concurrent BDS and Drug Product (DP) Formulation Study

This study was performed in conjunction with the study described in Section 6.2 above. Formulation compositions

TABLE 14

| Condition | Sample Name | Fomulation | Average of 3 Runs for Total Cumulative Counts/mL Size (um) | | | | | | |
|---|---|---|---|---|---|---|---|---|---|
| | | | 2 | 5 | 7.5 | 10 | 15 | 20 | 25 |
| No Shaking | Placebo | 4 | 47 | 10 | 7 | 5 | 5 | 3 | 2 |
| | | 9 | 73 | 30 | 17 | 8 | 5 | 2 | 0 |
| | | 14 | 73 | 17 | 12 | 10 | 3 | 0 | 0 |
| | AGS22M6 | 4 | 382 | 77 | 32 | 15 | 2 | 2 | 0 |
| | | 9 | 135 | 45 | 28 | 18 | 7 | 0 | 0 |
| | | 14 | 365 | 138 | 68 | 47 | 15 | 3 | 2 |
| Shaking at for 24 hrs | Placebo | 4 | 298 | 127 | 78 | 47 | 23 | 3 | 0 |
| | | 9 | 365 | 155 | 88 | 60 | 13 | 2 | 0 |
| | | 14 | 407 | 118 | 47 | 25 | 5 | 0 | 0 |
| | AGS22M6 | 4 | 368 | 127 | 62 | 42 | 18 | 5 | 2 |
| | | 9 | 557 | 192 | 108 | 73 | 20 | 3 | 2 |
| | | 14 | 967 | 333 | 165 | 97 | 32 | 12 | 2 |

Figure 2C:
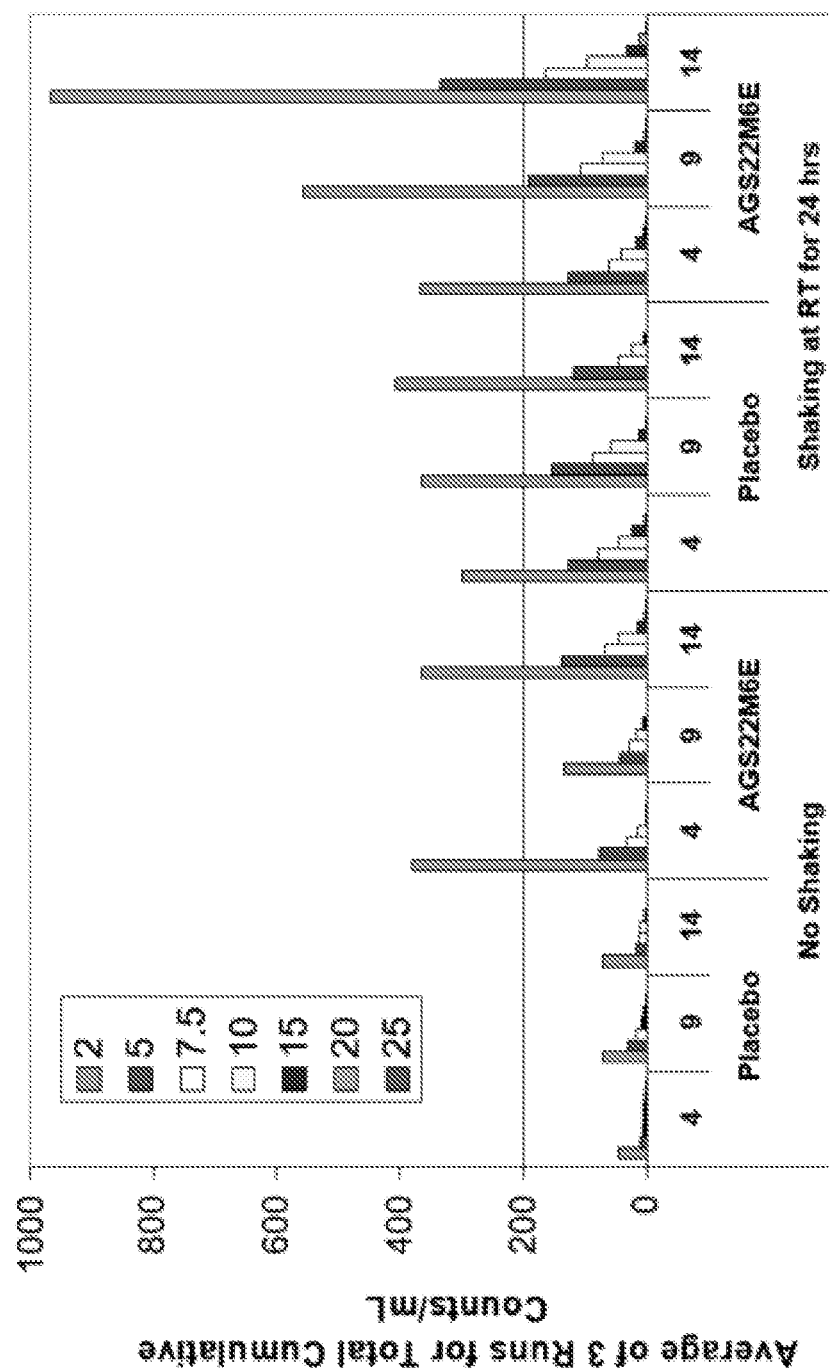
FIG. 2C depicts the total cumulative counts per mL as measured by HIAC for the formulations F4, F9, and F14.

Formulations F9 and F14 showed slightly elevated cumulative counts post-agitation, with F4 showing comparability pre- and post agitation, as charted in FIG. 2C (all counts for 10 and 25 um are below the USP limit).

and the materials used for this study are the same as those described in Section 6.2.

The material requirements and sample map are shown in the table below.

TABLE 15

| Concentration (mg/mL) | Condition | # of Vials | Fill Volume | Total Fill volume | Total Protein (mg) | Total ml per formulation | Total mg per formulation |
|---|---|---|---|---|---|---|---|
| 10 | BDS at 2-8° C. | 5 | 1 | 5.0 | 50 | | |
| 10 | BDS at −70° C. | 6 | 1 | 6.0 | 60 | | |
| 10 | DP at 2-8° C. | 8 | 5 | 40.0 | 400 | | |
| 10 | DP at 25° C./60% RH | 6 | 5 | 30.0 | 300 | | |
| 10 | DP at 40° C./75% RH | 6 | 5 | 30.0 | 300 | 111 | 1110 |

| # of Prot Concs to Test | # of Buffers to Test | Total # Vials | Total Fill Volume (mL) | Protein In Vials (mg) | Protein required (mg) |
|---|---|---|---|---|---|
| 1 | 3 | 93 | 333 | 3330 | 3996 |

The time points and assays are as described in the table below.

TABLE 16

| Analytical Assay | Pre-Lyo T = 0.1 | T = 0 1 Jun. 2010 | T = 2 wks 15 Jun. 2010 | T = 4 wks 29 Jun. 2010 | T = 8 wks 27 Jul. 2010 | T = 12 wks 24 Aug. 2010 |
|---|---|---|---|---|---|---|
| pH | X | X | | | | |
| Osmolality | X | X | | | | |
| Visual appearance (before reconstitution) | | X | X | X | X | X |
| Visual appearance (BDS or After reconstitution) | X | X | X | X | X | X |
| Reconstitution Time (DP only) | | X | X | X | X | X |
| A280 | X | X | X | X | X | X |
| Turbidity (A3 30) | X | X | X | X | X | X |
| Non-reduced SDS-PAGE | X | X | X | X | X | X |
| Reduced SDS-PAGE | X | X | X | X | X | X |
| SE-HPLC | X | X | X | X | X | X |
| RP-HPLC-NPI | X | X | X | X | X | X |
| Residual Moisture (DP only) | | X | | | | X |
| Potency &CIEF* | | | Provide samples for testing | | | |

Note:
Samples for the liquid arm of the study were frozen at −70° C. until samples from the lyophilized arm were prepared. Frozen liquid samples were then placed at conditions at the same time as lyophilized samples were placed at conditions, so as to make t = 0 identical for both liquid and lyophilized arms of the study.

The specific lyophilization cycle parameters are outlined in the table below. After lyophilization was complete, vials were stoppered under vacuum at 50 mT.

TABLE 17

| Step # | Step | Temperature or Ramp Rate | Time (min) | Pressure (mTorr) |
|---|---|---|---|---|
| 1 | Load/Equilibrate | 5° C. | 60 | |
| 2 | Ramp from 5° C. to 0° C. | 0.5° C./mi | 10 | |
| 3 | Hold | 0° C. | 60 | |
| 4 | Ramp from 0° C. to −45° C. | 1° C./min | 45 | |
| 5 | Hold | −45° C. | 840 | |
| 6 | Pump down | −45° C. | 60 | 50 |
| 7 | Ramp from −45° C. to - | 0.3° C./mi | 100 | 50 |
| 8 | Hold | −15° C. | 5040 | 50 |
| 9 | Ramp from −15° C. to 35 | 0.2° C./mi | 250 | 50 |
| 10 | Hold | 35° C. | 360 | 50 |
| 11 | Ramp from 35° C. to 5° C. | 0.5° C./mi | 60 | 50 |
| 12 | Hold | 5° C. hold | 60 | 50 |

Liquid Formulation 2-8° C. and −70° C. Stability Study Design

Formulations and placebo vials were placed upright in a freezer set to −70° C. and an incubator set to 2-8° C. At each time point, one active and one placebo vial for each formulation were removed from the storage conditions according to the sample map for analytical testing. After analytical testing, any remaining material was stored at 2-8° C., in case re-testing was needed. Aliquots were stored at −70° C. and were used for cIEF and activity testing.

Lyophilized Formulation 2-8° C., 25° C. and 40° C. Stability Study Design

Formulations and placebo vials were placed upright in an incubator set to 2-8° C., an incubator set to 25° C./60% RH and an incubator set to 40° C./75% RH. At each time point, one active and one placebo vial for each formulation were removed from storage condition according to the sample map for analytical testing. After analytical testing, any remaining material was stored at 2-8° C. in case re-testing was needed. Aliquots were stored at −70° C. and were used for cIEF and activity testing.

The formulation standard used in this study is the same as that in Section 6.2 above.

Lyophilization cycle analysis: A typical lyophilization cycle includes freezing, primary drying and secondary drying steps. During the freezing and drying process, the sublimation of ice can be followed by reference to several separate indicators, such as the readings of the thermocouple probes placed in placebo sample vials, the divergence and the later coincidence of the capacitance manometer and pirani gauge pressure readings, and the "dewpoint" measurement that tracks the change in the relative humidity in the chamber headspace.

By comparing the average product thermocouple temperature, the capacitance manometer/Pirani gauge reading difference and the dewpoint profile, it can be demonstrated that each correlates well with the others.

Stability of BDS formulations: Stability of BDS formulation at 2-8° C. and −70° C. storage conditions and at 2-8° C., 25° C. and 40° C. storage conditions were evaluated at T=0, 2, 4, 8, and 12 week time points. Liquid and reconstituted lyophilized samples were analyzed by concentration (A280), turbidity (A330), SE-HPLC, SDS-PAGE (R and NR) and RP-HPLC NPI at each time point. For lyophilized drug product (DP), osmolality was measured before lyophilization and after reconstitution at t=0 only; cake appearance and reconstitution time were measured at each time point; and Karl Fischer (residual moisture) was measured at T=0 and T=12 weeks only.

Visual appearance and reconstitution time: The cake formations for all three formulations were comparable. Both actives and placebos for all three formulations formed white, slightly cracked cakes with a shiny surface. All maintained intact structure. There were no differences between actives and placebos. There were no differences between these formulations. For all formulations stored at different conditions for 2, 4, 8 and 12 weeks, visual appearance of the cake was similar to T=0 as shown in the table below.

TABLE 18

|  | Formulation | Protein Concentration mg/ml | Cake Appearance | Reconstitution Time (seconds)^ | | | Visual Appearance |
|---|---|---|---|---|---|---|---|
|  |  |  |  | 40° C | 25° C. | 2-8° C. |  |
| 2 week | 4 | 10 | White cake, | 23 | 19 | 21 | Clear, |
|  | 9 | 10 | slightly | 17 | 21 | 25 | colorless, |
|  | 14 | 10 | cracked, shiny | 21 | 22 | 22 | no |
|  | 4 | Placebo | surface | 22 |  |  | particulates |
|  | 9 |  |  | 21 |  |  |  |
|  | 14 |  |  | 22 |  |  |  |
| 4 week | 4 | 10 | White cake, | 29 | 25 | 23 | Clear, |
|  | 9 | 10 | slightly | 17 | 23 | 21 | colorless, |
|  | 14 | 10 | cracked, shiny | 20 | 21 | 27 | no |
|  | 4 | Placebo | surface | 29 |  |  | particulates |
|  | 9 |  |  | 26 |  |  |  |
|  | 14 |  |  | 20 |  |  |  |
| 8 week | 4 | 10 | White cake, | 25 | 28 | 29 | Clear, |
|  | 9 | 10 | slightly | 25 | 23 | 31 | colorless, |
|  | 14 | 10 | cracked, shiny | 24 | 22 | 33 | no |
|  | 4 | Placebo | surface | 28 |  |  | particulates |
|  | 9 |  |  | 22 |  |  |  |
|  | 14 |  |  | 19 |  |  |  |
| 12 week | 4 | 10 | White cake, | 22 | 28 | 24 | Clear, |
|  | 9 | 10 | slightly | 20 | 22 | 27 | colorless, |
|  | 14 | 10 | cracked, shiny | 23 | 25 | 23 | no |
|  | 4 | Placebo | surface | 28 |  |  | particulates |
|  | 9 |  |  | 20 |  |  |  |
|  | 14 |  |  | 28 |  |  |  |

Moisture analysis: After lyophilization was completed, one active and one placebo vial from each formulation were allocated for residual moisture testing. As shown in the table below and FIG. 3A, the residual moistures of the actives and placebos for F4 and F14 were very close, ranging from 0.24 to 0.70%. F9 had higher residual moisture at every time point than F4 and F14.

TABLE 19

|  |  | % residual moisture | | | | SD | | | |
|---|---|---|---|---|---|---|---|---|---|
|  |  | t = 0 | t = 12 wk; 2-8° C. | t = 12 wk; 25° C. | t = 12 wk; 40° C. | T = 0 | 2-8° C. | 25° C. | 40° C. |
| Active | F4 | 0.24 | 0.25 | 0.42 | 0.54 | 0.03 | 0.01 | 0.02 | 0.03 |
|  | F9 | 0.76 | 0.55 | 0.61 | 0.75 | 0.02 | 0.00 | 0.02 | 0.02 |
|  | F1 | 0.24 | 0.24 | 0.29 | 0.55 | 0.01 | 0.02 | 0.01 | 0.01 |
| Placebo | F4 | 0.29 | 0.28 | 0.56 | 0.70 | 0.01 | 0.02 | 0.02 | 0.01 |
|  | F9 | 0.77 | 0.73 | 1.15 | 1.14 | 0.01 | 0.03 | 0.01 | 0.02 |
|  | F1 | 0.21 | 0.22 | 0.44 | 0.69 | 0.01 | 0.02 | 0.01 | 0.01 |

Results represent the average of three determinations on 1 vial

After samples were incubated at different conditions for 12 weeks, residual moistures for each formulation were tested again for both actives and placebos. The residual moistures for all three formulations stored at 2-8° C. for 12 weeks were similar to t=0. F4 and F14 had increased moisture relative to t=0 after stored at 25° C. and 40° C. for 12 weeks.

after inverting. Although effort was made to capture all condensation from sides of bottles, some condensation may have been trapped in cap of bottle; 2) some evaporation of sample might occur if a bottle has a flawed thread, although this issue was not seen in a previous study in which 4 mL drug substance was filled in these bottles and stored at 2-8° C. for 12 weeks.

TABLE 20

(12 week concurrent BDS and DP formulation study A280 and concentration data)

| Formulation | A280 | | | | | Concentration (mg/mL) | | | | |
|---|---|---|---|---|---|---|---|---|---|---|
| | 0 | 2 | 4 | 8 | 12 | 0 | 2 | 4 | 8 | 12 |
| BDS - Weeks at −70° C. | | | | | | | | | | |
| 4 | 0.757 | 0.737 | 0.735 | 0.740 | 0.727 | 10.4 | 10.1 | 10.1 | 10.2 | 10.0 |
| 9 | 0.735 | 0.725 | 0.749 | 0.727 | 0.736 | 10.1 | 10.0 | 10.3 | 10.0 | 10.1 |
| 14 | 0.743 | 0.740 | 0.746 | 0.764 | 0.742 | 10.2 | 10.2 | 10.3 | 10.5 | 10.2 |
| BDS - Weeks at 2-8° C. | | | | | | | | | | |
| 4 | 0.757 | 0.749 | 0.763 | 0.801 | 0.812 | 10.4 | 10.3 | 10.5 | 11.0 | 11.2 |
| 9 | 0.735 | 0.748 | 0.776 | 0.817 | 0.918 | 10.1 | 10.3 | 10.7 | 11.2 | 12.6 |
| 14 | 0.743 | 0.759 | 0.778 | 0.823 | 0.824 | 10.2 | 10.4 | 10.7 | 11.3 | 11.3 |

| Formulation | A280 | | | | | | Concentration (mg/mL) | | | | | |
|---|---|---|---|---|---|---|---|---|---|---|---|---|
| | 0 | 0.1 | 2 | 4 | 8 | 12 | 0 | 0.1 | 2 | 4 | 8 | 12 |
| Lyo DP - Weeks at 2- | | | | | | | | | | | | |
| 4 | 0.757 | 0.757 | 0.745 | 0.778 | 0.773 | 0.747 | 10.4 | 10.4 | 10.2 | 10.7 | 10.6 | 10.3 |
| 9 | 0.735 | 0.769 | 0.743 | 0.777 | 0.782 | 0.769 | 10.1 | 10.6 | 10.2 | 10.7 | 10.8 | 10.6 |
| 14 | 0.743 | 0.800 | 0.766 | 0.815 | 0.751 | 0.769 | 10.2 | 11.0 | 10.5 | 11.2 | 10.3 | 10.6 |
| Lyo DP - Weeks at | | | | | | | | | | | | |
| 4 | 0.757 | 0.757 | 0.751 | 0.765 | 0.761 | 0.751 | 10.4 | 10.4 | 10.3 | 10.5 | 10.5 | 10.3 |
| 9 | 0.735 | 0.769 | 0.751 | 0.778 | 0.768 | 0.774 | 10.1 | 10.6 | 10.3 | 10.7 | 10.6 | 10.6 |
| 14 | 0.743 | 0.800 | 0.743 | 0.784 | 0.770 | 0.765 | 10.2 | 11.0 | 10.2 | 10.8 | 10.6 | 10.5 |
| Lyo DP - Weeks at | | | | | | | | | | | | |
| 4 | 0.757 | 0.757 | 0.746 | 0.766 | 0.758 | 0.736 | 10.4 | 10.4 | 10.3 | 10.5 | 10.4 | 10.1 |
| 9 | 0.735 | 0.769 | 0.750 | 0.776 | 0.763 | 0.766 | 10.1 | 10.6 | 10.3 | 10.7 | 10.5 | 10.5 |
| 14 | 0.743 | 0.800 | 0.772 | 0.807 | 0.771 | 0.755 | 10.2 | 11.0 | 10.6 | 11.1 | 10.6 | 10.4 |

For all of the time points tested, after reconstitution with 4.7 mL of WFI, all of the reconstituted formulations and placebos were colorless and clear. No visible particles were observed. BDS samples stored at all conditions at all time points were clear and colorless too. No visible particles were observed.

A280 and osmolality analysis: Prior to filling and lyophilization, the protein concentrations of the formulations were checked in duplicate and found to within ±1 mg/mL of the target concentration of 10 mg/mL. After reconstitution with 4.7 mL of WFI, the protein concentrations of the formulations were within ±1 mg/mL of BDS before lyophilization (see Table 20 below, BDS, t=0). The osmolarities of the formulated samples and buffer were also tested in duplicate prior to filling and after reconstitution. The osmolarities before lyophilization and after reconstitution were between 187 and 194 mOsm/kg.

Figure 3A:
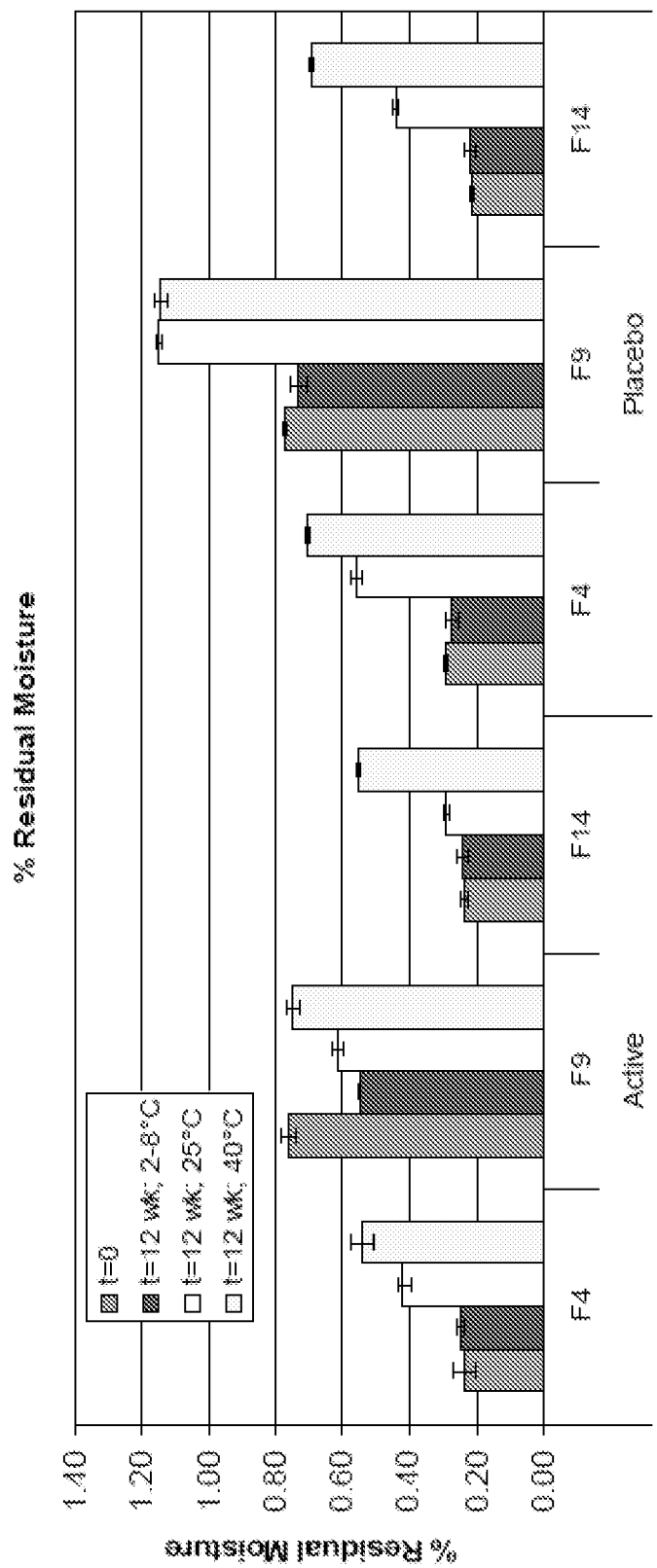
FIG. 3A depicts the results of the residual moisture analysis for the formulations F4, F9, and F14.
Figure 3B:
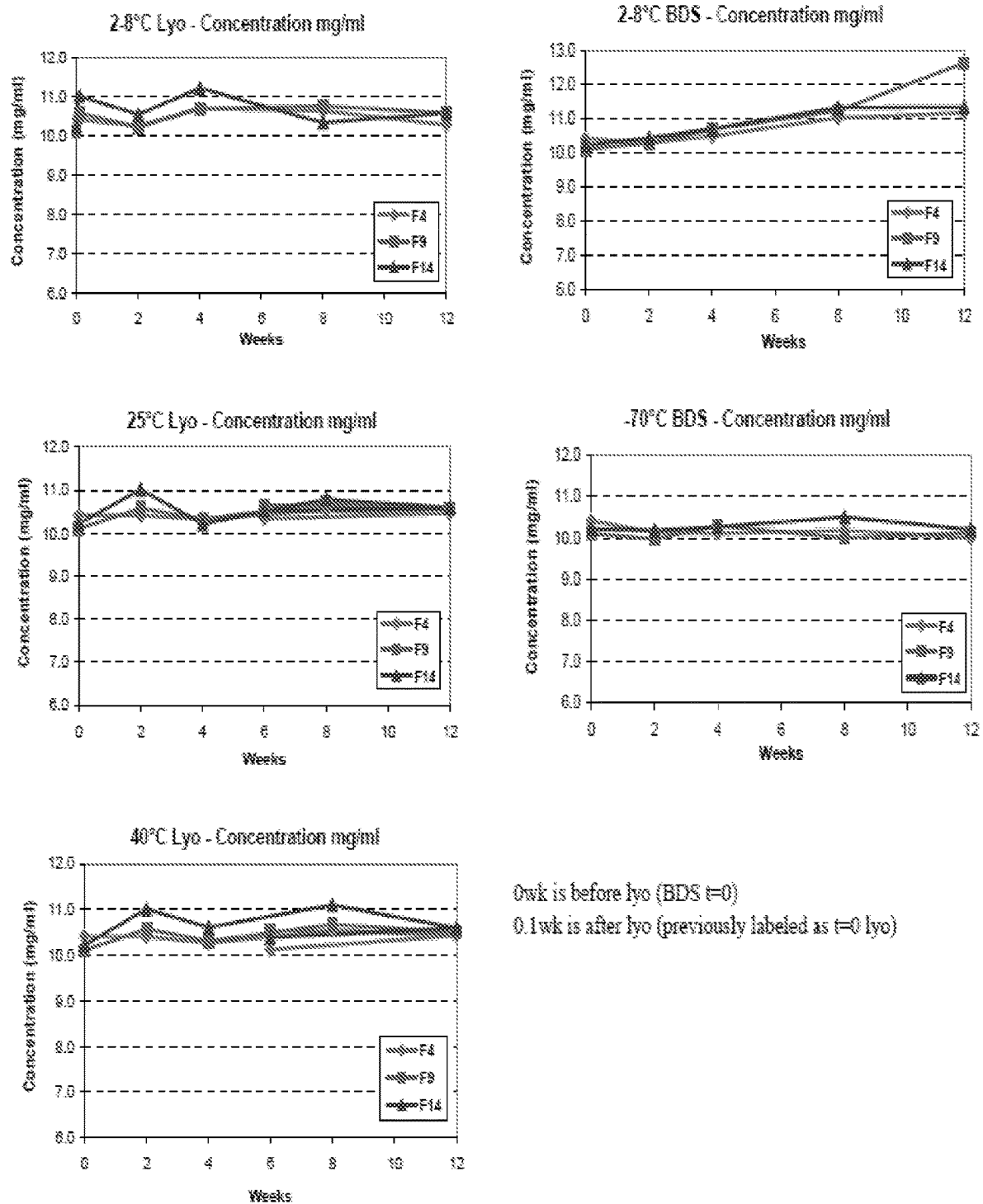
FIG. 3B depicts the A280 (concentration) results in the 12 week concurrent BDS and DP formulation study.
Figure 3C:
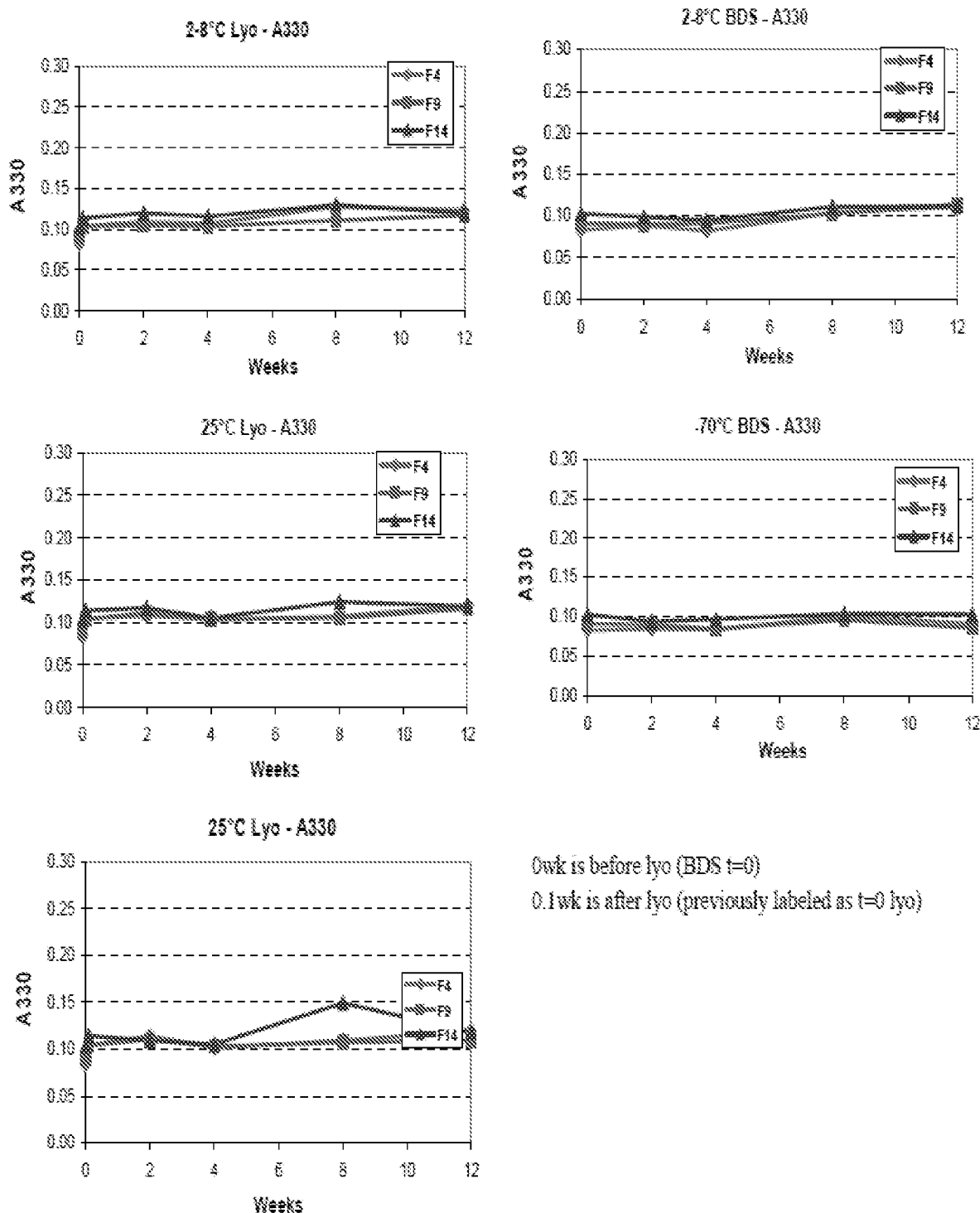
FIG. 3C depicts the A330 (turbidity) results in the 12 week concurrent BDS and DP formulation study.

The protein concentration results of BDS and DP samples stored at different conditions are shown in Table 20 below and FIG. 3B. There was no change in protein concentration under most conditions. However, BDS samples stored at 2-8° C. showed an unexpected increase of protein concentration. There were two possible reasons: 1) condensation that was present in vials may not be completely incorporated

TABLE 21

(12 week concurrent BDS and DP formulation study osmolatity data)

| | Formulation | Reading 1 | Reading 2 | Average | Placebo |
|---|---|---|---|---|---|
| T = 0, Lyo | 4 | 193 | 194 | 194 | 191 |
| | 9 | 197 | 195 | 196 | 192 |
| | 14 | 193 | 194 | 194 | 186 |
| T = 0, BDS | 4 | 189 | 190 | 190 | 188 |
| | 9 | 189 | 190 | 190 | 186 |
| | 14 | 188 | 186 | 187 | 180 |

A330 analysis: A330 measurements of both BDS and DP reconstituted active and placebo vials are shown in Table 22 below and FIG. 3C. The A330 value for the active vial was slightly higher than the placebo, indicating that the AGS-22M6E protein contributes to the formulation turbidity. There was no significant increase in turbidity for both the active and placebo samples storage at all conditions.

TABLE 22

| Formulation | 0 | 2 | 4 | 8 | 12 |
|---|---|---|---|---|---|
| BDS - Weeks at −70° C. | | | | | |
| 4 | 0.083 | 0.085 | 0.084 | 0.101 | 0.091 |
| 9 | 0.091 | 0.090 | 0.085 | 0.096 | 0.086 |
| 14 | 0.103 | 0.094 | 0.097 | 0.104 | 0.103 |
| 4 Placebo | 0.009 | | | | |
| 9 Placebo | 0.010 | | | | |
| 14 Placebo | 0.010 | | | | |
| BDS - Weeks at 2-8° C. | | | | | |
| 4 | 0.083 | 0.089 | 0.082 | 0.104 | 0.111 |
| 9 | 0.091 | 0.090 | 0.091 | 0.103 | 0.114 |
| 14 | 0.103 | 0.099 | 0.095 | 0.111 | 0.112 |
| 4 Placebo | 0.009 | 0.003 | 0.004 | 0.017 | 0.008 |
| 9 Placebo | 0.010 | 0.009 | 0.005 | 0.018 | 0.015 |
| 14 Placebo | 0.010 | 0.005 | 0.002 | 0.022 | 0.011 |

| Formulation | 0 | 0.1 | 2 | 4 | 8 | 12 |
|---|---|---|---|---|---|---|
| Lyo DP - Weeks at 2-8° C. | | | | | | |
| 4 | 0.083 | 0.104 | 0.109 | 0.107 | 0.128 | 0.124 |
| 9 | 0.091 | 0.104 | 0.105 | 0.104 | 0.111 | 0.117 |
| 14 | 0.103 | 0.114 | 0.120 | 0.116 | 0.130 | 0.120 |
| 4 Placebo | 0.009 | 0.009 | | | | |
| 9 Placebo | 0.010 | 0.030 | | | | |
| 14 Placebo | 0.010 | 0.020 | | | | |
| Lyo DP - Weeks at 25° C. | | | | | | |
| 4 | 0.083 | 0.104 | 0.108 | 0.103 | 0.107 | 0.120 |
| 9 | 0.091 | 0.104 | 0.111 | 0.104 | 0.105 | 0.116 |
| 14 | 0.103 | 0.114 | 0.117 | 0.105 | 0.124 | 0.119 |
| 4 Placebo | 0.009 | 0.009 | | | | |
| 9 Placebo | 0.010 | 0.030 | | | | |
| 14 Placebo | 0.010 | 0.020 | | | | |
| Lyo DP - Weeks at 40° C. | | | | | | |
| 4 | 0.083 | 0.104 | 0.114 | 0.101 | 0.109 | 0.119 |
| 9 | 0.091 | 0.104 | 0.110 | 0.103 | 0.107 | 0.109 |
| 14 | 0.103 | 0.114 | 0.109 | 0.105 | 0.149 | 0.118 |
| 4 Placebo | 0.009 | 0.009 | 0.012 | 0.008 | 0.015 | 0.016 |
| 9 Placebo | 0.010 | 0.030 | 0.013 | 0.013 | 0.020 | 0.017 |
| 14 Placebo | 0.010 | 0.020 | 0.007 | 0.009 | 0.014 | 0.014 |

0 wk is before lyo (BDS t = 0)
0.1 wk is after lyo (previously labeled as t = 0 lyo)

Figure 3D:
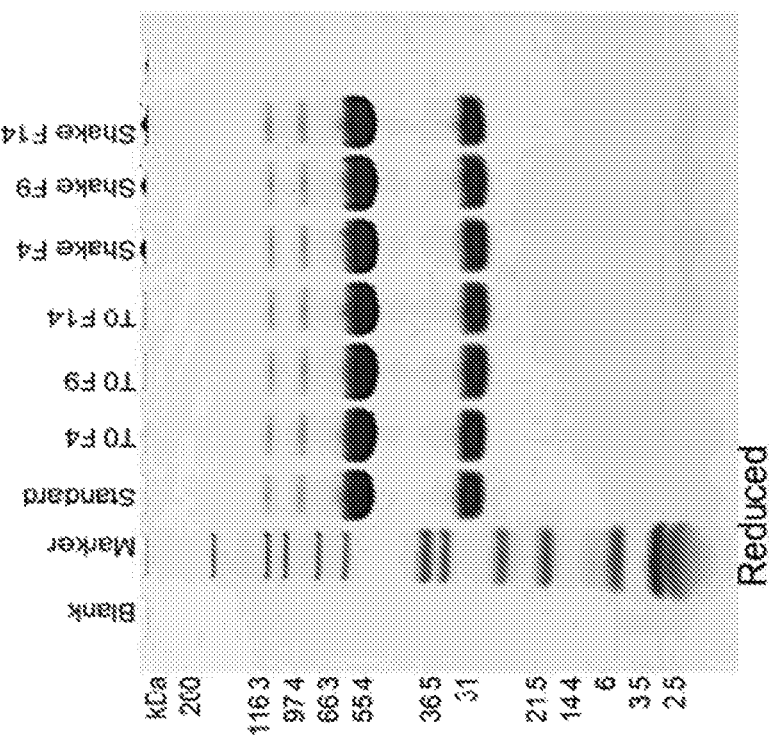
Figure 3D:
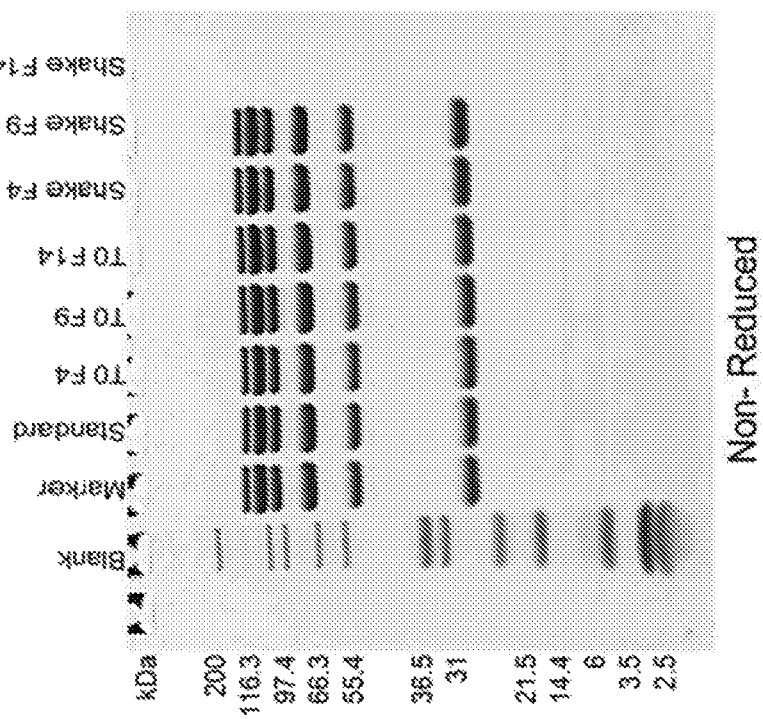
Figure 3E:
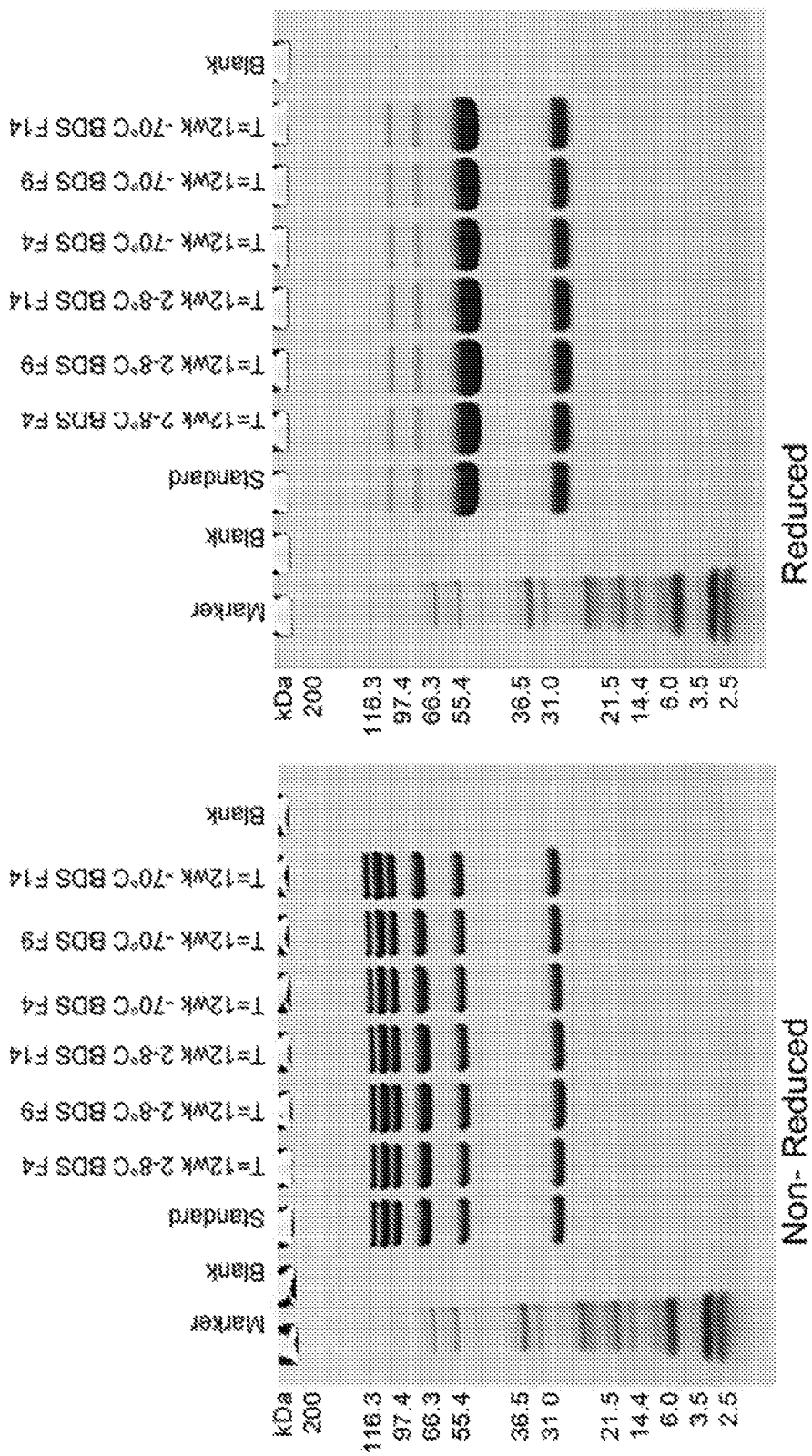
FIG. 3E depicts the results of the SDS-PAGE analysis of the BDS stored at −70° C. or 2-8° C. for 12 weeks.
Figure 3F:
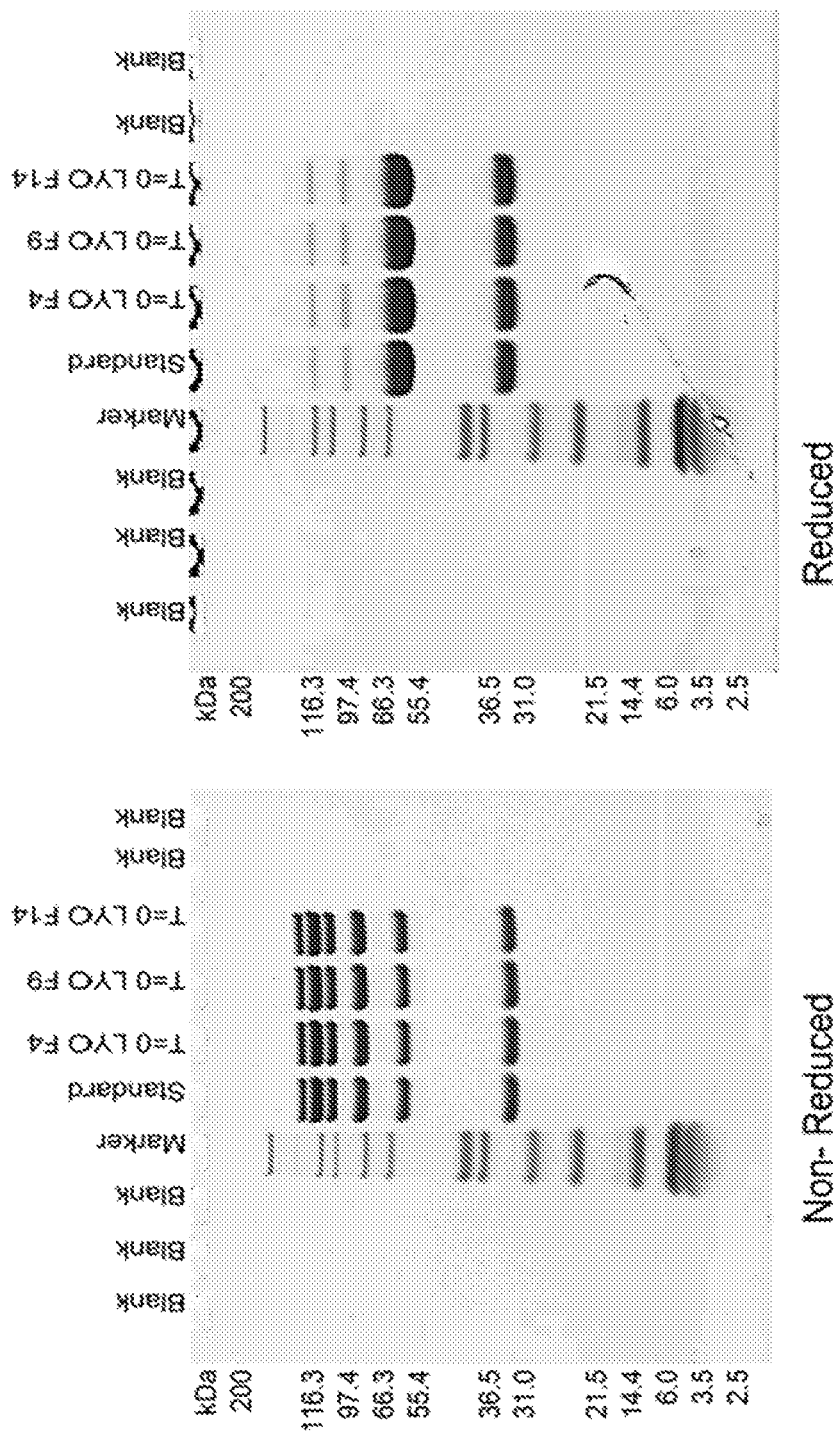
Figure 3G:
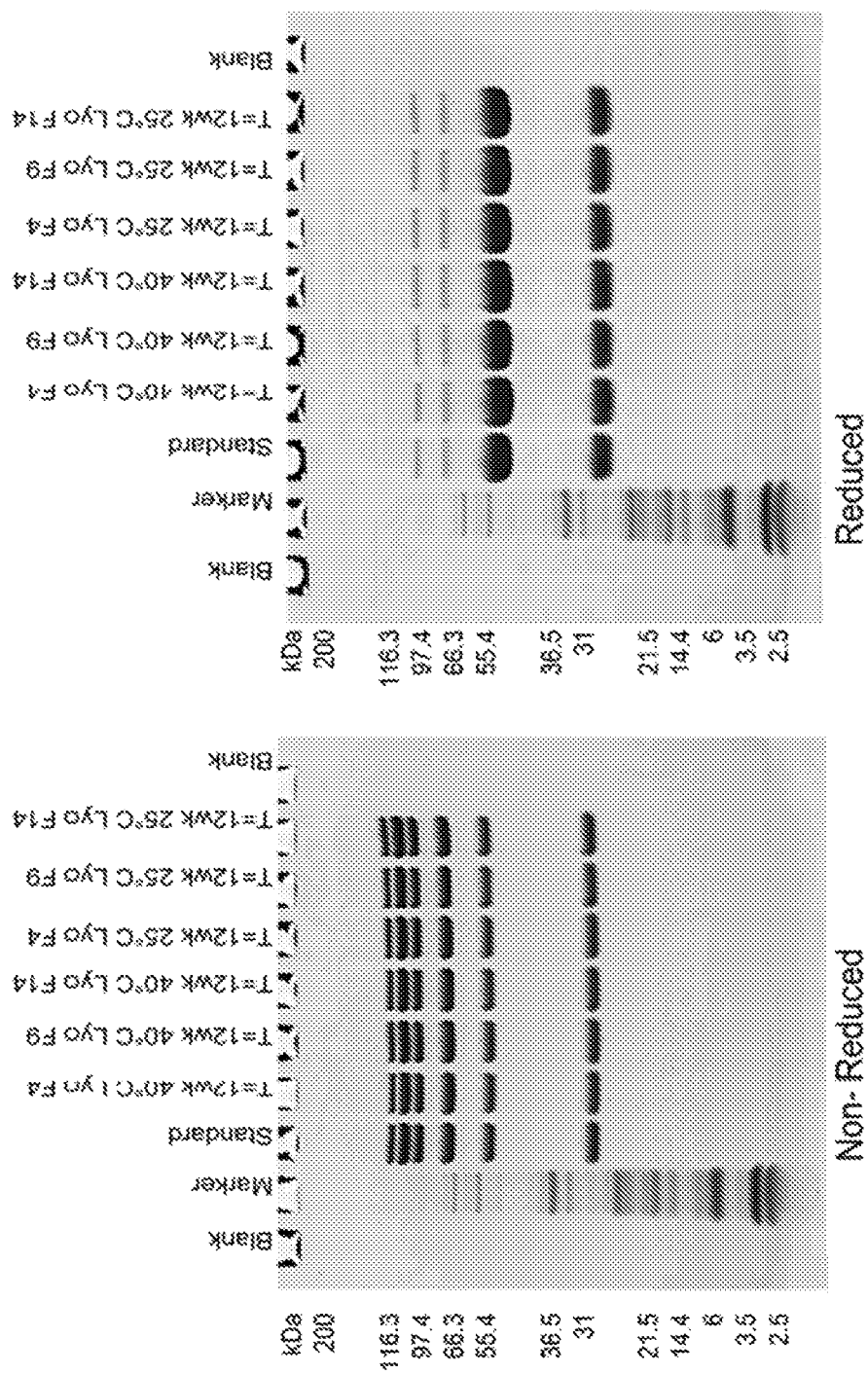
FIG. 3G depicts the results of the SDS-PAGE analysis of the DP (after lyophilization and reconstitution) stored at 25° C. or 40° C. for 12 weeks.
Figure 3H:
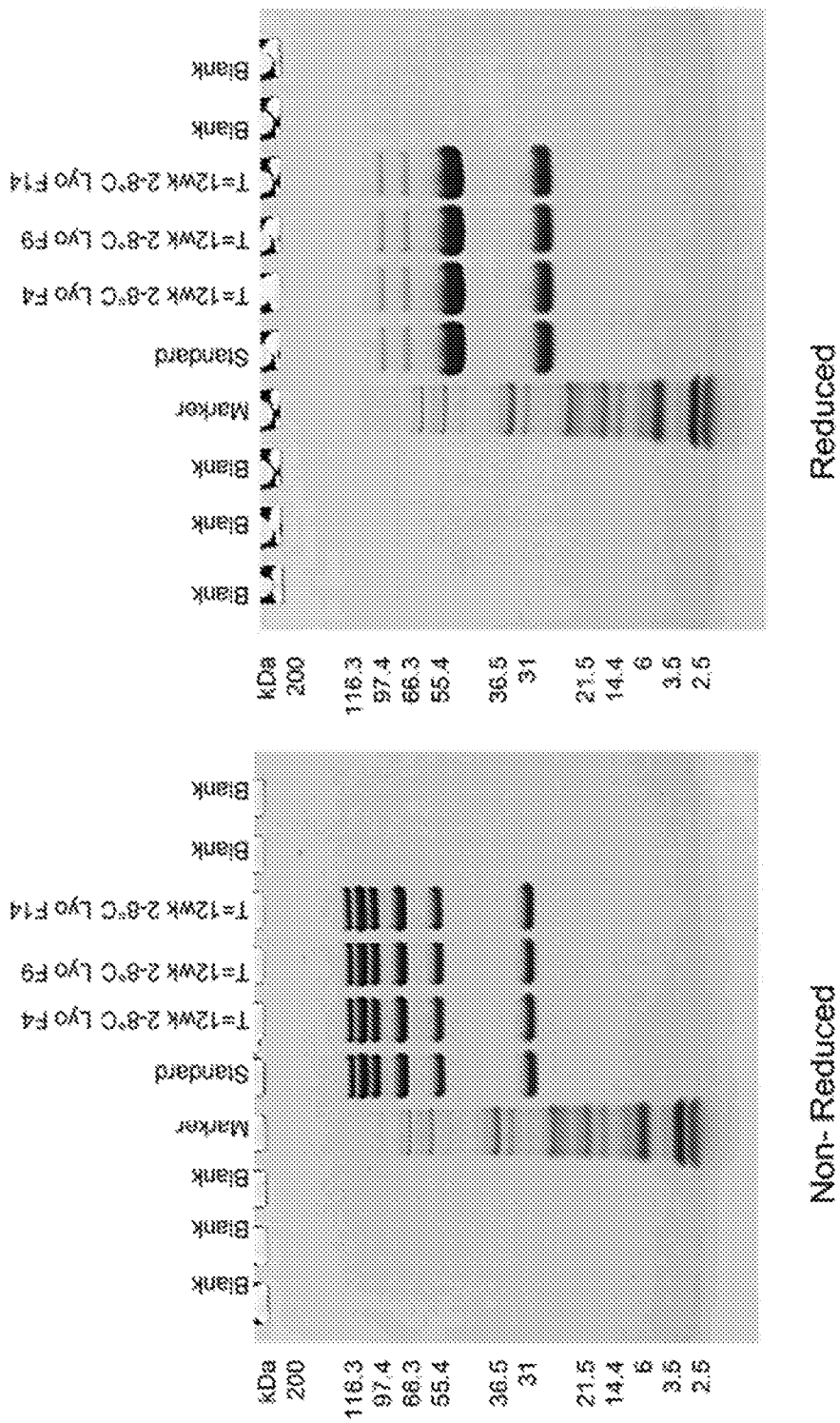
FIG. 3H depicts the results of the SDS-PAGE analysis of the DP (after lyophilization and reconstitution) stored at 2-8° C. for 12 weeks.

SDS-PAGE analysis: FIGS. 3D and 3E show the SDS-PAGE analysis for BDS T=0 (pre-lyophilization) and T=12 week samples at 2-8° C. and −70° C. storage conditions. FIG. 3F, 3G, 3H showed the SDS-PAGE analysis for DP at T=0 and T=12 week samples at 2-8° C., 25° C. and 40° C. storage conditions. No obvious changes were seen for all of the formulations after 12 weeks stored at all conditions.

RP-HPLC analysis: All of the BDS and DP samples in this study were also tested by RP-HPLC NPI method. There was no SGD1010 peak observed in any formulation at any condition (data not shown here). For all of the controls ran at each time point, the spike recoveries of SGD1010 in the formulation standard were about 100%. At T=4 week, 8 week, and 12 week time points, although a new dilution from 10 mM SGD1010 stock was used with freshly prepared diluent, the SGD1010 peak split, and the SGD1010 spiked into the formulation standard did not split (data not shown here). This was consistent throughout the sequence (data not shown here). The calculated recovery used the combined area of the split peaks.

SE-HPLC analysis: Table 23 below summarizes SE-HPLC data for the formulation standard run at each time point for this study. The data show the level of variation in percentages of main peak and post peaks across different runs for the same sample.

TABLE 23

| Formulation Standard | | | % of Total Integrated Area | | | Integrated Area | | | |
|---|---|---|---|---|---|---|---|---|---|
| Weeks | Injection | Main Peak Retention | Pre Peaks | Main Peak | Post Peaks | Pre Peaks | Main Peak | Post Peaks | Total |
| 0 wk | 1 | 19.6 | 1.3 | 95.8 | 2.9 | 423 | 30906 | 924 | 32253 |
| | 2 | 19.6 | 1.3 | 95.8 | 2.9 | 404 | 30758 | 934 | 32096 |
| | 3 | 19.5 | 1.3 | 96.0 | 2.7 | 410 | 30915 | 876 | 32200 |
| | avg | 19.5 | 1.3 | 95.9 | 2.8 | 412 | 30860 | 911 | 32183 |
| | % CV | 0.0 | 2.2 | 0.1 | 3.5 | 2.4 | 0.3 | 3.4 | 0.2 |
| 2 wk | 1 | 20.7 | 1.2 | 95.7 | 3.1 | 422 | 32516 | 1047 | 33986 |
| | 2 | 19.8 | 1.2 | 95.7 | 3.0 | 403 | 31099 | 986 | 32488 |
| | 3 | 19.7 | 1.2 | 95.7 | 3.1 | 405 | 31201 | 1007 | 32613 |
| | avg | 19.7 | 1.2 | 95.7 | 3.1 | 410 | 31606 | 1013 | 33029 |
| | % CV | 0.0 | 0.1 | 0.0 | 1.0 | 2.6 | 2.5 | 3.1 | 2.5 |
| 4 wk | 1 | 19.8 | 1.2 | 95.3 | 3.6 | 379 | 30322 | 1133 | 31834 |
| | 2 | 19.8 | 1.2 | 95.4 | 3.4 | 382 | 30449 | 1100 | 31931 |
| | 3 | 19.8 | 1.2 | 95.5 | 3.3 | 400 | 30918 | 1066 | 32384 |
| | avg | 19.8 | 1.2 | 95.4 | 3.4 | 387 | 30563 | 1100 | 32050 |
| | % CV | 0.0 | 2.0 | 0.1 | 3.9 | 3.0 | 1.0 | 3.0 | 0.9 |
| 8 wk | 1 | 20.2 | 1.2 | 95.5 | 3.3 | 411 | 31427 | 1074 | 32911 |
| | 2 | 20.2 | 1.2 | 95.6 | 3.1 | 407 | 31417 | 1033 | 32857 |
| | 3 | 20.1 | 1.3 | 95.7 | 3.0 | 417 | 31657 | 999 | 33073 |
| | avg | 20.2 | 1.2 | 95.6 | 3.1 | 412 | 31500 | 1035 | 32947 |
| | % CV | 0.1 | 0.8 | 0.1 | 3.9 | 1.2 | 0.4 | 3.6 | 0.3 |
| total | avg | 19.9 | 1.2 | 95.6 | 3.1 | 405 | 31132 | 1015 | 32552 |
| | stdev | 0.3 | 0.0 | 0.21 | 0.2 | 13.8 | 585.6 | 76.3 | 596.1 |
| | % CV | 1.7 | 2.6 | 0.22 | 7.7 | 3.4 | 1.9 | 7.5 | 1.8 |

TABLE 23-continued

| | | % of Total Integrated Area | | | | Integrated Area | | | |
|---|---|---|---|---|---|---|---|---|---|
| Sample | Weeks | Main Peak Retention | Pre Peaks | Main Peak | Post Peaks | Pre Peaks | Main Peak | Post Peaks | Total |
| Formulation | 0 | 19.5 | 1.3 | 95.9 | 2.8 | 412.1 | 30859.6 | 911.3 | 32183 |
| Standard | 2 | 19.7 | 1.2 | 95.7 | 3.1 | 409.9 | 31605.7 | 1013.4 | 33029 |
| Average | 4 | 19.8 | 1.2 | 95.4 | 3.4 | 386.7 | 30562.9 | 1100.0 | 32050 |
| | 8 | 20.2 | 1.2 | 95.6 | 3.1 | 411.6 | 31500.2 | 1035.2 | 32947 |
| | 12 | 19.4 | 1.2 | 95.1 | 3.6 | 384.5 | 29485.9 | 1125.2 | 30996 |

Table 24 below outlines the SE-HPLC data summarizing the percentage of HMW peaks, main peak and LMW peaks for BDS samples stored at 2-8° C. and −70° C. conditions for 12 Weeks (data not shown here). The variations of percentages of main peak and post peaks at different time points were very similar to the variations seen in formulation standard (data not shown here). Therefore, it can be concluded that no major changes occurred and that all 3 formulations were stable after 12 weeks at 2-8° and −70° C. in liquid form. No major differences were observed among the formulations.

Figure 3I:
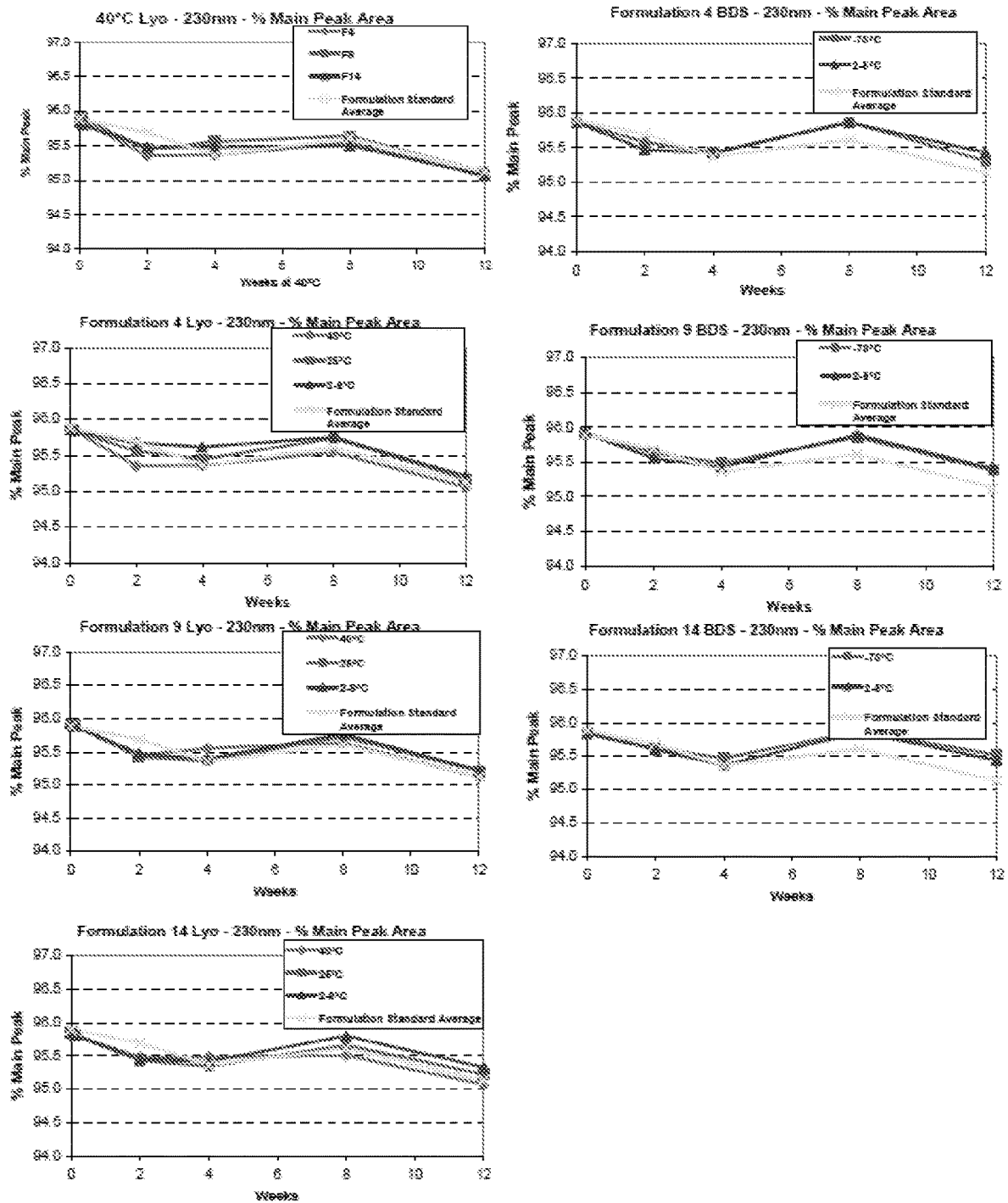
FIG. 3I depicts the results of the SE-HPLC analysis for the AGS-22M6E BDS stored at 2-8° C. and −70° C. and lyophilized AGS-22M6E stored at 2-8° C., 25° C./60% RH and 40° C./75% RH conditions for 12 Weeks.

Weeks. FIG. 3I shows SE-HPLC data in graphs for AGS-22M6E BDS and DP stored at different conditions. The variations of percentages of main peak and post peaks at different time points were very similar to the variations seen in formulation standard, indicating that no major changes occurred in the formulation samples. The SE-HPLC overlays for different DP formulations stored at different conditions were also analyzed (data not shown here). There were no differences observed before and after lyophilization. All 3 formulations were stable after 12 weeks at 2-8°, 25°, and 40° C. in lyophilized form. All formulations behaved simi-

TABLE 24

| | | % of Total Integrated Area | | | | Integrated Area | | | |
|---|---|---|---|---|---|---|---|---|---|
| Sample Name | Weeks at 2-8° C. | Main Peak Retention | Pre Peaks | Main Peak | Post Peaks | Pre Peaks | Main Peak | Post Peaks | Total |
| F4 | 0 | 19.6 | 1.3 | 95.9 | 2.9 | 412 | 31291 | 940 | 32642 |
| | 2 | 19.7 | 1.3 | 95.6 | 3.1 | 445 | 32429 | 1056 | 33930 |
| | 4 | 19.8 | 1.3 | 95.4 | 3.3 | 425 | 32200 | 1119 | 33744 |
| | 8 | 20.2 | 1.3 | 95.9 | 2.8 | 479 | 35060 | 1032 | 36571 |
| | 12 | 19.4 | 1.3 | 95.3 | 3.4 | 449 | 33754 | 1216 | 35419 |
| F9 | 0 | 19.6 | 1.3 | 95.9 | 2.8 | 413 | 31522 | 932 | 32866 |
| | 2 | 19.7 | 1.3 | 95.6 | 3.1 | 433 | 32137 | 1037 | 33607 |
| | 4 | 19.8 | 1.3 | 95.5 | 3.2 | 438 | 32540 | 1100 | 34078 |
| | 8 | 20.1 | 1.3 | 95.9 | 2.8 | 493 | 35546 | 1044 | 37082 |
| | 12 | 19.4 | 1.3 | 95.4 | 3.3 | 494 | 36686 | 1285 | 38465 |
| F14 | 0 | 19.6 | 1.3 | 95.8 | 2.9 | 439 | 32730 | 981 | 34150 |
| | 2 | 19.7 | 1.3 | 95.6 | 3.1 | 444 | 31954 | 1021 | 33418 |
| | 4 | 19.8 | 1.3 | 95.5 | 3.2 | 461 | 33355 | 1120 | 34936 |
| | 8 | 20.1 | 1.4 | 95.9 | 2.8 | 503 | 35252 | 1013 | 36768 |
| | 12 | 19.4 | 1.3 | 95.5 | 3.2 | 473 | 34069 | 1125 | 35667 |

| | | % of Total Integrated Area | | | | Integrated Area | | | |
|---|---|---|---|---|---|---|---|---|---|
| Sample Name | Weeks at 70° C. | Main Peak Retention | Pre Peaks | Main Peak | Post Peaks | Pre Peaks | Main Peak | Post Peaks | Total |
| F4 | 0 | 19.6 | 1.3 | 95.9 | 2.9 | 412 | 31291 | 940 | 32642 |
| | 2 | 19.7 | 1.3 | 95.5 | 3.2 | 434 | 31610 | 1069 | 33112 |
| | 4 | 19.8 | 1.3 | 95.4 | 3.3 | 427 | 31179 | 1070 | 32677 |
| | 8 | 20.1 | 1.3 | 95.9 | 2.8 | 439 | 31922 | 941 | 33302 |
| | 12 | 19.4 | 1.3 | 95.4 | 3.3 | 396 | 29995 | 1041 | 31432 |
| F9 | 0 | 19.6 | 1.3 | 95.9 | 2.8 | 413 | 31522 | 932 | 32866 |
| | 2 | 19.7 | 1.3 | 95.6 | 3.1 | 429 | 31119 | 1019 | 32567 |
| | 4 | 19.8 | 1.3 | 95.4 | 3.3 | 426 | 31384 | 1079 | 32889 |
| | 8 | 20.1 | 1.3 | 95.9 | 2.8 | 442 | 32178 | 938 | 33559 |
| | 12 | 19.4 | 1.3 | 95.4 | 3.3 | 397 | 30027 | 1051 | 31475 |
| F14 | 0 | 19.6 | 1.3 | 95.8 | 2.9 | 439 | 32730 | 981 | 34150 |
| | 2 | 19.7 | 1.3 | 95.6 | 3.1 | 431 | 31071 | 1000 | 32502 |
| | 4 | 19.8 | 1.3 | 95.4 | 3.3 | 437 | 31571 | 1097 | 33105 |
| | 8 | 20.1 | 1.3 | 95.9 | 2.8 | 454 | 32541 | 952 | 33947 |
| | 12 | 19.4 | 1.3 | 95.4 | 3.3 | 412 | 30512 | 1046 | 31970 |

Table 25 below outlines the SE-HPLC data, which summarizes the percentage of HMW peaks, main peak and LMW peaks for lyophilized AGS-22M6E stored at 2-8° C., 25° C./60% RH and 40° C./75% RH conditions for 12 larly and gave high quality product after lyophilization, in addition to acceptable stability profiles seen for the corresponding BDS in each case, both at T=0 and after shaking and freeze-thaw studies.

TABLE 25

| Sample Name | Weeks at 2-8° C. | Retention Time | % of Total Integrated Area | | | | Integrated Area | | |
|---|---|---|---|---|---|---|---|---|---|
| | | | Pre Peaks | Main Peak | Post Peaks | Pre Peaks | Main Peak | Post Peaks | Total |
| F4 | 0 | 19.6 | 1.3 | 95.9 | 2.9 | 412 | 31291 | 940 | 32642 |
| | 0.1 | 19.6 | 1.2 | 95.8 | 2.9 | 418 | 32092 | 972 | 33483 |
| | 2 | 19.7 | 1.2 | 95.7 | 3.1 | 400 | 31564 | 1027 | 32991 |
| | 4 | 19.8 | 1.2 | 95.6 | 3.2 | 413 | 33168 | 1106 | 34687 |
| | 8 | 20.1 | 1.3 | 95.8 | 2.9 | 449 | 32603 | 997 | 34049 |
| | 12 | 19.4 | 1.3 | 95.2 | 3.5 | 403 | 30358 | 1124 | 31885 |
| F9 | 0 | 19.6 | 1.3 | 95.9 | 2.8 | 413 | 31522 | 932 | 32866 |
| | 0.1 | 19.6 | 1.2 | 95.9 | 2.9 | 418 | 32453 | 972 | 33842 |
| | 2 | 19.8 | 1.3 | 95.5 | 3.2 | 432 | 31657 | 1068 | 33157 |
| | 4 | 19.8 | 1.3 | 95.4 | 3.3 | 441 | 32915 | 1145 | 34502 |
| | 8 | 20.1 | 1.3 | 95.8 | 2.9 | 459 | 33035 | 1000 | 34494 |
| | 12 | 19.4 | 1.3 | 95.2 | 3.5 | 411 | 31112 | 1149 | 32672 |
| F14 | 0 | 19.6 | 1.3 | 95.8 | 2.9 | 439 | 32730 | 981 | 34150 |
| | 0.1 | 19.6 | 1.3 | 95.8 | 2.9 | 450 | 33238 | 1005 | 34693 |
| | 2 | 19.8 | 1.3 | 95.4 | 3.2 | 461 | 32915 | 1110 | 34486 |
| | 4 | 19.8 | 1.3 | 95.4 | 3.3 | 472 | 34323 | 1178 | 35972 |
| | 8 | 20.1 | 1.3 | 95.8 | 2.9 | 468 | 33414 | 999 | 34881 |
| | 12 | 19.4 | 1.3 | 95.3 | 3.4 | 424 | 31239 | 1108 | 32771 |

| Sample Name | Weeks at 25° C. | Retention Time | % of Total Integrated Area | | | | Integrated Area | | |
|---|---|---|---|---|---|---|---|---|---|
| | | | Pre Peaks | Main Peak | Post Peaks | Pre Peaks | Main Peak | Post Peaks | Total |
| F4 | 0 | 19.6 | 1.3 | 95.9 | 2.9 | 412 | 31291 | 940 | 32642 |
| | 0.1 | 19.6 | 1.2 | 95.8 | 2.9 | 418 | 32092 | 972 | 33483 |
| | 2 | 19.8 | 1.2 | 95.6 | 3.2 | 406 | 31761 | 1069 | 33236 |
| | 4 | 19.8 | 1.2 | 95.4 | 3.3 | 410 | 32451 | 1138 | 33999 |
| | 8 | 20.2 | 1.3 | 95.7 | 3.0 | 431 | 32611 | 1019 | 34061 |
| | 12 | 19.4 | 1.3 | 95.2 | 3.5 | 420 | 30805 | 1142 | 32367 |
| F9 | 0 | 19.6 | 1.3 | 95.9 | 2.8 | 413 | 31522 | 932 | 32866 |
| | 0.1 | 19.6 | 1.2 | 95.9 | 2.9 | 418 | 32453 | 972 | 33842 |
| | 2 | 19.7 | 1.3 | 95.4 | 3.3 | 438 | 31863 | 1089 | 33389 |
| | 4 | 19.8 | 1.3 | 95.4 | 3.4 | 440 | 32810 | 1155 | 34405 |
| | 8 | 20.2 | 1.3 | 95.7 | 3.0 | 454 | 32933 | 1015 | 34402 |
| | 12 | 19.4 | 1.3 | 95.2 | 3.5 | 417 | 31201 | 1153 | 32770 |
| F14 | 0 | 19.6 | 1.3 | 95.8 | 2.9 | 439 | 32730 | 981 | 34150 |
| | 0.1 | 19.6 | 1.3 | 95.8 | 2.9 | 450 | 33238 | 1005 | 34693 |
| | 2 | 19.7 | 1.3 | 95.4 | 3.2 | 456 | 32561 | 1104 | 34121 |
| | 4 | 19.8 | 1.3 | 95.3 | 3.3 | 470 | 33734 | 1180 | 35383 |
| | 8 | 20.1 | 1.4 | 95.7 | 3.0 | 480 | 33192 | 1027 | 34698 |
| | 12 | 19.4 | 1.3 | 95.2 | 3.4 | 445 | 31605 | 1142 | 33192 |

| Sample Name | Weeks at 40° C. | Retention Time | % of Total Integrated Area | | | | Integrated Area | | |
|---|---|---|---|---|---|---|---|---|---|
| | | | Pre Peaks | Main Peak | Post Peaks | Pre Peaks | Main Peak | Post Peaks | Total |
| F4 | 0 | 19.6 | 1.3 | 95.9 | 2.9 | 412 | 31291 | 940 | 32642 |
| | 0.1 | 19.6 | 1.2 | 95.8 | 2.9 | 418 | 32092 | 972 | 33483 |
| | 2 | 19.8 | 1.3 | 95.4 | 3.4 | 414 | 31498 | 1120 | 33032 |
| | 4 | 19.8 | 1.3 | 95.4 | 3.3 | 448 | 32735 | 1144 | 34327 |
| | 8 | 20.2 | 1.4 | 95.5 | 3.1 | 455 | 32159 | 1045 | 33659 |
| | 12 | 19.4 | 1.4 | 95.1 | 3.5 | 450 | 30523 | 1137 | 32109 |
| F9 | 0 | 19.6 | 1.3 | 95.9 | 2.8 | 413 | 31522 | 932 | 32866 |
| | 0.1 | 19.6 | 1.2 | 95.9 | 2.9 | 418 | 32453 | 972 | 33842 |
| | 2 | 19.8 | 1.3 | 95.4 | 3.3 | 428 | 32091 | 1103 | 33622 |
| | 4 | 19.8 | 1.2 | 95.6 | 3.2 | 414 | 32985 | 1120 | 34518 |
| | 8 | 20.2 | 1.3 | 95.6 | 3.1 | 426 | 32104 | 1039 | 33569 |
| | 12 | 19.4 | 1.3 | 95.1 | 3.6 | 422 | 30813 | 1158 | 32393 |
| F14 | 0 | 19.6 | 1.3 | 95.8 | 2.9 | 439 | 32730 | 981 | 34150 |
| | 0.1 | 19.6 | 1.3 | 95.8 | 2.9 | 450 | 33238 | 1005 | 34693 |
| | 2 | 19.7 | 1.3 | 95.5 | 3.2 | 436 | 32383 | 1099 | 33918 |
| | 4 | 19.8 | 1.3 | 95.5 | 3.2 | 450 | 33290 | 1126 | 34866 |
| | 8 | 20.2 | 1.5 | 95.5 | 3.0 | 507 | 32935 | 1044 | 34486 |
| | 12 | 19.4 | 1.5 | 95.1 | 3.5 | 475 | 30996 | 1132 | 32604 |

6.4 Example 4—Lyophilization Cycle Development

Formulation F4 described in above sections was selected for this further lyophilization cycle development study. The lyophilization cycle parameters are shown in the table below. After lyophilization was complete, vials were stoppered under vacuum at 50 mT. The tray of vials was removed from the lyophilizer and vials were individually crimped with aluminum seals.

TABLE 26

| Step # | Step | Temperature or Ramp Rate | Time (min) | Pressure (mTorr) |
|---|---|---|---|---|
| 1 | Load/Equilibrate | 5° C. | 60 | |
| 2 | Ramp from 5° C. to 0° C. | 0.5° C./min | 10 | |
| 3 | Hold | 0° C. | 60 | |
| 4 | Ramp from 0° C. to −45° C. | 1° C./min | 45 | |
| 5 | Hold | −45° C. | 120 | |
| 6 | Pump down | −45° C. | 60 | 50 |
| 7 | Ramp from −45° C. to −15° C. | 0.3° C./min | 100 | 50 |
| 8 | Hold | −15° C. | 2710 | 50 |
| 9 | Ramp from −15° C. to 35° C. | 0.2° C./min | 250 | 50 |
| 10 | Hold | 35° C. | 420 | 50 |
| 11 | Ramp from 35° C. to 5° C. | 0.5° C./min | 60 | 50 |
| 12 | Hold | 5° C. hold | 60 | 50 |

Lyophilized Formulation Study Design

For each fill volume configuration, 5 product vials were filled in addition to 5 placebo vials. 2 vials from each of the active product and placebo were tested for each fill volume at T=0 (1 vial was tested for residual moisture and 1 vial was reconstituted and tested using the assays described in the study summary). In addition, 2 vials from each of active and placebo were probed for temperature monitoring during the freeze-drying process.

The formulation standard used for this study was the AGS-22M6E starting material at 12.8 mg/mL in 5.0% Sucrose, 0.02% Tween 20, pH 6.0.

Results

Lyophilization cycle analysis: The total conservative cycle time was 2.6 days, which is significantly shorter than the 4.7 day cycle time established for a 5 mL fill volume (see Section 6.3 above). The 2.6 day cycle time however for the present study is not representative of an optimized cycle time for either fill volume. Upon careful evaluation of the individual readouts associated with the cycle, an estimate of an optimized cycle time for either fill volume could be made. Since the dew point monitor is responding to the moisture evolving from both fill volumes, it was not used in this study to estimate a more optimal drying time for the 3.0 mL or 1.5 mL fill volume. Similarly, the Pirani Gauge, although normally an excellent indicator of end point of primary drying time, in this instance, only provides a guide as it too is responding to the sublimation of ice from all vials on the shelf. Instead, for the purpose of this study, monitoring product temperature provides the most reliable tool for estimating the drying times for each individual fill volume. In this study, thermocouple probes were placed in both active and placebo vials and close concordance between product temperature profiles for active and placebo was observed for both fill volumes.

With this assurance that product temperature gives accurate measurement of drying time, comparison of data for the two fill volumes (data not shown here) demonstrates that the 1.5 mL fill volume dries in approximately 1.3 days, which is considerably faster than the 3.0 mL fill volume which dries in approximately 1.8 days.

Cake appearance: All cakes were perfect cakes, very slightly contracted, with a shiny surface. They all maintained intact structure. In most vials, there were no cracks in the cakes. When the vials were inverted, the cakes did not remain adherent to the vials, but tumbled intact in the vials. In some vials, fine cracks were observed around the edge of the meniscus circle where the cake was attached to the vial. There was no difference between the cake formation for actives and placebos, for both fill volumes. The cake appearance was also comparable to the cake appearance recorded for 5 mL fill volume lyophilized product in the study of Section 6.3.

A280 analysis: Prior to filling and lyophilization, the protein concentration of the formulation was checked in duplicate and found to be close to the target concentration of 10 mg/mL. After reconstitution with 2.8 mL and 1.4 mL of WFI respectively, the protein concentrations for the 3.0 mL and 1.5 mL fill formulations were also close to those before lyophilization (see the table below).

TABLE 27

| Sample | Dilution Factor (df) | A330 nm | A280 nm | [protein] mg/mL | Average (mg/mL) |
|---|---|---|---|---|---|
| Pre-lyo | 20 | 0.00026 | 0.73176 | 10.06 | 10.1 |
| | | 0.00000 | 0.74046 | 10.19 | |
| F4 10 mg/mL, T = 0, 3 mL | 20 | 0.00126 | 0.82283 | 11.30 | 11.3 |
| | | 0.00000 | 0.81551 | 11.22 | |
| F4 10 mg/mL, T = 0, 1.5 mL | 20 | 0.00429 | 0.78214 | 10.70 | 10.7 |

Residual moisture, reconstitution time, A330, osmolality and visual appearance: After lyophilization was complete, one vial of each fill volume from the active and placebo vials was allocated for residual moisture testing. As shown in Table 28 below, the residual moistures of the actives ranged from 0.18% for the 3.0 mL fill to 0.29% for the 1.5 mL fill. Residual moistures were determined to be slightly higher for the placebos, at 0.34% for both fill volumes. Reconstitution times were less than 1 min for all vials tested, with slightly higher times recorded for the 3.0 mL fill volumes (average 36 s) compared to the 1.5 mL fill volume samples (average 20 s). There was no appreciable difference observed in reconstitution time between active and placebo vials. Similarly, visual appearance for all reconstituted samples, both active and placebo, was reported as clear and colorless with no particulates.

TABLE 28

| Condition | Lyo Fill Volume | Reconstitution Time^ (sec) | | Turbidity (A330) | | Osmolality (mOsm/ky)[1] | | % Residual Moisture* | |
|---|---|---|---|---|---|---|---|---|---|
| | | Active | Placebo | Active | Placebo | Active | Placebo | Active | Placebo |
| T = 0 | 3.0 | 38 | 35 | 0.0645 | 0.0139 | 194 | 186 | 0.18 | 0.34 |
| | 1.5 | 22 | 18 | 0.0555 | 0.0097 | 190 | 189 | 0.29 | 0.34 |
| Pre-Lyo | | | | 0.0610 | 0.0142 | 190 | 181 | | |
| | | | | 0.0492 | 0.0089 | | | | |

The turbidity (A330) measurements of active and placebo vials are also shown in the above table. As shown, for both pre- and post lyophilization samples, the A330 values for the active vial was slightly higher than the placebo, confirming earlier results discussed in Section 6.3, where AGS-22M6E was shown to contribute to the formulation turbidity.

The osmolarities of the formulated samples and buffer were tested in duplicate prior to filling and after reconstitution. Table 28 above summarizes this data, showing that there was no appreciable difference in osmolality before lyophilization or after reconstitution. They were also comparable to the osmolality determined for the 5.0 mL fill configuration samples in Section 6.3.

Figure 4:
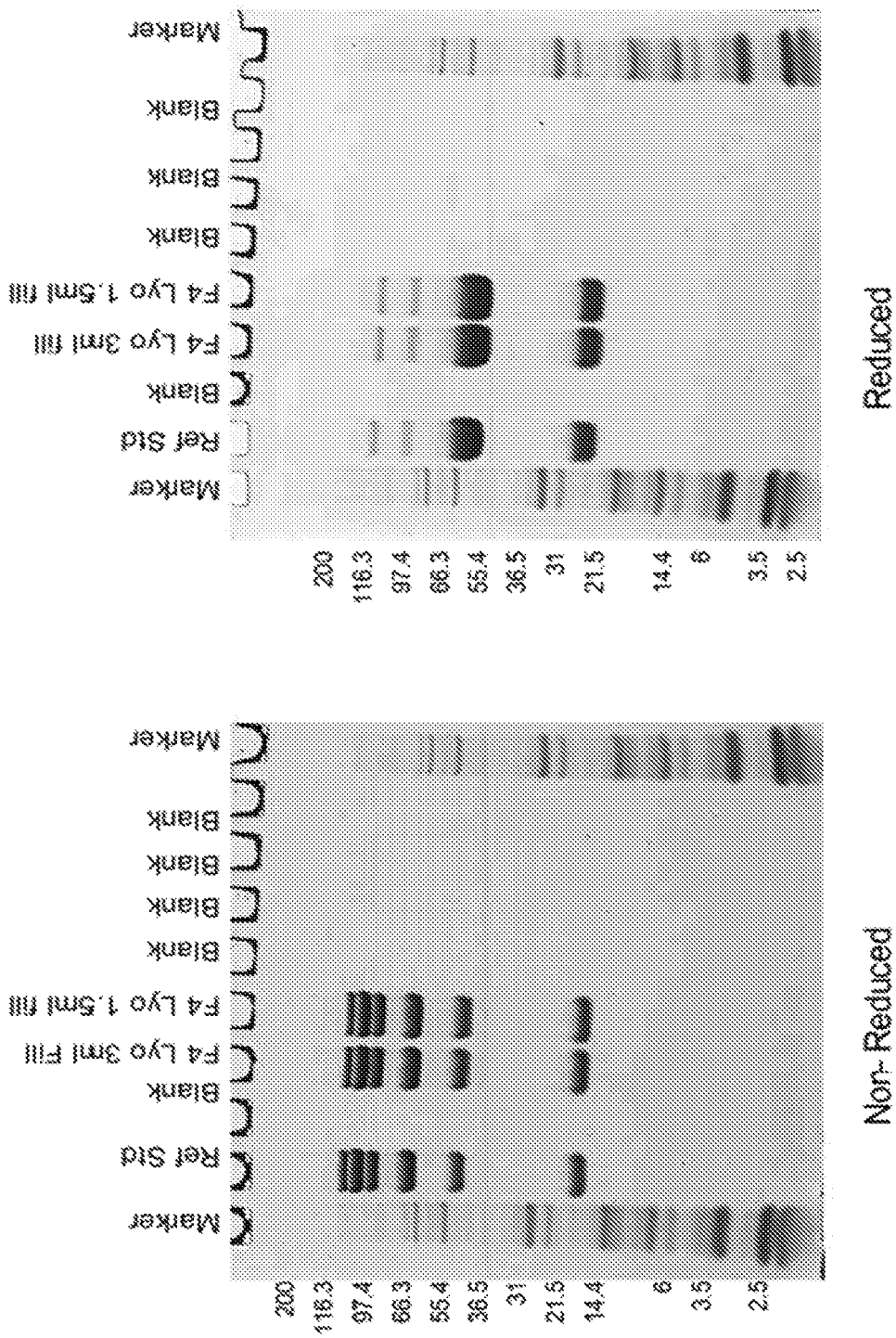
FIG. 4 depicts the results of the SDS-PAGE analysis for lyophilized formulation of F4 at both 3.0 and 1.5 mL fill volumes.

FIG. 4 shows the SDS-PAGE analysis for each fill volume, both reduced and non-reduced, as compared to the formulation standard. The results demonstrate that changing the fill volume did not have any impact on the SDS-PAGE profile.

Table 29 below summarizes the SEC-HPLC data, including the percentages of HMW peaks, main peaks and LMW peaks for samples lyophilized at each fill volume. Regardless of the fill volume evaluated, lyophilized samples behaved similarly and there was no difference in main peak areas measured before and after lyophilization. No changes were observed for either fill volume and that profiles were comparable to the 5 mL fill volume lyophilized in study described in Section 6.3.

TABLE 29

| | Peak Percentages (%) | | | | Peak Area (mAu) | | | |
|---|---|---|---|---|---|---|---|---|
| | Main Peak | | | | | | | |
| Sample Name | Retention Time | Pre Peaks | Main Peak | Post Peaks | Pre Peaks | Main Peak | Post Peaks | Total |
| Reference standard | 19.8 | 1.4 | 95.2 | 3.4 | 429 | 29155 | 1045 | 30629 |
| F4, active, lyo, 3.0 mL fill | 19.8 | 1.3 | 95.4 | 3.3 | 481 | 34059 | 1174 | 35714 |
| F4, active, lyo, 1.5 mL fill | 19.8 | 1.4 | 95.1 | 3.5 | 487 | 32359 | 1198 | 34043 |

From the foregoing, it will be appreciated that, although specific embodiments have been described herein for the purpose of illustration, various modifications may be made without deviating from the spirit and scope of what is provided herein. All of the references referred to above are incorporated herein by reference in their entireties.

7. SEQUENCE LISTING

The present specification is being filed with a computer readable form (CRF) copy of the Sequence Listing. The CRF entitled "14369-244-228_SEQ_LISTING.txt", which was created on Oct. 11, 2019 and is 39,693 bytes in size, is incorporated herein by reference in its entirety.

What is claimed is:

1. A pharmaceutical composition comprising
   (a) an antibody drug conjugate comprising an antibody or antigen binding fragment thereof that binds to 191P4D12 conjugated to one or more units of monomethyl auristatin E (MMAE), wherein the antibody or antigen binding fragment thereof comprises a heavy chain variable region comprising complementarity determining region H1 (CDR H1), CDR H2, and CDR H3 in the heavy chain variable region set forth in SEQ ID NO: 7 and a light chain variable region comprising CDR L1, CDR L2, and CDR L3 in the light chain variable region set forth in SEQ ID NO: 8; and
   (b) a pharmaceutically acceptable excipient comprising L-histidine in a range of 5 to 50 mM, polysorbate-20 (TWEEN-20) in a range of 0.001 to 0.1% (w/v), trehalose dihydrate in a range of 4 to 7% (w/v), and hydrochloric acid (HCl), wherein the pharmaceutical composition has a pH in a range of 5.5 to 6.5 at 15° C. to 27° C.

2. The pharmaceutical composition of claim 1, wherein
   (a) the antibody or antigen binding fragment thereof comprises CDR H1 comprising the amino acid sequence of SEQ ID NO: 9, CDR H2 comprising the amino acid sequence of SEQ ID NO: 10, CDR H3 comprising the amino acid sequence of SEQ ID NO: 11, CDR L1 comprising the amino acid sequence of SEQ ID NO: 12, CDR L2 comprising the amino acid sequence of SEQ ID NO: 13, and CDR L3 comprising the amino acid sequence of SEQ ID NO: 14;
   (b) the antibody or antigen binding fragment thereof comprises a heavy chain variable region comprising the amino acid sequence ranging from the 20th amino acid (glutamic acid) to the 136th amino acid (serine) of SEQ ID NO: 7 and a light chain variable region comprising the amino acid sequence ranging from the 23rd amino acid (aspartic acid) to the 130th amino acid (arginine) of SEQ ID NO: 8; or
   (c) the antibody comprises a heavy chain comprising the amino acid sequence ranging from the 20th amino acid (glutamic acid) to the 466th amino acid (lysine) of SEQ ID NO: 7 and a light chain comprising the amino acid sequence ranging from the 23rd amino acid (aspartic acid) to the 236th amino acid (cysteine) of SEQ ID NO: 8.

3. The pharmaceutical composition of claim 1, wherein
   (a) the antigen binding fragment is an Fab, F(ab')$_2$, Fv, or scFv fragment;

(b) the antibody is a fully human antibody; or
(c) the antibody or antigen binding fragment thereof is recombinantly produced.

4. The pharmaceutical composition of claim 1, wherein the antibody drug conjugate has the following structure:

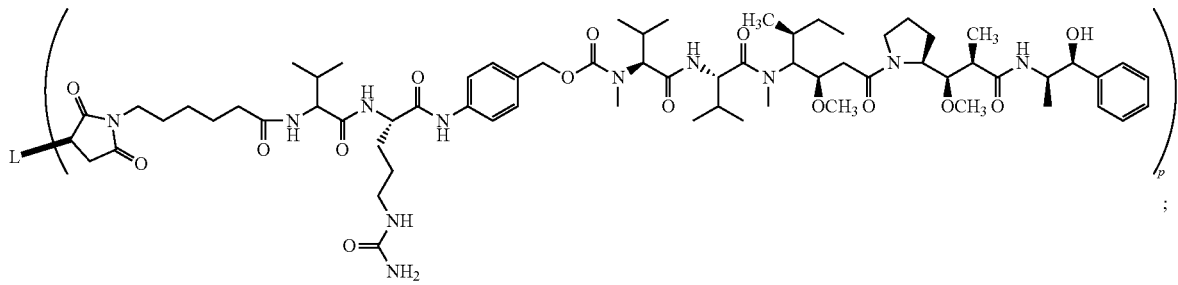

wherein L- represents the antibody or antigen binding fragment thereof and (i) p is from 1 to 10 or (ii) p is from 2 to 8.

5. The pharmaceutical composition of claim 1, wherein the antibody or antigen binding fragment thereof is linked to each unit of monomethyl auristatin E (MMAE) via a linker.

6. The pharmaceutical composition of claim 5, wherein the linker is an enzyme-cleavable linker, and wherein the linker forms a bond with a sulfur atom of the antibody or antigen binding fragment thereof.

7. The pharmaceutical composition of claim 5, wherein the linker has a formula of: -$A_a$-$W_w$—$Y_y$—; wherein -A- is a stretcher unit, a is 0 or 1; —W— is an amino acid unit, w is an integer ranging from 0 to 12; and —Y— is a spacer unit, y is 0, 1, or 2.

8. The pharmaceutical composition of claim 7, wherein the stretcher unit has the structure of Formula (1) below; the amino acid unit is valine citrulline; and the spacer unit is a PAB group comprising the structure of Formula (2) below:

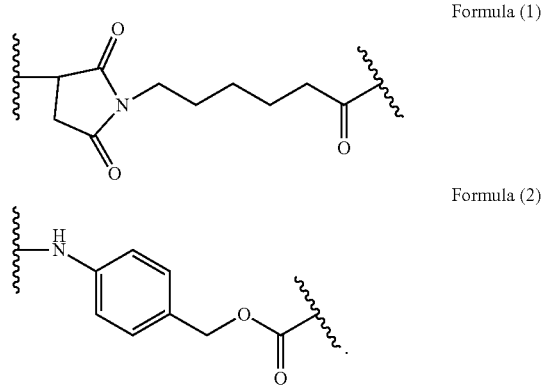

9. The pharmaceutical composition of claim 7, wherein the stretcher unit forms a bond with a sulfur atom of the antibody or antigen binding fragment thereof; and wherein the spacer unit is linked to MMAE via a carbamate group.

10. The pharmaceutical composition of claim 1, comprising the antibody drug conjugate at a concentration of (i) from 1 to 20 mg/mL; (ii) from 5 to 15 mg/mL; (iii) from 8 to 12 mg/mL; or (iv) about 10 mg/mL.

11. The pharmaceutical composition of claim 1, wherein the L-histidine is present (i) in the range of 10 to 40 mM; (ii) in the range of 15 to 35 mM; (iii) in the range of 15 to 30 mM; (iv) in the range of 15 to 25 mM; or (v) at about 20 mM.

12. The pharmaceutical composition of claim 1, wherein the polysorbate-20 (TWEEN-20) is present (i) in the range of 0.0025 to 0.075% (v/v); (ii) in the range of 0.005 to 0.05% (v/v); (iii) in the range of 0.01 to 0.03% (v/v); or (iv) at about 0.02% (v/v).

13. The pharmaceutical composition of claim 1, wherein the trehalose dihydrate is present (i) in the range of 4 to 6% (w/v); or (ii) at about 5.5%.

14. The pharmaceutical composition of claim 1, wherein the pharmaceutical composition has a pH (i) in the range of 5.7 to 6.3, or (ii) about 6.0; and wherein the pH is taken (i) at 15° C. to 27° C., or (ii) at 25° C.

15. The pharmaceutical composition of claim 1, wherein the pH is adjusted by HCl.

16. The pharmaceutical composition of claim 1, comprising about 20 mM L-histidine, about 0.02% (w/v) polysorbate-20 (TWEEN-20), and about 5.5% (w/v) trehalose dihydrate.

17. The pharmaceutical composition of claim 16, wherein the pH is 6.0 at room temperature or at 25° C.

18. The pharmaceutical composition of claim 16, wherein the antibody drug conjugate is at a concentration of about 10 mg/mL.

19. The pharmaceutical composition of claim 1, wherein
(a) the pharmaceutical composition is in a liquid form or is lyophilized; or
(b) the pharmaceutical composition is stored at −80° C., 4° C., 25° C., or 37° C.

20. A lyophilized composition made by freeze-drying the pharmaceutical composition of claim 1.

21. A method of treating cancer in a human subject, comprising administering to the subject an effective amount of the pharmaceutical composition of claim 1, wherein the cancer has tumor cells expressing 191P4D12.

22. The method of claim 21, wherein the cancer is colon cancer, pancreatic cancer, ovarian cancer, lung cancer, bladder cancer, urothelial cancer, breast cancer, esophageal cancer, head cancer, neck cancer, or non-small cell lung cancer.

23. The method of claim 22, wherein the bladder cancer is advanced bladder cancer, advanced urothelial cancer, metastatic bladder cancer, or metastatic urothelial cancer.

24. The method of claim 21, further comprising administering to the subject a second therapeutic agent, wherein the second therapeutic agent is an immune checkpoint inhibitor.

25. The method of claim 24, wherein the immune checkpoint inhibitor is
(a) a PD-1 inhibitor or a PD-L1 inhibitor;
(b) nivolumab; or (c) selected from a group consisting of atezolizumab, avelumab, and durvalumab.

26. The method of claim 21, wherein the antibody drug conjugate in the pharmaceutical composition is administered at a dose of (i) 1 to 10 mg/kg of the subject's body weight; (ii) 1 to 5 mg/kg of the subject's body weight; (iii) 1 to 2.5 mg/kg of the subject's body weight; (iv) 1 to 1.25 mg/kg of the subject's body weight; or (v) about 1 mg/kg or about 1.25 mg/kg of the subject's body weight.

27. The method of claim 26, wherein the pharmaceutical composition is administered by an intravenous (IV) injection or infusion.

28. The method of claim 27, wherein the pharmaceutical composition is administered by an intravenous (IV) injection or infusion over about 30 minutes on Days 1 and 8 of every three-week cycle.

29. The method of claim 28, further comprising administering an immune checkpoint inhibitor by an intravenous (IV) injection or infusion on Day 1 of every three-week cycle, wherein the immune checkpoint inhibitor is administered in an amount of about 100 mg to about 1500 mg over about 30 minutes or 60 minutes.

30. The method of claim 27, wherein the pharmaceutical composition is administered by an intravenous (IV) injection or infusion over about 30 minutes on Days 1, 8 and 15 of every four-week cycle.

31. The method of claim 30, further comprising administering an immune checkpoint inhibitor by an intravenous (IV) injection or infusion.

* * * * *

SEQUENCE LISTING

```
<160> NUMBER OF SEQ ID NOS: 23

<210> SEQ ID NO 1
<211> LENGTH: 3464
<212> TYPE: DNA
<213> ORGANISM: Homo sapiens
<220> FEATURE:
<221> NAME/KEY: CDS
<222> LOCATION: (264)...(1796)
<220> FEATURE:
<221> NAME/KEY: misc_feature
<222> LOCATION: (1)...(3464)
<223> OTHER INFORMATION: 191P4D12

<400> SEQUENCE: 1
ggccgtcgtt gttggccaca gcgtgggaag cagctctggg ggagctcgga gctcccgatc      60
acggcttctt gggggtagct acggctgggt gtgtagaacg gggccggggc tggggctggg     120
tcccctagtg gagacccaag tgcgagaggc aagaactctg cagcttcctg ccttctgggt     180
cagttcctta ttcaagtctg cagccggctc ccagggagat ctcggtggaa cttcagaaac     240
gctgggcagt ctgcctttca acc atg ccc ctg tcc ctg gga gcc gag atg tgg    293
                          Met Pro Leu Ser Leu Gly Ala Glu Met Trp
                            1               5                  10 ggg cct gag gcc tgg ctg ctg ctg cta ctg ctg gca tca ttt aca         341
```

-continued

```
                  Gly Pro Glu Ala Trp Leu Leu Leu Leu Leu Leu Ala Ser Phe Thr
                                   15                  20                  25 ggc cgg tgc ccc gcg ggt gag ctg gag acc tca gac gtg gta act gtg           389
Gly Arg Cys Pro Ala Gly Glu Leu Glu Thr Ser Asp Val Val Thr Val
                30                  35                  40 gtg ctg ggc cag gac gca aaa ctg ccc tgc ttc tac cga ggg gac tcc           437
Val Leu Gly Gln Asp Ala Lys Leu Pro Cys Phe Tyr Arg Gly Asp Ser
            45                  50                  55 ggc gag caa gtg ggg caa gtg gca tgg gct cgg gtg gac gcg ggc gaa           485
Gly Glu Gln Val Gly Gln Val Ala Trp Ala Arg Val Asp Ala Gly Glu
        60                  65                  70 ggc gcc cag gaa cta gcg cta ctg cac tcc aaa tac ggg ctt cat gtg           533
Gly Ala Gln Glu Leu Ala Leu Leu His Ser Lys Tyr Gly Leu His Val
    75                  80                  85                  90 agc ccg gct tac gag ggc cgc gtg gag cag ccg ccg ccc cca cgc aac           581
Ser Pro Ala Tyr Glu Gly Arg Val Glu Gln Pro Pro Pro Arg Asn
                95                 100                 105 ccc ctg gac ggc tca gtg ctc ctg cgc aac gca gtg cag gcg gat gag           629
Pro Leu Asp Gly Ser Val Leu Leu Arg Asn Ala Val Gln Ala Asp Glu
            110                 115                 120 ggc gag tac gag tgc cgg gtc agc acc ttc ccc gcc ggc agc ttc cag           677
Gly Glu Tyr Glu Cys Arg Val Ser Thr Phe Pro Ala Gly Ser Phe Gln
        125                 130                 135 gcg cgg ctg cgg ctc cga gtg ctg gtg cct ccc ctg ccc tca ctg aat           725
Ala Arg Leu Arg Leu Arg Val Leu Val Pro Pro Leu Pro Ser Leu Asn
    140                 145                 150 cct ggt cca gca cta gaa gag ggc cag ggc ctg acc ctg gca gcc tcc           773
Pro Gly Pro Ala Leu Glu Glu Gly Gln Gly Leu Thr Leu Ala Ala Ser
155                 160                 165                 170 tgc aca gct gag ggc agc cca gcc ccc agc gtg acc tgg gac acg gag           821
Cys Thr Ala Glu Gly Ser Pro Ala Pro Ser Val Thr Trp Asp Thr Glu
                175                 180                 185 gtc aaa ggc aca acg tcc agc cgt tcc ttc aag cac tcc cgc tct gct           869
Val Lys Gly Thr Thr Ser Ser Arg Ser Phe Lys His Ser Arg Ser Ala
            190                 195                 200 gcc gtc acc tca gag ttc cac ttg gtg cct agc cgc agc atg aat ggg           917
Ala Val Thr Ser Glu Phe His Leu Val Pro Ser Arg Ser Met Asn Gly
        205                 210                 215 cag cca ctg act tgt gtg gtg tcc cat cct ggc ctg ctc cag gac caa           965
Gln Pro Leu Thr Cys Val Val Ser His Pro Gly Leu Leu Gln Asp Gln
    220                 225                 230 agg atc acc cac atc ctc cac gtg tcc ttc ctt gct gag gcc tct gtg          1013
Arg Ile Thr His Ile Leu His Val Ser Phe Leu Ala Glu Ala Ser Val
235                 240                 245                 250 agg ggc ctt gaa gac caa aat ctg tgg cac att ggc aga gaa gga gct          1061
Arg Gly Leu Glu Asp Gln Asn Leu Trp His Ile Gly Arg Glu Gly Ala
                255                 260                 265 atg ctc aag tgc ctg agt gaa ggg cag ccc cct ccc tca tac aac tgg          1109
Met Leu Lys Cys Leu Ser Glu Gly Gln Pro Pro Pro Ser Tyr Asn Trp
            270                 275                 280 aca cgg ctg gat ggg cct ctg ccc agt ggg gta cga gtg gat ggg gac          1157
Thr Arg Leu Asp Gly Pro Leu Pro Ser Gly Val Arg Val Asp Gly Asp
        285                 290                 295 act ttg ggc ttt ccc cca ctg acc act gag cac agc ggc atc tac gtc          1205
Thr Leu Gly Phe Pro Pro Leu Thr Thr Glu His Ser Gly Ile Tyr Val
    300                 305                 310 tgc cat gtc agc aat gag ttc tcc tca agg gat tct cag gtc act gtg          1253
Cys His Val Ser Asn Glu Phe Ser Ser Arg Asp Ser Gln Val Thr Val
315                 320                 325                 330
```

| | |
|---|---|
| gat gtt ctt gac ccc cag gaa gac tct ggg aag cag gtg gac cta gtg<br>Asp Val Leu Asp Pro Gln Glu Asp Ser Gly Lys Gln Val Asp Leu Val<br>335                  340               345 | 1301 |
| tca gcc tcg gtg gtg gtg gtg ggt gtg atc gcc gca ctc ttg ttc tgc<br>Ser Ala Ser Val Val Val Val Gly Val Ile Ala Ala Leu Leu Phe Cys<br>350                355                360 | 1349 |
| ctt ctg gtg gtg gtg gtg gtg ctc atg tcc cga tac cat cgg cgc aag<br>Leu Leu Val Val Val Val Val Leu Met Ser Arg Tyr His Arg Arg Lys<br>        365                370               375 | 1397 |
| gcc cag cag atg acc cag aaa tat gag gag gag ctg acc ctg acc agg<br>Ala Gln Gln Met Thr Gln Lys Tyr Glu Glu Glu Leu Thr Leu Thr Arg<br>380                  385               390 | 1445 |
| gag aac tcc atc cgg agg ctg cat tcc cat cac acg gac ccc agg agc<br>Glu Asn Ser Ile Arg Arg Leu His Ser His His Thr Asp Pro Arg Ser<br>395                400               405              410 | 1493 |
| cag ccg gag gag agt gta ggg ctg aga gcc gag ggc cac cct gat agt<br>Gln Pro Glu Glu Ser Val Gly Leu Arg Ala Glu Gly His Pro Asp Ser<br>              415               420               425 | 1541 |
| ctc aag gac aac agt agc tgc tct gtg atg agt gaa gag ccc gag ggc<br>Leu Lys Asp Asn Ser Ser Cys Ser Val Met Ser Glu Glu Pro Glu Gly<br>430                  435               440 | 1589 |
| cgc agt tac tcc acg ctg acc acg gtg agg gag ata gaa aca cag act<br>Arg Ser Tyr Ser Thr Leu Thr Thr Val Arg Glu Ile Glu Thr Gln Thr<br>        445                450               455 | 1637 |
| gaa ctg ctg tct cca ggc tct ggg cgg gcc gag gag gag gaa gat cag<br>Glu Leu Leu Ser Pro Gly Ser Gly Arg Ala Glu Glu Glu Glu Asp Gln<br>460                  465               470 | 1685 |
| gat gaa ggc atc aaa cag gcc atg aac cat ttt gtt cag gag aat ggg<br>Asp Glu Gly Ile Lys Gln Ala Met Asn His Phe Val Gln Glu Asn Gly<br>475                  480               485              490 | 1733 |
| acc cta cgg gcc aag ccc acg ggc aat ggc atc tac atc aat ggg cgg<br>Thr Leu Arg Ala Lys Pro Thr Gly Asn Gly Ile Tyr Ile Asn Gly Arg<br>              495               500               505 | 1781 |
| gga cac ctg gtc tga cccaggcctg cctcccttcc ctaggcctgg ctccttctgt<br>Gly His Leu Val<br>              510 | 1836 |
| tgacatggga gattttagct catcttgggg gcctccttaa acaccccat ttcttgcgga | 1896 |
| agatgctccc catcccactg actgcttgac ctttacctcc aacccttctg ttcatcggga | 1956 |
| gggctccacc aattgagtct ctcccaccat gcatgcaggt cactgtgtgt gtgcatgtgt | 2016 |
| gcctgtgtga gtgttgactg actgtgtgtg tgtggagggg tgactgtccg tggaggggtg | 2076 |
| actgtgtccg tggtgtgtat tatgctgtca tatcagagtc aagtgaactg tggtgtatgt | 2136 |
| gccacgggat ttgagtggtt gcgtgggcaa cactgtcagg gtttggcgtg tgtgtcatgt | 2196 |
| ggctgtgtgt gacctctgcc tgaaaaagca ggtattttct cagacccag agcagtatta | 2256 |
| atgatgcaga ggttggagga gagaggtgga gactgtggct cagacccagg tgtgcgggca | 2316 |
| tagctggagc tggaatctgc ctccggtgtg agggaacctg tctcctacca cttcggagcc | 2376 |
| atgggggcaa gtgtgaagca gccagtccct gggtcagcca gaggcttgaa ctgttacaga | 2436 |
| agccctctgc cctctggtgg cctctgggcc tgctgcatgt acatattttc tgtaaatata | 2496 |
| catgcgccgg gagcttcttg caggaatact gctccgaatc acttttaatt tttttctttt | 2556 |
| ttttttcttg cccttttccat tagttgtatt tttatttat ttttatttt attttttttt | 2616 |
| agagatggag tctcactatg ttgctcaggc tggccttgaa ctcctgggct caagcaatcc | 2676 |
| tcctgcctca gcctccctag tagctgggac tttaagtgta caccactgtg cctgctttga | 2736 |
| atcctttacg aagagaaaaa aaaaattaaa gaaagccttt agatttatcc aatgtttact | 2796 |

```
actgggattg cttaaagtga ggcccctcca acaccagggg gttaattcct gtgattgtga    2856
aaggggctac ttccaaggca tcttcatgca ggcagcccct tgggagggca cctgagagct    2916
ggtagagtct gaaattaggg atgtgagcct cgtggttact gagtaaggta aaattgcatc    2976
caccattgtt tgtgatacct tagggaattg cttggacctg gtgacaaggg ctcctgttca    3036
atagtggtgt tggggagaga gagagcagtg attatagacc gagagagtag gagttgaggt    3096
gaggtgaagg aggtgctggg ggtgagaatg tcgcctttcc ccctgggttt tggatcacta    3156
attcaaggct cttctggatg tttctctggg ttggggctgg agttcaatga ggtttatttt    3216
tagctggccc acccagatac actcagccag aatacctaga tttagtaccc aaactcttct    3276
tagtctgaaa tctgctggat ttctggccta agggagaggc tcccatcctt cgttccccag    3336
ccagcctagg acttcgaatg tggagcctga agatctaaga tcctaacatg tacattttat    3396
gtaaatatgt gcatatttgt acataaaatg atattctgtt tttaaataaa cagacaaaac    3456
ttgaaaaa                                                             3464
```

<210> SEQ ID NO 2
<211> LENGTH: 510
<212> TYPE: PRT
<213> ORGANISM: Homo sapiens
<220> FEATURE:
<221> NAME/KEY: misc_feature
<222> LOCATION: (1)...(510)
<223> OTHER INFORMATION: 191P4D12

<400> SEQUENCE: 2

```
Met Pro Leu Ser Leu Gly Ala Glu Met Trp Gly Pro Glu Ala Trp Leu
 1               5                  10                  15

Leu Leu Leu Leu Leu Leu Ala Ser Phe Thr Gly Arg Cys Pro Ala Gly
                20                  25                  30

Glu Leu Glu Thr Ser Asp Val Val Thr Val Val Leu Gly Gln Asp Ala
            35                  40                  45

Lys Leu Pro Cys Phe Tyr Arg Gly Asp Ser Gly Glu Gln Val Gly Gln
        50                  55                  60

Val Ala Trp Ala Arg Val Asp Ala Gly Glu Gly Ala Gln Glu Leu Ala
 65                  70                  75                  80

Leu Leu His Ser Lys Tyr Gly Leu His Val Ser Pro Ala Tyr Glu Gly
                85                  90                  95

Arg Val Glu Gln Pro Pro Pro Arg Asn Pro Leu Asp Gly Ser Val
                100                 105                 110

Leu Leu Arg Asn Ala Val Gln Ala Asp Glu Gly Glu Tyr Glu Cys Arg
            115                 120                 125

Val Ser Thr Phe Pro Ala Gly Ser Phe Gln Ala Arg Leu Arg Leu Arg
        130                 135                 140

Val Leu Val Pro Pro Leu Pro Ser Leu Asn Pro Gly Pro Ala Leu Glu
145                 150                 155                 160

Glu Gly Gln Gly Leu Thr Leu Ala Ala Ser Cys Thr Ala Glu Gly Ser
                165                 170                 175

Pro Ala Pro Ser Val Thr Trp Asp Thr Glu Val Lys Gly Thr Thr Ser
            180                 185                 190

Ser Arg Ser Phe Lys His Ser Arg Ser Ala Ala Val Thr Ser Glu Phe
        195                 200                 205

His Leu Val Pro Ser Arg Ser Met Asn Gly Gln Pro Leu Thr Cys Val
    210                 215                 220
```

-continued

| | | | | | | | | | | | | | | |
|---|---|---|---|---|---|---|---|---|---|---|---|---|---|---|
|Val|Ser|His|Pro|Gly|Leu|Leu|Gln|Asp|Gln|Arg|Ile|Thr|His|Ile|Leu|
|225| | | | |230| | | | |235| | | | |240|

His Val Ser Phe Leu Ala Glu Ala Ser Val Arg Gly Leu Glu Asp Gln
               245                 250                 255

Asn Leu Trp His Ile Gly Arg Glu Gly Ala Met Leu Lys Cys Leu Ser
               260                 265                 270

Glu Gly Gln Pro Pro Ser Tyr Asn Trp Thr Arg Leu Asp Gly Pro
       275                 280                 285

Leu Pro Ser Gly Val Arg Val Asp Gly Asp Thr Leu Gly Phe Pro Pro
290                 295                 300

Leu Thr Thr Glu His Ser Gly Ile Tyr Val Cys His Val Ser Asn Glu
305                 310                 315                 320

Phe Ser Ser Arg Asp Ser Gln Val Thr Val Asp Val Leu Asp Pro Gln
               325                 330                 335

Glu Asp Ser Gly Lys Gln Val Asp Leu Val Ser Ala Ser Val Val Val
               340                 345                 350

Val Gly Val Ile Ala Ala Leu Leu Phe Cys Leu Leu Val Val Val Val
               355                 360                 365

Val Leu Met Ser Arg Tyr His Arg Arg Lys Ala Gln Gln Met Thr Gln
370                 375                 380

Lys Tyr Glu Glu Glu Leu Thr Leu Thr Arg Glu Asn Ser Ile Arg Arg
385                 390                 395                 400

Leu His Ser His His Thr Asp Pro Arg Ser Gln Pro Glu Glu Ser Val
               405                 410                 415

Gly Leu Arg Ala Glu Gly His Pro Asp Ser Leu Lys Asp Asn Ser Ser
               420                 425                 430

Cys Ser Val Met Ser Glu Glu Pro Glu Gly Arg Ser Tyr Ser Thr Leu
               435                 440                 445

Thr Thr Val Arg Glu Ile Glu Thr Gln Thr Glu Leu Leu Ser Pro Gly
               450                 455                 460

Ser Gly Arg Ala Glu Glu Glu Glu Asp Gln Asp Glu Gly Ile Lys Gln
465                 470                 475                 480

Ala Met Asn His Phe Val Gln Glu Asn Gly Thr Leu Arg Ala Lys Pro
               485                 490                 495

Thr Gly Asn Gly Ile Tyr Ile Asn Gly Arg Gly His Leu Val
               500                 505                 510

<210> SEQ ID NO 3
<211> LENGTH: 1432
<212> TYPE: DNA
<213> ORGANISM: Homo sapiens
<220> FEATURE:
<221> NAME/KEY: CDS
<222> LOCATION: (32)...(1432)
<220> FEATURE:
<221> NAME/KEY: misc_feature
<222> LOCATION: (1)...(1432)
<223> OTHER INFORMATION: Ha22-2(2,4)6.1 heavy chain

<400> SEQUENCE: 3

```
ggtgatcagc actgaacaca gaggactcac c atg gag ttg ggg ctg tgc tgg          52
                                  Met Glu Leu Gly Leu Cys Trp
                                   1               5 gtt ttc ctt gtt gct att tta gaa ggt gtc cag tgt gag gtg cag ctg        100
Val Phe Leu Val Ala Ile Leu Glu Gly Val Gln Cys Glu Val Gln Leu
         10                  15                  20 gtg gag tct ggg gga ggc ttg gta cag cct ggg ggg tcc ctg aga ctc        148
Val Glu Ser Gly Gly Gly Leu Val Gln Pro Gly Gly Ser Leu Arg Leu
```

|  |  |  |  |  |  |  |  |  |  |  |  |  |  |  |  |
|---|---|---|---|---|---|---|---|---|---|---|---|---|---|---|---|
| | | 25 | | | | 30 | | | | | 35 | | | | |
| tcc | tgt | gca | gcc | tct | gga | ttc | acc | ttc | agt | agc | tat | aac | atg | aac | tgg | 196
| Ser | Cys | Ala | Ala | Ser | Gly | Phe | Thr | Phe | Ser | Ser | Tyr | Asn | Met | Asn | Trp |
| 40 | | | | 45 | | | | | 50 | | | | | 55 | | gtc cgc cag gct cca ggg aag ggg ctg gag tgg gtt tca tac att agt    244
Val Arg Gln Ala Pro Gly Lys Gly Leu Glu Trp Val Ser Tyr Ile Ser
            60                  65                  70 agt agt agt agt acc ata tac tac gca gac tct gtg aag ggc cga ttc    292
Ser Ser Ser Ser Thr Ile Tyr Tyr Ala Asp Ser Val Lys Gly Arg Phe
            75                  80                  85 acc atc tcc aga gac aat gcc aag aac tca ctg tct ctg caa atg aac    340
Thr Ile Ser Arg Asp Asn Ala Lys Asn Ser Leu Ser Leu Gln Met Asn
            90                  95                 100 agc ctg aga gac gag gac acg gct gtg tat tac tgt gcg aga gca tac    388
Ser Leu Arg Asp Glu Asp Thr Ala Val Tyr Tyr Cys Ala Arg Ala Tyr
        105                 110                 115 tac tac ggt atg gac gtc tgg ggc caa ggg acc acg gtc acc gtc tcc    436
Tyr Tyr Gly Met Asp Val Trp Gly Gln Gly Thr Thr Val Thr Val Ser
120                 125                 130                 135 tca gcc tcc acc aag ggc cca tcg gtc ttc ccc ctg gca ccc tcc tcc    484
Ser Ala Ser Thr Lys Gly Pro Ser Val Phe Pro Leu Ala Pro Ser Ser
                140                 145                 150 aag agc acc tct ggg ggc aca gcg gcc ctg ggc tgc ctg gtc aag gac    532
Lys Ser Thr Ser Gly Gly Thr Ala Ala Leu Gly Cys Leu Val Lys Asp
                155                 160                 165 tac ttc ccc gaa ccg gtg acg gtg tcg tgg aac tca ggc gcc ctg acc    580
Tyr Phe Pro Glu Pro Val Thr Val Ser Trp Asn Ser Gly Ala Leu Thr
        170                 175                 180 agc ggc gtg cac acc ttc ccg gct gtc cta cag tcc tca gga ctc tac    628
Ser Gly Val His Thr Phe Pro Ala Val Leu Gln Ser Ser Gly Leu Tyr
    185                 190                 195 tcc ctc agc agc gtg gtg acc gtg ccc tcc agc agc ttg ggc acc cag    676
Ser Leu Ser Ser Val Val Thr Val Pro Ser Ser Leu Gly Thr Gln
200                 205                 210                 215 acc tac atc tgc aac gtg aat cac aag ccc agc aac acc aag gtg gac    724
Thr Tyr Ile Cys Asn Val Asn His Lys Pro Ser Asn Thr Lys Val Asp
                220                 225                 230 aag aga gtt gag ccc aaa tct tgt gac aaa act cac aca tgc cca ccg    772
Lys Arg Val Glu Pro Lys Ser Cys Asp Lys Thr His Thr Cys Pro Pro
            235                 240                 245 tgc cca gca cct gaa ctc ctg ggg gga ccg tca gtc ttc ctc ttc ccc    820
Cys Pro Ala Pro Glu Leu Leu Gly Gly Pro Ser Val Phe Leu Phe Pro
        250                 255                 260 cca aaa ccc aag gac acc ctc atg atc tcc cgg acc cct gag gtc aca    868
Pro Lys Pro Lys Asp Thr Leu Met Ile Ser Arg Thr Pro Glu Val Thr
265                 270                 275 tgc gtg gtg gtg gac gtg agc cac gaa gac cct gag gtc aag ttc aac    916
Cys Val Val Val Asp Val Ser His Glu Asp Pro Glu Val Lys Phe Asn
280                 285                 290                 295 tgg tac gtg gac ggc gtg gag gtg cat aat gcc aag aca aag ccg cgg    964
Trp Tyr Val Asp Gly Val Glu Val His Asn Ala Lys Thr Lys Pro Arg
                300                 305                 310 gag gag cag tac aac agc acg tac cgt gtg gtc agc gtc ctc acc gtc   1012
Glu Glu Gln Tyr Asn Ser Thr Tyr Arg Val Val Ser Val Leu Thr Val
            315                 320                 325 ctg cac cag gac tgg ctg aat ggc aag gag tac aag tgc aag gtc tcc   1060
Leu His Gln Asp Trp Leu Asn Gly Lys Glu Tyr Lys Cys Lys Val Ser
        330                 335                 340 aac aaa gcc ctc cca gcc ccc atc gag aaa acc atc tcc aaa gcc aaa   1108

-continued

```
Asn Lys Ala Leu Pro Ala Pro Ile Glu Lys Thr Ile Ser Lys Ala Lys
            345                 350                 355 ggg cag ccc cga gaa cca cag gtg tac acc ctg ccc cca tcc cgg gag      1156
Gly Gln Pro Arg Glu Pro Gln Val Tyr Thr Leu Pro Pro Ser Arg Glu
360                 365                 370                 375 gag atg acc aag aac cag gtc agc ctg acc tgc ctg gtc aaa ggc ttc      1204
Glu Met Thr Lys Asn Gln Val Ser Leu Thr Cys Leu Val Lys Gly Phe
                380                 385                 390 tat ccc agc gac atc gcc gtg gag tgg gag agc aat ggg cag ccg gag      1252
Tyr Pro Ser Asp Ile Ala Val Glu Trp Glu Ser Asn Gly Gln Pro Glu
            395                 400                 405 aac aac tac aag acc acg cct ccc gtg ctg gac tcc gac ggc tcc ttc      1300
Asn Asn Tyr Lys Thr Thr Pro Pro Val Leu Asp Ser Asp Gly Ser Phe
        410                 415                 420 ttc ctc tat agc aag ctc acc gtg gac aag agc agg tgg cag cag ggg      1348
Phe Leu Tyr Ser Lys Leu Thr Val Asp Lys Ser Arg Trp Gln Gln Gly
    425                 430                 435 aac gtc ttc tca tgc tcc gtg atg cat gag gct ctg cac aac cac tac      1396
Asn Val Phe Ser Cys Ser Val Met His Glu Ala Leu His Asn His Tyr
440                 445                 450                 455 acg cag aag agc ctc tcc ctg tcc ccg ggt aaa tga                       1432
Thr Gln Lys Ser Leu Ser Leu Ser Pro Gly Lys
                460                 465

<210> SEQ ID NO 4
<211> LENGTH: 466
<212> TYPE: PRT
<213> ORGANISM: Homo sapiens
<220> FEATURE:
<221> NAME/KEY: misc_feature
<222> LOCATION: (1)...(466)
<223> OTHER INFORMATION: Ha22-2(2,4)6.1 heavy chain

<400> SEQUENCE: 4

Met Glu Leu Gly Leu Cys Trp Val Phe Leu Val Ala Ile Leu Glu Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Asn Met Asn Trp Val Arg Gln Ala Pro Gly Lys Gly Leu
    50                  55                  60

Glu Trp Val Ser Tyr Ile Ser Ser Ser Ser Thr Ile Tyr Tyr Ala
65                  70                  75                  80

Asp Ser Val Lys Gly Arg Phe Thr Ile Ser Arg Asp Asn Ala Lys Asn
                85                  90                  95

Ser Leu Ser Leu Gln Met Asn Ser Leu Arg Asp Glu Asp Thr Ala Val
            100                 105                 110

Tyr Tyr Cys Ala Arg Ala Tyr Tyr Gly Met Asp Val Trp Gly Gln
        115                 120                 125

Gly Thr Thr Val Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190
```

-continued

```
Leu Gln Ser Ser Gly Leu Tyr Ser Leu Ser Ser Val Val Thr Val Pro
            195                 200                 205
Ser Ser Ser Leu Gly Thr Gln Thr Tyr Ile Cys Asn Val Asn His Lys
210                 215                 220
Pro Ser Asn Thr Lys Val Asp Lys Arg Val Glu Pro Lys Ser Cys Asp
225                 230                 235                 240
Lys Thr His Thr Cys Pro Pro Cys Pro Ala Pro Glu Leu Leu Gly Gly
                245                 250                 255
Pro Ser Val Phe Leu Phe Pro Pro Lys Pro Lys Asp Thr Leu Met Ile
                260                 265                 270
Ser Arg Thr Pro Glu Val Thr Cys Val Val Val Asp Val Ser His Glu
            275                 280                 285
Asp Pro Glu Val Lys Phe Asn Trp Tyr Val Asp Gly Val Glu Val His
290                 295                 300
Asn Ala Lys Thr Lys Pro Arg Glu Glu Gln Tyr Asn Ser Thr Tyr Arg
305                 310                 315                 320
Val Val Ser Val Leu Thr Val Leu His Gln Asp Trp Leu Asn Gly Lys
                325                 330                 335
Glu Tyr Lys Cys Lys Val Ser Asn Lys Ala Leu Pro Ala Pro Ile Glu
                340                 345                 350
Lys Thr Ile Ser Lys Ala Lys Gly Gln Pro Arg Glu Pro Gln Val Tyr
            355                 360                 365
Thr Leu Pro Pro Ser Arg Glu Glu Met Thr Lys Asn Gln Val Ser Leu
370                 375                 380
Thr Cys Leu Val Lys Gly Phe Tyr Pro Ser Asp Ile Ala Val Glu Trp
385                 390                 395                 400
Glu Ser Asn Gly Gln Pro Glu Asn Asn Tyr Lys Thr Thr Pro Pro Val
                405                 410                 415
Leu Asp Ser Asp Gly Ser Phe Phe Leu Tyr Ser Lys Leu Thr Val Asp
                420                 425                 430
Lys Ser Arg Trp Gln Gln Gly Asn Val Phe Ser Cys Ser Val Met His
            435                 440                 445
Glu Ala Leu His Asn His Tyr Thr Gln Lys Ser Leu Ser Leu Ser Pro
450                 455                 460
Gly Lys
465
```

<210> SEQ ID NO 5
<211> LENGTH: 735
<212> TYPE: DNA
<213> ORGANISM: Homo sapiens
<220> FEATURE:
<221> NAME/KEY: CDS
<222> LOCATION: (25)...(735)
<220> FEATURE:
<221> NAME/KEY: misc_feature
<222> LOCATION: (1)...(735)
<223> OTHER INFORMATION: Ha22-2(2,4)6.1 light chain

<400> SEQUENCE: 5

```
agtcagaccc agtcaggaca cagc atg gac atg agg gtc ccc gct cag ctc        51
                         Met Asp Met Arg Val Pro Ala Gln Leu
                           1               5 ctg ggg ctc ctg ctg ctc tgg ttc cca ggt tcc aga tgc gac atc cag       99
Leu Gly Leu Leu Leu Leu Trp Phe Pro Gly Ser Arg Cys Asp Ile Gln
 10                  15                  20                  25 atg acc cag tct cca tct tcc gtg tct gca tct gtt gga gac aga gtc     147
Met Thr Gln Ser Pro Ser Ser Val Ser Ala Ser Val Gly Asp Arg Val
```

```
                       30                  35                  40
acc atc act tgt cgg gcg agt cag ggt att agc ggc tgg tta gcc tgg      195
Thr Ile Thr Cys Arg Ala Ser Gln Gly Ile Ser Gly Trp Leu Ala Trp
             45                  50                  55 tat cag cag aaa cca ggg aaa gcc cct aag ttc ctg atc tat gct gca      243
Tyr Gln Gln Lys Pro Gly Lys Ala Pro Lys Phe Leu Ile Tyr Ala Ala
             60                  65                  70 tcc act ttg caa agt ggg gtc cca tca agg ttc agc ggc agt gga tct      291
Ser Thr Leu Gln Ser Gly Val Pro Ser Arg Phe Ser Gly Ser Gly Ser
     75                  80                  85 ggg aca gat ttc act ctc acc atc agc agc ctg cag cct gaa gat ttt      339
Gly Thr Asp Phe Thr Leu Thr Ile Ser Ser Leu Gln Pro Glu Asp Phe
 90                  95                 100                 105 gca act tac tat tgt caa cag gct aac agt ttc cct ccc act ttc ggc      387
Ala Thr Tyr Tyr Cys Gln Gln Ala Asn Ser Phe Pro Pro Thr Phe Gly
                    110                 115                 120 gga ggg acc aag gtg gag atc aaa cga act gtg gct gca cca tct gtc      435
Gly Gly Thr Lys Val Glu Ile Lys Arg Thr Val Ala Ala Pro Ser Val
                125                 130                 135 ttc atc ttc ccg cca tct gat gag cag ttg aaa tct gga act gcc tct      483
Phe Ile Phe Pro Pro Ser Asp Glu Gln Leu Lys Ser Gly Thr Ala Ser
            140                 145                 150 gtt gtg tgc ctg ctg aat aac ttc tat ccc aga gag gcc aaa gta cag      531
Val Val Cys Leu Leu Asn Asn Phe Tyr Pro Arg Glu Ala Lys Val Gln
    155                 160                 165 tgg aag gtg gat aac gcc ctc caa tcg ggt aac tcc cag gag agt gtc      579
Trp Lys Val Asp Asn Ala Leu Gln Ser Gly Asn Ser Gln Glu Ser Val
170                 175                 180                 185 aca gag cag gac agc aag gac agc acc tac agc ctc agc agc acc ctg      627
Thr Glu Gln Asp Ser Lys Asp Ser Thr Tyr Ser Leu Ser Ser Thr Leu
                190                 195                 200 acg ctg agc aaa gca gac tac gag aaa cac aaa gtc tac gcc tgc gaa      675
Thr Leu Ser Lys Ala Asp Tyr Glu Lys His Lys Val Tyr Ala Cys Glu
            205                 210                 215 gtc acc cat cag ggc ctg agc tcg ccc gtc aca aag agc ttc aac agg      723
Val Thr His Gln Gly Leu Ser Ser Pro Val Thr Lys Ser Phe Asn Arg
    220                 225                 230 gga gag tgt tag                                                      735
Gly Glu Cys
235

<210> SEQ ID NO 6
<211> LENGTH: 236
<212> TYPE: PRT
<213> ORGANISM: Homo sapiens
<220> FEATURE:
<221> NAME/KEY: misc_feature
<222> LOCATION: (1)...(236)
<223> OTHER INFORMATION: Ha22-2(2,4)6.1 light chain

<400> SEQUENCE: 6

Met Asp Met Arg Val Pro Ala Gln Leu Leu Gly Leu Leu Leu Leu Trp
 1               5                  10                  15

Phe Pro Gly Ser Arg Cys Asp Ile Gln Met Thr Gln Ser Pro Ser Ser
                20                  25                  30

Val Ser Ala Ser Val Gly Asp Arg Val Thr Ile Thr Cys Arg Ala Ser
            35                  40                  45

Gln Gly Ile Ser Gly Trp Leu Ala Trp Tyr Gln Gln Lys Pro Gly Lys
        50                  55                  60

Ala Pro Lys Phe Leu Ile Tyr Ala Ala Ser Thr Leu Gln Ser Gly Val
```

```
                65                  70                  75                  80
Pro Ser Arg Phe Ser Gly Ser Gly Ser Gly Thr Asp Phe Thr Leu Thr
                    85                  90                  95

Ile Ser Ser Leu Gln Pro Glu Asp Phe Ala Thr Tyr Tyr Cys Gln Gln
                100                 105                 110

Ala Asn Ser Phe Pro Pro Thr Phe Gly Gly Gly Thr Lys Val Glu Ile
                115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
                180                 185                 190

Ser Thr Tyr Ser Leu Ser Ser Thr Leu Thr Leu Ser Lys Ala Asp Tyr
                195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 7
<211> LENGTH: 466
<212> TYPE: PRT
<213> ORGANISM: Homo sapiens
<220> FEATURE:
<221> NAME/KEY: misc_feature
<222> LOCATION: (1)...(466)
<223> OTHER INFORMATION: Ha22-2(2,4)6.1 heavy chain

<400> SEQUENCE: 7

Met Glu Leu Gly Leu Cys Trp Val Phe Leu Val Ala Ile Leu Glu Gly
1               5                   10                  15

Val Gln Cys Glu Val Gln Leu Val Glu Ser Gly Gly Gly Leu Val Gln
                20                  25                  30

Pro Gly Gly Ser Leu Arg Leu Ser Cys Ala Ala Ser Gly Phe Thr Phe
            35                  40                  45

Ser Ser Tyr Asn Met Asn Trp Val Arg Gln Ala Pro Gly Lys Gly Leu
    50                  55                  60

Glu Trp Val Ser Tyr Ile Ser Ser Ser Ser Thr Ile Tyr Tyr Ala
65                  70                  75                  80

Asp Ser Val Lys Gly Arg Phe Thr Ile Ser Arg Asp Asn Ala Lys Asn
                85                  90                  95

Ser Leu Ser Leu Gln Met Asn Ser Leu Arg Asp Glu Asp Thr Ala Val
                100                 105                 110

Tyr Tyr Cys Ala Arg Ala Tyr Tyr Tyr Gly Met Asp Val Trp Gly Gln
                115                 120                 125

Gly Thr Thr Val Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
                180                 185                 190
```

```
Leu Gln Ser Ser Gly Leu Tyr Ser Leu Ser Val Val Thr Val Pro
            195                 200                 205

Ser Ser Ser Leu Gly Thr Gln Thr Tyr Ile Cys Asn Val Asn His Lys
210                 215                 220

Pro Ser Asn Thr Lys Val Asp Lys Arg Val Glu Pro Lys Ser Cys Asp
225                 230                 235                 240

Lys Thr His Thr Cys Pro Pro Cys Pro Ala Pro Glu Leu Leu Gly Gly
            245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
            275                 280                 285

Asp Pro Glu Val Lys Phe Asn Trp Tyr Val Asp Gly Val Glu Val His
            290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
            325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
            355                 360                 365

Thr Leu Pro Pro Ser Arg Glu Glu Met Thr Lys Asn Gln Val Ser Leu
            370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
            405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
            435                 440                 445

Glu Ala Leu His Asn His Tyr Thr Gln Lys Ser Leu Ser Leu Ser Pro
            450                 455                 460

Gly Lys
465

<210> SEQ ID NO 8
<211> LENGTH: 236
<212> TYPE: PRT
<213> ORGANISM: Homo sapiens
<220> FEATURE:
<221> NAME/KEY: misc_feature
<222> LOCATION: (1)...(236)
<223> OTHER INFORMATION: Ha22-2(2,4)6.1 light chain

<400> SEQUENCE: 8

Met Asp Met Arg Val Pro Ala Gln Leu Leu Gly Leu Leu Leu Leu Trp
1               5                   10                  15

Phe Pro Gly Ser Arg Cys Asp Ile Gln Met Thr Gln Ser Pro Ser Ser
            20                  25                  30

Val Ser Ala Ser Val Gly Asp Arg Val Thr Ile Thr Cys Arg Ala Ser
            35                  40                  45

Gln Gly Ile Ser Gly Trp Leu Ala Trp Tyr Gln Gln Lys Pro Gly Lys
        50                  55                  60
```

```
Ala Pro Lys Phe Leu Ile Tyr Ala Ala Ser Thr Leu Gln Ser Gly Val
 65                  70                  75                  80

Pro Ser Arg Phe Ser Gly Ser Gly Ser Gly Thr Asp Phe Thr Leu Thr
                 85                  90                  95

Ile Ser Ser Leu Gln Pro Glu Asp Phe Ala Thr Tyr Tyr Cys Gln Gln
            100                 105                 110

Ala Asn Ser Phe Pro Pro Thr Phe Gly Gly Gly Thr Lys Val Glu Ile
        115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
210                 215                 220

Ser Pro Val Thr Lys Ser Phe Asn Arg Gly Glu Cys
225                 230                 235
```

```
<210> SEQ ID NO 9
<211> LENGTH: 5
<212> TYPE: PRT
<213> ORGANISM: Homo sapiens
<220> FEATURE:
<223> OTHER INFORMATION: CDR1 of heavy chain

<400> SEQUENCE: 9

Ser Tyr Asn Met Asn
1               5

<210> SEQ ID NO 10
<211> LENGTH: 17
<212> TYPE: PRT
<213> ORGANISM: Homo sapiens
<220> FEATURE:
<223> OTHER INFORMATION: CDR2 of heavy chain

<400> SEQUENCE: 10

Tyr Ile Ser Ser Ser Ser Ser Thr Ile Tyr Tyr Ala Asp Ser Val Lys
1               5                   10                  15

Gly

<210> SEQ ID NO 11
<211> LENGTH: 8
<212> TYPE: PRT
<213> ORGANISM: Homo sapiens
<220> FEATURE:
<223> OTHER INFORMATION: CDR3 of heavy chain

<400> SEQUENCE: 11

Ala Tyr Tyr Tyr Gly Met Asp Val
1               5

<210> SEQ ID NO 12
<211> LENGTH: 11
<212> TYPE: PRT
<213> ORGANISM: Homo sapiens
```

```
<220> FEATURE:
<223> OTHER INFORMATION: CDR1 of light chain

<400> SEQUENCE: 12

Arg Ala Ser Gln Gly Ile Ser Gly Trp Leu Ala
1               5                   10

<210> SEQ ID NO 13
<211> LENGTH: 7
<212> TYPE: PRT
<213> ORGANISM: Homo sapiens
<220> FEATURE:
<223> OTHER INFORMATION: CDR2 of light chain

<400> SEQUENCE: 13

Ala Ala Ser Thr Leu Gln Ser
1               5

<210> SEQ ID NO 14
<211> LENGTH: 9
<212> TYPE: PRT
<213> ORGANISM: Homo sapiens
<220> FEATURE:
<223> OTHER INFORMATION: CDR3 of light chain

<400> SEQUENCE: 14

Gln Gln Ala Asn Ser Phe Pro Pro Thr
1               5

<210> SEQ ID NO 15
<211> LENGTH: 4
<212> TYPE: PRT
<213> ORGANISM: Artificial Sequence
<220> FEATURE:
<223> OTHER INFORMATION: linker

<400> SEQUENCE: 15

Gly Phe Leu Gly
1

<210> SEQ ID NO 16
<211> LENGTH: 8
<212> TYPE: PRT
<213> ORGANISM: Artificial Sequence
<220> FEATURE:
<223> OTHER INFORMATION: VH CDR1 according to IMGT

<400> SEQUENCE: 16

Gly Phe Thr Phe Ser Ser Tyr Asn
1               5

<210> SEQ ID NO 17
<211> LENGTH: 8
<212> TYPE: PRT
<213> ORGANISM: Artificial Sequence
<220> FEATURE:
<223> OTHER INFORMATION: VH CDR2 according to IMGT

<400> SEQUENCE: 17

Ile Ser Ser Ser Ser Ser Thr Ile
1               5

<210> SEQ ID NO 18
<211> LENGTH: 10
<212> TYPE: PRT
<213> ORGANISM: Artificial Sequence
<220> FEATURE:
```

<223> OTHER INFORMATION: VH CDR3 according to IMGT

<400> SEQUENCE: 18

Ala Arg Ala Tyr Tyr Tyr Gly Met Asp Val
1               5                   10

<210> SEQ ID NO 19
<211> LENGTH: 6
<212> TYPE: PRT
<213> ORGANISM: Artificial Sequence
<220> FEATURE:
<223> OTHER INFORMATION: VL CDR1 according to IMGT

<400> SEQUENCE: 19

Gln Gly Ile Ser Gly Trp
1               5

<210> SEQ ID NO 20
<211> LENGTH: 3
<212> TYPE: PRT
<213> ORGANISM: Artificial Sequence
<220> FEATURE:
<223> OTHER INFORMATION: VL CDR2 according to IMGT

<400> SEQUENCE: 20

Ala Ala Ser
1

<210> SEQ ID NO 21
<211> LENGTH: 9
<212> TYPE: PRT
<213> ORGANISM: Artificial Sequence
<220> FEATURE:
<223> OTHER INFORMATION: VL CDR3 according to IMGT

<400> SEQUENCE: 21

Gln Gln Ala Asn Ser Phe Pro Pro Thr
1               5

<210> SEQ ID NO 22
<211> LENGTH: 117
<212> TYPE: PRT
<213> ORGANISM: Artificial Sequence
<220> FEATURE:
<223> OTHER INFORMATION: heavy chain variable region (VH), the 20th
      amino acid (glutamic acid) to the 136th amino acid (serine) of SEQ
      ID NO:7

<400> SEQUENCE: 22

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asn Met Asn Trp Val Arg Gln Ala Pro Gly Lys Gly Leu Glu Trp Val
        35                  40                  45

```
Ser Tyr Ile Ser Ser Ser Ser Thr Ile Tyr Ala Asp Ser Val
    50              55                  60

Lys Gly Arg Phe Thr Ile Ser Arg Asp Asn Ala Lys Asn Ser Leu Ser
65              70                  75                  80

Leu Gln Met Asn Ser Leu Arg Asp Glu Asp Thr Ala Val Tyr Tyr Cys
                85                  90                  95

Ala Arg Ala Tyr Tyr Tyr Gly Met Asp Val Trp Gly Gln Gly Thr Thr
            100                 105                 110

Val Thr Val Ser Ser
        115

<210> SEQ ID NO 23
<211> LENGTH: 108
<212> TYPE: PRT
<213> ORGANISM: Artificial Sequence
<220> FEATURE:
<223> OTHER INFORMATION: light chain variable region (VL), the 23rd
      amino acid (aspartic acid) to the 130th amino acid (arginine) of
      SEQ ID NO:8

<400> SEQUENCE: 23

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Gly Trp
            20                  25                  30

Leu Ala Trp Tyr Gln Gln Lys Pro Gly Lys Ala Pro Lys Phe Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Pro
                85                  90                  95

Thr Phe Gly Gly Gly Thr Lys Val Glu Ile Lys Arg
            100                 105
```